US008765731B2

(12) United States Patent
Henderson et al.

(10) Patent No.: US 8,765,731 B2
(45) Date of Patent: Jul. 1, 2014

(54) BENZIMIDAZOLE ANALOGUES FOR THE TREATMENT OR PREVENTION OF FLAVIVIRUS INFECTIONS

(71) Applicant: Vertex Pharmaceuticals Incorporated, Cambridge, MA (US)

(72) Inventors: James A. Henderson, Cambridge, MA (US); John Maxwell, Hingham, MA (US); Louis Vaillancourt, Mascouche (CA); Mark Morris, Somerville, MA (US); Ronald Grey, Jr., Mansfield, MA (US); Simon Giroux, Cambridge, MA (US); Laval Chan Chun Kong, Kirkland (CA); Sanjoy Kumar Das, Pierrefonds (CA); Bingan Liu, Laval (CA); Carl Poisson, Montreal (CA); Caroline Cadilhac, Montreal (CA); Monica Bubenik, Mascouche (CA); T. Jagadeeswar Reddy, Pierrefonds (CA); Guy Falardeau, Laval (CA); Constantin Yannopoulos, Notre-Dame de l'Ile Perrot (CA); Jian Wang, Newton, MA (US); Oswy Z. Pereira, Kirkland (CA); Youssef L. Bennani, Lorraine (CA); Albert C. Pierce, Cambridge, MA (US); Govinda Rao Bhisetti, Lexington, MA (US); Kevin M. Cottrell, Cambridge, MA (US); Valerie Marone, Norton, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/678,854

(22) Filed: Nov. 16, 2012

(65) Prior Publication Data
US 2013/0157997 A1    Jun. 20, 2013

Related U.S. Application Data

(63) Continuation of application No. 12/838,350, filed on Jul. 16, 2010, now Pat. No. 8,354,419.

(60) Provisional application No. 61/317,017, filed on Mar. 24, 2010, provisional application No. 61/226,152, filed on Jul. 16, 2009.

(51) Int. Cl.
*A61K 31/4184* (2006.01)
*A61K 31/496* (2006.01)
*A61K 31/4545* (2006.01)
*A61K 31/506* (2006.01)
*A61K 31/4439* (2006.01)
*C07D 495/04* (2006.01)
*C07D 417/14* (2006.01)
*C07D 413/14* (2006.01)
*C07D 409/14* (2006.01)
*C07D 405/14* (2006.01)

(52) U.S. Cl.
USPC .......... 514/210.18; 514/394; 514/232.5; 514/212.08; 514/363; 514/375; 514/387; 514/254.06; 514/275; 514/218; 548/305.4; 548/136; 548/217; 548/303.7; 548/300.7; 544/80; 544/370; 544/331; 540/525; 540/575

(58) Field of Classification Search
USPC .............. 514/252.11, 394, 316, 253.09, 269, 514/338, 210.18, 232.5, 212.08, 363, 375, 514/387, 254.06, 275, 218; 548/305.4, 136, 548/217, 303.7, 300.7; 544/357, 364, 319, 544/80, 370, 331; 546/187, 273.4; 540/525, 540/575
See application file for complete search history.

(56) References Cited

U.S. PATENT DOCUMENTS 8,354,419 B2 *    1/2013    Henderson et al. .......... 514/269
2009/0170859 A1 *  7/2009    Tsantrizos et al. ............ 514/249

FOREIGN PATENT DOCUMENTS

| WO | 2004014313 | 2/2004 |
| WO | 2004014852 | 2/2004 |
| WO | 2006133326 | 12/2006 |
| WO | 2008021927 | 2/2008 |
| WO | 2008021928 | 2/2008 |
| WO | 2008021936 | 2/2008 |
| WO | 2008144380 | 11/2008 |
| WO | 2009020825 | 2/2009 |
| WO | 2009020828 | 2/2009 |
| WO | 2009102318 | 8/2009 |
| WO | 2009102325 | 8/2009 |
| WO | 2009102568 | 8/2009 |
| WO | 2009102633 | 8/2009 |
| WO | 2010017401 | 2/2010 |

(Continued)

OTHER PUBLICATIONS

International Search Report, PCT/US2010/042340, dated Mar. 11, 2011.

*Primary Examiner* — Kristin Vajda
(74) *Attorney, Agent, or Firm* — Min Lin

(57) ABSTRACT

Compounds represented by formula I:

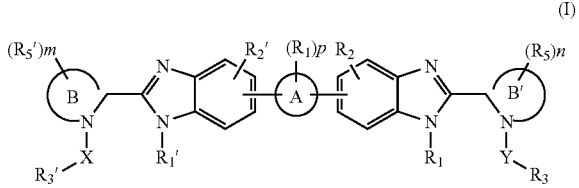

or pharmaceutically acceptable salts and solvates thereof, wherein A, B, B', X, Y, $R_1$, $R_1'$, $R_2$, $R_2'$, $R_3$, $R_3'$, $R_5$, $R_5'$, $R_6$, m, n, or p are as defined herein, are useful for treating flaviviridae viral infections.

22 Claims, No Drawings

(56) References Cited

FOREIGN PATENT DOCUMENTS

| | | |
|---|---|---|
| WO | 2010038790 | 4/2010 |
| WO | 2010038791 | 4/2010 |
| WO | 2010138488 | 4/2010 |
| WO | 2010065668 | 6/2010 |
| WO | 2010065674 | 6/2010 |
| WO | 2010065681 | 6/2010 |
| WO | 2010091413 | 8/2010 |
| WO | 2010094977 | 8/2010 |
| WO | 2010096302 | 8/2010 |
| WO | 2010096462 | 8/2010 |
| WO | 2010096777 | 8/2010 |
| WO | 2010038368 | 9/2010 |
| WO | 2010099527 | 9/2010 |
| WO | 2010111483 | 9/2010 |
| WO | 2010111534 | 9/2010 |
| WO | 2010111673 | 9/2010 |
| WO | 2010117635 | 10/2010 |
| WO | 2010117704 | 10/2010 |
| WO | 2010117977 | 10/2010 |
| WO | 2010120621 | 10/2010 |
| WO | 2010120935 | 10/2010 |
| WO | 2010122162 | 10/2010 |
| WO | 2010132538 | 11/2010 |
| WO | 2010132601 | 11/2010 |
| WO | 2010138791 | 12/2010 |
| WO | 2010144646 | 12/2010 |
| WO | 2011004276 | 1/2011 |
| WO | 2011028596 | 3/2011 |
| WO | 2011050146 | 4/2011 |
| WO | 2011059850 | 5/2011 |
| WO | 2011059887 | 5/2011 |
| WO | 2011060000 | 5/2011 |
| WO | 2011075439 | 6/2011 |
| WO | 2011075615 | 6/2011 |
| WO | 2011081918 | 7/2011 |
| WO | 2011082077 | 7/2011 |
| WO | 2011091417 | 7/2011 |
| WO | 2011091446 | 7/2011 |
| WO | 2011109037 | 9/2011 |
| WO | 2011112429 | 9/2011 |
| WO | 2011127350 | 10/2011 |
| WO | 2011149856 | 12/2011 |
| WO | 2011150243 | 12/2011 |
| WO | 2011153396 | 12/2011 |
| WO | 2011156543 | 12/2011 |
| WO | 2012018325 | 2/2012 |
| WO | 2012021591 | 2/2012 |
| WO | 2012021704 | 2/2012 |
| WO | 2012039717 | 3/2012 |
| WO | 2012040389 | 3/2012 |
| WO | 2012040923 | 4/2012 |
| WO | 2012040924 | 4/2012 |
| WO | 2012041014 | 4/2012 |
| WO | 2012041227 | 4/2012 |
| WO | 2012050918 | 4/2012 |
| WO | 2012058125 | 5/2012 |
| WO | 2012122716 | 9/2012 |
| WO | 2012125926 | 9/2012 |
| WO | 2012135581 | 10/2012 |
| WO | 2012166716 | 12/2012 |

\* cited by examiner

BENZIMIDAZOLE ANALOGUES FOR THE TREATMENT OR PREVENTION OF FLAVIVIRUS INFECTIONS

RELATED APPLICATIONS

This application claims the benefit of U.S. application Ser. No. 12/838,350, filed on Jul. 16, 2010 which claims the benefit of U.S. Provisional Application No. 61/226,152 filed on Jul. 16, 2009, and U.S. Provisional Application No. 61/317,017 filed on Mar. 24, 2010, the entire teachings of each of which are incorporated herein by reference.

BACKGROUND OF THE INVENTION

The present invention relates to novel compounds and a method for the treatment or prevention of *Flavivirus* infections using novel compounds.

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has close relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 bp coding for a polyprotein of 3009-3030 amino-acids, which is cleaved co and post-translationally into mature viral proteins (core, E1, E2, p7, NS2, NS3, NS4A, NS4B, NS5A, NS5B). It is believed that the structural glycoproteins, E1 and E2, are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

Combination of pegylated interferon plus ribavirin is the treatment of choice for chronic HCV infection. This treatment does not provide sustained viral response (SVR) in a majority of patients infected with the most prevalent genotype (1a and 1b). Furthermore, significant side effects prevent compliance to the current regimen and may require dose reduction or discontinuation in some patients.

There is therefore a great need for the development of anti-viral agents for use in treating or preventing *Flavivirus* infections.

SUMMARY OF THE INVENTION

The present invention is directed to compounds described herein, e.g., compounds represented by formulas (I), (II), (III), (IV), (IIIA), (IIIA'), (IIB), (IVA), (VA), (V), (VI), (VII), (VIII), (IX), (X) and (XI) described herein.

In one embodiment, the present invention is directed to a method treating or preventing a Hepatitis C viral infection in a human comprising administering to the human a therapeutically effective amount of a compound described herein.

In another embodiment, the present invention is directed to a pharmaceutical composition comprising at least one compound described herein and at least one pharmaceutically acceptable carrier or excipients.

The present invention is also directed to the use of a compound described herein for treating or preventing a Hepatitis C viral infection in a human.

DETAILED DESCRIPTION OF THE INVENTION

In one aspect, the present invention provides a compound of formula (I):

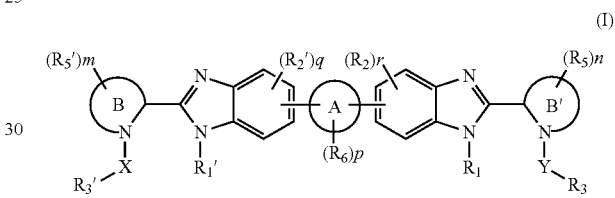

wherein,

A is $C_{2-4}$ alkenyl, $C_{2-5}$ alkynyl, $C_{3-10}$ cycloalkyl, $C_{6-14}$ aryl, or 4-12 membered heterocycle, 5-12 membered heteroaryl;

B and B' are each independently a 4-7 membered heterocycle;

$R_1$ and $R_1'$ are each independently H, $C_{1-6}$ alkyl, $C_{2-6}$ alkenyl, or $C_{2-6}$ alkynyl;

$R_2$ and $R_2'$ are each independently H, halogen, $C_{1-6}$ alkyl, or $C_{1-6}$ alkoxy;

X and Y are each independently

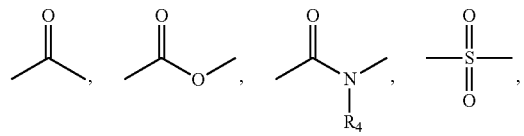

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, halogen, $C_{1-4}$ alkyl, hydroxyl, $C_{1-4}$ alkoxy, or $C_{1-4}$ halogenated alkyl;

$R_6$ is H, halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl or any two occurrence of $R_6$ on adjacent carbons can be taken together with the carbons to which they are attached to form a 5-7 cycloalkyl which is unsubstituted or substituted one or more times by $R^{10}$ or a 5-7 membered heterocycle which is unsubstituted or substituted one or more times by $R^{12}$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

m, and n, are each independently 0, 1, 2, 3 or 4;

p is 0, 1, 2, 3 or 4;

q, and r are each independently 0, 1, 2 or 3.

$R^{10}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{12}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; or a pharmaceutically acceptable salts thereof.

In another aspect, there is provided a method for treating or preventing a Flaviviridae viral infection in a patient comprising administering to the patient a therapeutically effective amount of a compound, composition or combination of the invention.

In another aspect, there is provided a pharmaceutical composition comprising at least one compound of the invention and at least one pharmaceutically acceptable carrier or excipient.

In another aspect, there is provided a combination comprising a compound of the invention and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In a further aspect, there is provided the use of a compound, composition or combination of the invention for treating or preventing a Flaviviridae viral infection in a human.

In still another aspect, there is provided the use of a compound, composition or combination of the invention for the manufacture of a medicament for treating or preventing a viral Flaviviridae infection in a human.

In one embodiment, compounds of the present invention comprise those wherein the following embodiments are present, either independently or in combination.

In accordance with a further embodiment, the compounds of the present invention are represented by formula (II)

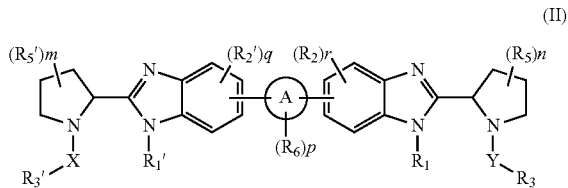

(II)

or pharmaceutically acceptable salts thereof;

In accordance with a further embodiment, the compounds of the present invention are represented by formula (III):

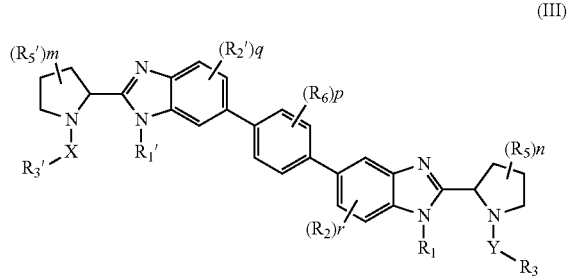

(III)

or pharmaceutically acceptable salts thereof;

In accordance with a further embodiment the compounds of the present invention are represented by formula (IV):

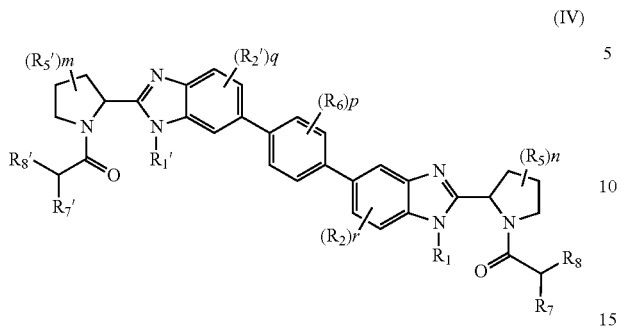

(IV)

or pharmaceutically acceptable salts thereof;
wherein
R$_7$ and R$_7$' are each independently C$_{1-8}$ alkyl, C$_{2-8}$ alkenyl, C$_{2-8}$ alkynyl, phenyl, benzyl, 5-6 membered heteroaryl, 6-7 membered heteroaralkyl, 3-6 membered heterocycle, or 4-7 membered heterocycle-alkyl; and
R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

According to a further embodiment, A is phenyl, thiophene, pyridine, pyrimidine, or triazole.

According to a further embodiment, A is phenyl, or thiophene.

According to a further embodiment, A is phenyl.

According to a further embodiment, B and B' in formulas (I) are each independently a pyrrolidine or a piperidine.

According to a further embodiment, B in formulas (I) is a pyrrolidine.

According to a further embodiment, B in formulas (I) is a piperidine.

According to a further embodiment, B' in formulas (I) is a pyrrolidine.

According to a further embodiment, B' in formulas (I) is a piperidine.

According to a further embodiment, X, is

According to a further embodiment X is

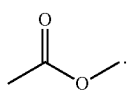

According to a further embodiment X is

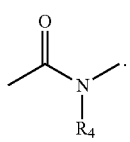

According to a further embodiment X is

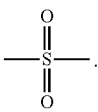

According to a further embodiment, X is a bond
According to a further embodiment, Y is

According to a further embodiment, Y is

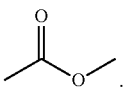

According to a further embodiment, Y is

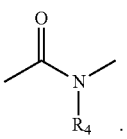

According to a further embodiment, Y is

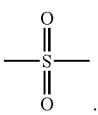

According to a further embodiment, Y is a bond.
According to a further embodiment, m and/or n are each independently 0, 1, 2, or 3.
According to a further embodiment, m and/or n are each independently 0, 1, or 2
According to a further embodiment, m and/or n are each independently 0, or 1.
According to a further embodiment, m and/or n are each independently 2.
According to a further embodiment, m and/or n are each independently 1.
According to a further embodiment, m and/or n are each independently 0.
According to a further embodiment, p is 0, 1, 2, or 3.
According to a further embodiment, p is 0, 1, or 2.
According to a further embodiment, p is 0 or 1.
According to a further embodiment, p is 0.
According to a further embodiment, p is 1.
According to a further embodiment, p is 2.
According to a further embodiment, R$_1$ and R$_1$' are each independently H.
According to a further embodiment, q and r are each independently 0, 1, or 2.

According to a further embodiment, q and r are each independently 0, or 1.

According to a further embodiment, q and r are each independently 1.

According to a further embodiment, q and r are each independently 0.

According to a further embodiment, $R_2$ and $R_2'$ are each independently H or Halogen.

According to a further embodiment, $R_2$ and $R_2'$ are each independently H or fluoro.

According to a further embodiment, $R_2$ and $R_2$ are each independently fluoro.

According to a further embodiment, $R_2$ and $R_2'$, are each independently H.

According to a further embodiment, $R_5$ and $R_5'$, are each independently H, Halogen, methyl, ethyl, t-butoxy-, or hydroxyl.

According to a further embodiment, $R_5$ and $R_5'$ are each independently H or Halogen.

According to a further embodiment, $R_5$ and $R_5'$ are each independently H or fluoro.

According to a further embodiment, $R_5$ and $R_5'$ are fluoro.

According to a further embodiment, $R_5$ and $R_5'$ are fluoro and m, and n, are 2.

According to a further embodiment, $R_5$ and $R_5'$ are each independently H.

According to a further embodiment, $R_6$ is halogen, $C_{1-3}$ alkyl, hydroxyl, cyano, benzyloxy, or $C_{1-3}$ alkoxy.

According to a further embodiment, $R_6$ is chloro, fluoro, methyl, hydroxyl, benzyloxy, cyano, or methoxy.

According to a further embodiment, $R_6$ is fluoro, methyl, or methoxy, and p is 2.

According to a further embodiment, $R_6$ is H.

According to a further embodiment, $R_3$ and $R_3'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

According to a further embodiment, $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 5-6 membered heterocycle which is unsubstituted or substituted one or more times by $R^{12}$, or 6-8 membered heterocycle-alkyl which is unsubstituted or substituted one or more times by $R^{12}$.

According to a further embodiment, $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 5-6 membered heterocycle which is unsubstituted or substituted one or more times by $R^{12}$, or 6-7 membered heterocycle-alkyl which is unsubstituted or substituted one or more times by $R^{12}$.

According to a further embodiment, $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$.

According to a further embodiment, $R_3$ and $R_3'$ are each independently phenyl which is unsubstituted or substituted one or more times by $R^{11}$.

According to a further embodiment, $R_3$ and $R_3'$ are each independently benzyl which is unsubstituted or substituted one or more times by $R^{11}$.

According to a further embodiment, $R_3$ and $R_3'$ are each independently benzyl.

According to a further embodiment, $R_3$ and $R_3'$ are each independently, $C_{1-12}$ alkyl which is unsubstituted or substituted one or more times by $R^{10}$.

According to a further embodiment, $R_3$ and $R_3'$ are each independently methyl, ethyl, propyl, isopropyl, butyl, sec-butyl, tert-butyl, pentyl, 2-methylbutyl, 3-methylbutyl, cyclopropyl, cyclobutyl, cyclopentyl, cyclohexyl, or cyclohexyl $(CH_2)$—, which in each case is unsubstituted or substituted one or more times by $R^{10}$.

According to a further embodiment, $R_3$ and $R_3'$ are each independently methyl, ethyl, propyl, isopropyl, butyl, sec-butyl, tert-butyl, pentyl, 2-methylbutyl, 3-methylbutyl, cyclopropyl, cyclobutyl, cyclopentyl, cyclohexyl, or cyclohexyl $(CH_2)$—.

According to a further embodiment, $R_3$ and $R_3'$ are each independently tert-butyl.

According to a further embodiment, $R_3$ and $R_3'$ are each independently H.

According to a further embodiment, $R_3$ and $R_3'$ are each independently 3-6 membered heterocycle which is unsubstituted or substituted one or more times by $R^{12}$.

According to a further embodiment, $R_3$ and $R_3'$ are each independently tetrahydrofuranyl.

According to a further embodiment, $R_3$ and $R_3'$ are each independently 4-8 membered heterocycle-alkyl which is unsubstituted or substituted one or more times by $R^{12}$.

According to a further embodiment, $R^{10}$ is halogen, —$OR_a$, OXO, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$. are each independently H or methyl.

According to a further embodiment, $R^{10}$ is —$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —$NR_bSO_2R_a$, or —$NR_bSO_2NR_aR_b$, wherein $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is —$NR_aR_b$, —$NR_dC(=O)NR_aR_b$, —$NR_bC(=O)R_a$, —$NR_bC(=O)OR_a$, or —$NR_bSO_2R_a$, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is —$NR_aR_b$, —$NR_dC(=O)NR_aR_b$, —$NR_bC(=O)R_a$, —$NR_bC(=O)OR_a$, or —$NR_bSO_2R_a$, wherein $R_a$ is $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$ are each independently H or methyl.

According to a further embodiment, $R^{10}$ is —$NR_aR_b$, —$NR_bC(=O)R_a$, wherein $R_a$-$R_b$ are each independently H, $C_{1-6}$ alkyl, $C_{2-6}$ alkenyl, $C_{2-6}$ alkynyl, or $C_{7-8}$ aralkyl.

According to a further embodiment, $R^{10}$ is —$NR_bC(=O)OR_a$, wherein $R_a$-$R_b$ are each independently H, $C_{1-6}$ alkyl, $C_{2-6}$ alkenyl, $C_{2-6}$ alkynyl, or $C_{7-8}$ aralkyl.

According to a further embodiment, $R^{10}$ is —$NR_bC(=O)OR_a$, wherein $R_a$ is $C_{1-6}$ alkyl, $C_{2-6}$ alkenyl, $C_{2-6}$ alkynyl, or $C_{7-8}$ aralkyl, and $R_b$ is H or methyl.

According to a further embodiment, $R^{10}$ is —$NR_bC(=O)OR_a$, wherein $R_a$ is $C_{1-6}$ alkyl, $C_{2-6}$ alkenyl, $C_{2-6}$ alkynyl, or $C_{7-8}$ aralkyl, and $R_b$ is H.

According to a further embodiment, $R^{10}$ is halogen, —$OR_a$, oxo, —$C(=O)OR_a$, —$C(O)NR_aR_b$, —$C(=O)OH$, —$C(=O)R_a$, —$OC(=O)NR_aR_b$, —$OC(=O)R_a$, —$OC(=O)OR_a$, hydroxyl, cyano, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is —$OR_a$, —$OC(=O)NR_aR_b$, —$OC(=O)R_a$, —$OC(=O)OR_a$, hydroxyl, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is oxo, —$C(=O)OR_a$, —$C(O)NR_aR_b$, —$C(=O)OH$, —$C(=O)R_a$, cyano, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is halogen, —$OR_a$, oxo, —$C(=O)OR_a$, —$C(O)NR_aR_b$, —$C(=O)OH$, —$OC(=O)NR_aR_b$, hydroxyl, cyano, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is $OR_a$, —$C(=O)OR_a$, —$C(O)NR_aR_b$, —$C(=O)OH$, —$OC(=O)NR_aR_b$, hydroxyl, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{10}$ is halogen, hydroxyl, or —$NH_2$.

According to a further embodiment, $R^{10}$ is halogen.

According to a further embodiment, $R^{11}$ is halogen, —$OR_a$, —$NR_aR_b$, —$C(=O)OR_a$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, —$OC(=O)R_a$, —$OC(=O)OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$, are each independently H or methyl.

According to a further embodiment, $R^{11}$ is halogen, —$OR_a$, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{11}$ is halogen, —$OR_a$, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, is $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$ are each independently H or methyl.

According to a further embodiment, $R^{11}$ is halogen, —$OR_a$, —$NR_aR_b$, hydroxyl, cyano, $C_{1-6}$ alkyl, wherein $R_a$-$R_b$ are each independently H, $C_{1-3}$ alkyl.

According to a further embodiment, $R^{11}$ is halogen, hydroxyl, cyano, or —$NH_2$.

According to a further embodiment, $R^{11}$ is halogen.

According to a further embodiment, $R^{12}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$, are each independently H or methyl.

According to a further embodiment, $R^{12}$ is halogen, —$OR_a$, oxo, —$NR_aR_b$, —C(=O)$OR_a$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{12}$ is halogen, —$OR_a$, oxo, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

According to a further embodiment, $R^{12}$ is halogen, —$OR_a$, oxo, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$ is $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$ are each independently H or methyl.

According to a further embodiment, $R^{12}$ is halogen, —$OR_a$, oxo, —$NR_aR_b$, hydroxyl, cyano, $C_{1-6}$ alkyl, wherein $R_a$-$R_b$ are each independently H, $C_{1-3}$ alkyl.

According to a further embodiment, $R^{12}$ is halogen.

According to a further embodiment, $R_8$ and $R_8'$ in formula (IV), are each independently —$NR_aR_b$, —$NR_bC$(=O)$R_a$, —$NR_bC$(=O)$OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ in formula (IV), are each independently —$NR_aR_b$, —$NR_bC$(=O)$OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ in formula (IV), are each independently —$NR_bC$(=O)$OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

According to a further embodiment, $R_8$ and $R_8'$ in formula (IV), are each independently —$NR_bC$(=O)$OR_a$, wherein $R_a$-$R_b$ are each independently H, $C_{1-6}$ alkyl, phenyl, tetrahydrofuran, or benzyl.

According to a further embodiment, $R_8$ and $R_8'$ in formula (IV), are each independently —$NR_bC$(=O)$OR_a$, wherein $R_a$ is $C_{1-6}$ alkyl, tetrahydrofuran, or benzyl, and $R_b$ is H.

According to a further embodiment, $R_8$ and $R_8'$ in formula (IV), are each independently —$NR_bC$(=O)$OR_a$, wherein $R_a$ is $C_{1-6}$ alkyl, tetrahydrofuran, or benzyl, and $R_b$ is methyl.

According to a further embodiment, $R_8$ and $R_8'$ in formula (IV), are each independently —$NR_bC$(=O)$OR_a$, wherein $R_a$ is $C_{1-6}$ alkyl and $R_b$ is H, or methyl.

According to a further embodiment, $R_8$ and $R_8'$ in formula (IV), are each independently —$NR_bC$(=O)$OR_a$, wherein $R_a$ is $C_{1-6}$ alkyl and $R_b$ is H.

According to a further embodiment, $R_7$ and $R_7'$ in formula (IV), are each independently phenyl.

According to a further embodiment, $R_7$ and $R_7'$ in formula (IV), are each independently benzyl.

According to a further embodiment, $R_7$ and $R_7'$ in formula (IV), are each independently, $C_{1-6}$ alkyl.

According to a further embodiment, $R_7$ and $R_7'$ in formula (IV), are each independently methyl, ethyl, propyl, isopropyl, butyl, sec-butyl, tert-butyl, pentyl, 2-methylbutane, 3-methylbutane, cyclopropyl, cyclobutyl, cyclopentyl, or cyclohexyl.

According to a further embodiment, $R_7$ and $R_7'$ in formula (IV), are each independently methyl.

According to a further embodiment, $R_7$ and $R_7'$ in formula (IV), are each independently ethyl.

According to a further embodiment, $R_7$ and $R_7'$ in formula (IV), are each independently propyl.

According to a further embodiment, $R_7$ and $R_7'$ in formula (IV), are each independently isopropyl.

According to a further embodiment, $R_7$ and $R_7'$ in formula (IV), are each independently butyl.

According to a further embodiment, $R_7$ and $R_7'$ in formula (IV), are each independently tert-butyl.

According to a further embodiment, $R_7$ and $R_7'$ in formula (IV), are each independently cyclopropyl.

According to a further embodiment, $R_7$ and $R_7'$ in formula (IV), are each independently cyclobutyl.

According to a further embodiment, $R_7$ and $R_7'$ in formula (IV), are each independently cyclopentyl.

According to a further embodiment, $R_7$ and $R_7'$ in formula (IV), are each independently cyclohexyl.

In accordance with a further embodiment of the invention, the compounds of the present invention are selected from the compounds of the invention, wherein:
$R_1$ and $R_1'$ are H;
$R_2$ and $R_2'$ are each independently H, or halogen;
q and r are each independently 0, or 1.
X and Y are each independently

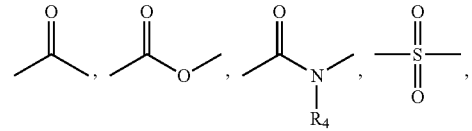

or a bond;
$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, or halogen;

$R_6$ is H, halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl, wherein $R_a$-$R_d$ are each independently H, $C_{1-6}$ alkyl, $C_{2-6}$ alkenyl, $C_{2-6}$ alkynyl, or $C_{7-16}$ aralkyl;

m, and n, are each independently 0, 1, or 2;

p is 0, 1, or 2;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of the invention, wherein:

$R_1$ and $R_1'$ are H;

$R_2$ and $R_2'$ are each independently H, or halogen;

q and r are each independently 0, or 1.

X and Y are each independently

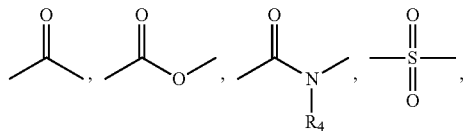

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, or halogen;

$R_6$ is H, halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl, wherein $R_a$-$R_d$ are each independently H, $C_{1-6}$ alkyl, $C_{2-6}$ alkenyl, $C_{2-6}$ alkynyl, or $C_{7-16}$ aralkyl;

m, and n, are each independently 0, 1, or 2;

p is 0, 1, or 2;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$. are each independently H or methyl;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$. are each independently H or methyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$. are each independently H or methyl.

In accordance with a further embodiment of the invention, the compounds of the present invention are selected from the compounds of the invention wherein:

$R_1$ and $R_1'$ are H;
$R_2$ and $R_2'$ are each independently H, or halogen;
q and r are each independently 0, or 1;
X and Y are each independently

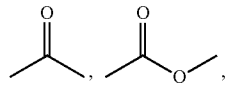

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, or halogen;
$R_6$ is H, halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —$SO_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl, wherein $R_a$-$R_d$ are each independently H, $C_{1-6}$ alkyl, $C_{2-6}$ alkenyl, $C_{2-6}$ alkynyl, or $C_{7-16}$ aralkyl;

m, and n, are each independently 0, 1, or 2;
p is 0, 1, or 2;
$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —$SO_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of the invention, wherein:

$R_1$ and $R_1'$ are H;
$R_2$ and $R_2'$ are each independently H, or halogen;
q and r are each independently 0, or 1;
X and Y are each independently

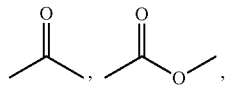

or a bond;

$R_3$ and $R_3'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, or halogen;

$R_6$ is H, halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl, wherein $R_a$-$R_d$ are each independently H, $C_{1-6}$ alkyl, $C_{2-6}$ alkenyl, $C_{2-6}$ alkynyl, or $C_{7-16}$ aralkyl;

m, and n, are each independently 0, 1, or 2;

p is 0, 1, or 2;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of the invention, wherein:

$R_1$ and $R_1'$ are H;

$R_2$ and $R_2'$ are each independently H, or halogen;

q and r are each independently 0, or 1;

X and Y are

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, or halogen;

$R_6$ is H, halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl, wherein $R_a$-$R_d$ are each independently H, $C_{1-6}$ alkyl, $C_{2-6}$ alkenyl, $C_{2-6}$ alkynyl, or $C_{7-16}$ aralkyl;

m, and n, are each independently 0, 1, or 2;

p is 0, 1, or 2;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)

$R_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of formula (IV), wherein:

R$_1$ and R$_1$' are H;
R$_2$ and R$_2$' are each independently H or Halogen;
q and r are each independently 0, or 1.
R$_5$ and R$_5$' are each independently H or Halogen;
R$_6$ is halogen, C$_{1-3}$ alkyl, hydroxyl, cyano, benzyloxy, or C$_{1-3}$ alkoxy;
m, and n, are each independently 0, 1, or 2;
p is 0, 1, or 2;
R$_7$ and R$_7$' are each independently C$_{1-8}$ alkyl, C$_{2-8}$ alkenyl, C$_{2-8}$ alkynyl, phenyl, benzyl, 5-6 membered heteroaryl, 6-7 membered heteroaralkyl, 3-6 membered heterocycle, or 4-7 membered heterocycle-alkyl; and
R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of formula (IV), wherein:

R$_1$ and R$_1$' are H;
R$_2$ and R$_2$' are H;
R$_5$ and R$_5$' are H;
R$_6$ is halogen, C$_{1-3}$ alkyl, hydroxyl, cyano, benzyloxy, or C$_{1-3}$ alkoxy;
P is 0, 1, or 2.
R$_7$ and R$_7$' are each independently C$_{1-8}$ alkyl, C$_{2-8}$ alkenyl, C$_{2-8}$ alkynyl, phenyl, benzyl, 5-6 membered heteroaryl, 6-7 membered heteroaralkyl, 3-6 membered heterocycle, or 4-7 membered heterocycle-alkyl; and
R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In accordance with a further embodiment of the invention, the compounds of the present invention are selected from the compounds of formula (IV), wherein:

R$_1$ and R$_1$' are each H;
R$_2$ and R$_2$' are each H;
R$_5$ and R$_5$' are each H;
R$_6$ is halogen, C$_{1-3}$ alkyl, hydroxyl, cyano, benzyloxy, or C$_{1-3}$ alkoxy;
p is 0, 1, or 2.

R$_7$ and R$_7$' are each independently C$_{1-8}$ alkyl, C$_{2-8}$ alkenyl, C$_{2-8}$ alkynyl; and
R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention R$_1$ is halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, —P(=O)OR$_a$OR$_b$, C$_{1-6}$ alkyl which is unsubstituted or substituted one or more times by R$^{10}$, C$_{2-6}$ alkenyl which is unsubstituted or substituted one or more times by R$^{10}$, C$_{2-6}$ alkynyl which is unsubstituted or substituted one or more times by R$^{10}$;

In one embodiment in the compounds of the present invention, herein as valency allows in B, B', R$_a$-R$_d$, R$_1$, R$_2$, R$_2$', R$_3$, R$_3$', R$_4$, R$_4$', R$^{10}$, R$^{11}$ and R$^{12}$ each of alkyl, alkenyl, alkynyl, alkoxy, aryl, aralkyl, heteroaryl, heteroaralkyl, heterocycle, or heterocycle-alkyl is independently unsubstituted or substituted one or more times by halogen, —OR$_{a''}$, oxo, —NR$_{a''}$R$_{b''}$, =NO—R$_{c''}$, —C(=O)OR$_{a''}$, —C(O)NR$_{a''}$R$_{b''}$, —C(=O)OH, —C(=O)R$_{a''}$, —C(=NOR$_c$)R$_{a''}$, —C(=NR$_c$)NR$_{a''}$R$_{b''}$, —NR$_{d''}$C(=O)NR$_{a''}$R$_{b''}$, —NR$_{b''}$C(=O)R$_{a''}$, —NR$_{d''}$C(=NR$_c$)NR$_{a''}$R$_{b''}$, —NR$_{b''}$C(=O)OR$_{a''}$, —OC(=O)NR$_{a''}$R$_{b''}$, —OC(=O)R$_{a''}$, —OC(=O)OR$_{a''}$, hydroxyl, nitro, azido, cyano, —S(O)$_{0-3}$R$_{a''}$, —SO$_2$NR$_{a''}$R$_{b''}$, —NR$_{b''}$SO$_2$R$_{a''}$; wherein R$_{a''}$-R$_{d''}$ are each independently H, C$_{1-12}$ alkyl.

In one embodiment in the compounds of the present invention p is 0, 1 or 2.

In one embodiment in the compounds of the present invention p is 0 or 1.

In one embodiment in the compounds of the present invention p is 0.

In one embodiment in the compounds of the present invention p is 2.

In one embodiment in the compounds of the present invention R$_4$ and R$_4$' are H.

In one embodiment in the compounds of the present invention R$_1$ is halogen, C$_{1-3}$ alkyl, hydroxyl, cyano, or C$_{1-3}$ alkoxy.

In one embodiment in the compounds of the present invention R$_1$ is chloro, fluoro, methyl, hydroxyl, cyano, or methoxy.

In one embodiment in the compounds of the present invention n R$_1$ is H.

In one embodiment in the compounds of the present invention R$^{10}$ is halogen, —OR$_a$, oxo, —C(=O)OR$_a$, —C(O)NR$_a$R$_b$, —C(=O)OH, —C(=O)R$_a$, —OC(=O)NR$_a$R$_b$, —OC(=O)R$_a$, —OC(=O)OR$_a$, hydroxyl, cyano, wherein R$_a$-R$_b$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention R$^{11}$ is halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —$NR_bSO_2R_a$, or —$NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, —$OR_a$, —$NR_aR_b$, —$C(=O)OR_a$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, —$OC(=O)R_a$, —$OC(=O)OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, —$OR_a$, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{11}$ is halogen, —$OR_a$, —$NR_aR_b$, hydroxyl, cyano, $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, —$OR_a$, oxo, —$NR_aR_b$, —$C(=O)OR_a$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, —$OC(=O)R_a$, —$OC(=O)OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, —$OR_a$, oxo, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention $R^{12}$ is halogen, —$OR_a$, oxo, —$NR_aR_b$, hydroxyl, cyano, $C_{1-6}$ alkyl, wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one or more times by halogen, —$OR_{a'}$, —$NR_{a'}R_{b'}$, —$C(=O)OR_{a'}$, —$C(O)NR_{a'}R_{b'}$, —$C(=O)OH$, hydroxyl, nitro, azido, cyano; wherein $R_{a'}$-$R_{d'}$ are each independently H, $C_{1-12}$ alkyl.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by halogen.

In one embodiment in the compounds of the present invention wherein as valency allows in B, B', $R_a$-$R_d$, $R_1$, $R_2$, $R_2'$, $R_3$, $R_3'$, $R_4$, $R_4'$, $R^{10}$, $R^{11}$ and $R^{12}$ each of alkyl, alkenyl, alkynyl, alkoxy, aryl, aralkyl, heteroaryl, heteroaralkyl, heterocycle, or heterocycle-alkyl is independently unsubstituted or substituted one time by fluoro.

The use of a compound of the present invention for treating an Hepatitis C viral infection in a human. The use of a compound of the present invention further comprising administering at least one additional agent. The use of a compound of the present invention wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

The use of a compound of the present invention, wherein said at least one additional agent is selected from ribavirin and interferon-α.

The use of a compound of the present invention for the manufacture of a medicament.

A pharmaceutical formulation comprising at least one compound of the present invention and at least one pharmaceutically acceptable carrier or excipient.

The use of a compound of the present invention for treating an Hepatitis C viral infection in a human. The use of a compound of the present invention further comprising administering at least one additional agent. The use of a compound of the present invention wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). The use of a compound of the present invention wherein said at least one additional agent is selected from ribavirin and interferon-α.

The use of a compound of the present invention for the manufacture of a medicament.

A pharmaceutical formulation comprising at least one compound of the present invention and at least one pharmaceutically acceptable carrier or excipient.

According to an aspect of the invention, the compounds of the invention are selected from:

| # | name |
|---|---|
| 1. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 2. | ((S)-1-{(S)-2-[5-(3-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 3. | ((S)-1-{(S)-2-[5-(4-{2-[(S)-4,4-Difluoro-1-((S)-2-methoxycarbonylamino-3-methyl-butyryl)-pyrrolidin-2-yl]-1H-benzoimidazol-5-yl}-phenyl)-1H-benzoimidazol-2-yl]-4,4-difluoro-pyrrolidine-1-carbonyl}-2-methyl-propyl)-carbamic acid methyl ester |
| 4. | [(S)-1-((S)-2-{5-[4-(2-{(S)-1-[(S)-2-(Methoxycarbonyl-methyl-amino)-3-methyl-butyryl]-pyrrolidin-2-yl}-1H-benzoimidazol-5-yl)-phenyl]-1H-benzoimidazol-2-yl}-pyrrolidine-1-carbonyl)-2-methyl-propyl]-methyl-carbamic acid methyl ester |
| 5. | ((S)-1-{(S)-2-[5-(2-Cyano-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 6. | ((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyridin-2-yl)-1H-benzoimidazol-2-yl]-pyrrolidine-1-carbonyl}-2-methyl-propyl)-carbamic acid methyl ester |
| 7. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2-methyl-phenyl)-1H-benzoimidazol-2-yl]-pyrrolidine-1-carbonyl}-2-methyl-propyl)-carbamic acid methyl ester |
| 8. | ((S)-1-{(S)-2-[5-(2-Methoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 9. | ((S)-1-{(S)-2-[5-(2-Fluoro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 10. | ((S)-1-{(S)-2-[5-(2-Chloro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 11. | ((S)-1-{(S)-2-[5-(2-Cyano-6-{2-[(S)-1-((S)-2-methoxycarbonylamino-3-methyl-butyryl)-pyrrolidin-2-yl]-1H-benzoimidazol-5-yl}-pyridin-3-yl)-1H-benzoimidazol-2-yl]-pyrrolidine-1-carbonyl}-2-methyl-propyl)-carbamicacid methyl ester |
| 12. | (S)-1-{(S)-2-[5-(2,5-Dimethoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 13. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,3-dimethyl-phenyl)-1H-benzoimidazol-2-yl]-pyrrolidine-1-carbonyl}-2-methyl-propyl)-carbamic acid methyl ester |
| 14. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-dimethyl-phenyl)-1H-benzoimidazol-2-yl]-pyrrolidine-1-carbonyl}-2-methyl-propyl)-carbamicacid methyl ester |
| 15. | ((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 16. | (2S,2'S)-tert-butyl-2,2'-(5,5'-(thiophene-2,5-diyl)bis(1H-benzo[d]imidazole-5,2-diyl))dipyrrolidine-1-carboxylate |
| 17. | Dimethyl-(2S,2'S)-1,1'-((2S,2'S)-2,2'-(5,5'-(thiophene-2,5-diyl)bis(1H-benzo[d]imidazole-5,2-diyl))bis(pyrrolidine-2,1-diyl))bis(3-methyl-1-oxobutane-2,1-diyl)dicarbamate |
| 18. | methyl N-[(1S)-1-[(2S)-2-[5-[4-[2-[(2S)-1-[(2S)-2-(methoxycarbonylamino)-3-methyl-butanoyl]pyrrolidin-2-yl]-1H-benzimidazol-5-yl]-2-thienyl]-1H-benzimidazol-2-yl]pyrrolidine-1-carbonyl]-2-methyl-propyl]carbamate |
| 19. | ((S)-1-{(S)-2-[5-(4-Benzyloxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 20. | ((S)-1-{(S)-2-[5-(4-Hydroxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 21. | ((S)-1-{(S)-2-[6-(1-{2-[(S)-1-((S)-2-Methoxycarbonylamino-3-methyl-butyryl)-pyrrolidin-2-yl]-3H-benzoimidazol-5-yl}-1H-[1,2,3]triazol-4-yl)-1H-benzoimidazol-2-yl]-pyrrolidine-1-carbonyl}-2-methyl-propyl)-carbamic acid methyl ester |
| 22. | (2R,2'R,5S,5'S)-tert-butyl 5,5'-(6,6'-(1,4-phenylene)bis(1H-benzo[d]imidazole-6,2-diyl))bis(2-ethylpyrrolidine-1-carboxylate) |
| 23. | 1,4-bis(2-((2S,5R)-5-ethylpyrrolidin-2-yl)-1H-benzo[d]imidazol-6-yl)benzene |
| 24. | ((S)-1-{(2R,5S)-2-Ethyl-5-[5-(4-{2-[(2S,5R)-5-ethyl-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 25. | ((S)-1-{(2S,4R)-4-tert-butoxy-2-[5-(4-{2-[(2S,4R)-4-tert-butoxy-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 26. | ((S)-1-{(2S,4R)-4-Hydroxy-2-[5-(4-{2-[(2S,4R)-4-hydroxy-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 27. | Dimethyl (2S,2'S)-1,1'-((2S,2'S)-2,2'-(5,5'-(1,4-phenylene)bis(6-fluoro-1H-benzo[d]imidazole-5,2-diyl))bis(pyrrolidine-2,1-diyl))bis(3-methyl-1-oxobutane-2,1-diyl)dicarbamate |
| 28. | (S)-2-{5-[2-((S)-1-Benzyloxycarbonyl-piperidin-2-yl)-1H-benzoimidazol-5-ylethynyl]-1H-benzoimidazol-2-yl}-piperazine-1,4-dicarboxylic acid 1-benzyl ester 4-tert-butyl ester |
| 29. | (S)-2-{5-[2-((S)-1-Benzyloxycarbonyl-4-tert-butyloxycarbonyl-piperazin-2-yl)-1H-benzoimidazol-5-ylethynyl]-1H-benzoimidazol-2-yl}-piperazine-1,4-dicarboxylic acid 1-benzyl ester 4-tert-butyl ester |

-continued

| # | name |
|---|---|
| 30. | (S)-2-{5-[2-((S)-1-Benzyloxycarbonyl-piperidin-2-yl)-1H-benzoimidazol-5-ylethynyl]-1H-benzoimidazol-2-yl}-piperidine-1-carboxylic acid benzyl ester |
| 31. | (S)-2-{5-[2-((S)-1-Benzyloxycarbonyl-pyrrolidin-2-yl)-1H-benzoimidazol-5-ylethynyl]-1H-benzoimidazol-2-yl}-pyrrolidine-1-carboxylic acid benzyl ester |
| 32. | [(S)-5-(5-{2-[(S)-1-((R)-tetrahydro-furan-2-carbonyl)-pyrrolidin-2-yl]-1H-benzoimidazol-5-ylethynyl}-1H-benzoimidazol-2-yl)-pyrrolidin-1-yl]-(R)-tetrahydrofuran-2-yl-methanone |
| 33. | {(R)-2-[(S)-2-(5-{2-[(S)-1-((R)-2-Methoxycarbonylamino-2-phenyl-acetyl)-pyrrolidin-2-yl]-1H-benzoimidazol-5-ylethynyl}-1H-benzoimidazol-2-yl)-pyrrolidin-1-yl]-2-oxo-1-phenyl-ethyl}-carbamic acid methylester |
| 34. | (S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carboxylic acid tert-butyl ester |
| 35. | ((S)-2-Methyl-1-{(S)-2-[5-((S)-2-pyrrolidin-2-yl-1H-benzoimidazol-5-ylethynyl)-1H-benzoimidazol-2-yl]-pyrrolidine-1-carbonyl}-propyl)-carbamic acid methyl ester |
| 36. | {(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2,2-dimethyl-propyl}-carbamic acid methyl ester |
| 37. | {(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2-methyl-propyl}-carbamic acid methyl ester |
| 38. | {(S)-2-Methyl-1-[(S)-2-(5-{2-[(S)-1-((R)-tetrahydro-furan-2-carbonyl)-pyrrolidin-2-yl]-1H-benzoimidazol-5-ylethynyl}-1H-benzoimidazol-2-yl)-pyrrolidine-1-carbonyl]-propyl}-carbamic acid methyl ester |
| 39. | {(S)-1-[(S)-2-(5-{2-[(S)-1-((R)-2-Methoxycarbonylamino-2-phenyl-acetyl)-pyrrolidin-2-yl]-1H-benzoimidazol-5-ylethynyl}-1H-benzoimidazol-2-yl)-pyrrolidine-1-carbonyl]-2-methyl-propyl}-carbamic acid methyl ester |
| 40. | (S)-2-(5-{(E)-4-[2-((S)-1-Benzyloxycarbonyl-piperidin-2-yl)-1H-benzoimidazol-5-yl]-but-1-en-3-ynyl}-1H-benzoimidazol-2-yl)-piperidine-1-carboxylic acid benzyl ester |
| 41. | (S)-2-(5-{4-[2-((S)-1-Benzyloxycarbonyl-piperidin-2-yl)-1H-benzoimidazol-5-yl]-buta-1,3-diynyl}-1H-benzoimidazol-2-yl)-piperidine-1-carboxylic acid benzyl ester |
| 42. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-difluoro-phenyl)-1H-benzoimidazol-2-yl]-pyrrolidine-1-carbonyl}-2-methyl-propyl)-carbamicacid methyl ester |
| 43. | Methyl N-[(1S)-1-[(2S)-2-[5-[5-[2-[(2S)-1-[(2S)-2-(methoxycarbonylamino)-3-methyl-butanoyl]pyrrolidin-2-yl]-1H-benzimidazol-5-yl]-3-methyl-2-pyridyl]-1H-benzimidazol-2-yl]pyrrolidine-1-carbonyl]-2-methyl-propyl]carbamate |
| 44. | Dimethyl-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate |
| 45. | bis((S)-tetrahydrofuran-3-yl)-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate |
| 46. | Dimethyl-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate |
| 47. | bis((S)-tetrahydrofuran-3-yl)-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate |

In another aspect, the present invention provides a compound described in the following embodiments.

In one embodiment, the compounds of the present invention is represented by formula (IIIA):

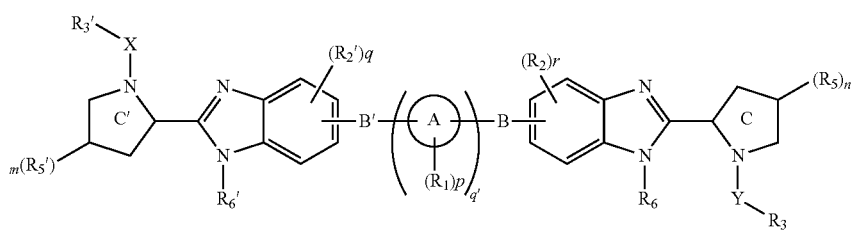

(IIIA)

or pharmaceutically acceptable salts thereof, wherein:
each A is independently $C_{6-14}$ aryl, 4-12 membered heterocycle, $C_{3-10}$ cycloalkyl, or 5-12 membered heteroaryl;
B and B' are each independently absent, $C_{1-6}$ alkyl, $C_{2-6}$ alkenyl, or $C_{2-6}$ alkynyl;
$R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;
$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_2$, and $R_2$ are each independently halogen, $C_{1-10}$ alkyl, $C_{1-6}$ halogenated alkyl, $-(CH_2)_{1-6}OH$, $-OR_a$, $-C(=O)OR_a$, $-NR_aR_b$, $-NR_bC(=O)R_a$, $-C(O)NR_aR_b$, $-S(O)_{0-3}R_a$, $C_{6-12}$ aryl, or 5-12 membered heteroaryl;

$R_3$ and $R_3'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

X and Y are each independently

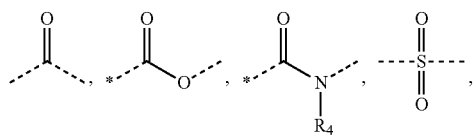

or a bond;
wherein the asterisk (*) indicates the point of attachment to the nitrogen of ring C or C';

$R_4$ is H, $C_{1-6}$ alkyl, or halogenated $C_{1-6}$ alkyl;

$R_5$ and $R_5'$ are each independently halogen, $-C(O)NR_aR_b$, $-(CH_2)_{1-6}OH$, $C_{1-6}$ alkyl, $C_{1-6}$ halogenated alkyl, or $C_{6-14}$ aryl; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_6$ and $R_6'$ are each independently H, $C_{1-6}$ alkyl, $-(CH_2)_{1-6}OH$, $C_{2-6}$ alkenyl, or $C_{2-6}$ alkynyl;

m and n, combined are 1, 2, 3 or 4;
p is 0, 1, 2, 3 or 4;
q' is 0, 1 or 2;
q and r are each independently 0, 1, 2, 3 or 4;
$R^{10}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$;

$R^{11}$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In another embodiment, the compounds of the present invention is represented by formula (IIIA'):

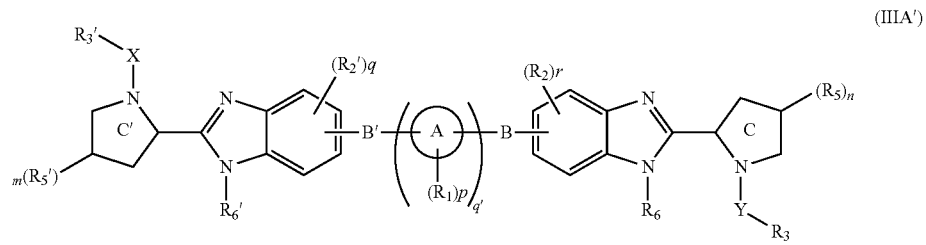

(IIIA')

or pharmaceutically acceptable salts thereof, wherein:
B and B' are each independently absent or $-(C\equiv C)-$;
$R_5$ and $R_5'$ are each independently halogen, $-C(O)NR_aR_b$, $-(CH_2)_{1-6}OH$, $C_{1-6}$ alkyl, $C_{1-6}$ halogenated alkyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and the remainder of the variables are as described above for formula (IIIA).

In another embodiment, the compounds of the present invention are represented by formula (IIIB):

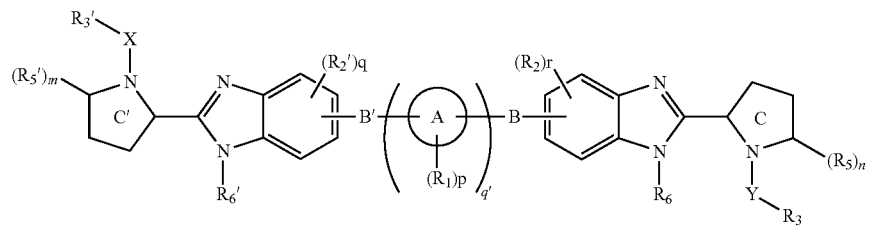

(IIB)

or pharmaceutically acceptable salts thereof, wherein
each A is independently $C_{6-14}$ aryl, 4-12 membered heterocycle, $C_{3-10}$ cycloalkyl, or 5-12 membered heteroaryl;

B and B' are each independently absent, $C_{1-6}$ alkyl, $C_{2-6}$ alkenyl, or $C_{2-6}$ alkynyl;

$R_1$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, —$P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_{2'}$ and $R_2$ are each independently halogen, $C_{1-10}$ alkyl, $C_{1-6}$ halogenated alkyl, —$(CH_2)_{1-6}OH$, —$OR_a$, —$C(=O)OR_a$, —$NR_aR_b$, —$NR_bC(=O)R_a$, —$C(O)NR_aR_b$, —$S(O)_{0-3}R_a$, $C_{6-12}$ aryl, or 5-12 membered heteroaryl;

$R_3$ and $R_3'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

X and Y are each independently

![four structural fragments showing acyl, carbonate-like, carbamoyl with $R_4$, and sulfonyl groups]

or a bond;
wherein the asterisk (*) indicates the point of attachment to the nitrogen of ring C or C';

$R_4$ is H, $C_{1-6}$ alkyl, or halogenated $C_{1-6}$ alky;

$R_5$ and $R_5'$ are each independently halogen, —$NR_aR_b$, —$C(O)NR_aR_b$, —$(CH_2)_{1-6}OH$, $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_6$ and $R_6'$ are each independently H, $C_{1-6}$ alkyl, —$(CH_2)_{1-6}OH$, $C_{2-6}$ alkenyl, or $C_{2-6}$ alkynyl;

m, and n, combined are 1, 2, 3 or 4;
p is 0, 1, 2, 3 or 4;
q' is 0, 1 or 2;
q and r are each independently 0, 1, 2, 3 or 4;

$R^{10}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl; and R$^{12}$ is halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In another embodiment, the compounds of the present invention are represented by formula (IVA):

stituted or substituted one or more times by R$^{11}$, benzyl which is unsubstituted or substituted one or more times by R$^{11}$, 5-6 membered heteroaryl which is unsubstituted or substituted one or more times by R$^{11}$, 6-7 membered heteroaralkyl which is unsubstituted or substituted one or more times by R$^{11}$, 3-6 membered heterocycle which is unsubstituted or substituted one or more times by R$^{12}$, or 4-7 membered heterocycle-alkyl which is unsubstituted or substituted one or more times by R$^{12}$;

R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, or —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl;

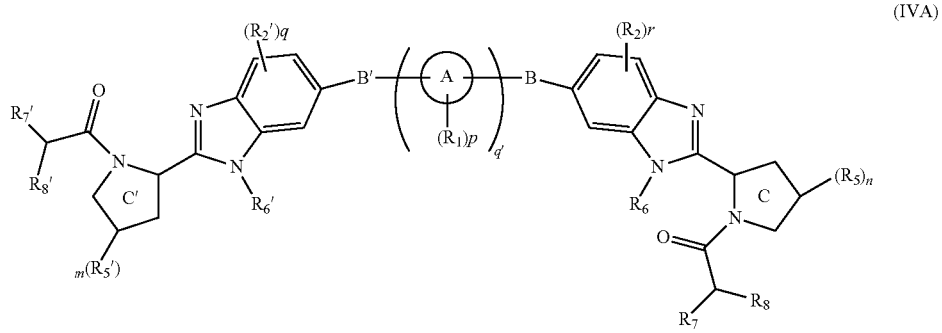

(IVA)

or pharmaceutically acceptable salts thereof, wherein:

R$_7$ and R$_7$' are each independently C$_{1-8}$ alkyl which is unsubstituted or substituted one or more times by R$^{10}$, C$_{2-8}$ alkenyl which is unsubstituted or substituted one or more times by R$^{10}$, C$_{2-8}$ alkynyl which is unsubstituted or substituted one or more times by R$^{10}$, phenyl which is unsubm and n combined are 0, 1, 2, 3 or 4;

and the remainder of the variables are as described above for formula (IIIA).

In another embodiment, the compounds of the present invention are represented by formula (VA):

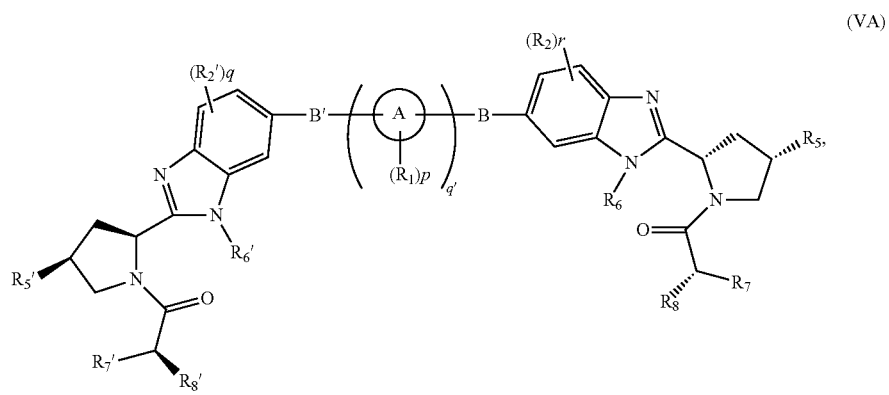

(VA)

or pharmaceutically acceptable salts thereof, wherein the variables are as described above for formula (IVA).

In another embodiment, the compounds of the present invention are represented by formula (V):

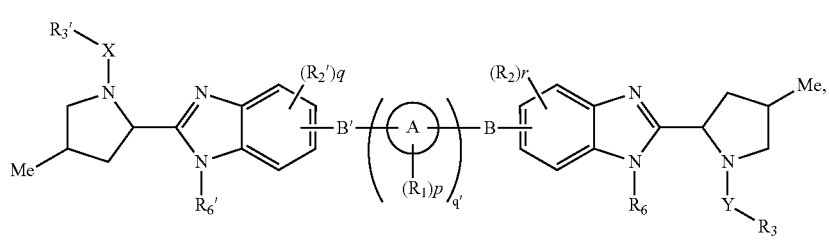

(V)

or pharmaceutically acceptable salts thereof, wherein the variables are as described above for formula (IIIA).

In another embodiment, the compounds of the present invention are represented by formula (VI):

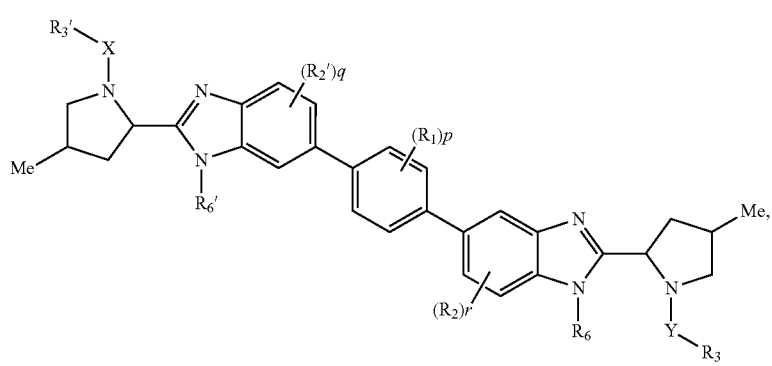

(VI)

or pharmaceutically acceptable salts thereof, wherein the variables are as described above for formula (V).

In another embodiment, the compounds of the present invention are represented by formula (VII):

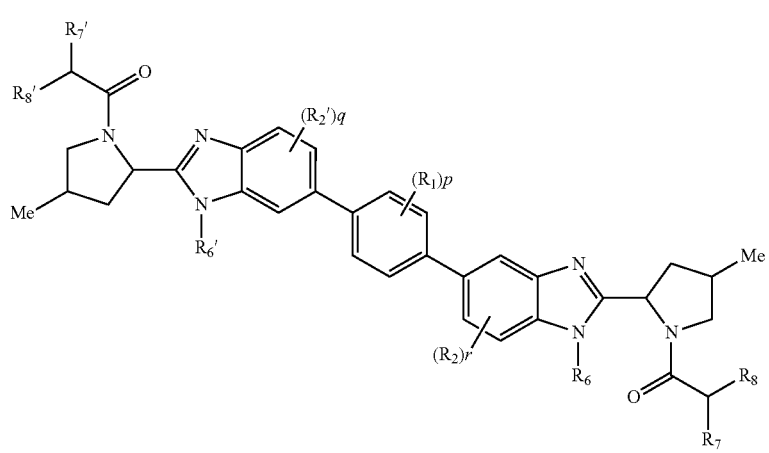

(VII)

or pharmaceutically acceptable salts thereof, wherein $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$;

$R_8$ and $R_8'$ are each independently —$NR_aR_b$, —$NR_aC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

and the remainder of the variables are as described above for formula (VI).

In another embodiment, the compounds of the present invention are represented by formula (VIII):

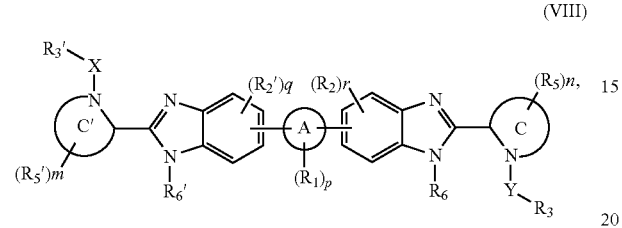

(VIII)

or pharmaceutically acceptable salts thereof, wherein

C and C' are each independently a 4-7 membered heterocycle;

$R_1$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, —$P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_2$ and $R_2'$ are each independently halogen, $C_{1-10}$ alkyl, $C_{1-6}$ halogenated alkyl, —$(CH_2)_{1-6}OH$, —$OR_a$, —$C(=O)OR_a$, —$NR_aR_b$, —$NR_bC(=O)R_a$, —$C(O)NR_aR_b$, —$S(O)_{0-3}R_a$, $C_{6-12}$ aryl, or 5-12 membered heteroaryl;

$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

X and Y are each independently

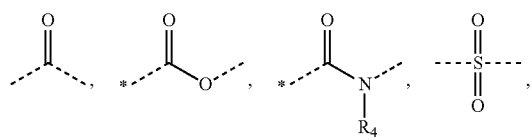

or a bond;

wherein the asterisk (*) indicates the point of attachment to the nitrogen of ring C or C';

$R_3$ and $R_3'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently halogen, —$NR_aR_b$, —$C(O)NR_aR_b$, —$(CH_2)_{1-6}OH$, $C_{1-6}$ alkyl, $C_{1-6}$ halogenated alkyl, hydroxyl, $C_{6-14}$ aryl, or $C_{1-6}$ alkoxy; wherein two occurrence of $R_5$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_5'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$;

$R_6$ and $R_6'$ are each independently H, $C_{1-6}$ alkyl, —$(CH_2)_{1-6}OH$, $C_{2-6}$ alkenyl, or $C_{2-6}$ alkynyl;

m, and n, are each independently 0, 1, 2, 3 or 4;

q and r are each independently 0, 1, 2, or 3;

$R^{10}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{12}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

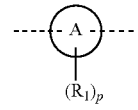

is selected from the group consisting of:

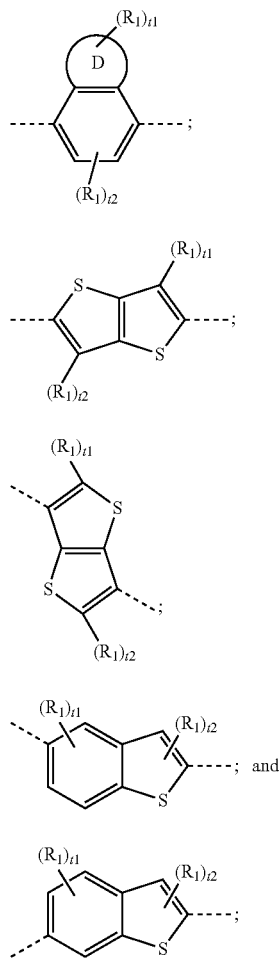

wherein D is a 5-7 cycloalkyl which is unsubstituted or substituted by (R$_1$)$_{t1}$, a 5-7 membered heterocycle which is unsubstituted or substituted by (R$_1$)$_{t1}$ or a 5-7 membered heteroaryl which is unsubstituted or substituted by (R$_1$)$_{t1}$;

p is 0, 1, 2, 3 or 4; and t1+t2=p.

In another embodiment, the compounds of the present invention are represented by formula (IX):

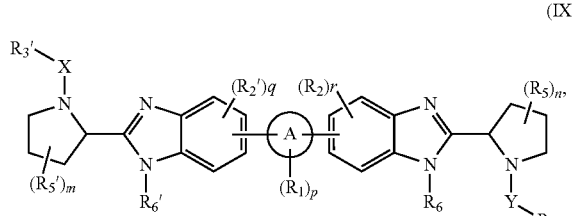

or pharmaceutically acceptable salts thereof, wherein the variables are as described above for formula (VIII).

In another embodiment, the compounds of the present invention are represented by formula (X):

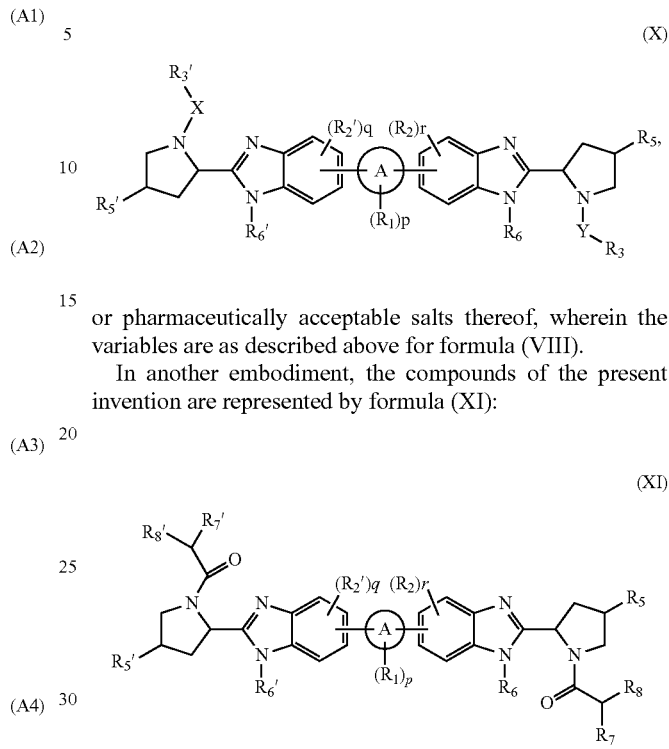

or pharmaceutically acceptable salts thereof, wherein the variables are as described above for formula (VIII).

In another embodiment, the compounds of the present invention are represented by formula (XI):

or pharmaceutically acceptable salts thereof, wherein:

R$_7$ and R$_7$' are each independently C$_{1-8}$ alkyl which is unsubstituted or substituted one or more times by R$^{10}$, C$_{2-8}$ alkenyl which is unsubstituted or substituted one or more times by R$^{10}$, C$_{2-8}$ alkynyl which is unsubstituted or substituted one or more times by R$^{10}$, phenyl which is unsubstituted or substituted one or more times by R$^{11}$, benzyl which is unsubstituted or substituted one or more times by R$^{11}$, 5-6 membered heteroaryl which is unsubstituted or substituted one or more times by R$^{11}$, 6-7 membered heteroaralkyl which is unsubstituted or substituted one or more times by R$^{11}$, 3-6 membered heterocycle which is unsubstituted or substituted one or more times by R$^{12}$, or 4-7 membered heterocycle-alkyl which is unsubstituted or substituted one or more times by R$^{12}$;

R$_8$ and R$_8$' are each independently —NR$_a$R$_b$, —NR$_d$C(=O) NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, or —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl; and the remainder of the variables are as described above for formula (VIII).

According to a 1$^{st}$ embodiment, each A in formula (IIIA), (IIIA'), (IIB), (IVA), (VA) and (V), is independently cyclopropyl, cyclohexyl, pyrrolidinyl, pyrazolidinyl, imidazolidinyl, piperazinyl, piperadinyl, phenyl, naphthalenyl, thienyl, furanyl, pyrrolyl, pyrazolyl, imidazolyl, thiazolyl, thiadiazolyl, oxazolyl, oxadiazolyl, pyridyl, pyrimidyl, pyrazinyl, pyridazinyl, indolyl, indazolyl, benzimidazolyl, benzoxazolyl, benzodioxolyl, benzothiazolyl, benzothiadiazolyl, benzothiophenyl, dihydrobenzodioxinyl, thienofuranyl, thienothienyl, thienopyrrolyl, quinolinyl, quinoxalinyl, quinazolinyl, cinnolinyl, or triazolyl; and wherein each A is independently substituted with $(R_1)_p$.

According to a further embodiment, each A in formula (IIIA), (IIIA'), (IIB), (IVA), (VA) and (V), is independently cyclopropyl, cyclohexyl, pyrrolidinyl, pyrazolidinyl, imidazolidinyl, piperazinyl, piperadinyl, phenyl, naphthalenyl, thienyl, furanyl, pyrrolyl, pyrazolyl, imidazolyl, thiazolyl, thiadiazolyl, oxazolyl, oxadiazolyl, pyridyl, pyrimidyl, pyrazinyl, pyridazinyl, indolyl, indazolyl, benzimidazolyl, benzoxazolyl, benzodioxolyl, benzothiazolyl, benzothiadiazolyl, dihydrobenzodioxinyl, thienofuranyl, thienothienyl, thienopyrrolyl, quinolinyl, quinoxalinyl, quinazolinyl, cinnolinyl, or triazolyl; and wherein each A is independently substituted with $(R_1)_p$.

According to another further embodiment, each A in formula (IIIA), (IIIA'), (IIB), (IVA), (VA) and (V), independently cyclopropyl, cyclohexyl, phenyl, or naphthalene, wherein each A is independently substituted with $(R_1)_p$.

According to another further embodiment, each A in formula (IIIA), (IIIA'), (IIB), (IVA), (VA) and (V), is independently selected from the group consisting of:

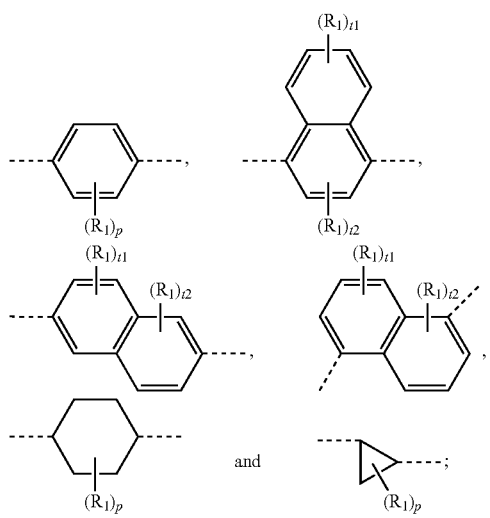

wherein t1+t2=p.

According to another further embodiment, each A in formula (IIIA), (IIIA'), (IIB), (IVA), (VA) and (V), is:

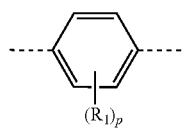

According to another further embodiment, each A in formula (IIIA), (IIIA'), (IIB), (IVA), (VA) and (V), is independently piperazinyl, piperadinyl, thienyl, furanyl, pyrrolyl, pyrazolyl, imidazolyl, thiazolyl, oxazolyl, thiadiazolyl, pyrrolidinyl, pyridyl, pyrimidinyl, pyrazinyl, pyridazinyl, benzoxazolyl, benzodioxolyl, benzothiazolyl, benzothiadiazolyl, benzothiophenyl, dihydrobenzodioxinyl, thienofuranyl, thienothienyl, quinolinyl, or triazolyl, each of which is substituted with $(R_1)_p$.

According to another further embodiment, each A in formula (IIIA), (IIIA'), (IIB), (IVA), (VA) and (V), is independently piperazinyl, piperadinyl, thienyl, furanyl, pyrrolyl, pyrazolyl, imidazolyl, thiazolyl, oxazolyl, thiadiazolyl, pyrrolidinyl, pyridyl, pyrimidinyl, pyrazinyl, pyridazinyl, benzoxazolyl, benzodioxolyl, benzothiazolyl, benzothiadiazolyl, dihydrobenzodioxinyl, thienofuranyl, thienothienyl, quinolinyl, or triazolyl, each of which is substituted with $(R_1)_p$.

According to another further embodiment, each A in formula (IIIA), (IIIA'), (IIB), (IVA), (VA) and (V), is independently selected from the group consisting of:

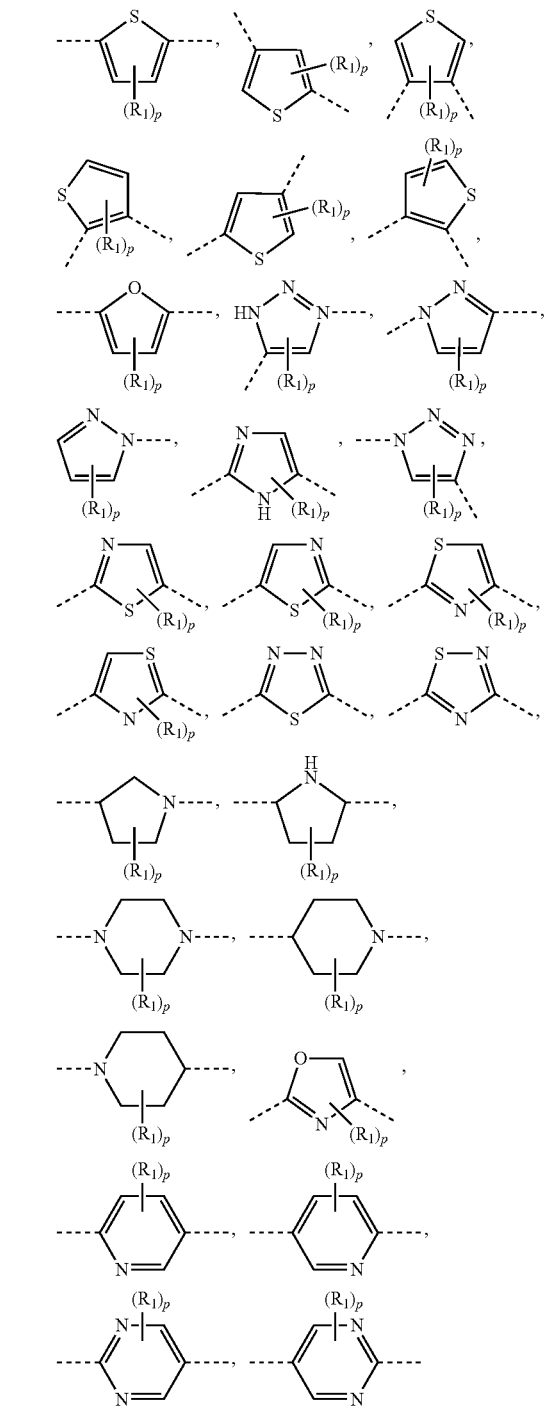

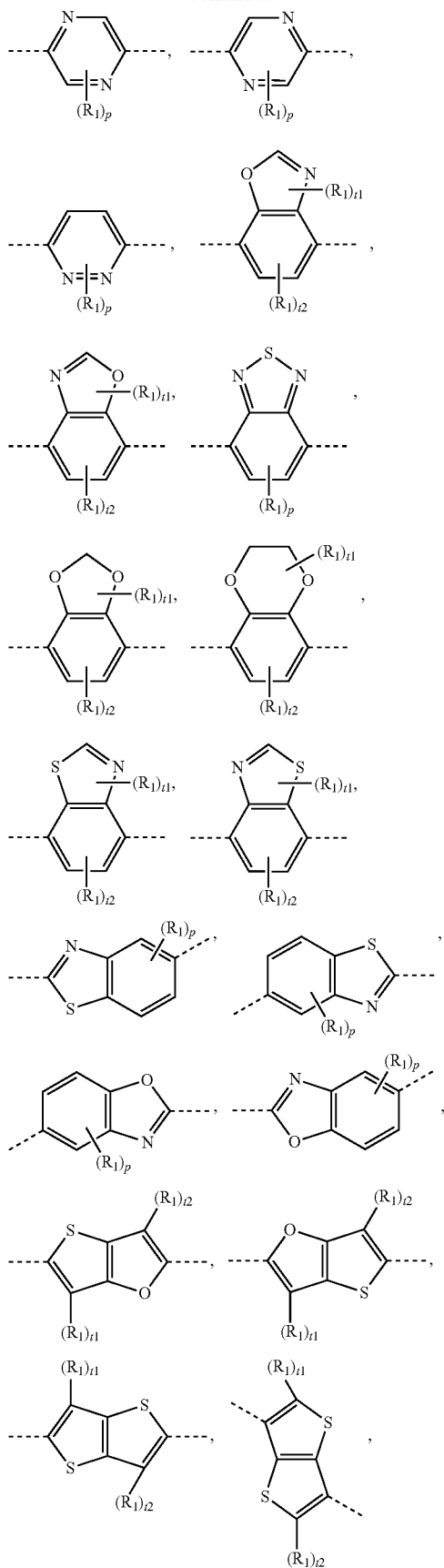
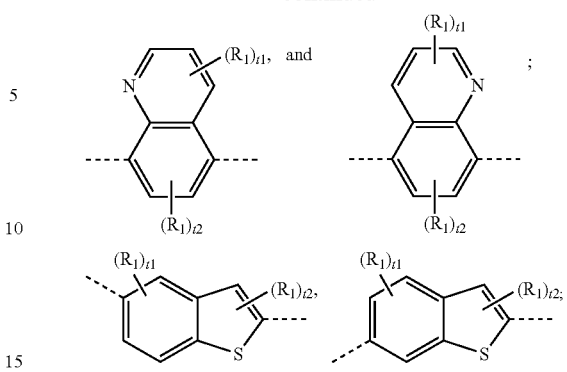
and
t1+t2=p
According to another further embodiment, each A in formula (IIIA), (IIIA'), (IIB), (IVA), (VA) and (V), is independently selected from the group consisting of:
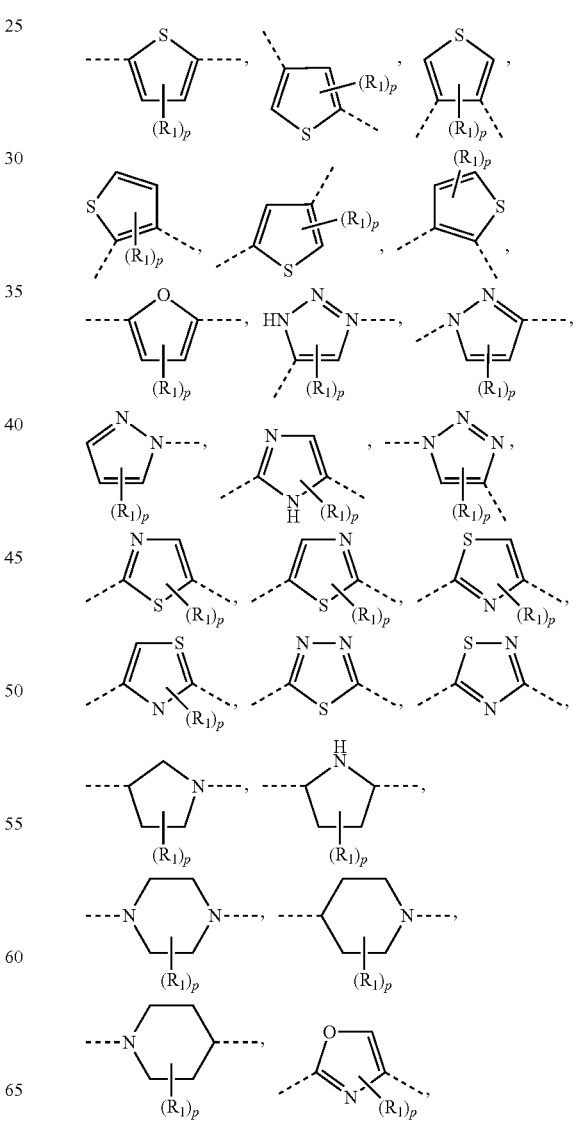

-continued
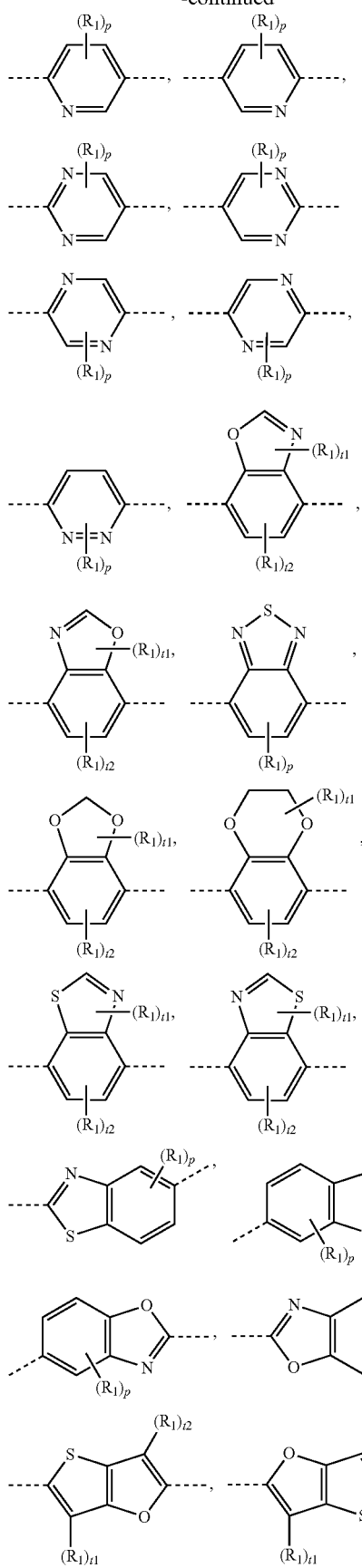
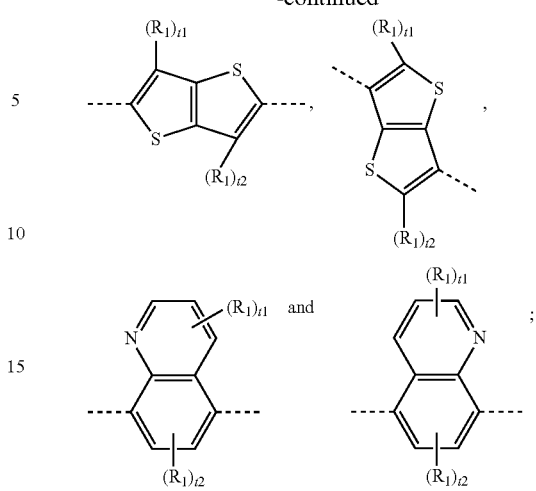
and t1+t2=p.
According to another further embodiment, each A in formula (IIIA), (IIIA'), (IIB), (IVA), (VA), (V), (VIII), (IX), (X) and (XI), is independently selected from the group consisting of:
(A1a)
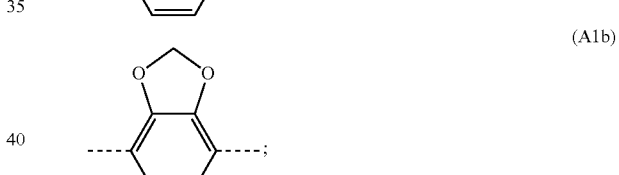
(A1b)
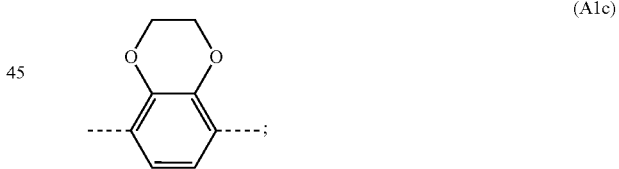
(A1c)
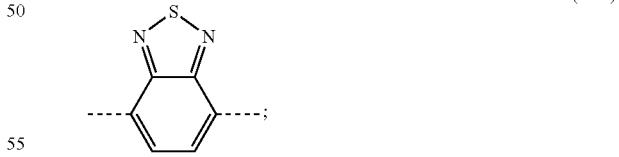
(A1d)
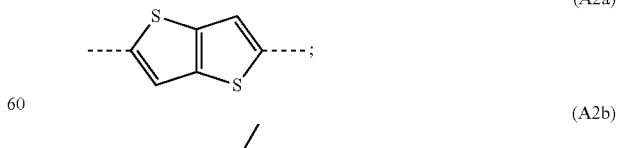
(A2a)
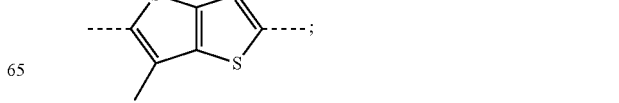
(A2b)

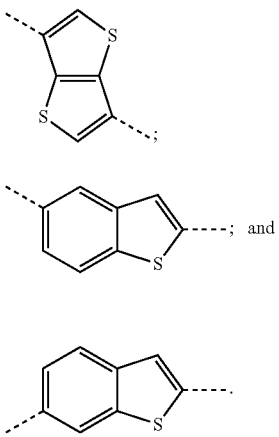

(A3a)

(A4a) ; and (A5a)

According to another further embodiment, each A in formula (IIIA), (IIIA'), (IIB), (IVA), (VA) and (V), is independently a 5-12 membered heteroaryl wherein the hetero atom(s) are selected from the group consisting of oxygen and sulphur; wherein each A is independently substituted with $(R_1)_p$.

The remainder of the variables for any embodiments described in the 1$^{st}$ embodiment are as described in formulas (IIIA), (IIIA'), (IIB), (IVA), (VA), (V), (VIII), (IX), (X) and (XI).

According to a 2$^{nd}$ embodiment, B and B' in formulas (IIIA), (IIIA'), (IIB), (IVA), (VA) and (V), are independently absent, $C_{1-6}$ alkyl or $C_{2-6}$ alkynyl; and the remainder of the variables are as described in formula (IIIA), (IIIA'), (IIB), (IVA), (VA) and (V) or any embodiments in the 1$^{st}$ embodiment described above.

According to a 3$^{rd}$ embodiment, B and B' in formulas (IIIA), (IIIA'), (IIB), (IVA), (VA) and (V), are independently absent, —(CH$_2$)$_2$— or —(C≡C)—; and the remainder of the variables are as described in formula (IIIA), (IIIA'), (IIB), (IVA), (VA) and (V) or in any embodiments in the 1$^{st}$ embodiment described above.

According to a 4$^{th}$ embodiment, B and B' in formulas (IIIA), (IIIA'), (IIB), (IVA), (VA) and (V), are independently absent or —(C≡C)—; and the remainder of the variables are as described in formula (IIIA), (IIIA'), (IIB), (IVA), (VA) and (V) or in any embodiments in the 1$^{st}$ embodiment described above.

According to a 5$^{th}$ embodiment, for formula (IIIA), (IIIA'), (IIB), (IVA), (VA), (V), (VI), (VII), (VIII), (IX), (X) and (XI), the distance between C and C' is between about 16 Å to about 24 Å in length. The remainder of the variables are as described in formulas (IIIA), (IIIA'), (IIB), (IVA), (VA), (V), (VI), (VII), (VIII), (IX), (X) and (XI) or in the 1$^{st}$ to 4$^{th}$ embodiments described above.

According to a 6$^{th}$ embodiment,

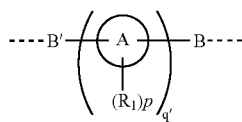

in formulas (IIIA), (IIIA'), (IIB), (IVA), (VA) and (V), is selected from the group consisting of:

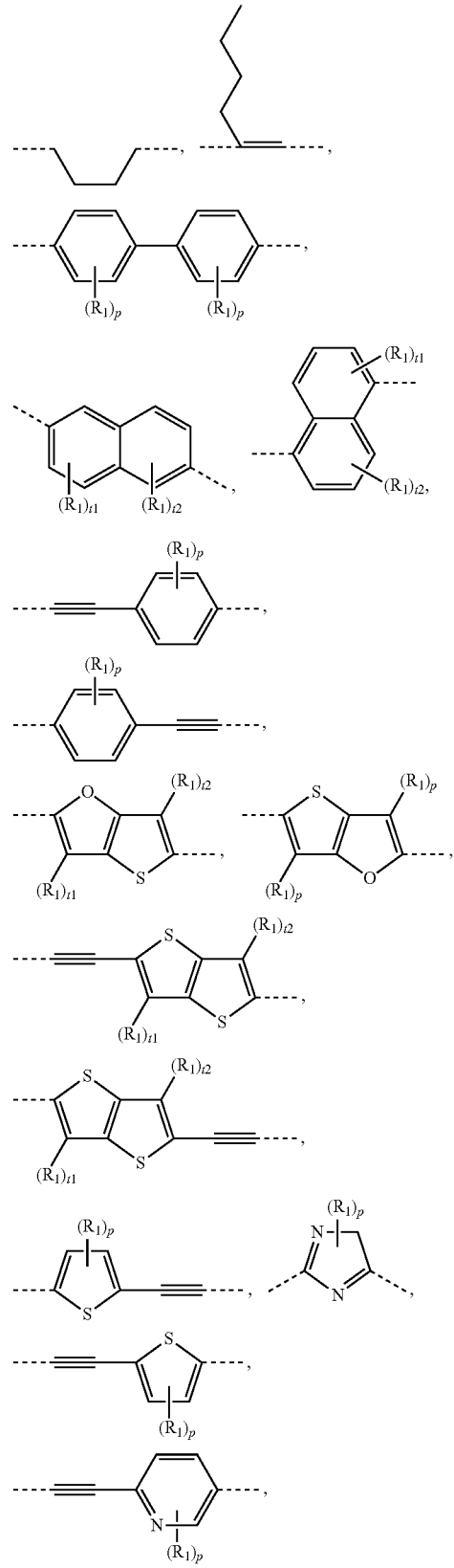

-continued
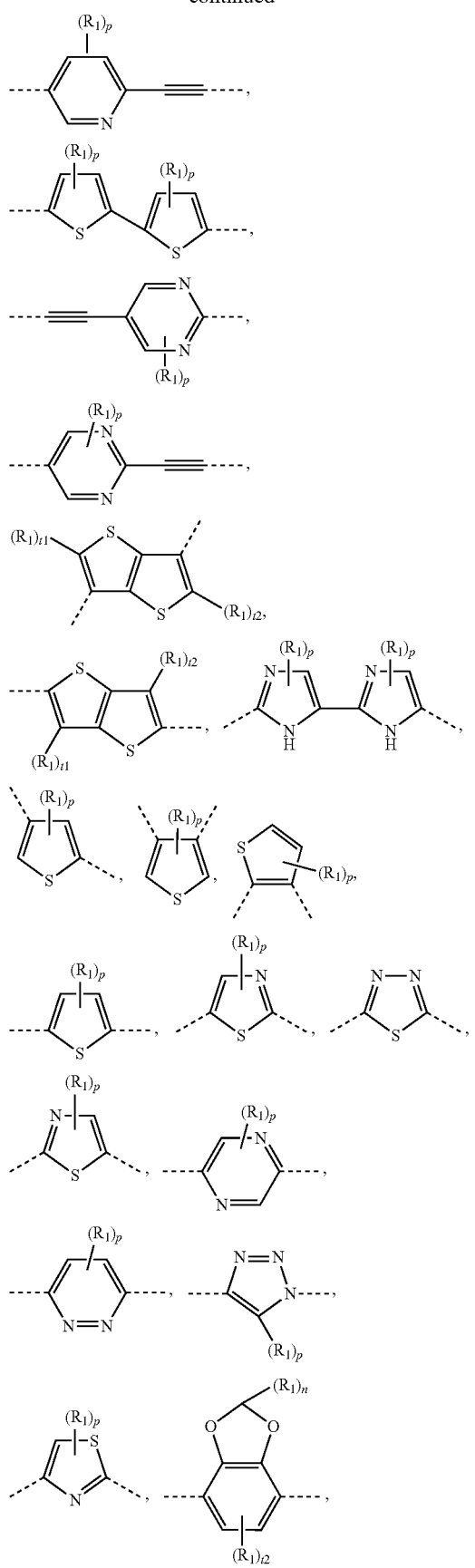
-continued
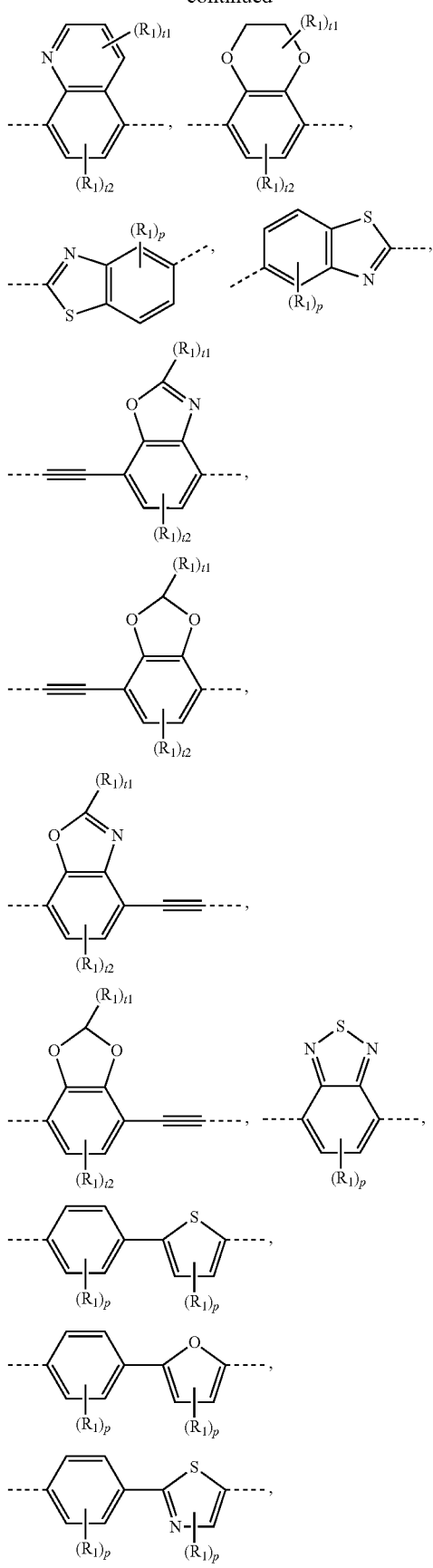

-continued

-continued
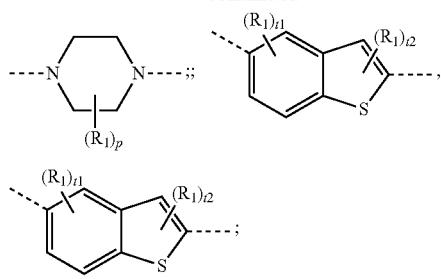
and
t1+t2=p; and the remainder of the variables are as described above in formulas (IIIA), (IIIA'), (IIB), (IVA), (VA) and (V), or in the 1st to 5th embodiment described above.
In a further embodiment of the 6th embodiment,
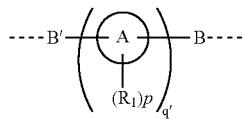
in formulas (IIIA), (IIIA'), (IIB), (IVA), (VA) and (V), is selected from the group consisting of:
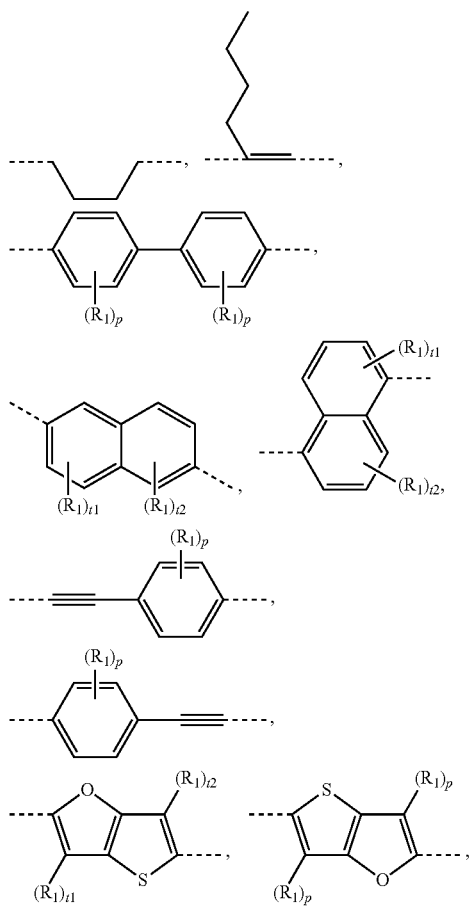
-continued
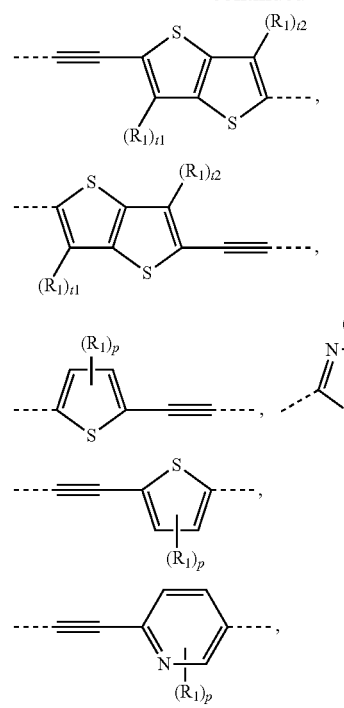
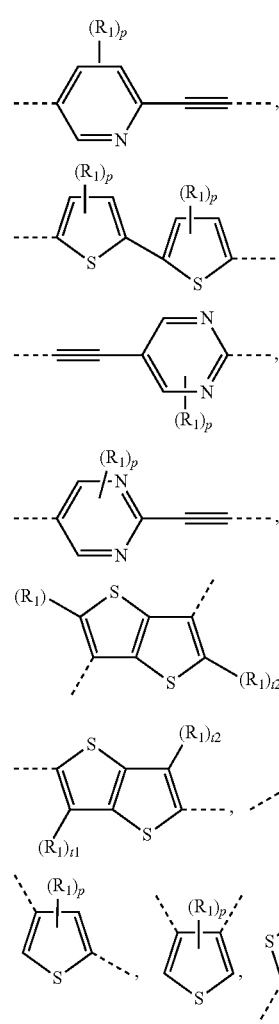

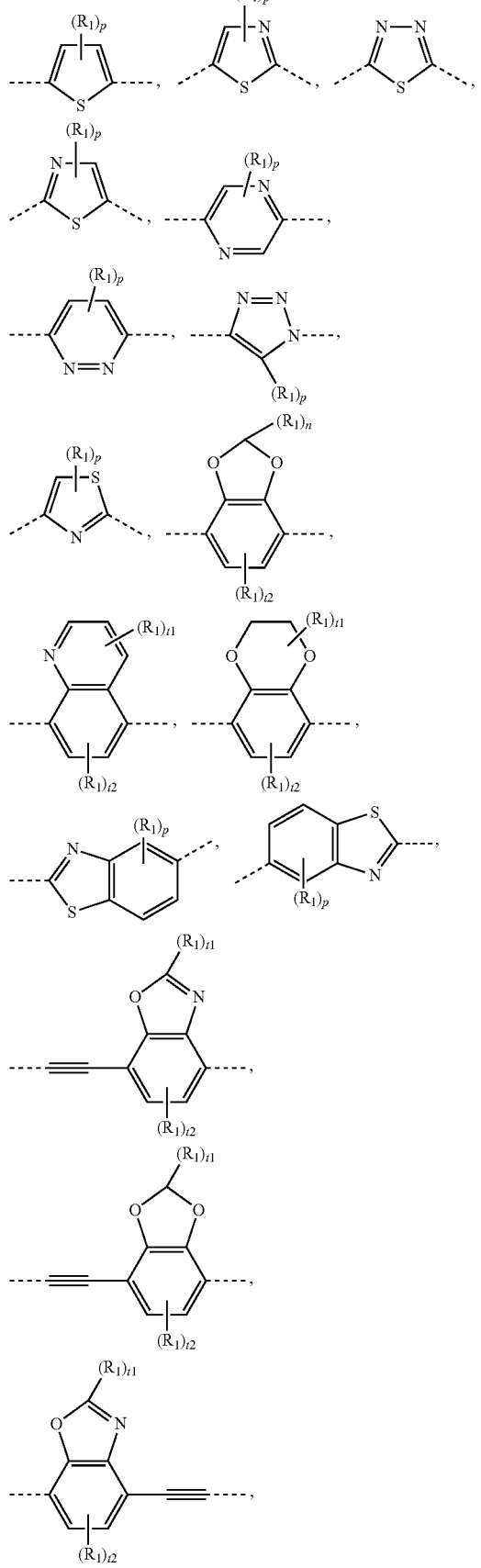
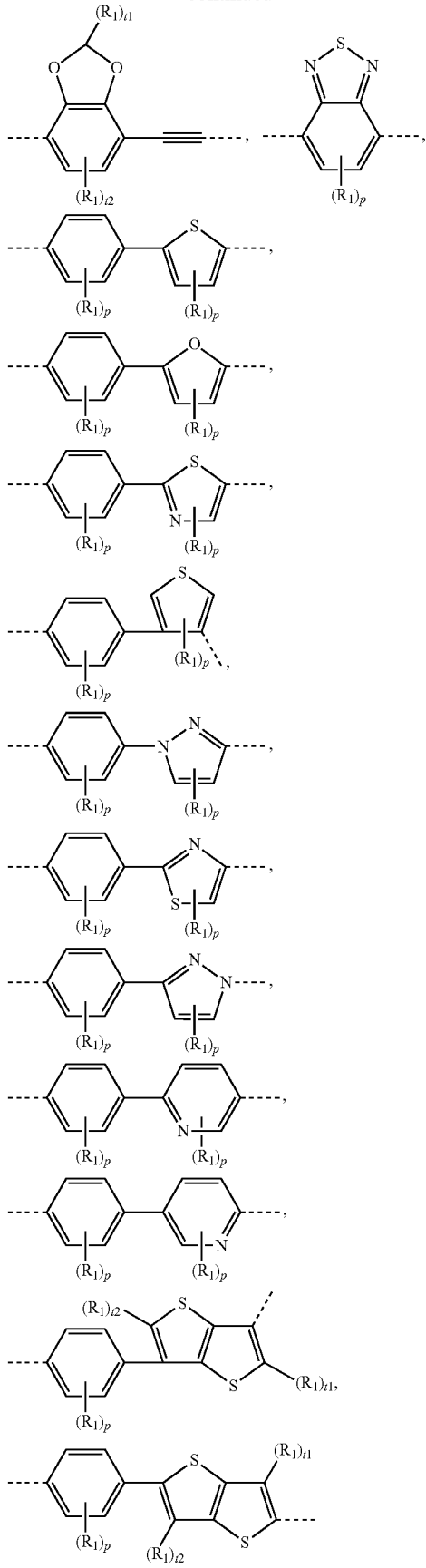

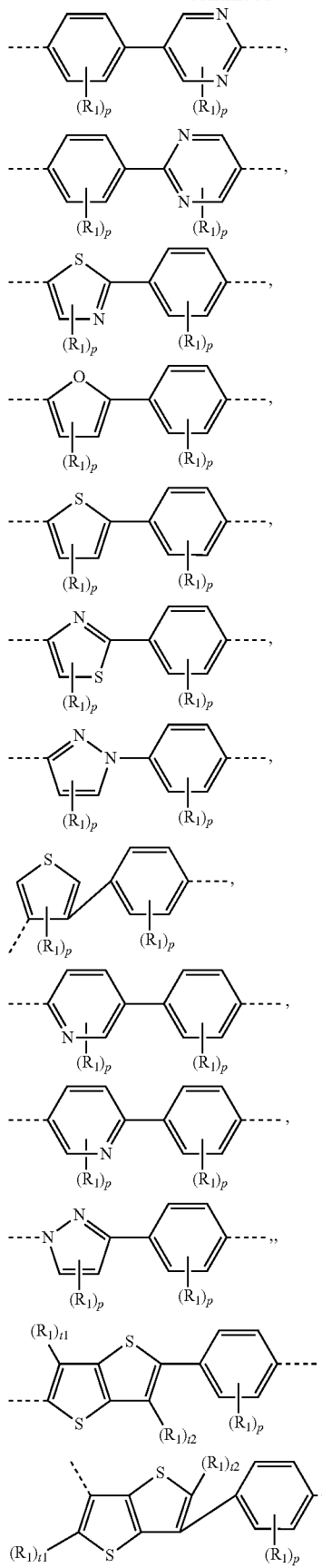
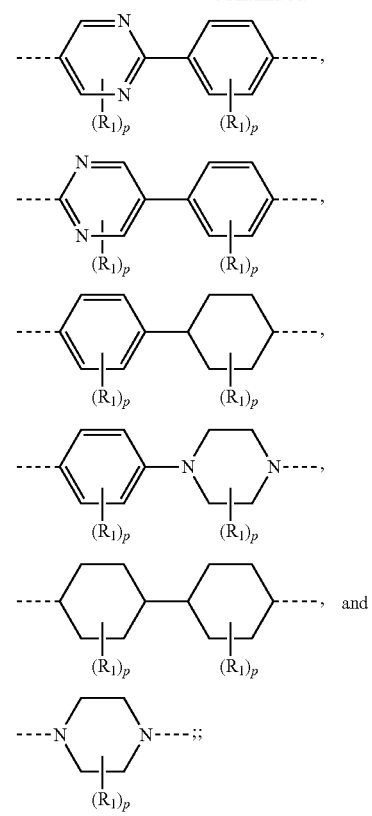
and
t1+t2=p; and the remainder of the variables are as described above in formulas (IIIA), (IIIA'), (IIB), (IVA), (VA) and (V), or in the 1st to 5th embodiment described above.
According to a 7th embodiment,
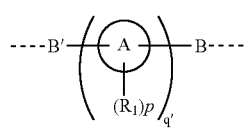
in formulas (IIIA), (IIIA'), (IIB), (IVA), (VA) and (V), is selected from the group consisting of:
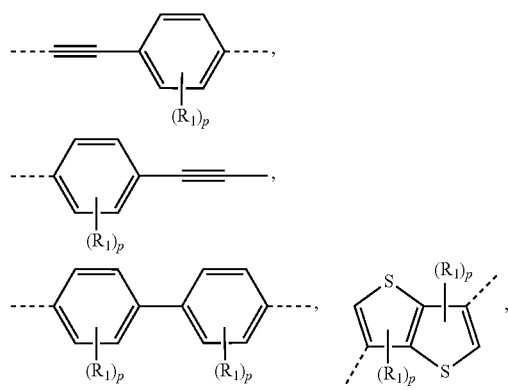

-continued

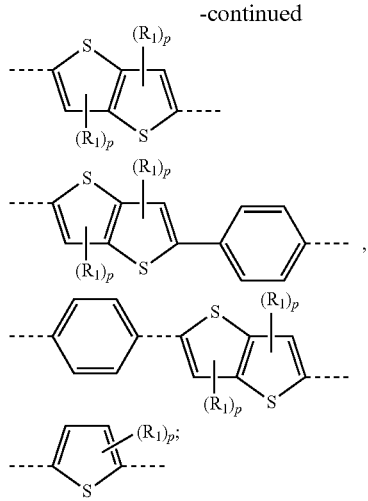

and
t1+t2=p; and the remainder of the variables are as described above in formulas (IIIA), (IIIA'), (IIB), (IVA), (VA) and (V), or in the $1^{st}$ to $5^{th}$ embodiment described above.

According to a $8^{th}$ embodiment,

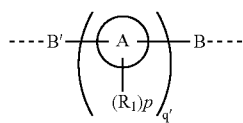

in formulas (IIIA), (IIIA'), (IIB), (IVA), (VA) and (V), is selected from the group consisting of:

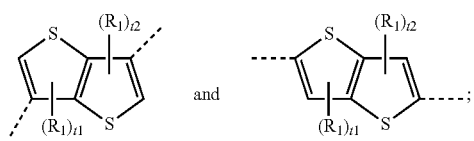

and
t1+t2=p; and the remainder of the variables are as described above in formulas (IIIA), (IIIA'), (IIB), (IVA), (VA) and (V), or in the $1^{st}$ to $5^{th}$ embodiment described above.

In a further embodiments of the $8^{th}$ embodiment,

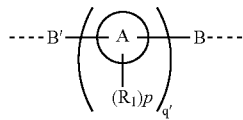

in formulas (IIIA), (IIIA'), (IIB), (IVA), (VA) and (V), is

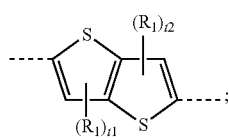

and t1+t2=p; and the remainder of the variables are as described above in formulas (IIIA), (IIIA'), (IIB), (IVA), (VA) and (V), or in the $1^{st}$ to $5^{th}$ embodiment described above.

According to a further embodiment of the $8^{th}$ embodiment,

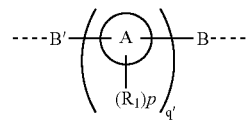

in formulas (IIIA), (IIIA'), (IIB), (IVA), (VA) and (V), is

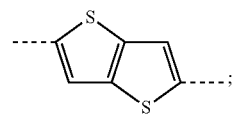

and the remainder of the variables are as described above in formulas (IIIA), (IIIA'), (IIB), (IVA), (VA) and (V), or in the $1^{st}$ to $5^{th}$ embodiment described above.

According to another further embodiment of the $8^{th}$ embodiment,

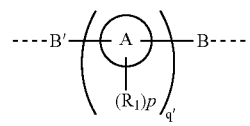

in formulas (IIIA), (IIIA'), (IIB), (IVA), (VA) and (V), is

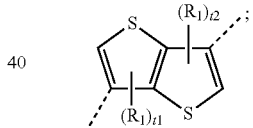

t1+t2=p; and the remainder of the variables are as described above in formulas (IIIA), (IIIA'), (IIB), (IVA), (VA) and (V), or in the $1^{st}$ to $5^{th}$ embodiment described above.

According to another further embodiment of the $8^{th}$ embodiment,

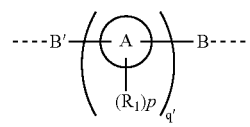

in formulas (IIIA), (IIIA'), (IIB), (IVA), (VA) and (V), is

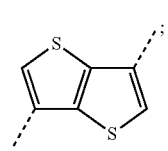

and the remainder of the variables are as described above in formulas (IIIA), (IIIA'), (IIB), (IVA), (VA) and (V), or in the $1^{st}$ to $5^{th}$ embodiment described above.

According to a $9^{th}$ embodiment,

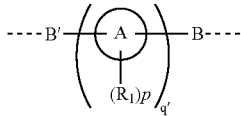

in formulas (IIIA), (IIIA'), (IIB), (IVA), (VA) and (V), is

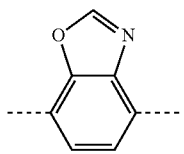

(A1a); and the remainder of the variables are as described above in formulas (IIIA), (IIIA'), (IIB), (IVA), (VA) and (V), or in the $1^{st}$ to $5^{th}$ embodiment described above.

According to a $10^{th}$ embodiment,

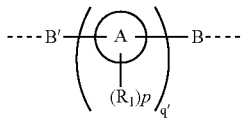

in formulas (IIIA), (IIIA'), (IIB), (IVA), (VA) and (V), is

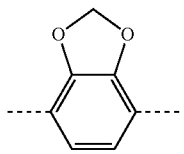

(A1b); and the remainder of the variables are as described above in formulas (IIIA), (IIIA'), (IIB), (IVA), (VA) and (V), or in the $1^{st}$ to $5^{th}$ embodiment described above.

According to a $11^{th}$ embodiment,

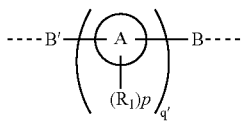

in formulas (IIIA), (IIIA'), (IIB), (IVA), (VA) and (V), is

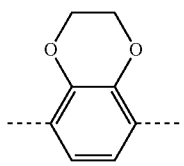

(A1c); and the remainder of the variables are as described above in formulas (IIIA), (IIIA'), (IIB), (IVA), (VA) and (V), or in the $1^{st}$ to $5^{th}$ embodiment described above.

According to a $12^{th}$ embodiment,

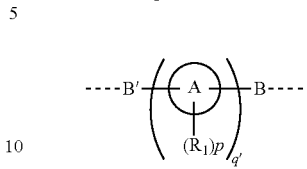

in formulas (IIIA), (IIIA'), (IIB), (IVA), (VA) and (V), is

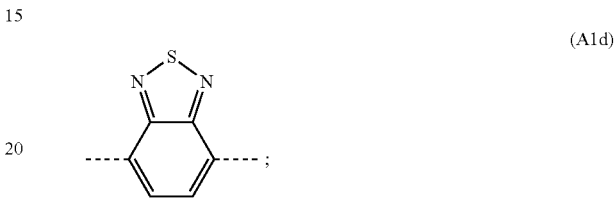

and the remainder of the variables are as described above in formulas (IIIA), (IIIA'), (IIB), (IVA), (VA) and (V), or in the $1^{st}$ to $5^{th}$ embodiment described above.

According to a $13^{th}$ embodiment, $R_1$ in formulas (IIIA), (IIIA'), (IIB), (IVA), (VA), (V), (VI), (VII), (VIII), (IX), (X) and (XI), is halogen, $C_{1-4}$ alkyl which is unsubstituted or substituted one or more times by $R^{10}$, —C(=O)$OR_a$, —C(O)$NR_aR_b$, hydroxyl, cyano, or $C_{1-3}$ alkoxy; and the remainder of the variables are as described above in formulas (IIIA), (IIIA'), (IIB), (IVA), (VA), (V), (VI), (VII), (VIII), (IX), (X) and (XI), or in the $1^{st}$ to $12^{th}$ embodiment described above.

According to a $14^{th}$ embodiment, $R_1$ in formulas (IIIA), (IIIA'), (IIB), (IVA), (VA), (V), (VI), (VII), (VIII), (IX), (X) and (XI), is chloro, fluoro, bromo, methyl, ethyl, propyl, butyl, —CH$_2$OH, difluoromethyl, trifluoromethyl, hydroxyl, cyano, or methoxy; and the remainder of the variables are as described above in formulas (IIIA), (IIIA'), (IIB), (IVA), (VA), (V), (VI), (VII), (VIII), (IX), (X) and (XI), or in the $1^{st}$ to $12^{th}$ embodiment described above.

According to a $15^{th}$ embodiment, each $R_2$' in formulas (IIIA), (IIIA'), (IIB), (IVA), (VA), (V), (VI), (VII), (VIII), (IX), (X) and (XI), is independently fluoro or methyl. Alternatively, q in formulas (IIIA), (IIIA'), (IIB), (IVA), (VA), (V), (VI), (VII), (VIII), (IX), (X) and (XI), is 0. The remainder of the variables are as described above in formulas (IIIA), (IIIA'), (IIB), (IVA), (VA), (V), (VI), (VII), (VIII), (IX), (X) and (XI), or in the $1^{st}$ to $14^{th}$ embodiment described above.

According to a $16^{st}$ embodiment, each $R_2$ in formulas (IIIA), (IIIA'), (IIB), (IVA), (VA), (V), (VI), (VII), (VIII), (IX), (X) and (XI), is independently fluoro or methyl. Alternatively, r in formulas (IIIA), (IIIA'), (IIB), (IVA), (VA), (V), (VI), (VII), (VIII), (IX), (X) and (XI), is 0. The remainder of the variables are as described above in formulas (IIIA), (IIIA'), (IIB), (IVA), (VA), (V), (VI), (VII), (VIII), (IX), (X) and (XI), or in the $1^{st}$ to $15^{th}$ embodiment described above.

According to a $17^{th}$ embodiment, $R_6$ and $R_6$' in formulas (IIIA), (IIIA'), (IIB), (IVA), (VA), (V), (VI), (VII), (VIII), (IX), (X) and (XI), are H or methyl; and the remainder of the variables are as described above in formulas (IIIA), (IIIA'), (IIB), (IVA), (VA), (V), (VI), (VII), (VIII), (IX), (X) and (XI), or in the $1^{st}$ to $16^{th}$ embodiment described above.

According to a $18^{th}$ embodiment, $R_5$ and $R_5$' in formulas (IIIA), (IIIA'), (IVA) and (VA), (IIB), (VIII), (IX), (X) and (XI), are each independently halogen, methyl, ethyl, isopropyl, di-fluoromethyl, di-fluoroethyl, trifluoromethyl, tri-fluoroethyl, —CH$_2$OH, —NR$_a$N$_b$, t-butoxy-, or hydroxyl or two R$_5$ groups together with the atoms to which they are attached form fused cyclopropyl, spiro cyclopropyl or

two R$_5$' groups together with the atoms to which they are attached form fused cyclopropyl, spiro cyclopropyl or

In a further embodiment, R$_5$ and R$_5$' in formulas (IIIA), (IIIA'), (IVA) and (VA), are each independently halogen, methyl, ethyl, isopropyl, di-fluoromethyl, di-fluoroethyl, trifluoromethyl, tri-fluoroethyl, —CH$_2$OH, —NR$_a$N$_b$, or t-butoxy-; or two R$_5$ groups together with the atoms to which they are attached form fused cyclopropyl, spiro cyclopropyl; or

two R$_5$' groups together with the atoms to which they are attached form fused cyclopropyl, spiro cyclopropyl or

and the remainder of the variables are as described above in formulas (IIIA), (IIIA'), (IIB), (IVA), (VA), (VIII), (IX), (X) and (XI), or in the 1$^{st}$ to 17$^{th}$ embodiment described above.

According to a 19$^{th}$ embodiment, R$_5$ and R$_5$' in formulas (IIIA), (IIIA'), (IIB), (IVA), (VA), (VIII), (IX), (X) and (XI), each independently methyl, methoxy, ethyl, di-fluoromethyl, trifluoromethyl, or two R$_5$ groups together with the atoms to which they are attached form fused cyclopropyl or spiro cyclopropyl or two R$_5$' groups together with the atoms to which they are attached form fused cyclopropyl or spiro cyclopropyl; and the remainder of the variables are as described above in formulas (IIIA), (IIIA'), (IIB), (IVA), (VA), (VIII), (IX), (X) and (XI), or in the 1$^{st}$ to 17$^{th}$ embodiment described above. In a further embodiment, R$_5$ and R$_5$' in formulas (IIIA), (IIIA'), (IVA) and (VA), each independently methyl, ethyl, di-fluoromethyl, trifluoromethyl, or two R$_5$ groups together with the atoms to which they are attached form fused cyclopropyl or spiro cyclopropyl or two R$_5$' groups together with the atoms to which they are attached form fused cyclopropyl or spiro cyclopropyl; and the remainder of the variables are as described above in formulas (IIIA), (IIIA'), (IIB), (IVA), (VA), (VIII), (IX), (X) and (XI), or in the 1$^{st}$ to 17$^{th}$ embodiment described above.

According to a 19$^{th}$ embodiment, R$_5$ and R$_5$' in formulas (IIIA), (IIIA'), (IIB), (IVA), (VA), (VIII), (IX), (X) and (XI), and the remainder of the variables are as described above in formulas (IIIA), (IIIA'), (IIB), (IVA), (VA), (VIII), (IX), (X) and (XI), or in the 1$^{st}$ to 17$^{th}$ embodiment described above.

According to a 20$^{th}$ embodiment, m and n in formulas (IIIA), (IIIA'), (IIB), (IVA), (VIII) and (IX), are 1 or 2; and the remainder of the variables are as described above in formulas (IIIA), (IIIA'), (IIB), (IVA), (VIII) and (IX) or in the 1$^{st}$ to 17$^{th}$ embodiment described above. In a further embodiment, m and n are 1.

According to a 21$^{st}$ embodiment, X and Y in formulas (IIIA), (IIIA'), (IIB), (V), (VI), (VIII), (IX) and (X),

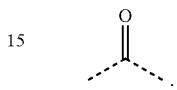

According to a 22$^{nd}$ embodiment, R$_3$ and R$_3$' in formulas (IIIA), (IIIA'), (IIB), (V), (VI), (VIII), (IX) and (X), are each independently, C$_{1-8}$ alkyl which is unsubstituted or substituted one or more times by R$^{10}$, C$_{2-8}$ alkenyl which is unsubstituted or substituted one or more times by R$^{10}$, C$_{2-8}$ alkynyl which is unsubstituted or substituted one or more times by R$^{10}$, phenyl which is unsubstituted or substituted one or more times by R$^{11}$, C$_{7-8}$ aralkyl which is unsubstituted or substituted one or more times by R$^{11}$, 5-6 membered heteroaryl which is unsubstituted or substituted one or more times by R$^{11}$, 6-8 membered heteroaralkyl which is unsubstituted or substituted one or more times by R$^{11}$, 3-6 membered heterocycle which is unsubstituted or substituted one or more times by R$^{12}$, or 4-8 membered heterocycle-alkyl which is unsubstituted or substituted one or more times by R$^{12}$; and the remainder of the variables are as described above in formulas (IIIA), (IIIA'), (IIB), (V), (VI), (VIII), (IX) and (X) or in the 1$^{st}$ to 21$^{st}$ embodiments described above.

In a further embodiment, R$_3$ and R$_3$' are each independently, C$_{1-6}$ alkyl which is unsubstituted or substituted one or more times by R$^{10}$, C$_{2-6}$ alkenyl which is unsubstituted or substituted one or more times by R$^{10}$, C$_{2-6}$ alkynyl which is unsubstituted or substituted one or more times by R$^{10}$, phenyl which is unsubstituted or substituted one or more times by R$^{11}$, benzyl which is unsubstituted or substituted one or more times by R$^{11}$, 5-6 membered heteroaryl which is unsubstituted or substituted one or more times by R$^{11}$, 6-7 membered heteroaralkyl which is unsubstituted or substituted one or more times by R$^{11}$, 5-6 membered heterocycle which is unsubstituted or substituted one or more times by R$^{12}$, or 6-7 membered heterocycle-alkyl which is unsubstituted or substituted one or more times by R$^{12}$. The remainder of the variables are as described above in formulas (IIIA), (IIIA'), (IIB), (V), (VI), (VIII), (IX) and (X) or in the 1$^{st}$ to 21$^{st}$ embodiments described above.

In another further embodiment, R$_3$ and R$_3$' are each independently, C$_{1-6}$ alkyl which is unsubstituted or substituted one or more times by R$^{10}$, C$_{2-6}$ alkenyl which is unsubstituted or substituted one or more times by R$^{10}$, C$_{2-6}$ alkynyl which is unsubstituted or substituted one or more times by R$^{10}$. The remainder of the variables are as described above in formulas (IIIA), (IIIA'), (IIB), (V), (VI), (VIII), (IX) and (X) or in the 1$^{st}$ to 21$^{st}$ embodiments described above.

In a 23$^{rd}$ embodiment, R$_3$ and R$_3$' in formulas (IIIA), (IIIA'), (IIB), (V), (VI), (VIII), (IX) and (X), are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl (CH$_2$)—, which are unsubstituted or substituted one or more times by $R^{10}$. The remainder of the variables are as described above in formulas (IIIA), (IIIA'), (IIB), (V), (VI), (VIII), (IX) and (X) or in the $1^{st}$ to $21^{st}$ embodiments described above.

In a $24^{th}$ embodiment, $R_3$ and $R_3'$ in formulas (IIIA), (IIIA'), (IIB), (V), (VI), (VIII), (IX) and (X), are each independently phenyl which is unsubstituted or substituted one or more times by $R^{11}$. The remainder of the variables are as described above in formulas (IIIA), (IIIA'), (IIB), (V), (VI), (VIII), (IX) and (X) or in the $1^{st}$ to $21^{st}$ embodiments described above.

In a $25^{th}$ embodiment, $R_3$ and $R_3'$ in formulas (IIIA), (IIIA'), (IIB), (V), (VI), (VIII), (IX) and (X), are each independently benzyl which is unsubstituted or substituted one or more times by $R^{11}$. The remainder of the variables are as described above in formulas (IIIA), (IIIA'), (IIB), (V), (VI), (VIII), (IX) and (X) or in the $1^{st}$ to $21^{st}$ embodiments described above.

In a $26^{th}$ embodiment, $R^{10}$ in formulas (IIIA), (IIIA'), (IIB), (IVA), (VA), (V), (VI), (VII), (VIII), (IX), (X) and (XI), is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NOR_c) $R_a$, —C(=$NR_c$)$NR_aR_b$, —$NR_dC$(=O)$NR_aR_b$, —$NR_bC$ (=O)$R_a$, —$NR_dC$(=$NR_c$)$NR_aR_b$, —$NR_bC$(=O)$OR_a$, —OC(=O)$NR_aR_b$, —OC(=O)$R_a$, hydroxyl, nitro, azido, cyano, —S(O)$_{0-3}R_a$, —SO$_2NR_aR_b$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl. The remainder of the variables are as described above in formulas (IIIA), (IIIA'), (IIB), (IVA), (VA), (V), (VI), (VII), (VIII), (IX), (X) and (XI) or in the $1^{st}$ to $25^{th}$ embodiments described above.

In a further embodiment, $R^{10}$ in formulas (IIIA), (IIIA'), (IIB), (IVA), (VA), (V), (VI), (VII), (VIII), (IX), (X) and (XI), —$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —$NR_bSO_2R_a$, or —$NR_bSO_2NR_aR_b$. The remainder of the variables are as described above in formulas (IIIA), (IIIA'), (IIB), (IVA), (VA), (V), (VI), (VII), (VIII), (IX), (X) and (XI) or in the $1^{st}$ to $25^{th}$ embodiments described above.

In another further embodiment, $R^{10}$ is —$NR_aR_b$, —$NR_dC$(=O)$NR_aR_b$, —$NR_bC$(=O)$R_a$, —$NR_bC$(=O)$OR_a$, or —$NR_bSO_2R_a$. The remainder of the variables are as described in formulas (IIIA), (IIIA'), (IIB), (IVA), (VA), (V), (VI), (VII), (VIII), (IX), (X) and (XI) or in the $1^{st}$ to $25^{th}$ embodiments described above.

In a $27^{th}$ embodiment, $R_a$-$R_d$ in formulas (IIIA), (IIIA'), (IIB), (IVA), (VA), (V), (VI), (VII), (VIII), (IX), (X) and (XI), are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl. The remainder of the variables are as described above in formulas (IIIA), (IIIA'), (IIB), (IVA), (VA), (V), (VI), (VII), (VIII), (IX), (X) and (XI) or in the $1^{st}$ to $26^{th}$ embodiments described above.

In a further embodiment, $R_a$ and $R_c$ in formulas (IIIA), (IIIA'), (IIB), (IVA), (VA), (V), (VI), (VII), (VIII), (IX), (X) and (XI), are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$, are each independently H or $C_{1-3}$ alkyl. The remainder of the variables are as described above in formulas (IIIA), (IIIA'), (IIB), (IVA), (VA), (V), (VI), (VII), (VIII), (IX), (X) and (XI) or in the $1^{st}$ to $26^{th}$ embodiments described above.

In a $28^{th}$ embodiment, $R_a$-$R_d$ in formulas (IIIA), (IIIA'), (IIB), (IVA), (VA), (V), (VI), (VII), (VIII), (IX), (X) and (XI), $R_a$-$R_d$ are each independently H or $C_{1-3}$ alkyl. The remainder of the variables are as described above in formulas (IIIA), (IIIA'), (IIB), (IVA), (VA), (V), (VI), (VII), (VIII), (IX), (X) and (XI) or in the $1^{st}$ to $26^{th}$ embodiments described above.

In a $29^{th}$ embodiment, $R_8$ and $R_8'$ in formulas (IVA), (VA), (VII) and (XI), are $R_8$ and $R_8'$ are each independently —$NR_aR_b$, —$NR_bC$(=O)$R_a$, —$NR_bC$(=O)$OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl. The remainder of the variables are as described in formulas (IVA), (VA), (VII) and (XI) or in the $1^{st}$ to $28^{th}$ embodiments described above.

In a $30^{th}$ embodiment, $R_8$ and $R_8'$ in formulas (IVA), (VA), (VII) and (XI), are $R_8$ and $R_8'$ are each independently —$NR_bC$(=O)$OR_a$, wherein $R_a$-$R_b$ are each independently H, $C_{1-6}$ alkyl, phenyl, tetrahydrofuran, or benzyl. The remainder of the variables are as described in formulas (IVA), (VA), (VII) and (XI) or in the $1^{st}$ to $28^{th}$ embodiments described above.

In a $31^{st}$ embodiment, $R_7$ and $R_7'$ in formulas (IVA), (VA), (VII) and (XI), are each independently phenyl which is unsubstituted or substituted one or more times by $R^{11}$. The remainder of the variables are as described in formulas (IVA), (VA), (VII) and (XI) or in the $1^{st}$ to $30^{th}$ embodiments described above.

In a $32^{nd}$ embodiment, $R_7$ and $R_7'$ in formulas (IVA), (VA), (VII) and (XI), are each $R_7$ and $R_7'$ are each independently, $C_{1-6}$ alkyl which is unsubstituted or substituted one or more times by $R^{10}$. The remainder of the variables are as described in formulas (IVA), (VA), (VII) and (XI) or in the $1^{st}$ to $30^{th}$ embodiments described above.

In a further embodiment, $R_7$ and $R_7'$ are each independently methyl, ethyl, propyl, isopropyl, methoxyisopropyl, butyl, sec-butyl, tert-butyl, pentyl, 2-methylbutane, 3-methylbutane, cyclopropyl, cyclobutyl, cyclopentyl, or cyclohexyl. The remainder of the variables are as described in formulas (IVA), (VA), (VII) and (XI) or in the $1^{st}$ to $30^{th}$ embodiments described above.

In a $33^{rd}$ embodiment, for formulas (IVA), (VA), (VII) and (XI), $R_7$ and $R_8$ or $R_{7'}$ and $R_{8'}$ together with the carbon to which they are attached are each independently:

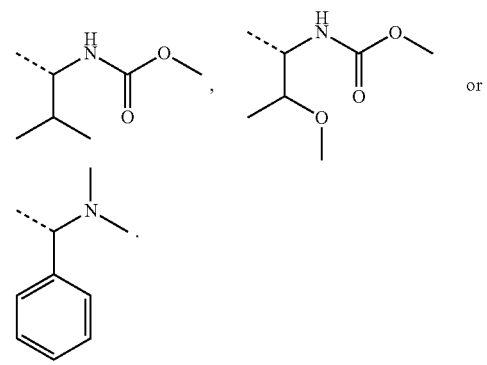

The remainder of the variables are as described in formulas (IVA), (VA), (VII) and (XI) or in the $1^{st}$ to $28^{th}$ embodiments described above.

In another aspect, the present invention provides compounds described in the following embodiments.

In one embodiment, the compounds of the present invention is represented by formula (I):

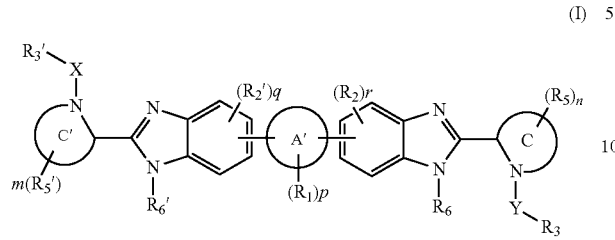

or pharmaceutically acceptable salts thereof, wherein,

A' is $C_{2-4}$ alkenyl, $C_{2-5}$ alkynyl, $C_{3-10}$ cycloalkyl, $C_{6-14}$ aryl, 4-12 membered heterocycle or 5-12 membered heteroaryl;

C and C' are each independently a 4-7 membered heterocycle;

$R_1$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, —$P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_2$, and $R_2'$ are each independently halogen, $C_{1-10}$ alkyl, $C_{1-6}$ halogenated alkyl, —$(CH_2)_{1-6}OH$, —$OR_a$, —$C(=O)OR_a$, —$NR_aR_b$, —$NR_bC(=O)R_a$, —$C(O)NR_aR_b$, —$S(O)_{0-3}R_a$, $C_{6-12}$ aryl, or 5-12 membered heteroaryl;

$R_3$ and $R_3'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_5$ and $R_5'$ are each independently H, halogen, —$NR_aR_b$, —$C(O)NR_aR_b$, —$(CH_2)_{1-6}OH$, $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_6$ and $R_6'$ are each independently H, $C_{1-6}$ alkyl, —$(CH_2)_{1-6}OH$, $C_{2-6}$ alkenyl, or $C_{2-6}$ alkynyl;

X and Y are each independently

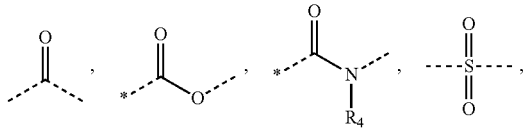

or a bond;

wherein the asterisk (*) indicates the point of attachment to the nitrogen of ring C or C';

$R_4$ is H, $C_{1-6}$ alkyl, or halogenated $C_{1-6}$ alky;

m, and n, combined are 1, 2, 3 or 4;

p is 0, 1, 2, 3 or 4;

q and r are each independently 0, 1, 2, 3 or 4;

$R^{10}$ is halogen, —$OR_a$, oxo, —$NR_aR_b$, =$NO$—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =$NO$—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

wherein

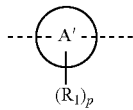

is not,

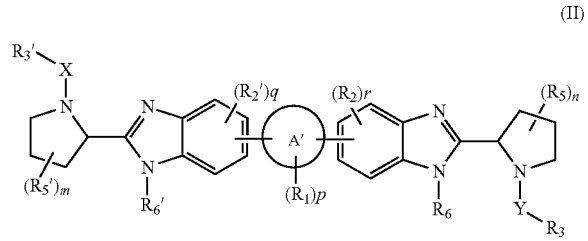

optionally substituted ethyl, phenyl, oxazolyl, furanyl, pyridyl, bicycle[2,2,2]octanyl, isoquinolinyl, and naphthyl.

In another embodiment, the compounds of the present invention are represented by formula (II):

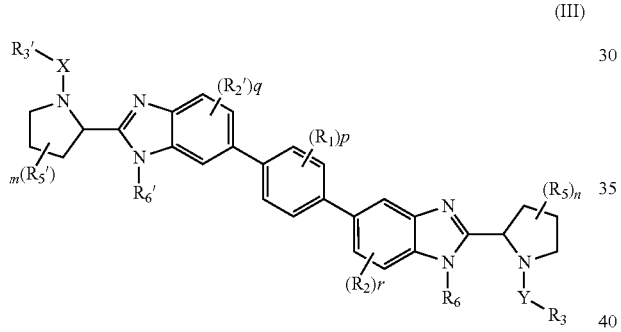

or pharmaceutically acceptable salts thereof, wherein the variables are as described above in formula (I).

In another embodiment, the compounds of the present invention are represented by formula (III):

(III)

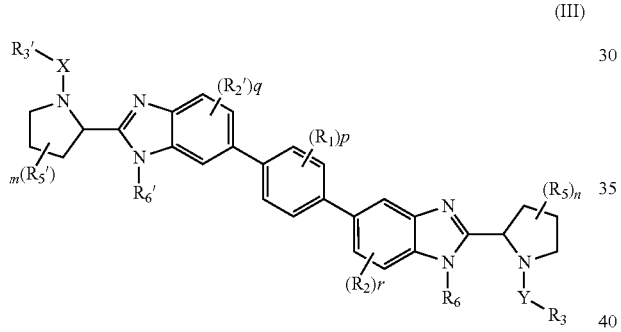

or pharmaceutically acceptable salts thereof, wherein two of $R_1$ on adjacent carbons can be taken together with the carbons to which they are attached to form a 5-7 cycloalkyl which is unsubstituted or substituted one or more times by $R^{10}$ or a 5-7 membered heterocycle which is unsubstituted or substituted one or more times by $R^{12}$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_2$ and $R_2'$ are each independently H, halogen, $C_{1-6}$ alkyl, or $C_{1-6}$ alkoxy;

X and Y are each independently

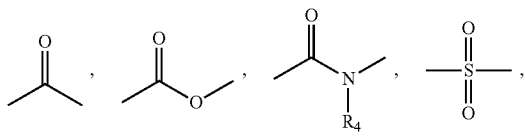

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, halogen, $C_{1-4}$ alkyl, hydroxyl, $C_{1-4}$ alkoxy, or $C_{1-4}$ halogenated alkyl;

$R_6$ and $R_6'$ are each independently H, $C_{1-6}$ alkyl, $C_{2-6}$ alkenyl, or $C_{2-6}$ alkynyl;

m, n, and p are each independently 0, 1, 2, 3 or 4;

q and r are each independently 0, 1, 2, or 3.

$R^{10}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{12}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In another embodiment, the compounds of the present invention are represented by formula (IV):

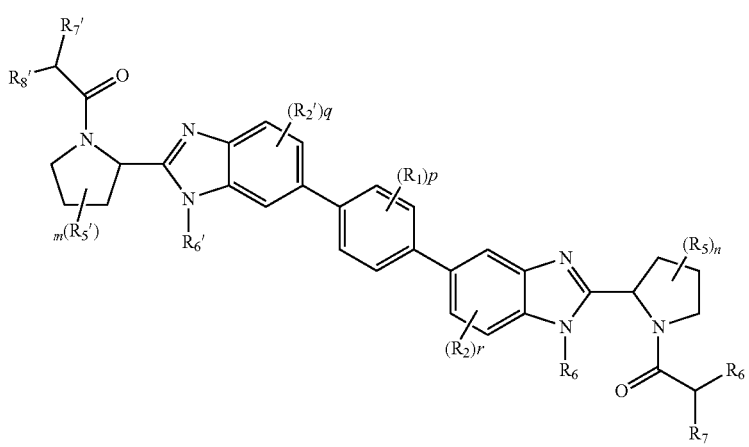

(IV)

or pharmaceutically acceptable salts thereof; wherein $R_7$ and $R_7'$ are each independently $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 3-6 membered heterocycle which is unsubstituted or substituted one or more times by $R^{12}$, or 4-7 membered heterocycle-alkyl which is unsubstituted or substituted one or more times by $R^{12}$;

$R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

The remainder of the variables in formula (IV) are as described above for formula (III).

In a first embodiment of the aspect, A' in formulas (I) and (II) is cyclopropyl, cyclohexyl, pyrrolidinyl, pyrazolidinyl, imidazolidinyl, piperazinyl, piperadinyl, phenyl, naphthalenyl, thienyl, pyrrolyl, pyrazolyl, imidazolyl, thiazolyl, thiadiazolyl, oxadiazolyl, pyrimidyl, pyrazinyl, pyridazinyl, indolyl, indazolyl, benzimidazolyl, benzoxazolyl, benzodioxolyl, benzothiazolyl, benzothiadiazolyl, benzothiophenyl, dihydrobenzodioxinyl, thienofuranyl, thienothienyl, thienopyrrolyl, quinolinyl, quinoxalinyl, quinazolinyl, cinnolinyl, or triazolyl; each of which is substituted with $(R_1)_p$. The remainder of the variables are as described above for formula (I) or (II).

In a further embodiment, A' in formulas (I) and (II) is thienyl, pyrimidyl, pyridazinyl, thiazolyl, N-methylimidazolyl, piperazinyl, thiadiazolyl, 1,4-diazepanyl or triazole. The remainder of the variables are as described above for formula (I) or (II).

In a further embodiment, A' in formulas (I) and (II) is thienyl. The remainder of the variables are as described above for formula (I) or (II).

In a second embodiment of the aspect, X and Y in formulas (I), (II) and (III) are

The remainder of the variables are as described above for formula (I), (II) and (III) or in the first embodiment described above.

In a third embodiment, $R_5$ and $R_5'$ in formulas (I), (II), (III) and (IV) are each independently H, halogen, methyl, ethyl, t-butoxy-, or hydroxyl. Alternatively, $R_5$ and $R_5'$ are fluoro. In another alternative, $R_5$ and $R_5'$ are H. The remainder of variables are as described in formulas (I), (II), (III) and (IV) or in the first or second embodiments described above.

In a fourth embodiment, $R_5$ and $R_5'$ in formulas (I), (II), (III) and (IV) are each independently halogen, methyl, ethyl, isopropyl, di-fluoromethyl, di-fluoroethyl, trifluoromethyl, tri-fluoroethyl, —$CH_2OH$, —$NR_aN_b$, t-butoxy-, or hydroxyl; or two $R_5$ groups together with the atoms to which they are attached form fused cyclopropyl, spiro cyclopropyl or

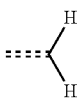

and/or two $R_5'$ groups with the atoms to which they are attached form fused cyclopropyl, spiro cyclopropyl or

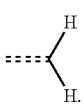

The remainder of variables are as described in formulas (I), (II), (III) and (IV) or in the first or second embodiments described above.

In a further embodiment, $R_5$ and $R_5'$ are each independently methyl, ethyl, methoxy, difluoromethyl, trifluoromethyl, or two $R_5$ groups together with the atoms to which they are attached form fused cyclopropyl or spiro cyclopropyl and/or two $R_5'$ groups together with the atoms to which they are attached form fused cyclopropyl or spiro cyclopropyl. The remainder of variables are as described in formulas (I), (II), (III) and (IV) or in the first or second embodiments described above.

In a fifth embodiment, $R_5$ and $R_5'$ in formulas (I), (II), (III) and (IV) are methyl. The remainder of variables are as described in formulas (I), (II), (III) and (IV) or in the first or second embodiments described above.

In a sixth embodiment, m and n in formulas (I), (II), (III) and (IV) are each independently 0, 1, or 2. Alternatively, m and n are 2. In another alternative, m and n are 1. The remainder of variables are as described in formulas (I), (II), (III) and (IV) or in the first to fifth embodiments described above.

In a seventh embodiment, $R_6$ are $R_6'$ in formulas (I), (II), (III) and (IV) are H or methyl. Alternatively, $R_6$ are $R_6'$ in formulas (I), (II), (III) and (IV) are H. The remainder of variables are as described in formulas (I), (II), (III) and (IV) or in the first to sixth embodiments described above.

In a eighth embodiment, $R_1$ in formulas (I), (II), (III) and (IV) is halogen, $C_{1-3}$ alkyl, hydroxyl, cyano, benzyloxy, or $C_{1-3}$ alkoxy. In a further embodiment, $R_1$ is chloro, fluoro, methyl, hydroxyl, benzyloxy, cyano, or methoxy. The remainder of variables are as described in formulas (I), (II), (III) and (IV) or in the first to seventh embodiments described above.

In a ninth embodiment, p in formulas (I), (II), (III) and (IV) is 2. Alternatively, p is 1. In another alternative, p is 0. The remainder of variables are as described in formulas (I), (II), (III) and (IV) or in the first to eighth embodiments described above.

In a tenth embodiment, $R_2$ and $R_2'$ in formulas (I), (II), (III) and (IV) are fluoro. Alternatively, $R_2$ and $R_2'$ in formulas (I), (II), (III) and (IV) are H. The remainder of variables are as described in formulas (I), (II), (III) and (IV) or in the first to ninth embodiments described above. In a further embodiment, $R_2$ and $R_2'$ are fluoro and q and r are 1.

In an eleventh embodiment, $R_3$ and $R_3'$ in formulas (I), (II), (III) and (IV) are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$. The remainder of variables are as described in formulas (I), (II), (III) and (IV) or in the first to tenth embodiments described above.

In a further embodiment, $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 5-6 membered heterocycle which is unsubstituted or substituted one or more times by $R^{12}$, or 6-7 membered heterocycle-alkyl which is unsubstituted or substituted one or more times by $R^{12}$. The remainder of variables are as described in formulas (I), (II), (III) and (IV) or in the first to tenth embodiments described above.

In another further embodiment, $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$. The remainder of variables are as described in formulas (I), (II), (III) and (IV) or in the first to tenth embodiments described above.

In another further embodiment, $R_3$ and $R_3'$ are each independently phenyl which is unsubstituted or substituted one or more times by $R^{11}$. The remainder of variables are as described in formulas (I), (II), (III) and (IV) or in the first to tenth embodiments described above.

In another further embodiment, $R_3$ and $R_3'$ are each independently benzyl which is unsubstituted or substituted one or more times by $R^{11}$.

In a twelfth embodiment, $R_3$ and $R_3'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl(CH$_2$)—, which are unsubstituted or substituted one or more times by $R^{10}$. The remainder of variables are as described in formulas (I), (II), (III) and (IV) or in the first to tenth embodiments described above.

In a thirteenth embodiment, for formula (IV), $R_7$ and $R_7'$ are each independently $C_{1-8}$ alkyl, $C_{2-8}$ alkenyl, $C_{2-8}$ alkynyl, phenyl, benzyl, 5-6 membered heteroaryl, 6-7 membered heteroaralkyl, 3-6 membered heterocycle, or 4-7 membered heterocycle-alkyl;

$R_8$ and $R_8'$ are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, —NR$_b$SO$_2$NR$_a$R$_b$, wherein R$_a$-R$_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and the remainder of the variables are as described in formula (IV) above or in the first to twelfth embodiments described above.

In a fourteenth embodiment, $R_8$ and $R_8'$ in formula (IV) are each independently —NR$_a$R$_b$, —NR$_b$C(=O)R$_a$, —NR$_b$C(=O)OR$_a$, wherein R$_a$-R$_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl. The remainder of the variables are as described in formula (IV) above or in the first to twelfth embodiments described above.

In a further embodiment, $R_8$ and $R_8'$ are each independently —NR$_b$C(=O)OR$_a$, wherein R$_a$-R$_b$ are each independently H, $C_{1-6}$ alkyl, phenyl, tetrahydrofuran, or benzyl. The remainder of the variables are as described in formula (IV) above or in the first to twelfth embodiments described above.

In a fifteenth embodiment, $R_7$ and $R_7'$ in formula (IV) are each independently phenyl. The remainder of the variables are as described in formula (IV) above or in the first to fourteenth embodiments described above.

In a sixteenth embodiment, $R_7$ and $R_7'$ in formula (IV) are each independently, $C_{1-6}$ alkyl. The remainder of the variables are as described in formula (IV) above or in the first to fourteenth embodiments described above. In a further embodiment, $R_7$ and $R_7'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, or cyclohexyl. The remainder of the variables are as described in formula (IV) above or in the first to fourteenth embodiments described above.

In a seventeenth embodiment, for formula (IV), $R_7$ and $R_8$ or $R_7'$ and $R_8'$ together with the carbon to which they are attached are each independently:

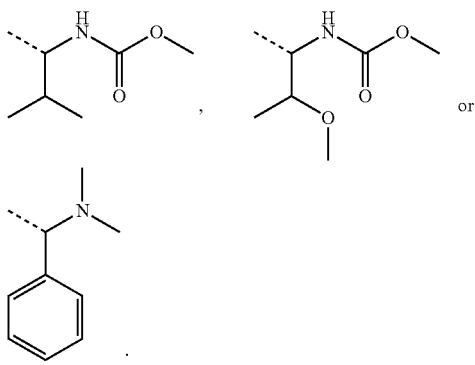

The remainder of the variables are as described in formula (IV) above or in the first to twelfth embodiments described above.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, $R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$ are each independently H or methyl.

Alternatively, $R^{10}$ is —$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —$NR_bSO_2R_a$, or —$NR_bSO_2NR_aR_b$, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In another alternative, $R^{10}$ is —$NR_aR_b$, —$NR_dC$(=O)$NR_aR_b$, —$NR_bC$(=O)$R_a$, —$NR_bC$(=O)$OR_a$, or —$NR_bSO_2R_a$, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In yet another alternative, $R^{10}$ is halogen, —$OR_a$, oxo, —C(=O)$OR_a$, —C(O)$NR_aR_b$, —C(=O)OH, —C(=O)$R_a$, —OC(=O)$NR_aR_b$, —OC(=O)$R_a$, —OC(=O)$OR_a$, hydroxyl, cyano, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, $R^{11}$ is halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$ are each independently H or methyl.

Alternatively, $R^{11}$ is halogen, —$OR_a$, —$NR_aR_b$, —C(=O)$OR_a$, —C(O)$NR_aR_b$, —C(=O)$R_a$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In another alternative, $R^{11}$ is halogen, —$OR_a$, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In yet another alternative, $R^{11}$ is halogen, —$OR_a$, —$NR_aR_b$, hydroxyl, cyano, $C_{1-6}$ alkyl, wherein $R_a$-$R_b$ are each independently H, $C_{1-3}$ alkyl.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$ are each independently H or methyl.

Alternatively, $R^{12}$ is halogen, —$OR_a$, oxo, —$NR_aR_b$, —C(=O)$OR_a$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, —OC(=O)$R_a$, —OC(=O)$OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In another alternative, $R^{12}$ is halogen, —$OR_a$, oxo, —$NR_aR_b$, —C(O)$NR_aR_b$, —C(=O)OH, —C(=O)$R_a$, —$NR_dC$(=O)$NR_aR_b$, —$NR_bC$(=O)$R_a$, —$NR_bC$(=O)$OR_a$, —OC(=O)$NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In yet another alternative, $R^{12}$ is halogen, —$OR_a$, oxo, —$NR_aR_b$, hydroxyl, cyano, $C_{1-6}$ alkyl, wherein $R_a$-$R_b$ are each independently H, $C_{1-3}$ alkyl.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

Alternatively, $R_a$ and $R_c$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, and $R_b$, and $R_d$. are each independently H or $C_{1-3}$ alkyl.

In another alternative, $R_a$-$R_d$ are each independently H or $C_{1-3}$ alkyl.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, the heterocyle in the groups (e.g., heterocycle and heterocycle-alkyl) represented by $R_3$, $R_3'$, $R_a$-$R_d$, $R_7$ and $R_7'$ are selected from the group consisting of morphonlinyl, morpholino, tetrahydrofuranyl, pyrrolidinyl, azepanyl, tetrahydropyranyl, oxazolinyl, piperazinyl and piperadinyl, each of which is optionally substituted with one or more times by halogen, $C_{1-3}$ alkyl, halogenated $C_{1-3}$ alkyl, oxo, hydroxyl, —C(=O)O—($C_{1-3}$ alkyl), $C_{1-3}$ alkoxy, or halogenated $C_{1-3}$ alkoxy. Alternatively, the heterocyle in the groups represented by $R_3$, $R_3'$, $R_a$-$R_d$, $R_7$ and $R_7'$ are selected from the group consisting of morphonlinyl, morpholino, tetrahydrofuranyl, pyrrolidinyl, azepanyl, tetrahydropyranyl and oxazolinyl, each of which is optionally substituted with one or more times by halogen, $C_{1-3}$ alkyl, halogenated $C_{1-3}$ alkyl, oxo, hydroxyl, —C(=O)O—($C_{1-3}$ alkyl), $C_{1-3}$ alkoxy, or halogenated $C_{1-3}$ alkoxy. In one embodiment, the heterocycle groups described above is optionally substituted with one or more times by oxo, hydroxyl or —C(=O)O—($C_{1-3}$ alkyl). Alternatively, the heterocycle groups described above is unsubstituted.

In a further embodiment, for formulas (I), (II), (III), (IV), (IIIA), (IIIA'), (IIB), (IVA), (VA), (V), (VI), (VII), (VIII), (IX), (X) and (XI) and any foregoing embodiments, the heteroaryl in the groups (e.g., heteroaryl and heteroaralkyl) represented by $R_3$, $R_3'$, $R_a$-$R_d$, $R_7$ and $R_7'$ are selected from the group consisting of furanyl, pyrazinyl, pyridazinyl, pyrimidinyl, pyridyl, pyrroly, thienyl, triazolyl, imidazolyl, indolyl, quinolinyl and isoquinolinyl, each of which is optionally substituted with halogen, $C_{1-3}$ alkyl, halogenated $C_{1-3}$ alkyl, hydroxyl, —C(=O)O—($C_{1-3}$ alkyl), $C_{1-3}$ alkoxy, or halogenated $C_{1-3}$ alkoxy. Alternatively, the heteroaryl in the groups (e.g., heteroaryl and heteroaralkyl) represented by $R_3$, $R_3'$, $R_a$-$R_d$, $R_7$ and $R_7'$ are selected from the group consisting of indolyl and pyrimidinyl, each of which is optionally substituted one or more times by halogen, $C_{1-3}$ alkyl, halogenated $C_{1-3}$ alkyl, hydroxyl, —C(=O)O—($C_{1-3}$ alkyl), $C_{1-3}$ alkoxy, or halogenated $C_{1-3}$ alkoxy. In one embodiment, the heteroaryl groups described above is unsubstituted.

In another aspect, the compounds of the present invention are selected from compounds shown in Table 1 or pharmaceutically acceptable salts thereof. In certain embodiments, the variables used herein are as defined in the specific embodiments as shown in Table 1.

TABLE 1

| Compound | Cmpd # |
|---|---|
|  | 1 |
|  | 2 |

TABLE 1-continued

| Compound | Cmpd # |
|---|---|
| | 3 |
| | 4 |
| | 5 |
| | 6 |

TABLE 1-continued

| Compound | Cmpd # |
|---|---|
| | 7 |
| | 8 |
| | 9 |
| | 10 |

TABLE 1-continued

| Compound | Cmpd # |
|---|---|
| | 11 |
| | 12 |
| | 13 |
| | 14 |

TABLE 1-continued

| Compound | Cmpd # |
|---|---|
| | 15 |
| | 16 |
| | 17 |
| | 18 |

TABLE 1-continued
| Compound | Cmpd # |
|---|---|
| 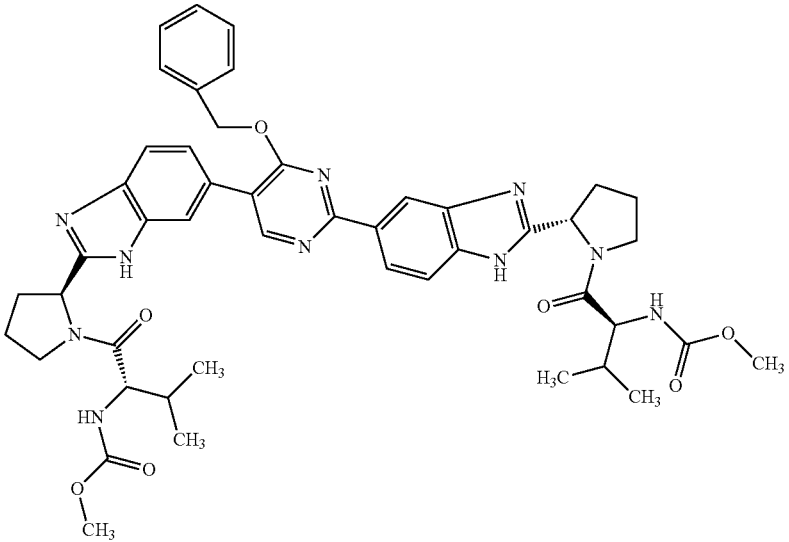 [SMILES: COC(=O)N[C@H](C(=O)N1CCC[C@H]1c1nc2cc(-c3ncc(-c4ccc5nc([C@@H]6CCCN6C(=O)[C@@H](NC(=O)OC)C(C)C)[nH]c5c4)c(OCc4ccccc4)n3)ccc2[nH]1)C(C)C] | 19 |
| 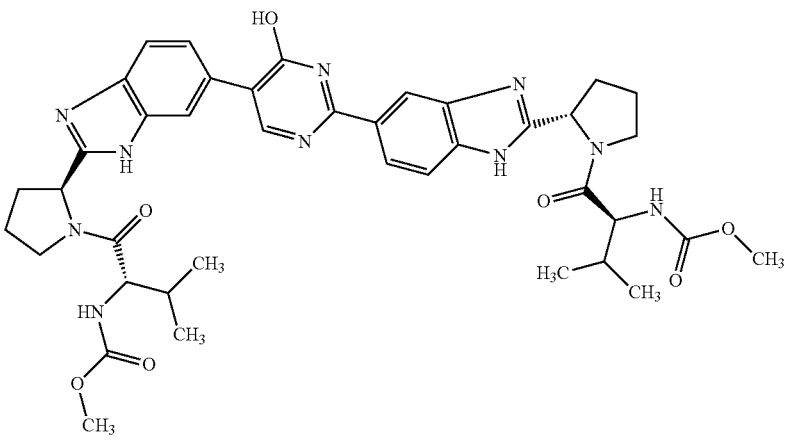 [SMILES: COC(=O)N[C@H](C(=O)N1CCC[C@H]1c1nc2cc(-c3ncc(-c4ccc5nc([C@@H]6CCCN6C(=O)[C@@H](NC(=O)OC)C(C)C)[nH]c5c4)c(O)n3)ccc2[nH]1)C(C)C] | 20 |
| 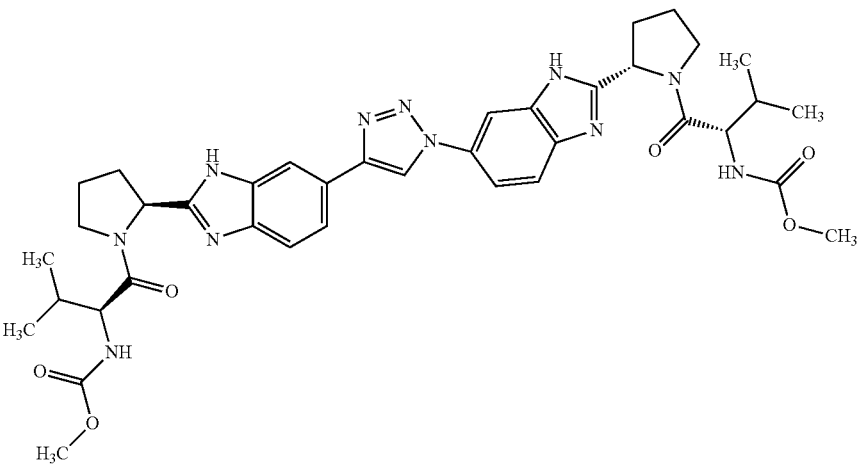 [SMILES: COC(=O)N[C@H](C(=O)N1CCC[C@H]1c1nc2ccc(-c3cn(-c4ccc5nc([C@@H]6CCCN6C(=O)[C@@H](NC(=O)OC)C(C)C)[nH]c5c4)nn3)cc2[nH]1)C(C)C] | 21 |

TABLE 1-continued

| Compound | Cmpd # |
|---|---|
| | 22 |
| | 23 |
| | 24 |
| | 25 |

TABLE 1-continued

| Compound | Cmpd # |
|---|---|
| | 26 |
| | 27 |
| | 28 |

TABLE 1-continued

| Compound | Cmpd # |
|---|---|
| | 29 |
| | 30 |
| | 31 |
| | 32 |

TABLE 1-continued

| Compound | Cmpd # |
|---|---|
| | 33 |
| | 34 |
| | 35 |

TABLE 1-continued
| Compound | Cmpd # |
|---|---|
| 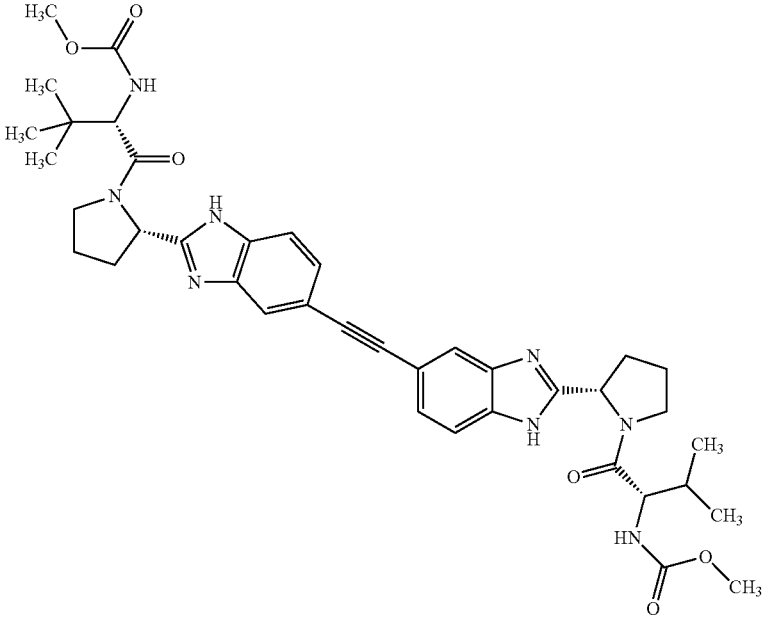 [SMILES: COC(=O)N[C@H](C(=O)N1CCC[C@H]1c1nc2cc(C#Cc3ccc4[nH]c([C@@H]5CCCN5C(=O)[C@@H](NC(=O)OC)C(C)(C)C)nc4c3)ccc2[nH]1)C(C)C] | 36 |
| 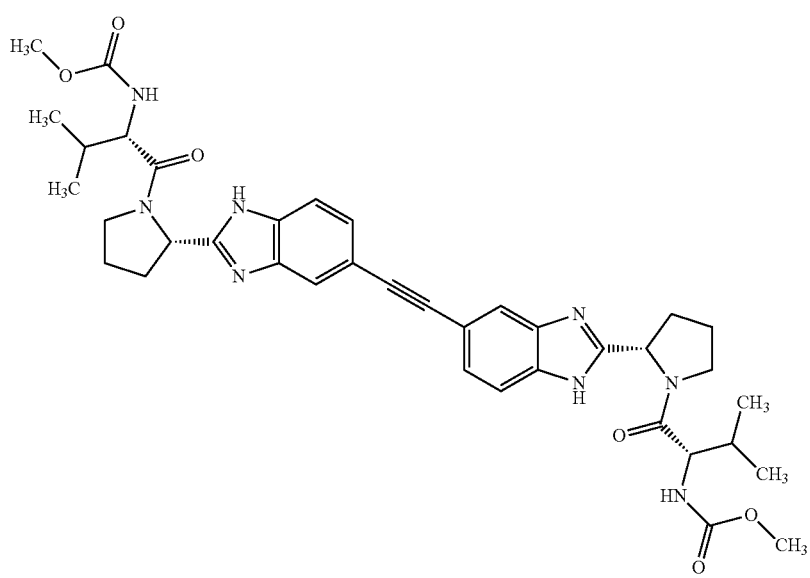 | 37 |

TABLE 1-continued
| Compound | Cmpd # |
|---|---|
| 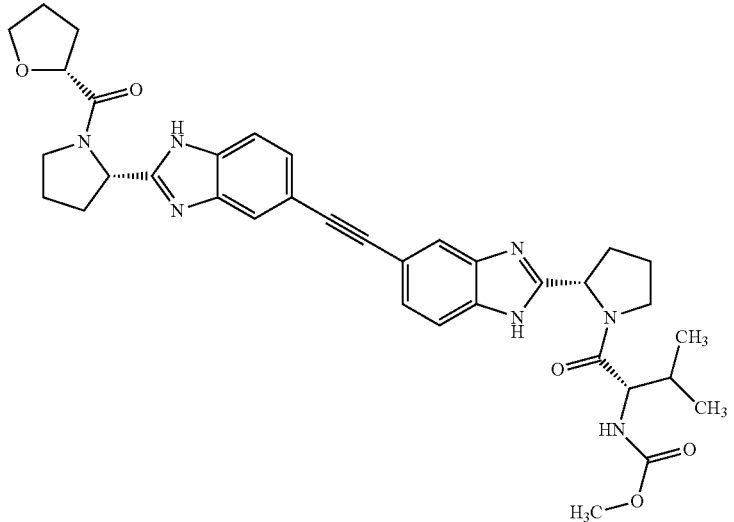 [SMILES: COC(=O)N[C@H](C(=O)N1CCC[C@H]1c1nc2cc(C#Cc3ccc4[nH]c([C@@H]5CCCN5C(=O)[C@H]5CCCO5)nc4c3)ccc2[nH]1)C(C)C] | 38 |
| 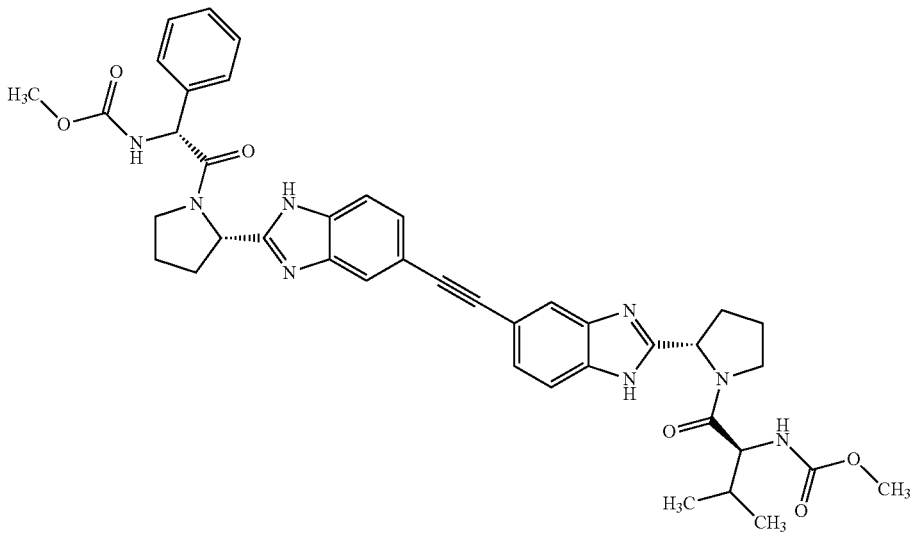 | 39 |

TABLE 1-continued
| Compound | Cmpd # |
|---|---|
| 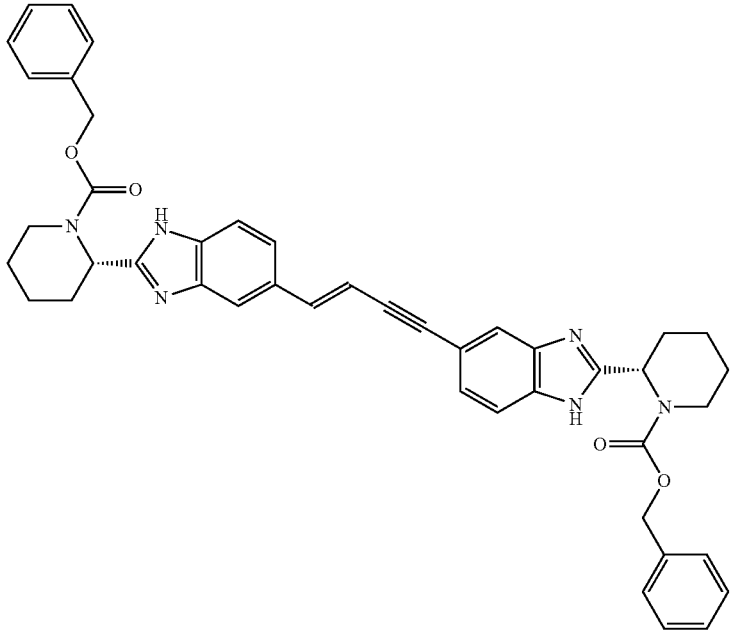 [SMILES: O=C(OCc1ccccc1)N1CCCC[C@H]1c1nc2cc(C#C/C=C/c3ccc4[nH]c([C@@H]5CCCCN5C(=O)OCc5ccccc5)nc4c3)ccc2[nH]1] | 40 |
| 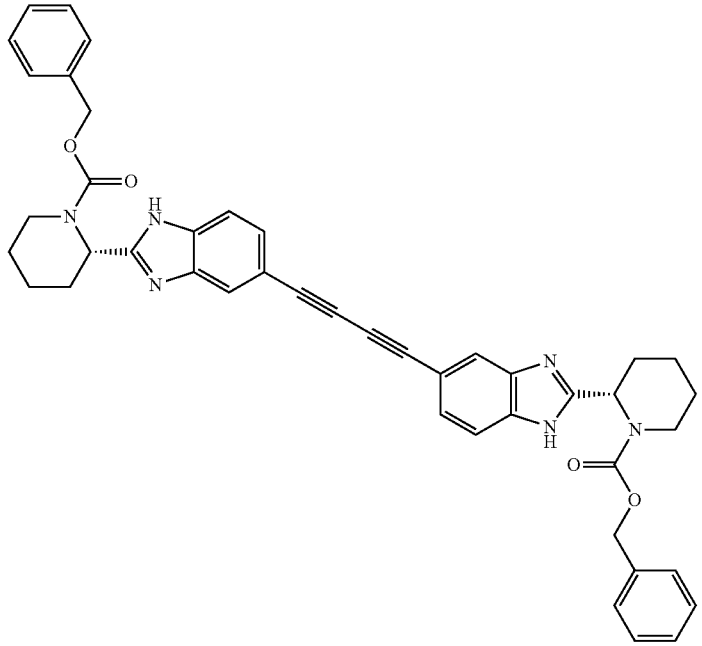 [SMILES: O=C(OCc1ccccc1)N1CCCC[C@H]1c1nc2cc(C#CC#Cc3ccc4[nH]c([C@@H]5CCCCN5C(=O)OCc5ccccc5)nc4c3)ccc2[nH]1] | 41 |
| 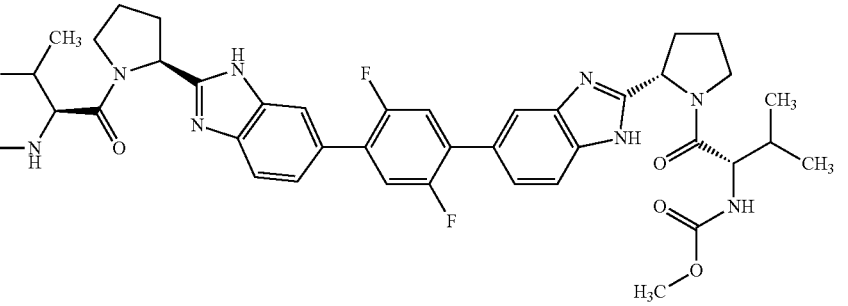 | 42 |

TABLE 1-continued
| Compound | Cmpd # |
|---|---|
| 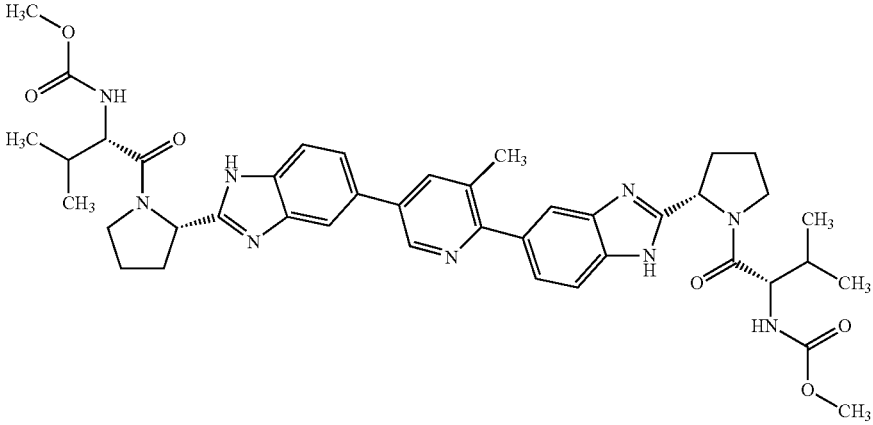 [SMILES: COC(=O)N[C@H](C(=O)N1CCC[C@H]1c1nc2cc(-c3cnc(-c4ccc5[nH]c([C@@H]6CCCN6C(=O)[C@@H](NC(=O)OC)C(C)C)nc5c4)c(C)c3)ccc2[nH]1)C(C)C] | 43 |
| 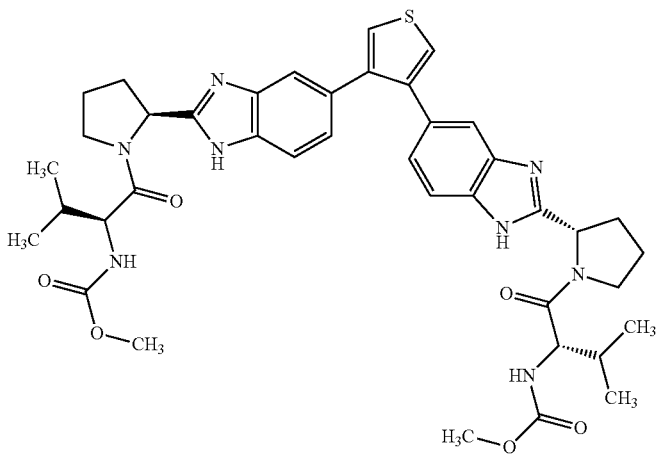 [SMILES: COC(=O)N[C@H](C(=O)N1CCC[C@H]1c1nc2cc(-c3cscc3-c3ccc4[nH]c([C@@H]5CCCN5C(=O)[C@@H](NC(=O)OC)C(C)C)nc4c3)ccc2[nH]1)C(C)C] | 44 |
| 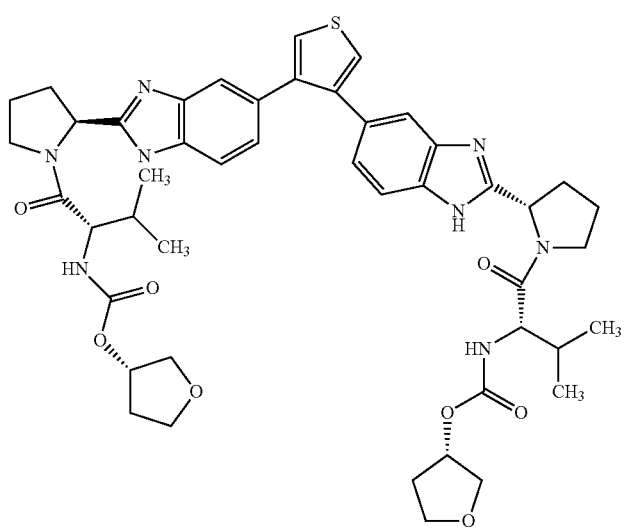 [SMILES: CC(C)[C@H](NC(=O)O[C@H]1CCOC1)C(=O)N1CCC[C@H]1c1nc2cc(-c3cscc3-c3ccc4[nH]c([C@@H]5CCCN5C(=O)[C@@H](NC(=O)O[C@H]5CCOC5)C(C)C)nc4c3)ccc2[nH]1] | 45 |

TABLE 1-continued

| Compound | Cmpd # |
|---|---|
| | 46 |
| | 47 |
| | 48 |

TABLE 1-continued

| Compound | Cmpd # |
|---|---|
| | 49 |
| | 50 |
| | 51 |
| | 52 |

TABLE 1-continued

| Compound | Cmpd # |
|---|---|
| | 53 |
| | 54 |
| | 55 |
| | 56 |
| | 57 |

| Compound | Cmpd # |
|---|---|
| | 58 |
| | 59 |
| | 60 |

TABLE 1-continued

| Compound | Cmpd # |
|---|---|
| | 61 |
| | 62 |
| | 63 |
| | 64 |

TABLE 1-continued

| Compound | Cmpd # |
|---|---|
| | 65 |
| | 66 |
| | 67 |
| | 68 |
| | 69 |

TABLE 1-continued

| Compound | Cmpd # |
|---|---|
| | 70 |
| | 71 |
| | 72 |
| | 73 |
| | 74 |

TABLE 1-continued

| Compound | Cmpd # |
| --- | --- |
| | 75 |
| | 76 |
| | 77 |
| | 78 |
| | 79 |

TABLE 1-continued

| Compound | Cmpd # |
|---|---|
| | 80 |
| | 81 |
| | 82 |
| | 83 |

TABLE 1-continued

| Compound | Cmpd # |
|---|---|
| | 84 |
| | 85 |
| | 86 |
| | 87 |

TABLE 1-continued

| Compound | Cmpd # |
|---|---|
| | 88 |
| | 89 |
| | 90 |
| | 91 |

TABLE 1-continued

| Compound | Cmpd # |
|---|---|
| | 92 |
| | 93 |
| | 94 |
| | 95 |

TABLE 1-continued

| Compound | Cmpd # |
|---|---|
| | 96 |
| | 97 |
| | 98 |
| | 99 |
| | 100 |

TABLE 1-continued

| Compound | Cmpd # |
|---|---|
| | 101 |
| | 102 |
| | 103 |
| | 104 |
| | 105 |

TABLE 1-continued

| Compound | Cmpd # |
|---|---|
| | 106 |
| | 107 |
| | 108 |
| | 109 |
| | 110 |

TABLE 1-continued
| Compound | Cmpd # |
|---|---|
| 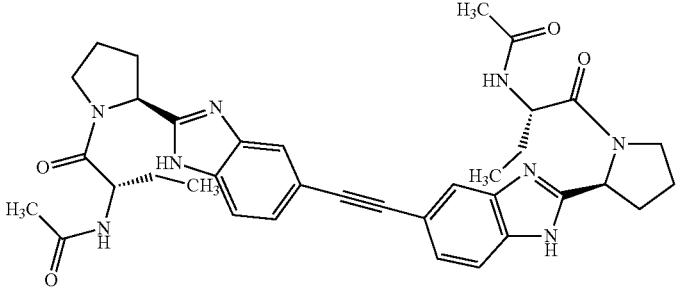 [SMILES: CC[C@H](NC(C)=O)C(=O)N1CCC[C@H]1c1nc2cc(C#Cc3ccc4[nH]c([C@@H]5CCCN5C(=O)[C@H](CC)NC(C)=O)nc4c3)ccc2[nH]1] | 111 |
| 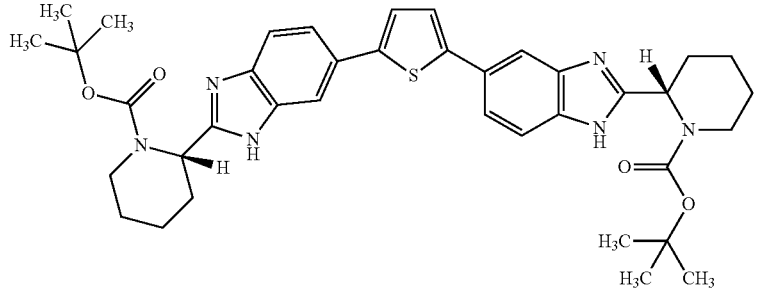 [SMILES: CC(C)(C)OC(=O)N1CCCC[C@H]1c1nc2cc(-c3ccc(-c4ccc5nc([C@@H]6CCCCN6C(=O)OC(C)(C)C)[nH]c5c4)s3)ccc2[nH]1] | 112 |
| 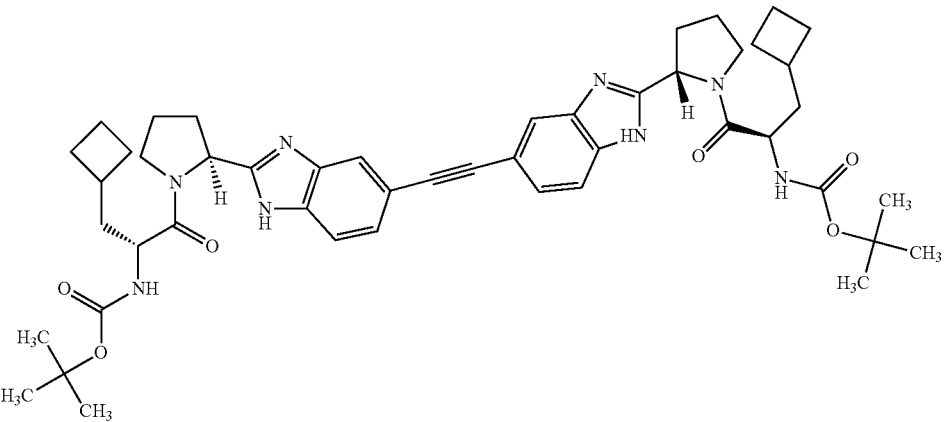 [SMILES: CC(C)(C)OC(=O)N[C@H](CC1CCC1)C(=O)N1CCC[C@H]1c1nc2cc(C#Cc3ccc4[nH]c([C@@H]5CCCN5C(=O)[C@@H](CC5CCC5)NC(=O)OC(C)(C)C)nc4c3)ccc2[nH]1] | 113 |
| 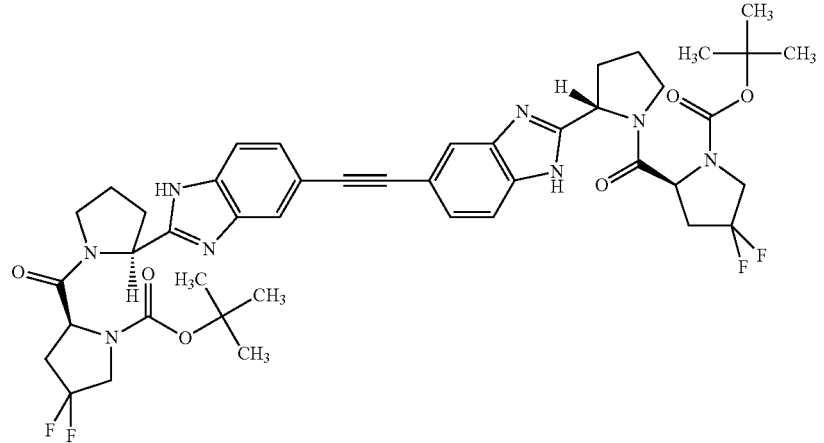 [SMILES: CC(C)(C)OC(=O)N1CC(F)(F)C[C@H]1C(=O)N1CCC[C@H]1c1nc2cc(C#Cc3ccc4[nH]c([C@@H]5CCCN5C(=O)[C@@H]5CC(F)(F)CN5C(=O)OC(C)(C)C)nc4c3)ccc2[nH]1] | 114 |

TABLE 1-continued
| Compound | Cmpd # |
|---|---|
| 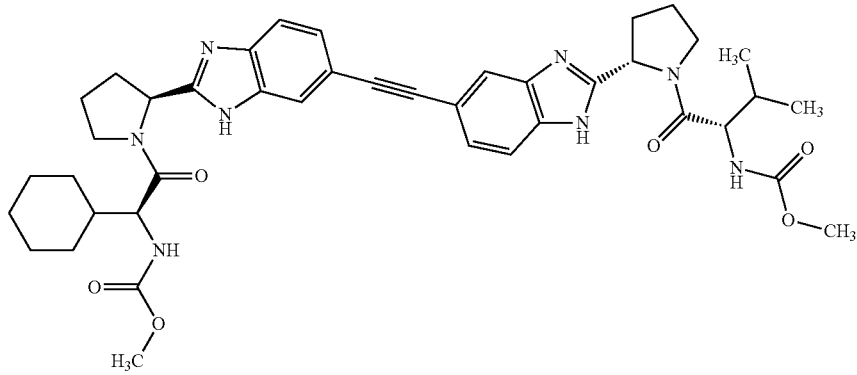 [SMILES: COC(=O)N[C@H](C(=O)N1CCC[C@H]1c1nc2cc(C#Cc3ccc4nc([C@@H]5CCCN5C(=O)[C@@H](NC(=O)OC)C5CCCCC5)[nH]c4c3)ccc2[nH]1)C(C)C] | 115 |
| 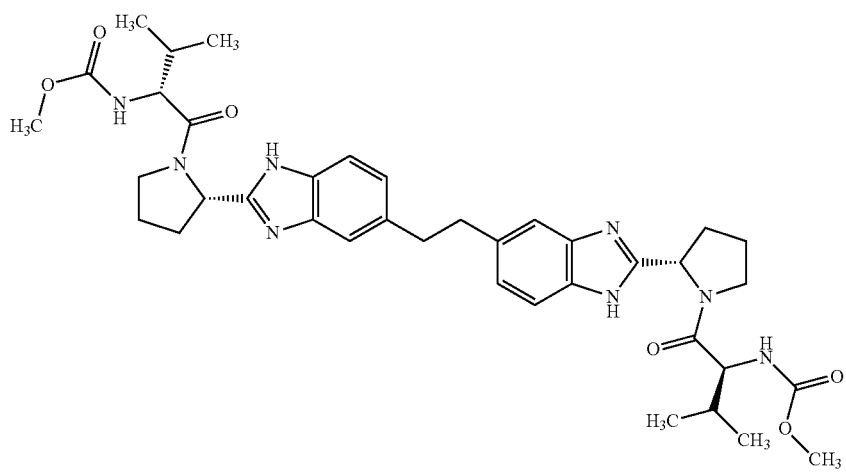 [SMILES: COC(=O)N[C@H](C(=O)N1CCC[C@H]1c1nc2cc(CCc3ccc4[nH]c([C@@H]5CCCN5C(=O)[C@H](NC(=O)OC)C(C)C)nc4c3)ccc2[nH]1)C(C)C] | 116 |
| 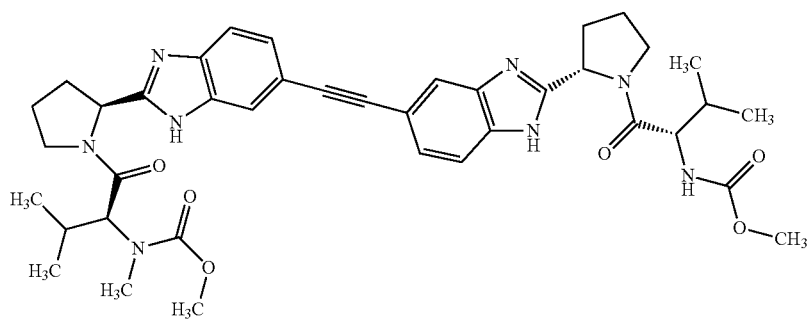 [SMILES: COC(=O)N[C@H](C(=O)N1CCC[C@H]1c1nc2cc(C#Cc3ccc4nc([C@@H]5CCCN5C(=O)[C@H](C(C)C)N(C)C(=O)OC)[nH]c4c3)ccc2[nH]1)C(C)C] | 117 |
| 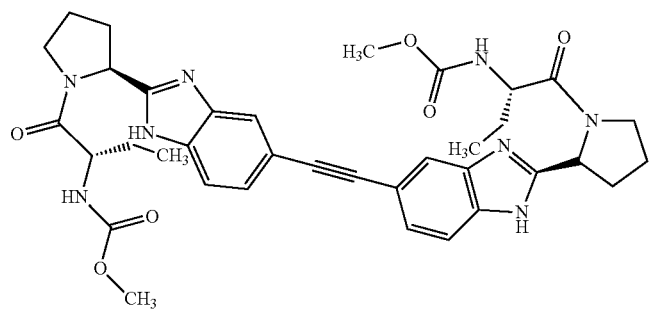 | 118 |

TABLE 1-continued

| Compound | Cmpd # |
|---|---|
| | 119 |
| | 120 |
| | 121 |
| | 122 |

TABLE 1-continued

| Compound | Cmpd # |
|---|---|
| | 123 |
| | 124 |
| | 125 |
| | 126 |
| | 127 |

TABLE 1-continued

| Compound | Cmpd # |
|---|---|
| | 128 |
| | 129 |
| | 130 |
| | 131 |

TABLE 1-continued

| Compound | Cmpd # |
|---|---|
| | 132 |
| | 133 |
| | 134 |
| | 135 |

TABLE 1-continued

| Compound | Cmpd # |
|---|---|
| | 136 |
| | 137 |
| | 138 |
| | 139 |
| | 140 |

TABLE 1-continued

| Compound | Cmpd # |
|---|---|
|  | 141 |
|  | 142 |
|  | 143 |

TABLE 1-continued

| Compound | Cmpd # |
|---|---|
| | 144 |
| | 145 |
| | 146 |
| | 147 |

TABLE 1-continued

| Compound | Cmpd # |
|---|---|
| | 148 |
| | 149 |
| | 150 |
| | 151 |

TABLE 1-continued

| Compound | Cmpd # |
|---|---|
| | 152 |
| | 153 |
| | 154 |

TABLE 1-continued

| Compound | Cmpd # |
|---|---|
| | 155 |
| | 156 |
| | 157 |

TABLE 1-continued

| Compound | Cmpd # |
|---|---|
| | 158 |
| | 159 |
| | 160 |

TABLE 1-continued

| Compound | Cmpd # |
|---|---|
| | 161 |
| | 162 |
| | 163 |

TABLE 1-continued
| Compound | Cmpd # |
|---|---|
| 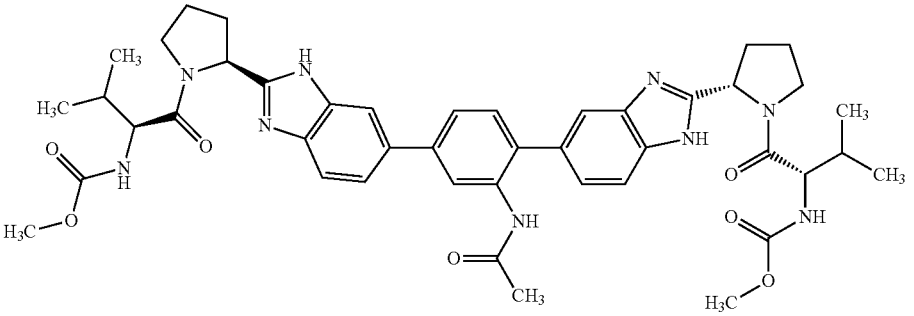 [SMILES: COC(=O)N[C@H](C(=O)N1CCC[C@H]1c1nc2cc(-c3ccc(-c4ccc5nc([C@@H]6CCCN6C(=O)[C@@H](NC(=O)OC)C(C)C)[nH]c5c4)cc3NC(C)=O)ccc2[nH]1)C(C)C] | 164 |
| 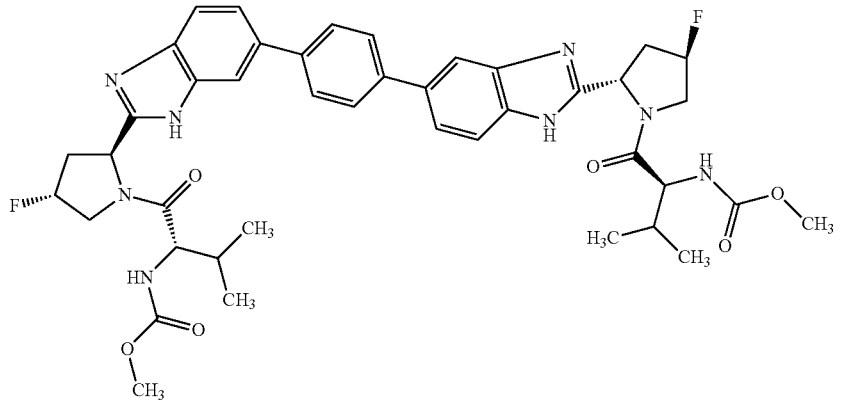 [SMILES: COC(=O)N[C@H](C(=O)N1C[C@H](F)C[C@H]1c1nc2cc(-c3ccc(-c4ccc5nc([C@@H]6C[C@@H](F)CN6C(=O)[C@@H](NC(=O)OC)C(C)C)[nH]c5c4)cc3)ccc2[nH]1)C(C)C] | 165 |
| 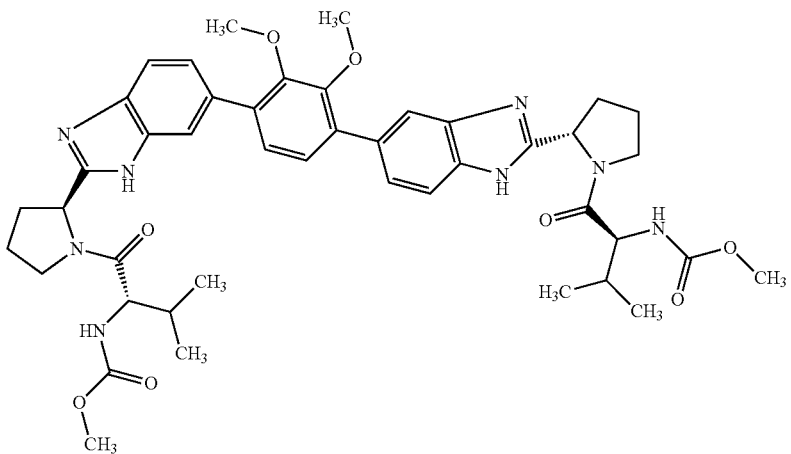 [SMILES: COC(=O)N[C@H](C(=O)N1CCC[C@H]1c1nc2cc(-c3ccc(-c4ccc5nc([C@@H]6CCCN6C(=O)[C@@H](NC(=O)OC)C(C)C)[nH]c5c4)c(OC)c3OC)ccc2[nH]1)C(C)C] | 166 |
| 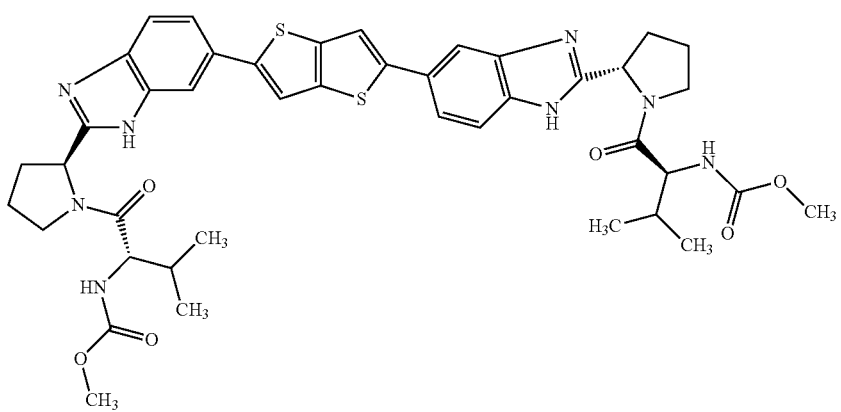 [SMILES: COC(=O)N[C@H](C(=O)N1CCC[C@H]1c1nc2cc(-c3cc4sc(-c5ccc6nc([C@@H]7CCCN7C(=O)[C@@H](NC(=O)OC)C(C)C)[nH]c6c5)cc4s3)ccc2[nH]1)C(C)C] | 167 |

TABLE 1-continued
| Compound | Cmpd # |
|---|---|
| 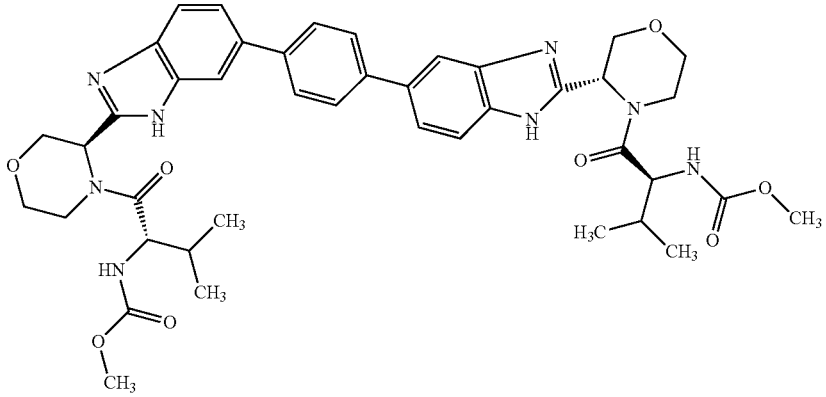 [SMILES: COC(=O)N[C@H](C(=O)N1CCOC[C@H]1c1nc2cc(-c3ccc(-c4ccc5nc([C@@H]6COCCN6C(=O)[C@@H](NC(=O)OC)C(C)C)[nH]c5c4)cc3)ccc2[nH]1)C(C)C] | 168 |
| 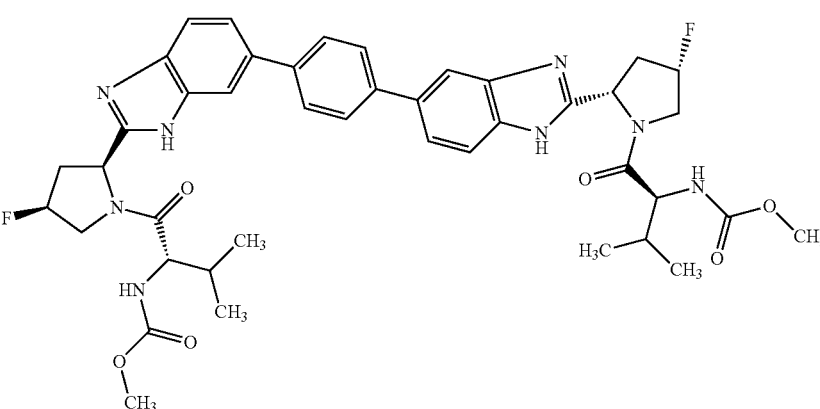 | 169 |
| 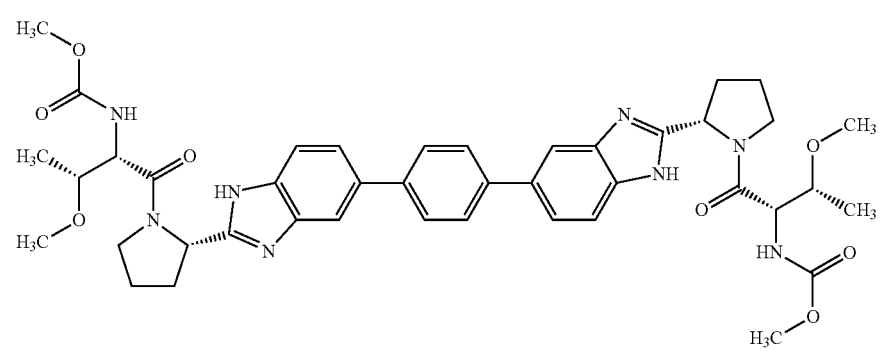 | 170 |
| 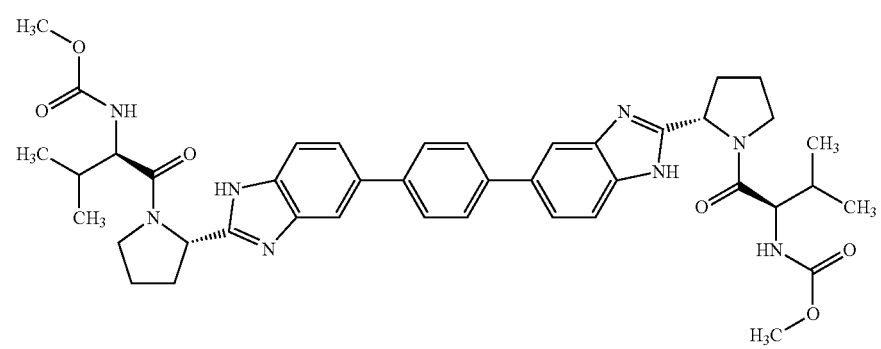 [SMILES: COC(=O)N[C@@H](C(=O)N1CCC[C@H]1c1nc2cc(-c3ccc(-c4ccc5[nH]c([C@@H]6CCCN6C(=O)[C@H](NC(=O)OC)C(C)C)nc5c4)cc3)ccc2[nH]1)C(C)C] | 171 |

TABLE 1-continued

| Compound | Cmpd # |
| --- | --- |
| | 172 |
| | 173 |
| | 174 |

TABLE 1-continued

| Compound | Cmpd # |
|---|---|
| | 175 |
| | 176 |
| | 177 |
| | 178 |

TABLE 1-continued

| Compound | Cmpd # |
|---|---|
| | 179 |
| | 180 |
| | 181 |
| | 182 |

TABLE 1-continued

| Compound | Cmpd # |
|---|---|
| | 183 |
| | 184 |
| | 185 |
| | 186 |

TABLE 1-continued

| Compound | Cmpd # |
|---|---|
| | 187 |
| | 188 |
| | 189 |
| | 190 |

TABLE 1-continued
| Compound | Cmpd # |
|---|---|
| 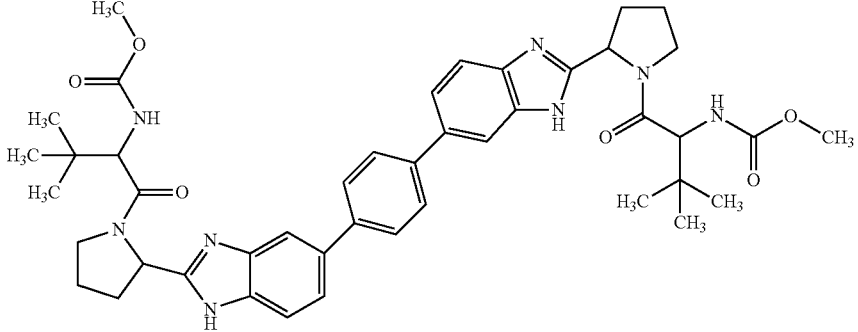 [SMILES: COC(=O)NC(C(=O)N1CCCC1c1nc2cc(-c3ccc(-c4ccc5nc(C6CCCN6C(=O)C(NC(=O)OC)C(C)(C)C)[nH]c5c4)cc3)ccc2[nH]1)C(C)(C)C] | 191 |
| 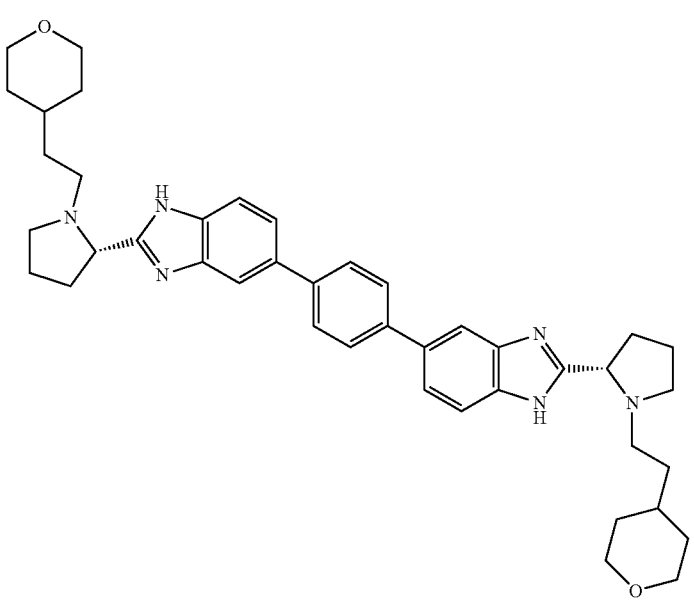 [SMILES: c1cc(-c2ccc3[nH]c([C@@H]4CCCN4CCC4CCOCC4)nc3c2)ccc1-c1ccc2[nH]c([C@@H]3CCCN3CCC3CCOCC3)nc2c1] | 192 |
| 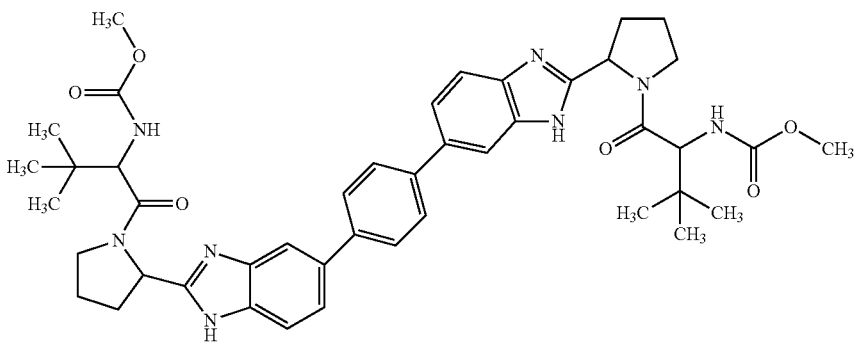 [SMILES: COC(=O)NC(C(=O)N1CCCC1c1nc2cc(-c3ccc(-c4ccc5nc(C6CCCN6C(=O)C(NC(=O)OC)C(C)(C)C)[nH]c5c4)cc3)ccc2[nH]1)C(C)(C)C] | 193 |

TABLE 1-continued

| Compound | Cmpd # |
|---|---|
| | 194 |
| | 195 |
| | 196 |
| | 197 |

TABLE 1-continued

| Compound | Cmpd # |
|---|---|
| | 198 |
| | 199 |
| | 200 |
| | 201 |

TABLE 1-continued
| Compound | Cmpd # |
|---|---|
| 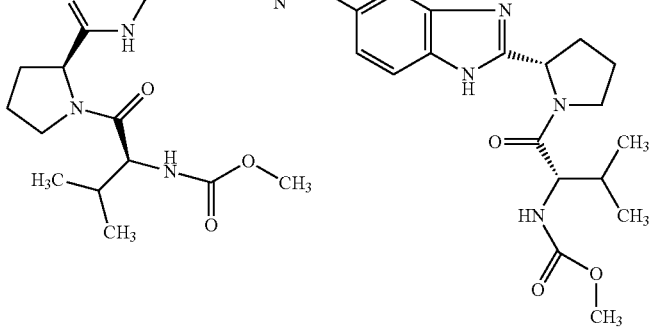 | 202 |
| 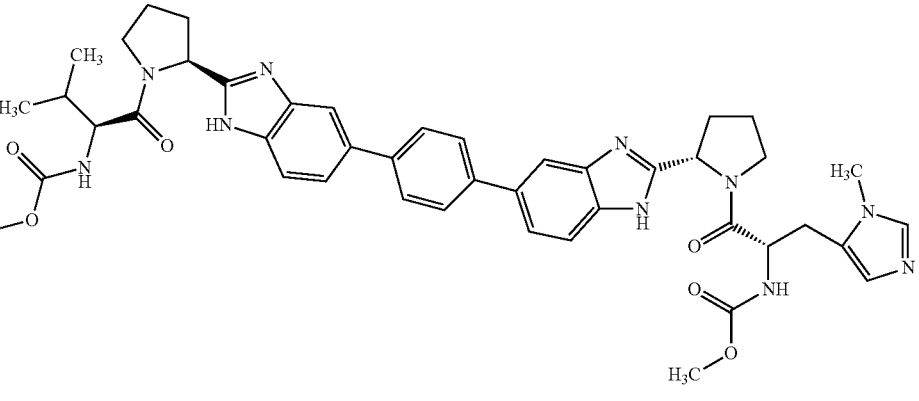 | 203 |
| 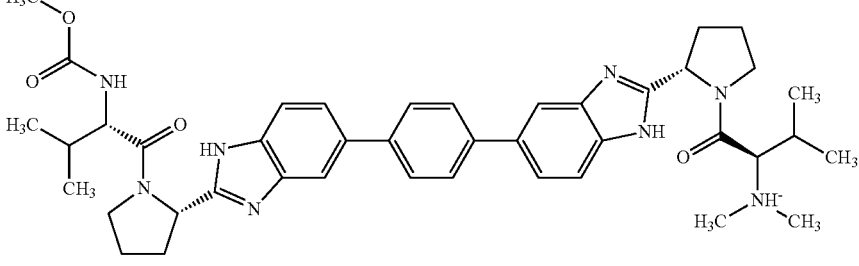 | 204 |
| 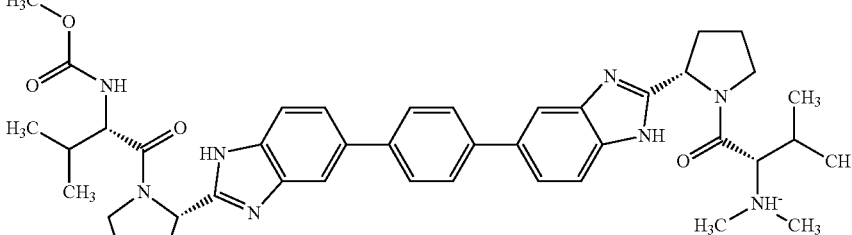 | 205 |

TABLE 1-continued

| Compound | Cmpd # |
|---|---|
| | 206 |
| | 207 |
| | 208 |
| | 209 |

TABLE 1-continued

| Compound | Cmpd # |
| --- | --- |
| | 210 |
| | 211 |
| | 212 |

TABLE 1-continued

| Compound | Cmpd # |
|---|---|
| | 213 |
| | 214 |
| | 215 |
| | 216 |

TABLE 1-continued
| Compound | Cmpd # |
|---|---|
|  | 217 |
|  | 218 |
| 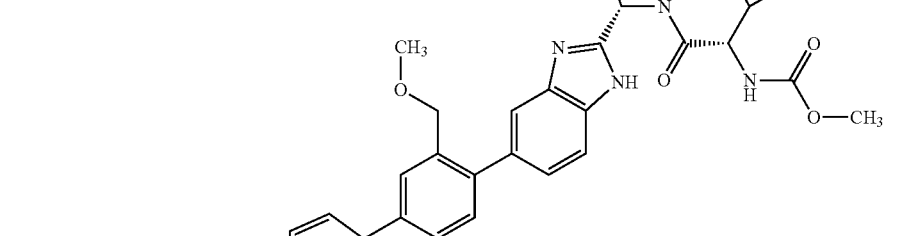 | 219 |

| Compound | Cmpd # |
|----------|--------|
| (structure) | 220 |
| (structure) | 221 |
| (structure) | 222 |

TABLE 1-continued

| Compound | Cmpd # |
|---|---|
| | 223 |
| | 224 |
| | 225 |
| | 226 |
| | 227 |

TABLE 1-continued

| Compound | Cmpd # |
|---|---|
| | 228 |
| | 229 |
| | 230 |

TABLE 1-continued

| Compound | Cmpd # |
|---|---|
| | 231 |
| | 232 |
| | 233 |
| | 234 |

TABLE 1-continued

| Compound | Cmpd # |
|---|---|
| | 235 |
| | 236 |
| | 237 |

TABLE 1-continued

| Compound | Cmpd # |
|---|---|
| | 238 |
| | 239 |
| | 240 |
| | 241 |

TABLE 1-continued
| Compound | Cmpd # |
|---|---|
| 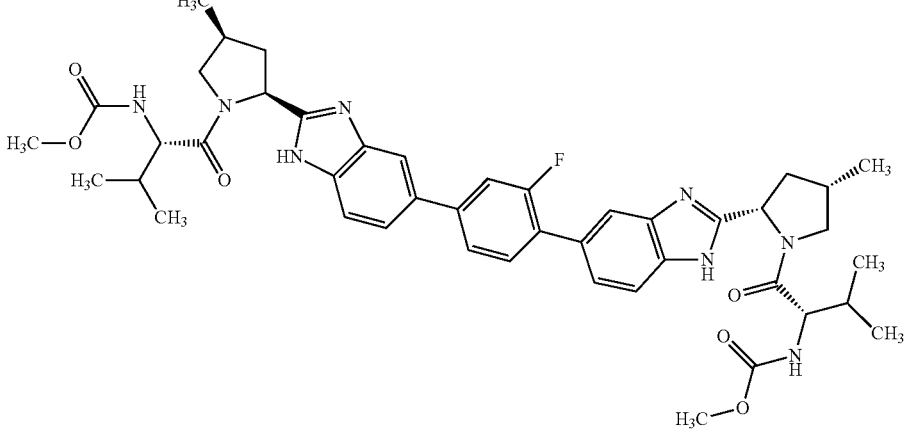 [SMILES: COC(=O)N[C@H](C(=O)N1C[C@@H](C)C[C@H]1c1nc2cc(-c3ccc(-c4ccc5[nH]c([C@@H]6C[C@H](C)CN6C(=O)[C@@H](NC(=O)OC)C(C)C)nc5c4)c(F)c3)ccc2[nH]1)C(C)C] | 242 |
| 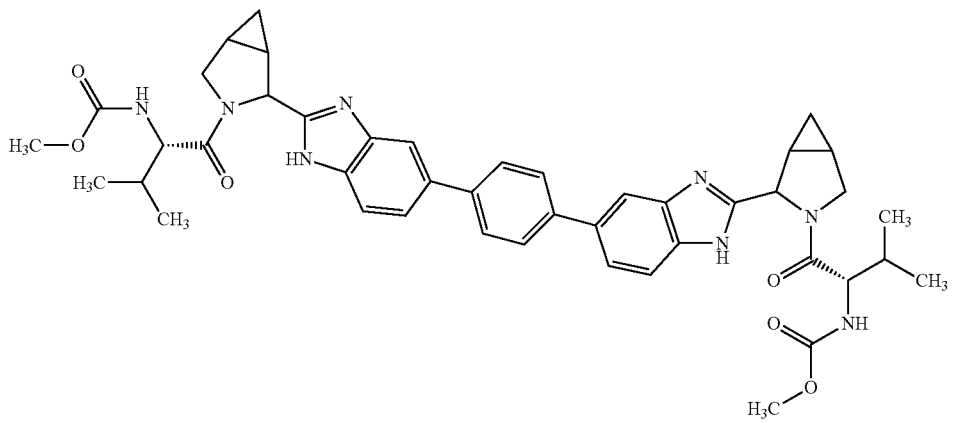 [SMILES: COC(=O)N[C@H](C(=O)N1CC2CC2C1c1nc2cc(-c3ccc(-c4ccc5[nH]c(C6C7CC7CN6C(=O)[C@@H](NC(=O)OC)C(C)C)nc5c4)cc3)ccc2[nH]1)C(C)C] | 243 |
| 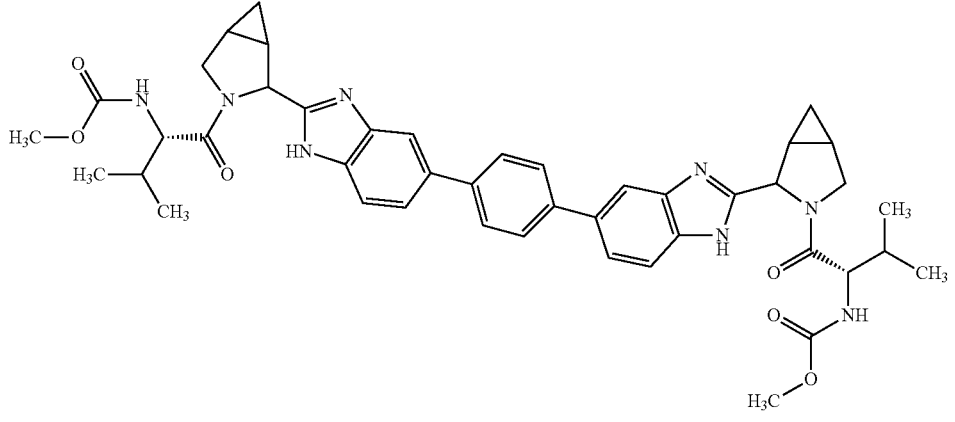 [SMILES: COC(=O)N[C@H](C(=O)N1CC2CC2C1c1nc2cc(-c3ccc(-c4ccc5[nH]c(C6C7CC7CN6C(=O)[C@@H](NC(=O)OC)C(C)C)nc5c4)cc3)ccc2[nH]1)C(C)C] | 244 |

TABLE 1-continued
| Compound | Cmpd # |
|---|---|
| 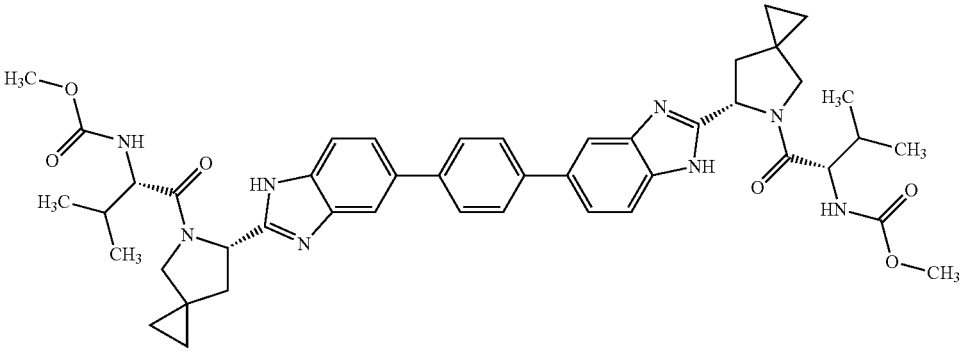 | 245 |
| 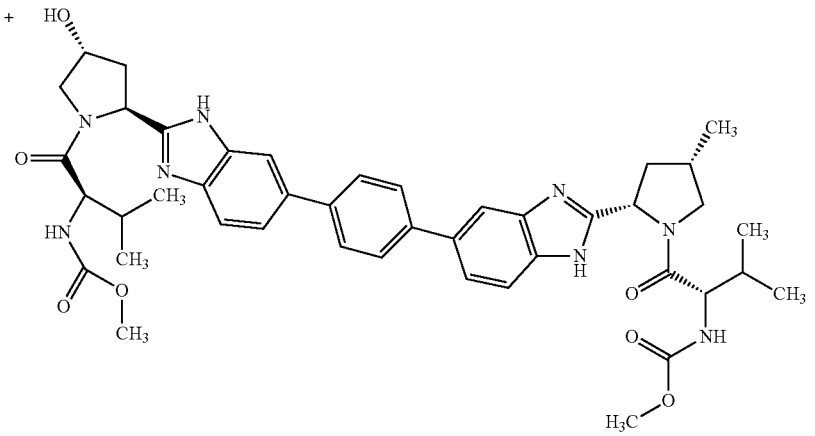 | 246 |
| 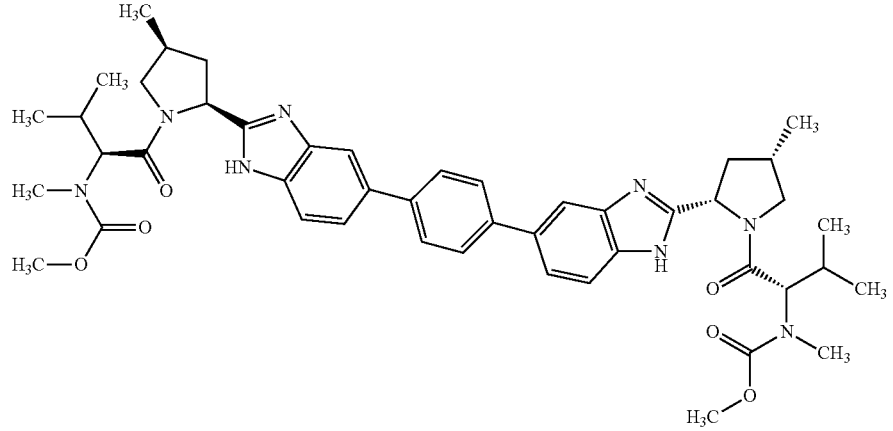 [SMILES: COC(=O)N[C@H](C(=O)N1C[C@@H](C)C[C@H]1c1nc2cc(-c3ccc(-c4ccc5[nH]c([C@@H]6C[C@H](C)CN6C(=O)[C@H](C(C)C)N(C)C(=O)OC)nc5c4)cc3)ccc2[nH]1)C(C)C] | 247 |

TABLE 1-continued

| Compound | Cmpd # |
|---|---|
| | 248 |
| | 249 |
| | 250 |
| | 251 |

TABLE 1-continued

| Compound | Cmpd # |
|---|---|
| | 252 |
| | 253 |
| | 254 |

TABLE 1-continued
| Compound | Cmpd # |
|---|---|
| 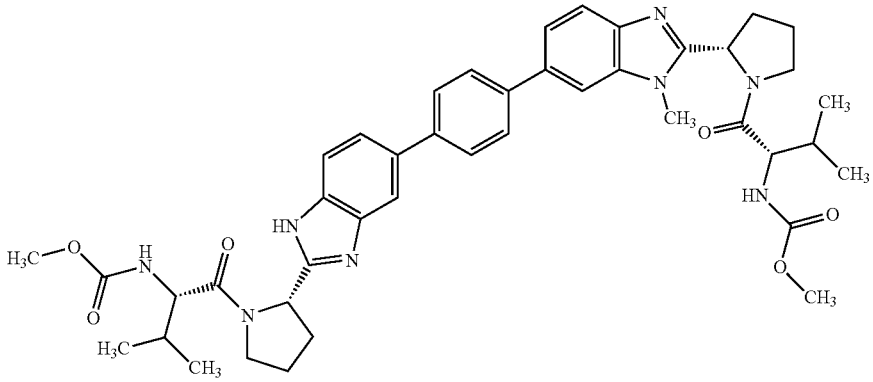 [SMILES: COC(=O)N[C@H](C(=O)N1CCC[C@H]1c1nc2cc(-c3ccc(-c4ccc5nc([C@@H]6CCCN6C(=O)[C@@H](NC(=O)OC)C(C)C)n(C)c5c4)cc3)ccc2[nH]1)C(C)C] | 255 |
| 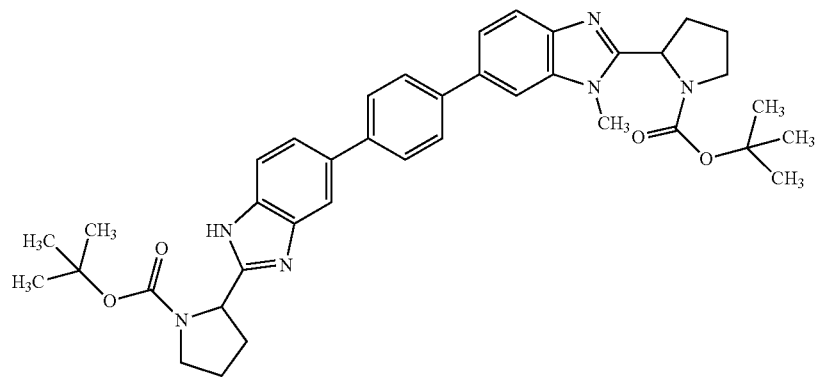 [SMILES: Cn1c(C2CCCN2C(=O)OC(C)(C)C)nc2ccc(-c3ccc(-c4ccc5[nH]c(C6CCCN6C(=O)OC(C)(C)C)nc5c4)cc3)cc21] | 256 |
| 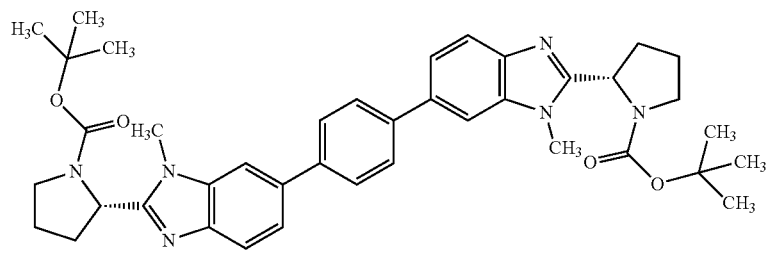 [SMILES: Cn1c([C@@H]2CCCN2C(=O)OC(C)(C)C)nc2ccc(-c3ccc(-c4ccc5nc([C@@H]6CCCN6C(=O)OC(C)(C)C)n(C)c5c4)cc3)cc21] | 257 |

TABLE 1-continued

| Compound | Cmpd # |
|---|---|
| | 258 |
| | 259 |
| | 260 |

TABLE 1-continued

| Compound | Cmpd # |
|---|---|
| | 261 |
| | 262 |
| | 263 |

TABLE 1-continued

| Compound | Cmpd # |
|---|---|
| | 264 |
| | 265 |
| | 266 |

TABLE 1-continued

| Compound | Cmpd # |
|---|---|
| | 267 |
| | 268 |
| | 269 |
| | 270 |

TABLE 1-continued

| Compound | Cmpd # |
|---|---|
| | 271 |
| | 272 |
| | 273 |
| | 274 |

| Compound | Cmpd # |
|---|---|
| | 275 |
| | 276 |
| | 277 |

TABLE 1-continued

| Compound | Cmpd # |
|---|---|
| | 278 |
| | 279 |
| | 280 |

| Compound | Cmpd # |
|---|---|
| | 281 |
| | 282 |
| | 283 |

TABLE 1-continued

| Compound | Cmpd # |
|---|---|
| | 284 |
| | 285 |
| | 286 |

TABLE 1-continued

| Compound | Cmpd # |
|---|---|
| | 287 |
| | 288 |
| | 289 |
| | 290 |

TABLE 1-continued

| Compound | Cmpd # |
|---|---|
| | 291 |
| | 292 |
| | 293 |

TABLE 1-continued

| Compound | Cmpd # |
|---|---|
| | 294 |
| | 295 |
| | 296 |

| Compound | Cmpd # |
|---|---|
| | 297 |
| | 298 |
| | 299 |
| | 300 |

TABLE 1-continued

| Compound | Cmpd # |
|---|---|
| | 301 |
| | 302 |
| | 303 |

TABLE 1-continued

| Compound | Cmpd # |
|---|---|
| | 304 |
| | 305 |
| | 306 |
| | 307 |

TABLE 1-continued

| Compound | Cmpd # |
|---|---|
| | 308 |
| | 309 |
| | 310 |
| | 311 |

TABLE 1-continued
| Compound | Cmpd # |
| --- | --- |
| 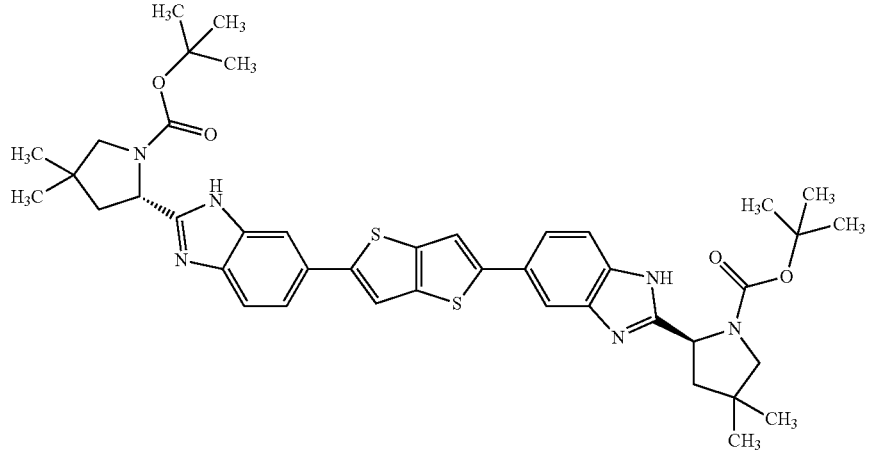 [SMILES: CC1(C)C[C@@H](c2nc3cc(-c4cc5sc(-c6ccc7nc([C@@H]8CC(C)(C)CN8C(=O)OC(C)(C)C)[nH]c7c6)cc5s4)ccc3[nH]2)N(C(=O)OC(C)(C)C)C1] | 312 |
| 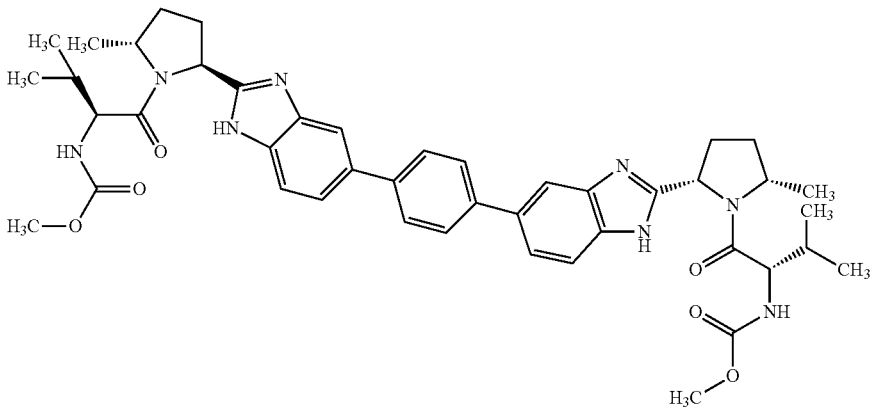 [SMILES: COC(=O)N[C@H](C(=O)N1[C@H](C)CC[C@H]1c1nc2cc(-c3ccc(-c4ccc5[nH]c([C@@H]6CC[C@H](C)N6C(=O)[C@@H](NC(=O)OC)C(C)C)nc5c4)cc3)ccc2[nH]1)C(C)C] | 313 |
| 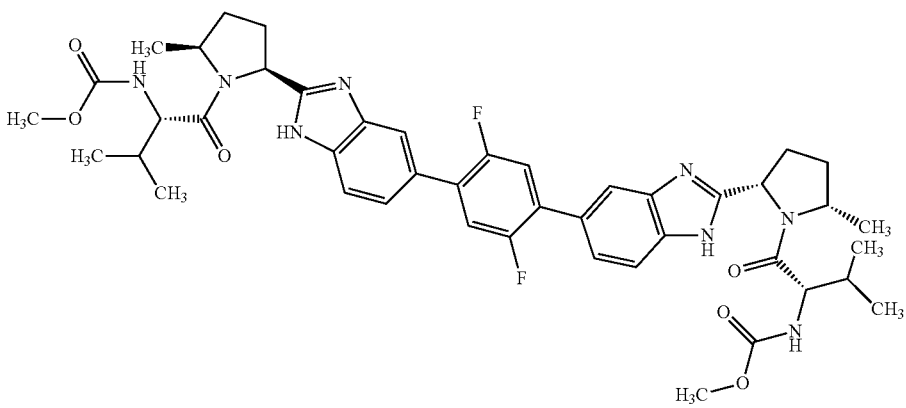 [SMILES: COC(=O)N[C@H](C(=O)N1[C@@H](C)CC[C@H]1c1nc2cc(-c3cc(F)c(-c4ccc5[nH]c([C@@H]6CC[C@H](C)N6C(=O)[C@@H](NC(=O)OC)C(C)C)nc5c4)cc3F)ccc2[nH]1)C(C)C] | 314 |

TABLE 1-continued

| Compound | Cmpd # |
|---|---|
| | 315 |
| | 316 |
| | 317 |

TABLE 1-continued

| Compound | Cmpd # |
|---|---|
| | 318 |
| | 319 |
| | 320 |
| | 321 |

TABLE 1-continued

| Compound | Cmpd # |
|---|---|
| | 322 |
| | 323 |
| | 324 |

TABLE 1-continued

| Compound | Cmpd # |
|---|---|
| | 325 |
| | 326 |
| | 327 |
| | 328 |

TABLE 1-continued

| Compound | Cmpd # |
|---|---|
| | 329 |
| | 330 |
| | 331 |
| | 332 |
| | 333 |

TABLE 1-continued

| Compound | Cmpd # |
|---|---|
| [chemical structure] | 334 |
| [chemical structure] | 335 |

Compounds shown in Table 1 are representative compounds of the present invention and have exhibited inhibitory activities against Hepatitis C virus in a cell culture assay, except for compounds 22, 23, 35, 308, 309 and 333-335. Compounds 22, 23, 35, 57, 308, and 309 are synthetic intermediates for inhibitory compounds of the present invention. Compounds 333-335 have not been tested for their inhibitory activities.

In one embodiment, the compounds of the present invention are selected from compounds 1, 2, 4-14, 25, 26-34, 36-39, 41-43, 48-67, 69-89, 91-100, 102-111, 113-145, 147, 148-152, 154, 161, 164, 166, 168, 170, 171, 175, 177-181, 189, 190-193, 195-198, 201, 203-208, 211-213, 216-218, 220, 225-228, 230-232, 234, 235, 236, 240, 241, 243, 244, 246, 250, 254-257, 259, 265, 267, 272, 308, 334 and 335.

In another aspect, the compounds of the present invention are described in the following embodiments.

In embodiment 1, a compound of formula (I):

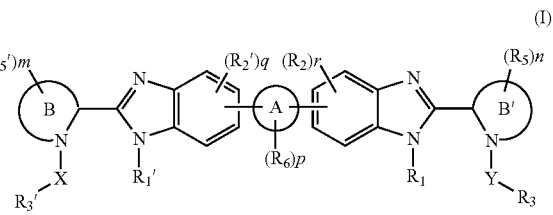

(I)

wherein,

A is $C_{2-4}$ alkenyl, $C_{2-5}$ alkynyl, $C_{3-10}$ cycloalkyl, $C_{6-14}$ aryl, 4-12 membered heterocycle or 5-12 membered heteroaryl;

B and B' are each independently a 4-7 membered heterocycle;

$R_1$ and $R_1'$ are each independently H, $C_{1-6}$ alkyl, $C_{2-6}$ alkenyl, or $C_{2-6}$ alkynyl;

$R_2$ and $R_2'$ are each independently H, halogen, $C_{1-6}$ alkyl, or $C_{1-6}$ alkoxy;

X and Y are each independently

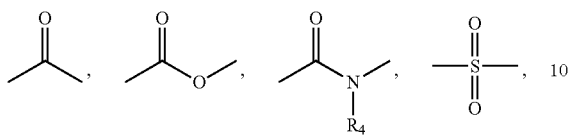

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, halogen, $C_{1-4}$ alkyl, hydroxyl, $C_{1-4}$ alkoxy, or $C_{1-4}$ halogenated alkyl;

$R_6$ is H, halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl or any two occurrence of $R_6$ on adjacent carbons can be taken together with the carbons to which they are attached to form a 5-7 cycloalkyl which is unsubstituted or substituted one or more times by $R^{10}$ or a 5-7 membered heterocycle which is unsubstituted or substituted one or more times by $R^{12}$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

m, n, and p are each independently 0, 1, 2, 3 or 4;

q and r are each independently 0, 1, 2, or 3.

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; or a pharmaceutically acceptable salts thereof.

In embodiment 1a, a compound of formula (I):

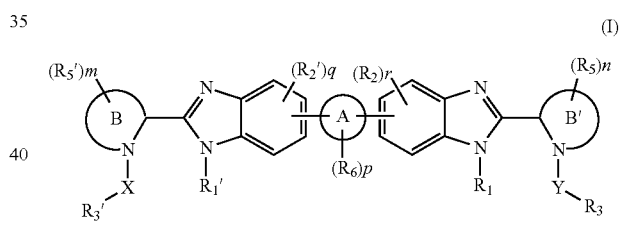

wherein,

A is $C_{2-4}$ alkenyl, $C_{2-5}$ alkynyl, $C_{3-10}$ cycloalkyl, $C_{6-14}$ aryl, 4-12 membered heterocycle or 5-12 membered heteroaryl;

B and B' are each independently a 4-7 membered heterocycle;

$R_1$ and $R_1'$ are each independently H, $C_{1-6}$ alkyl, $C_{2-6}$ alkenyl, or $C_{2-6}$ alkynyl;

$R_2$ and $R_2'$ are each independently H, halogen, $C_{1-6}$ alkyl, or $C_{1-6}$ alkoxy;

X and Y are each independently

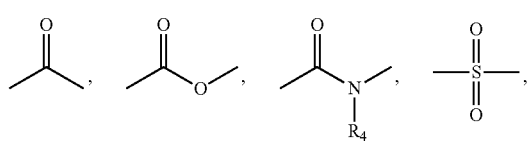

or a bond;

$R_3$ and $R_3'$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_4$ is H, $C_{1-6}$ alkyl, or halogenated $C_{1-6}$ alkyl, or can be merged with $R_3$ or $R_3'$ to form a 3-12 membered heterocycle;

$R_5$ and $R_5'$ are each independently H, halogen, $C_{1-4}$ alkyl, hydroxyl, $C_{1-4}$ alkoxy, or $C_{1-4}$ halogenated alkyl;

$R_6$ is H, halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, $C_{1-6}$ alkyl, $C_{2-6}$ alkenyl, $C_{2-6}$ alkynyl, or $C_{1-6}$ halogenated alkyl or any two occurrence of $R_6$ on adjacent carbons can be taken together with the carbons to which they are attached to form a 5-7 cycloalkyl which is unsubstituted or substituted one or more times by $R^{10}$ or a 5-7 membered heterocycle which is unsubstituted or substituted one or more times by $R^{12}$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

m, n, and p are each independently 0, 1, 2, 3 or 4;

q and r are each independently 0, 1, 2, or 3.

$R^{10}$ is halogen, —$OR_a$, oxo, —$NR_aR_b$, =$NO$—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R^{12}$ is halogen, —$OR_a$, oxo, —$NR_aR_b$, =$NO$—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}$ $R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; or a pharmaceutically acceptable salts thereof wherein

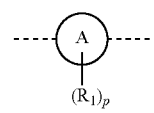

is not,

optionally substituted ethyl, phenyl, oxazolyl, or furanyl.

In embodiment 2, a compound according to embodiment 1, wherein said compound is of formula (II):

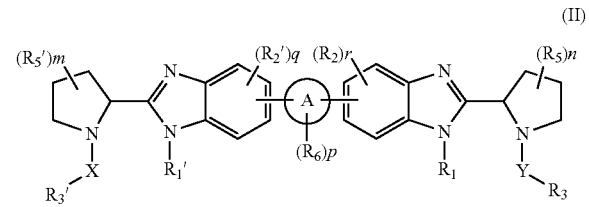

or pharmaceutically acceptable salts thereof;

In embodiment 3, a compound according to any one of embodiments 1 and 2, wherein A is —(C≡C)—, phenyl, thiophene, pyridine, pyrimidine, or triazole.

In embodiment 4, a compound according to any one of embodiments 1 and 2, wherein A is phenyl, thiophene, pyridine, pyrimidine, or triazole.

In embodiment 5, a compound according to embodiment 3, wherein A is phenyl, or thiophene.

In embodiment 6, a compound according to any one of embodiments 1 to 5, wherein said compound is of formula (III):

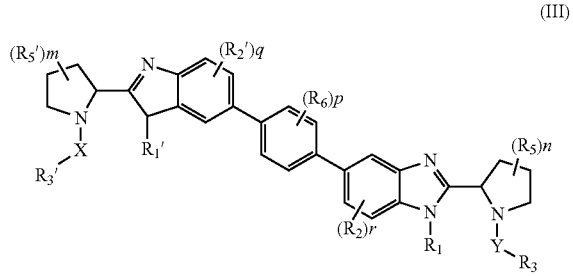

or pharmaceutically acceptable salts thereof;

In embodiment 7, a compound according to any one of embodiments 1 to 6, wherein X and Y are

In embodiment 8, a compound according to any one of embodiments 1 to 7, wherein $R_5$ and $R_5'$ in formulas (I), (II), (III), and (IV), are each independently H, Halogen, methyl, ethyl, t-butoxy-, or hydroxyl.

In embodiment 9, a compound according to embodiment 7, wherein $R_5$ and $R_5'$ in formulas (I), (II), (III), and (IV), are H.

In embodiment 10, a compound according to embodiment 7, wherein $R_5$ and $R_5'$ in formulas (I), (II), (III), and (IV), are fluoro.

In embodiment 11, a compound according to any one of embodiments 1 to 10, wherein m, or n, are each independently 0, 1, or 2.

In embodiment 12, a compound according to embodiment 10, wherein m, or n, are 2.

In embodiment 13, a compound according to embodiment 10, wherein m, or n, are 1.

In embodiment 14, a compound according to any one of embodiments 1 to 13, wherein $R_1$ and $R_1'$ are H.

In embodiment 15, a compound according to any one of embodiments 1 to 14, wherein $R_6$ is halogen, $C_{1-3}$ alkyl, hydroxyl, cyano, benzyloxy, or $C_{1-3}$ alkoxy.

In embodiment 16, a compound according to embodiment 15, wherein $R_6$ is chloro, fluoro, methyl, hydroxyl, benzyloxy, cyano, or methoxy.

In embodiment 17, a compound according to any one of embodiments 1 to 14, wherein $R_6$ is H.

In embodiment 18, a compound according to any one of embodiments 1 to 17, wherein p is 2.

In embodiment 19, a compound according to any one of embodiments 1 to 17, wherein p is 1.

In embodiment 20. a compound according to any one of embodiments 1 to 19, wherein $R_2$ and $R_2'$ are fluoro.

In embodiment 21, a compound according to any one of embodiments 1 to 19, wherein $R_2$ and $R_2'$ are H.

In embodiment 22, a compound according to any one of embodiments 1 to 21, wherein q and r are 1.

In embodiment 23, a compound according to any one of embodiments 1 to 22, wherein $R_3$ and $R_3'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

In embodiment 24, a compound according to embodiment 23, wherein $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 5-6 membered heterocycle which is unsubstituted or substituted one or more times by $R^{12}$, or 6-7 membered heterocycle-alkyl which is unsubstituted or substituted one or more times by $R^{12}$.

In embodiment 25, a compound according to embodiment 23, wherein $R_3$ and $R_3'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$.

In embodiment 26, a compound according to embodiment 23, wherein $R_3$ and $R_3'$ are each independently phenyl which is unsubstituted or substituted one or more times by $R^{11}$.

In embodiment 27, a compound according to embodiment 23, wherein $R_3$ and $R_3'$ are each independently benzyl which is unsubstituted or substituted one or more times by $R^{11}$.

In embodiment 28, a compound according to any one of embodiments 1 to 22, wherein $R_3$ and $R_3'$ are each independently, $C_{1-12}$ alkyl which is unsubstituted or substituted one or more times by $R^{10}$.

In embodiment 29, a compound according to embodiment 28, wherein $R_3$ and $R_3'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl($CH_2$)—, which are unsubstituted or substituted one or more times by $R^{10}$.

In embodiment 30, a compound according to any one of embodiments 1 to 29, wherein $R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_aC(=O)NR_aR_b$, —$NR_bC(=O)R_a$, —$NR_dC(=NR_c)NR_aR_b$, —$NR_bC(=O)OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl, and $R_b$, and $R_d$. are each independently H or methyl.

In embodiment 31, a compound according to any one of embodiments 1 to 29, wherein $R^{10}$ is —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, or —$NR_bSO_2NR_aR_b$, wherein $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 32, a compound according to embodiment 31, wherein $R^{10}$ is —$NR_aR_b$, —$NR_dC(=O)NR_aR_b$, —$NR_bC(=O)R_a$, —$NR_bC(=O)OR_a$, or —$NR_bSO_2R_a$, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 33, a compound according to any one of embodiments 1 to 29, wherein $R^{10}$ is halogen, —$OR_a$, oxo, —C(=O)$OR_a$, —C(O)$NR_aR_b$, —C(=O)OH, —C(=O)$R_a$, —OC(=O)$NR_aR_b$, —OC(=O)$R_a$, —OC(=O)$OR_a$, hydroxyl, cyano, wherein $R_a$-$R_b$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 34, a compound according to any one of embodiments 1 to 29, wherein $R_{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroalkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroalkyl, 3-12 membered heterocycle, or 4-18 membered heterocycle-alkyl, and $R_b$, and $R_d$ are each independently H or methyl.

In embodiment 35, a compound according to any one of embodiments 1 to 29, wherein $R^{11}$ is halogen, —$OR_a$, —$NR_aR_b$, —$C(=O)OR_a$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, —$OC(=O)R_a$, —$OC(=O)OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 36, a compound according to embodiment 35, wherein $R^{11}$ is halogen, —$OR_a$, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 37, a compound according to embodiment 35, wherein $R^{11}$ is halogen, —$OR_a$, —$NR_aR_b$, hydroxyl, cyano, $C_{1-6}$ alkyl, wherein $R_a$-$R_b$ are each independently H, $C_{1-3}$ alkyl.

In embodiment 38, a compound according to any one of embodiments 1 to 29, wherein $R^{12}$ is halogen, —$OR_a$, oxo, —$NR_aR_b$, =$NO$—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroalkyl, 3-12 membered heterocycle, or 4-18 membered heterocycle-alkyl, wherein $R_a$ and $R_c$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroalkyl, 3-12 membered heterocycle, or 4-18 membered heterocycle-alkyl, and $R_b$, and $R_d$ are each independently H or methyl.

In embodiment 39, a compound according to any one of embodiments 1 to 29, wherein $R^{12}$ is halogen, —$OR_a$, oxo, —$NR_aR_b$, —$C(=O)OR_a$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, —$OC(=O)R_a$, —$OC(=O)OR_a$, hydroxyl, cyano, —$SO_2NR_aR_b$, —$NR_bSO_2R_a$, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 40, a compound according to embodiment 39 wherein $R^{12}$ is halogen, —$OR_a$, oxo, —$NR_aR_b$, —$C(O)NR_aR_b$, —$C(=O)OH$, —$C(=O)R_a$, —$NR_dC(=O)NR_aR_b$, —$NR_bC(=O)R_a$, —$NR_bC(=O)OR_a$, —$OC(=O)NR_aR_b$, hydroxyl, cyano, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl, wherein $R_a$, $R_b$, and $R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

In embodiment 41, a compound according to embodiment 39, wherein $R^{12}$ is halogen, —$OR_a$, oxo, —$NR_aR_b$, hydroxyl, cyano, $C_{1-6}$ alkyl, wherein $R_a$-$R_b$ are each independently H, $C_{1-3}$ alkyl. In embodiment 42, a compound according to any one of embodiments 1 to 22, wherein wherein said compound is of formula (IV):

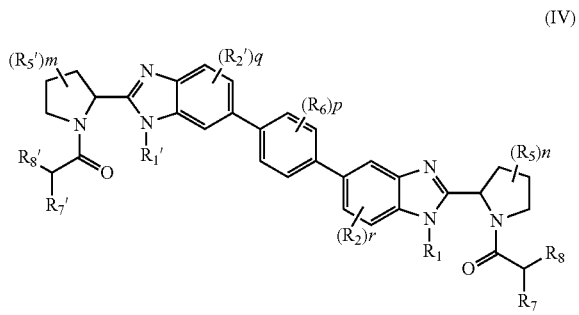

(IV)

or pharmaceutically acceptable salts thereof;
wherein
$R_7$ and $R_7'$ are each independently $C_{1-8}$ alkyl, $C_{2-8}$ alkenyl, $C_{2-8}$ alkynyl, phenyl, benzyl, 5-6 membered heteroaryl, 6-7 membered heteroaralkyl, 3-6 membered heterocycle, or 4-7 membered heterocycle-alkyl; and $R_8$ and $R_8'$ are each independently —$NR_aR_b$, —$NR_dC(=O)NR_aR_b$, —$NR_bC(=O)R_a$, —$NR_dC(=NR_c)NR_aR_b$, —$NR_bC(=O)OR_a$, —$NR_bSO_2R_a$, —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroalkyl, 3-12 membered heterocycle, or 4-18 membered heterocycle-alkyl.

In embodiment 43, a compound according to embodiment 42, wherein $R_8$ and $R_8'$ are each independently —$NR_aR_b$, —$NR_bC(=O)R_a$, —$NR_bC(=O)OR_a$, wherein $R_a$-$R_b$ are each independently H, $C_{1-6}$ alkyl, phenyl, benzyl, 5-6 membered heteroaryl, 6-8 membered heteroaralkyl, 5-6 membered heterocycle, or 6-8 membered heterocycle-alkyl.

In embodiment 44, a compound according to embodiment 43, wherein $R_8$ and $R_8'$ in formulas (IV), are each independently —NR$_b$C(=O)OR$_a$, wherein R$_a$-R$_b$ are each independently H, C$_{1-6}$ alkyl, phenyl, tetrahydrofuran, or benzyl.

In embodiment 45, a compound according to any one of embodiments 42 to 44, wherein R$_7$ and R$_7$' are each independently phenyl.

In embodiment 46, a compound according to any one of embodiments 42 to 44, wherein R$_7$ and R$_7$' are each independently, C$_{1-6}$ alkyl.

In embodiment 47, a compound according to embodiment 46, wherein R$_7$ and R$_7$' are each independently methyl, ethyl, propyl, isopropyl, butyl, sec-butyl, tert-butyl, pentyl, 2-methylbutane, 3-methylbutane, cyclopropyl, cyclobutyl, cyclopentyl, or cyclohexyl.

In embodiment 48, a compound selected from:

| # | name |
|---|------|
| 1. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 2. | ((S)-1-{(S)-2-[5-(3-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 3. | ((S)-1-{(S)-2-[5-(4-{2-[(S)-4,4-Difluoro-1-((S)-2-methoxycarbonylamino-3-methyl-butyryl)-pyrrolidin-2-yl]-1H-benzoimidazol-5-yl}-phenyl)-1H-benzoimidazol-2-yl]-4,4-difluoro-pyrrolidine-1-carbonyl}-2-methyl-propyl)-carbamic acid methyl ester |
| 4. | [(S)-1-((S)-2-{5-[4-(2-{(S)-1-[(S)-2-(Methoxycarbonyl-methyl-amino)-3-methyl-butyryl]-pyrrolidin-2-yl}-1H-benzoimidazol-5-yl)-phenyl]-1H-benzoimidazol-2-yl}-pyrrolidine-1-carbonyl)-2-methyl-propyl]-methyl-carbamic acid methyl ester |
| 5. | ((S)-1-{(S)-2-[5-(2-Cyano-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 6. | ((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyridin-2-yl)-1H-benzoimidazol-2-yl]-pyrrolidine-1-carbonyl}-2-methyl-propyl)-carbamic acid methyl ester |
| 7. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2-methyl-phenyl)-1H-benzoimidazol-2-yl]-pyrrolidine-1-carbonyl}-2-methyl-propyl)-carbamic acid methyl ester |
| 8. | ((S)-1-{(S)-2-[5-(2-Methoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 9. | ((S)-1-{(S)-2-[5-(2-Fluoro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 10. | ((S)-1-{(S)-2-[5-(2-Chloro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 11. | ((S)-1-{(S)-2-[5-(2-Cyano-6-{2-[(S)-1-((S)-2-methoxycarbonylamino-3-methyl-butyryl)-pyrrolidin-2-yl]-1H-benzoimidazol-5-yl}-pyridin-3-yl)-1H-benzoimidazol-2-yl]-pyrrolidine-1-carbonyl}-2-methyl-propyl)-carbamicacid methyl ester |
| 12. | (S)-1-{(S)-2-[5-(2,5-Dimethoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 13. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,3-dimethyl-phenyl)-1H-benzoimidazol-2-yl]-pyrrolidine-1-carbonyl}-2-methyl-propyl)-carbamic acid methyl ester |
| 14. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-dimethyl-phenyl)-1H-benzoimidazol-2-yl]-pyrrolidine-1-carbonyl}-2-methyl-propyl)-carbamicacid methyl ester |
| 15. | ((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 16. | (2S,2'S)-tert-butyl-2,2'-(5,5'-(thiophene-2,5-diyl)bis(1H-benzo[d]imidazole-5,2-diyl))dipyrrolidine-1-carboxylate |
| 17. | Dimethyl-(2S,2'S)-1,1'-((2S,2'S)-2,2'-(5,5'-(thiophene-2,5-diyl)bis(1H-benzo[d]imidazole-5,2-diyl))bis(pyrrolidine-2,1-diyl))bis(3-methyl-1-oxobutane-2,1-diyl)dicarbamate |
| 18. | methyl N-[(1S)-1-[(2S)-2-[5-[4-[2-[(2S)-1-[(2S)-2-(methoxycarbonylamino)-3-methyl-butanoyl]pyrrolidin-2-yl]-1H-benzimidazol-5-yl]-2-thienyl]-1H-benzimidazol-2-yl]pyrrolidine-1-carbonyl]-2-methyl-propyl]carbamate |
| 19. | ((S)-1-{(S)-2-[5-(4-Benzyloxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 20. | ((S)-1-{(S)-2-[5-(4-Hydroxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester |
| 21. | ((S)-1-{(S)-2-[6-(1-{2-[(S)-1-((S)-2-Methoxycarbonylamino-3-methyl-butyryl)-pyrrolidin-2-yl]-3H-benzoimidazol-5-yl}-1H-[1,2,3]triazol-4-yl)-1H-benzoimidazol-2-yl]-pyrrolidine-1-carbonyl}-2-methyl-propyl)-carbamic acid methyl ester |
| 22. | (2R,2'R,5S,5'S)-tert-butyl 5,5'-(6,6'-(1,4-phenylene)bis(1H-benzo[d]imidazole-6,2-diyl))bis(2-ethylpyrrolidine-1-carboxylate) |
| 23. | 1,4-bis(2-((2S,5R)-5-ethylpyrrolidin-2-yl)-1H-benzo[d]imidazol-6-yl)benzene |
| 24. | ((S)-1-{(2R,5S)-2-Ethyl-5-[5-(4-{2-[(2S,5R)-5-ethyl-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 25. | ((S)-1-{(2S,4R)-4-tert-butoxy-2-[5-(4-{2-[(2S,4R)-4-tert-butoxy-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 26. | ((S)-1-{(2S,4R)-4-Hydroxy-2-[5-(4-{2-[(2S,4R)-4-hydroxy-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester |
| 27. | Dimethyl (2S,2'S)-1,1'-((2S,2'S)-2,2'-(5,5'-(1,4-phenylene)bis(6-fluoro-1H-benzo[d]imidazole-5,2-diyl))bis(pyrrolidine-2,1-diyl))bis(3-methyl-1-oxobutane-2,1-diyl)dicarbamate |
| 28. | (S)-2-{5-[2-((S)-1-Benzyloxycarbonyl-piperidin-2-yl)-1H-benzoimidazol-5-ylethynyl]-1H-benzoimidazol-2-yl}-piperazine-1,4-dicarboxylic acid 1-benzyl ester 4-tert-butyl ester |
| 29. | (S)-2-{5-[2-((S)-1-Benzyloxycarbonyl-4-tert-butyloxycarbonyl-piperazin-2-yl)-1H-benzoimidazol-5-ylethynyl]-1H-benzoimidazol-2-yl}-piperazine-1,4-dicarboxylic acid 1-benzyl ester 4-tert-butyl ester |

| # | name |
|---|---|
| 30. | (S)-2-{5-[2-((S)-1-Benzyloxycarbonyl-piperidin-2-yl)-1H-benzoimidazol-5-ylethynyl]-1H-benzoimidazol-2-yl}-piperidine-1-carboxylic acid benzyl ester |
| 31. | (S)-2-{5-[2-((S)-1-Benzyloxycarbonyl-pyrrolidin-2-yl)-1H-benzoimidazol-5-ylethynyl]-1H-benzoimidazol-2-yl}-pyrrolidine-1-carboxylic acid benzyl ester |
| 32. | [(S)-5-(5-{2-[(S)-1-((R)-tetrahydro-furan-2-carbonyl)-pyrrolidin-2-yl]-1H-benzoimidazol-5-ylethynyl}-1H-benzoimidazol-2-yl)-pyrrolidin-1-yl]-(R)-tetrahydro-furan-2-yl-methanone |
| 33. | {(R)-2-[(S)-2-(5-{2-[(S)-1-((R)-2-Methoxycarbonylamino-2-phenyl-acetyl)-pyrrolidin-2-yl]-1H-benzoimidazol-5-ylethynyl}-1H-benzoimidazol-2-yl)-pyrrolidin-1-yl]-2-oxo-1-phenyl-ethyl}-carbamic acid methylester |
| 34. | (S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carboxylic acid tert-butyl ester |
| 35. | ((S)-2-Methyl-1-{(S)-2-[5-((S)-2-pyrrolidin-2-yl-1H-benzoimidazol-5-ylethynyl)-1H-benzoimidazol-2-yl]-pyrrolidine-1-carbonyl}-propyl)-carbamic acid methyl ester |
| 36. | {(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2,2-dimethyl-propyl}-carbamic acid methyl ester |
| 37. | {(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2-methyl-propyl}-carbamic acid methyl ester |
| 38. | {(S)-2-Methyl-1-[(S)-2-(5-{2-[(S)-1-((R)-tetrahydro-furan-2-carbonyl)-pyrrolidin-2-yl]-1H-benzoimidazol-5-ylethynyl}-1H-benzoimidazol-2-yl)-pyrrolidine-1-carbonyl]-propyl}-carbamic acid methyl ester |
| 39. | {(S)-1-[(S)-2-(5-{2-[(S)-1-((R)-2-Methoxycarbonylamino-2-phenyl-acetyl)-pyrrolidin-2-yl]-1H-benzoimidazol-5-ylethynyl}-1H-benzoimidazol-2-yl)-pyrrolidine-1-carbonyl]-2-methyl-propyl}-carbamic acid methyl ester |
| 40. | (S)-2-(5-{(E)-4-[2-((S)-1-Benzyloxycarbonyl-piperidin-2-yl)-1H-benzoimidazol-5-yl]-but-1-en-3-ynyl}-1H-benzoimidazol-2-yl)-piperidine-1-carboxylic acid benzyl ester |
| 41. | (S)-2-(5-{4-[2-((S)-1-Benzyloxycarbonyl-piperidin-2-yl)-1H-benzoimidazol-5-yl]-buta-1,3-diynyl}-1H-benzoimidazol-2-yl)-piperidine-1-carboxylic acid benzyl ester |
| 42. | ((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-difluoro-phenyl)-1H-benzoimidazol-2-yl]-pyrrolidine-1-carbonyl}-2-methyl-propyl)-carbamicacid methyl ester |
| 43. | Methyl N-[(1S)-1-[(2S)-2-[5-[5-[2-[(2S)-1-[(2S)-2-(methoxycarbonylamino)-3-methyl-butanoyl]pyrrolidin-2-yl]-1H-benzimidazol-5-yl]-3-methyl-2-pyridyl]-1H-benzimidazol-2-yl]pyrrolidine-1-carbonyl]-2-methyl-propyl]carbamate |
| 44. | Dimethyl-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate |
| 45. | bis((S)-tetrahydrofuran-3-yl)-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate |
| 46. | Dimethyl-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate |
| 47. | bis((S)-tetrahydrofuran-3-yl)-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate | or a pharmaceutically acceptable salt.

In embodiment 49, a compound according to any one of embodiments 1 to 48, for treating or preventing a Hepatitis C viral infection.

In embodiment 50, a pharmaceutical composition comprising at least one compound according to any one of embodiments 1 to 48 and at least one pharmaceutically acceptable carrier or excipient.

In embodiment 51, a pharmaceutical combination comprising at least one compound according to any one of embodiments 1 to 48 and at least one additional agent.

In embodiment 52, the pharmaceutical combination according to embodiment 51, wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In embodiment 53, the pharmaceutical combination according to embodiment 51, wherein said at least one additional agent is selected from ribavirin and interferon-α.

In embodiment 54, the pharmaceutical combination according to any one of embodiments 51 to 54, wherein said compound and said additional agent are in dosage unit forms suitable for sequential administration.

In embodiment 55, the pharmaceutical combination according to any one of embodiments 51 to 54, wherein said compound and said additional agent are in dosage unit forms suitable for simultaneous administration.

In embodiment 56, the use of a compound according to any one of embodiments 1 to 48 for treating an Hepatitis C viral infection in a human.

In embodiment 57, the use according to embodiment 56, further comprising administering at least one additional agent.

In embodiment 58, the use according to embodiment 57 wherein said at least one additional agent is selected from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In embodiment 59. the use according to embodiment 57, wherein said at least one additional agent is selected from ribavirin and interferon-α.

In embodiment 60, the use of a compound according to any one of embodiments 1 to 48 for the manufacture of a medicament.

In embodiment 61, a pharmaceutical formulation comprising at least one compound as defined in anyone of embodiments 1 to 48 and at least one pharmaceutically acceptable carrier or excipient.

In embodiment 62, compounds of the present invention are represented by formula (IA):

(IA)

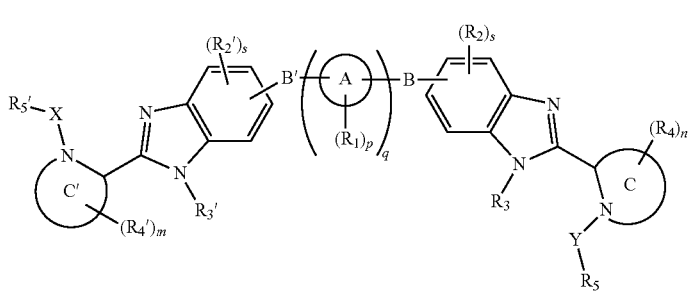

or pharmaceutically acceptable salts thereof, wherein each A is independently $C_{6-14}$ aryl, 4-12 membered heterocycle, $C_{3-10}$ cycloalkyl, or 5-12 membered heteroaryl;

B and B' are each independently absent, $C_{1-6}$ alkyl, $C_{2-6}$ alkenyl, or $C_{2-6}$ alkynyl; wherein B and B' are not both absent when q is 1;

C and C' are each independently a 4-7 membered heterocycle;

$R_1$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, —$P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

$R_{2'}$ and $R_2$ are independently halogen, $C_{1-10}$ alkyl, $C_{1-6}$ halogenated alkyl, —$(CH_2)_{1-6}OH$, —$OR_a$, —$C(=O)OR_a$, —$NR_aR_b$, —$NR_bC(=O)R_a$, —$C(O)NR_aR_b$, —$S(O)_{0-3}R_a$, $C_{6-12}$ aryl, or 5-12 membered heteroaryl;

$R_3$ and $R_3'$ are each independently H, $C_{1-6}$ alkyl, —$(CH_2)_{1-6}OH$, $C_{2-6}$ alkenyl, or $C_{2-6}$ alkynyl;

$R_4$ and $R_4'$ are each independently halogen, —$NR_aR_b$, —$C(O)NR_aR_b$, —$(CH_2)_{1-6}OH$, $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$;

X and Y are each independently

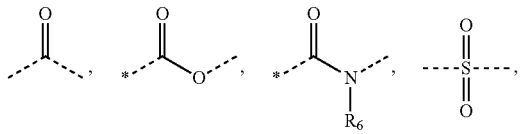

or a bond;

wherein the asterisk (*) indicates the point of attachment to the nitrogen of ring C or C';

$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_6$ is H, $C_{1-6}$ alkyl, or halogenated $C_{1-6}$ alkyl;

m, and n, are each independently 0, 1, 2, 3 or 4;

p is 0, 1, 2, 3 or 4;

q is 1 or 2;

each s is independently 0, 1, 2, 3 or 4;

$R^{10}$ is halogen, —$OR_a$, oxo, —$NR_aR_b$, =NO—$R_c$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$;

$R^{11}$ is halogen, —$OR_a$, —$NR_aR_b$, —$C(=O)OR_a$, —$C(O)NR_aR_b$, —$C(=O)OH$, —$C(=O)R_a$, —$C(=NOR_c)R_a$, —$C(=NR_c)NR_aR_b$, —$NR_dC(=O)NR_aR_b$, —$NR_bC(=O)R_a$, —$NR_dC(=NR_c)NR_aR_b$, —$NR_bC(=O)OR_a$, —$OC(=O)NR_aR_b$, —$OC(=O)R_a$, —$OC(=O)OR_a$, hydroxyl, nitro, azido, cyano, —$S(O)_{0-3}R_a$, —$SO_2NR_aR_b$, —$NR_bSO_2R_a$, —$NR_bSO_2NR_aR_b$, or —$P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —$C(=O)OR_a$, —$C(O)NR_aR_b$, —$C(=O)OH$, —$C(=O)$ $R_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In embodiment 63, the compounds of the present invention are represented by formula (IIA):

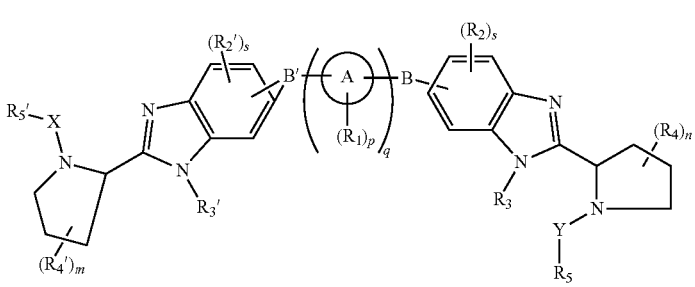

(IIA)

or a pharmaceutically acceptable salt thereof.

In embodiment 64, the compounds of the present invention are represented by formula (IIIA):

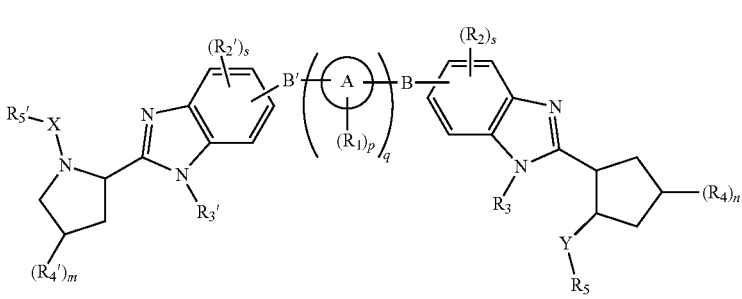

(IIIA)

or a pharmaceutically acceptable salt thereof, wherein each A is independently $C_{6-14}$ aryl, 4-12 membered heterocycle, $C_{3-10}$ cycloalkyl, or 5-12 membered heteroaryl;

B and B' are each independently absent, $C_{1-6}$ alkyl, $C_{2-6}$ alkenyl, or $C_{2-6}$ alkynyl;

R$_1$ is halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, —P(=O)OR$_a$OR$_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of R$_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;

R$_a$-R$_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

R$_{2'}$ and R$_2$ are each independently halogen, $C_{1-10}$ alkyl, $C_{1-6}$ halogenated alkyl, —(CH$_2$)$_{1-6}$OH, —OR$_a$, —C(=O)OR$_a$, —NR$_a$R$_b$, —NR$_b$C(=O)R$_a$, —C(O)NR$_a$R$_b$, —S(O)$_{0-3}$R$_a$, $C_{6-12}$ aryl, or 5-12 membered heteroaryl;

R$_3$ and R$_3'$ are each independently H, $C_{1-6}$ alkyl, —(CH$_2$)$_{1-6}$OH, $C_{2-6}$ alkenyl, or $C_{2-6}$ alkynyl;

R$_4$ and R$_4'$ are each independently halogen, —C(O)NR$_a$R$_b$, —(CH$_2$)$_{1-6}$OH, $C_{1-6}$ alkyl, $C_{1-6}$ halogenated alkyl, $C_{6-14}$ aryl, or $C_{1-6}$ alkoxy; wherein two occurrence of R$_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of R$_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein R$_a$-R$_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

X and Y are each independently

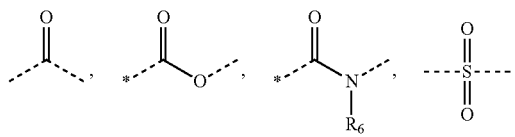

or a bond;
wherein the asterisk (*) indicates the point of attachment to the nitrogen of ring C or C';

$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_6$ is H, $C_{1-6}$ alkyl, or halogenated $C_{1-6}$ alkyl;
m, and n, combined are 1, 2, 3 or 4;
p is 0, 1, 2, 3 or 4;
q is 0, 1 or 2;
each s is independently 0, 1, 2, 3 or 4;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$;

$R^{11}$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In embodiment 65, the compounds of the present invention are represented by formula (IIIB):

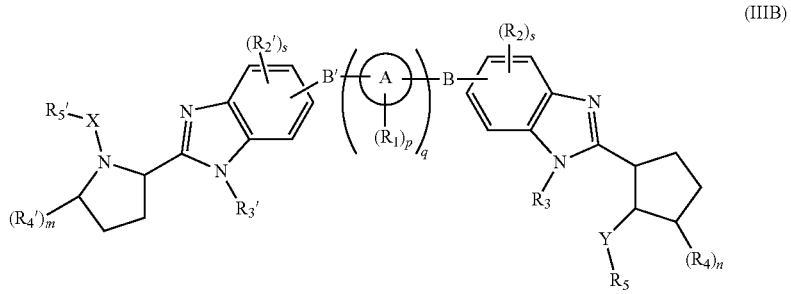

(IIIB)

or a pharmaceutically acceptable salt thereof, wherein
each A is independently $C_{6-14}$ aryl, 4-12 membered heterocycle, $C_{3-10}$ cycloalkyl, or 5-12 membered heteroaryl;
B and B' are each independently absent, $C_{1-6}$ alkyl, $C_{2-6}$ alkenyl, or $C_{2-6}$ alkynyl;
C and C' are each independently a 4-7 membered heterocycle;
$R_1$ is halogen, —$OR_a$, —$NR_aR_b$, —C(=O)$OR_a$, —C(O)$NR_aR_b$, —C(=O)OH, —C(=O)$R_a$, —C(=NO$R_c$)$R_a$, —C(=N$R_c$)$NR_aR_b$, —$NR_dC$(=O)$NR_aR_b$, —$NR_bC$(=O)$R_a$, —$NR_dC$(=N$R_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —$SO_2NR_aR_b$, —$NR_bSO_2R_a$, —$NR_bSO_2NR_aR_b$, —P(=O)$OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;
$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
$R_2'$ and $R_2$ are each independently halogen, $C_{1-10}$ alkyl, $C_{1-6}$ halogenated alkyl, —(CH$_2$)$_{1-6}$OH, —$OR_a$, —C(=O)$OR_a$, —$NR_aR_b$, —$NR_bC$(=O)$R_a$, —C(O)$NR_aR_b$, —S(O)$_{0-3}R_a$, $C_{6-12}$ aryl, or 5-12 membered heteroaryl;
$R_3$ and $R_3'$ are each independently H, $C_{1-6}$ alkyl, —(CH$_2$)$_{1-6}$OH, $C_{2-6}$ alkenyl, or $C_{2-6}$ alkynyl;
$R_4$ and $R_4'$ are each independently halogen, —$NR_aR_b$, —C(O)$NR_aR_b$, —(CH$_2$)$_{1-6}$OH, $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4'$ can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;

X and Y are each independently

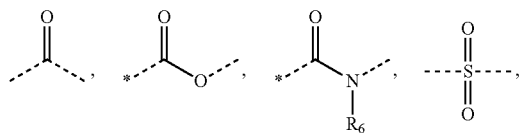

or a bond;

wherein the asterisk (*) indicates the point of attachment to the nitrogen of ring C or C';

$R_5$ and $R_5'$ are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;

$R_6$ is H, $C_{1-6}$ alkyl, or halogenated $C_{1-6}$ alky;

m, and n, combined are 1, 2, 3 or 4;

p is 0, 1, 2, 3 or 4;

q is 0, 1 or 2;

$R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NOR$_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —SO$_2$$NR_aR_b$, —$NR_b$SO$_2$$R_a$, —$NR_b$SO$_2$$NR_aR_b$, or —P(=O)$OR_aOR_b$;

$R^{11}$ is halogen, —$OR_a$, —$NR_aR_b$, —C(=O)$OR_a$, —C(O)$NR_aR_b$, —C(=O)OH, —C(=O)$R_a$, —C(=NOR$_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —SO$_2$$NR_aR_b$, —$NR_b$SO$_2$$R_a$, —$NR_b$SO$_2$$NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and $R^{12}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NOR$_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}$$R_a$, —SO$_2$$NR_aR_b$, —$NR_b$SO$_2$$R_a$, —$NR_b$SO$_2$$NR_aR_b$, or —P(=O)$OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

In embodiment 66, the compound according to any one of embodiments 62 to 65, wherein each A is independently cyclopropyl, cyclohexyl, pyrrolidinyl, pyrazolidinyl, imidazolidinyl, piperazinyl, piperadinyl, phenyl, naphthalenyl, thienyl, furanyl, pyrrolyl, pyrazolyl, imidazolyl, thiazolyl, thiadiazolyl, oxazolyl, oxadiazolyl, pyridyl, pyrimidyl, pyrazinyl, pyridazinyl, indolyl, indazolyl, benzimidazolyl, benzoxazolyl, benzodioxolyl, benzothiazolyl, benzothiadiazolyl, dihydrobenzodioxine, thienofuranyl, thienothienyl, thienopyrrolyl, quinolinyl, quinoxalinyl, quinazolinyl, cinnolinyl, or triazolyl; and wherein each A is independently substituted with $(R_1)_p$.

In embodiment 67, the compound according to embodiment 66, wherein each A is independently cyclopropyl, cyclohexyl, phenyl, or naphthalene, wherein each A is independently substituted with $(R_1)_p$.

In embodiment 68, The compound according to embodiment 67 wherein each A is independently selected from the group consisting of:

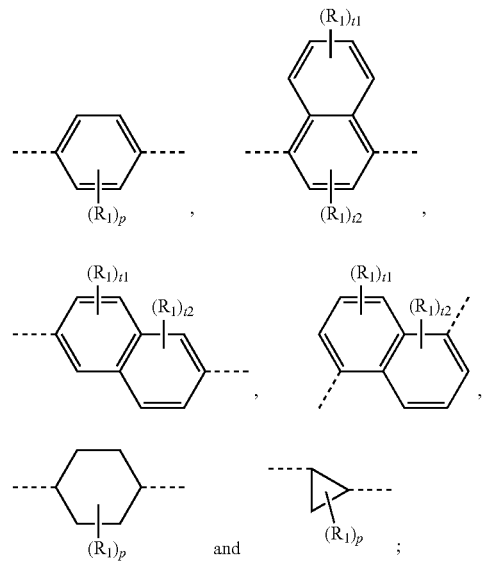

and
t1+t2=p.

In embodiment 69, the compound according to embodiment 68, wherein A is:

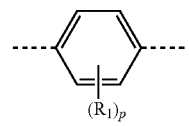

In embodiment 70. the compound according to embodiment 66, wherein each A is independently piperazinyl, piperadinyl, thienyl, furanyl, pyrrolyl, pyrazolyl, imidazolyl, thiazolyl, oxazolyl, thiadiazolyl, pyrrolidinyl, pyridyl, pyrimidinyl, pyrazinyl, pyridazinyl, benzoxazolyl, benzodioxolyl, benzothiazolyl, benzothiadiazolyl, dihydrobenzodioxinyl, thienofuranyl, thienothienyl, quinolinyl, or triazolyl.

In embodiment 71, the compound according to embodiment 71, wherein each A is independently selected from the group consisting of:
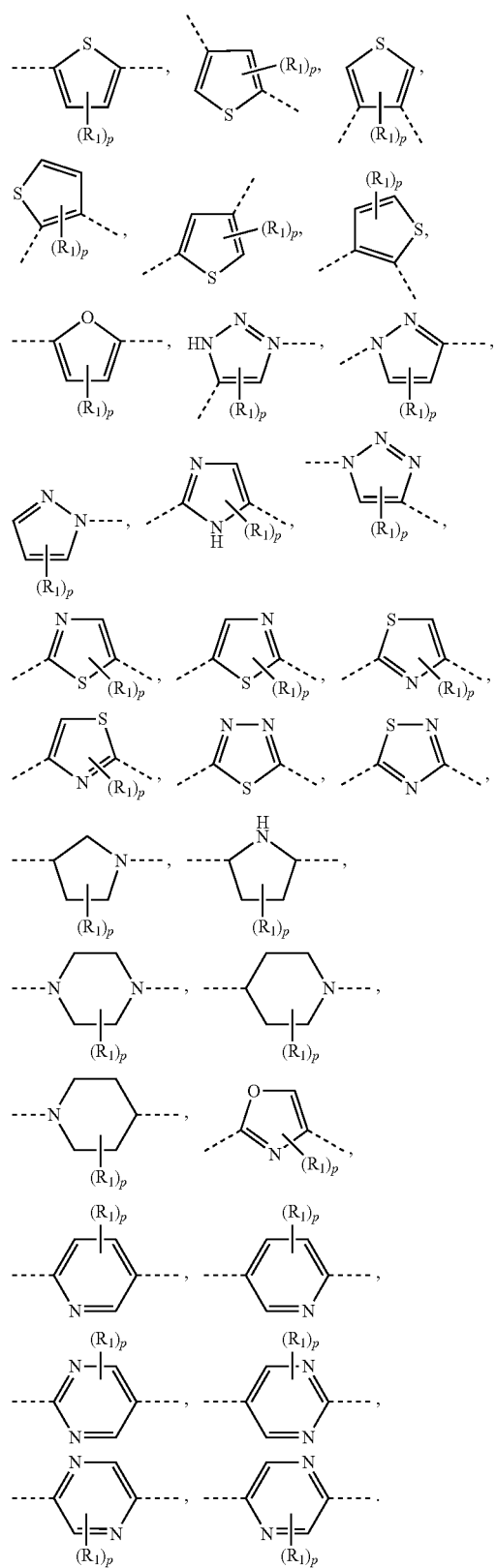
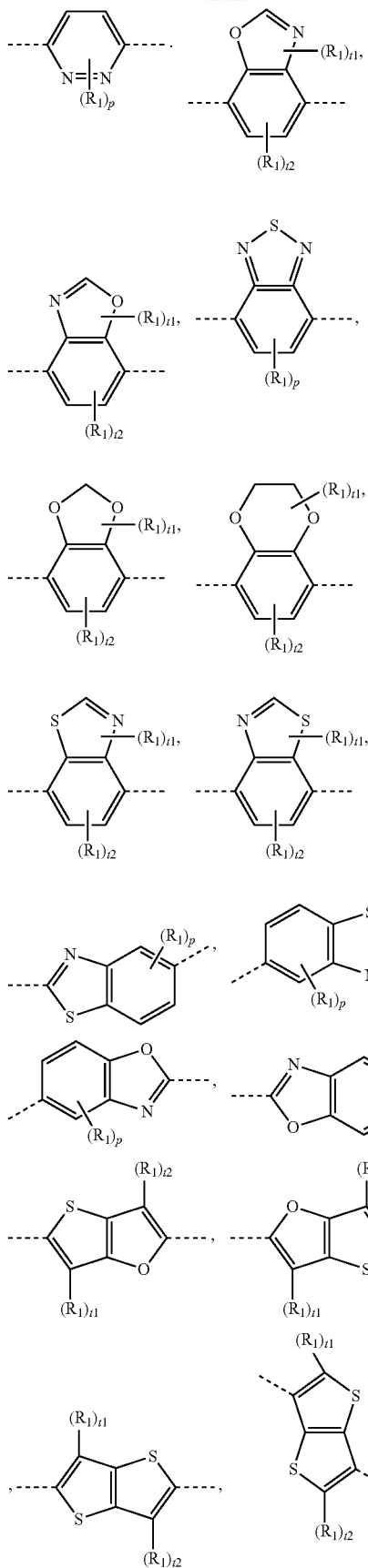

-continued

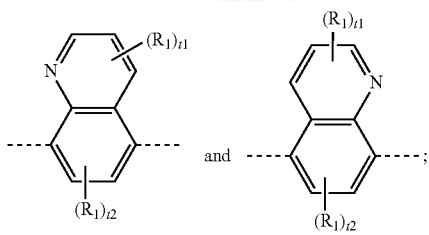

and t1+t2=p.

In embodiment 72, the compound according to any one of embodiments 62-65, wherein each A is independently a 5-12 membered heteroaryl wherein the heteroatom(s) are selected from the group consisting of oxygen and sulphur; wherein each A is independently substituted with $(R_1)_p$.

In embodiment 73, the compound according to any one of embodiments 62 to 72, wherein B and B' are independently absent, $C_{1-6}$ alkyl or $C_{2-6}$ alkynyl.

In embodiment 74, the compound according to embodiment 73, wherein B and B' are independently absent, —(CH$_2$)$_2$— or —(CC)—.

In embodiment 75, The compound according to embodiment 74, wherein B and B' are independently absent or —(CC)—.

In embodiment 76, The compound according to any one of embodiments 62 to 75, wherein the distance between C and C' is between about 16 Å and about 24 Å in length.

In embodiment 77, the compound according to any one of embodiments 62 to 76, wherein

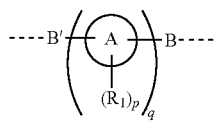

is selected from the group consisting of:

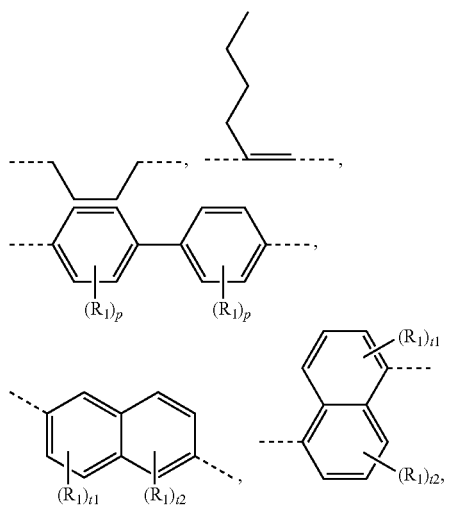

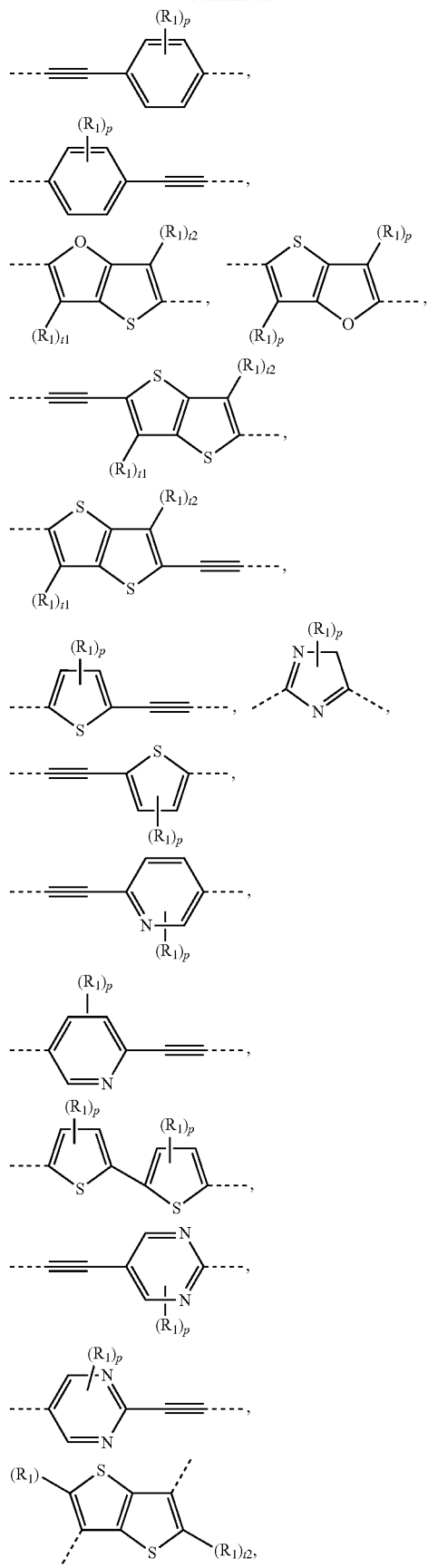

-continued
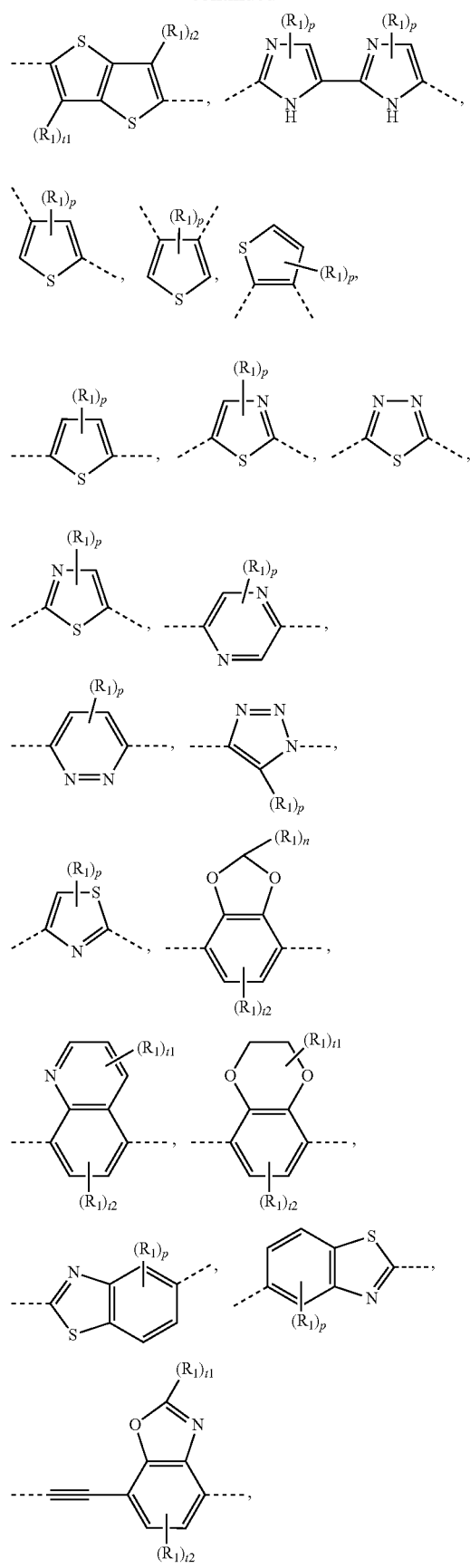
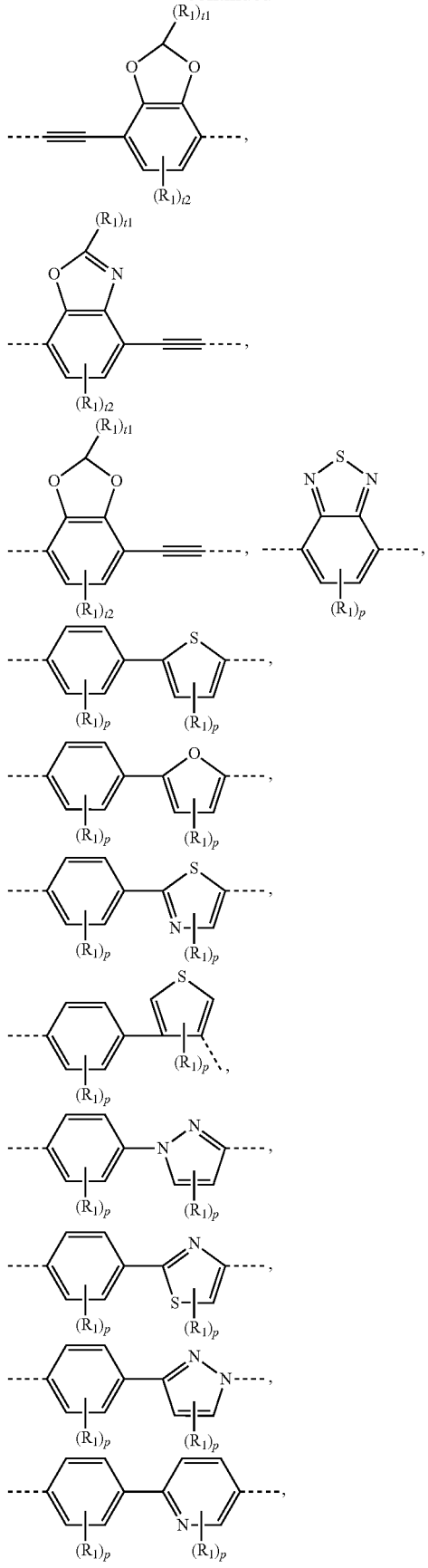

-continued
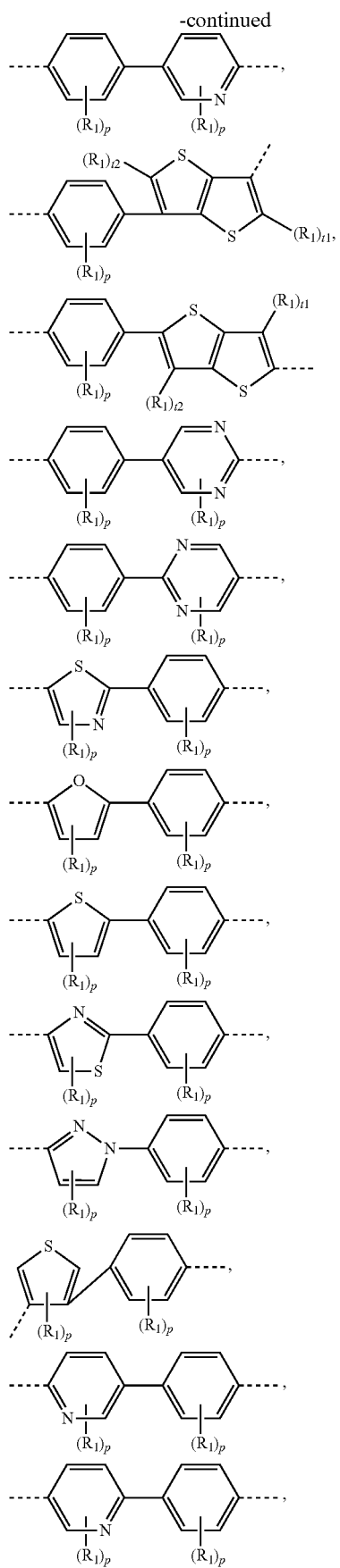
-continued
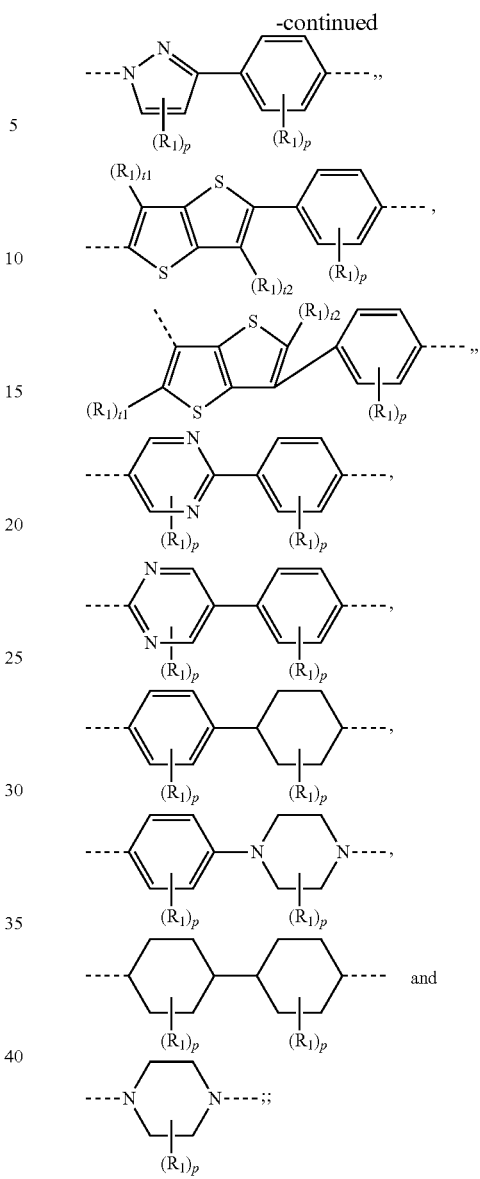
and
t1+t2=p.
In embodiment 78, The compound according to embodiment 77, wherein
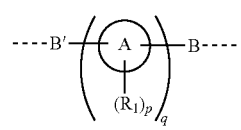
is selected from the group consisting of:
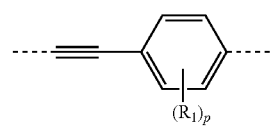

-continued

[chemical structure: phenyl with alkyne substituent, (R₁)ₚ]

[chemical structure: biphenyl with (R₁)ₚ on each ring]

[chemical structures: two thieno-thiophene regioisomers with (R₁)ₚ]

[chemical structure: thieno-thiophene-phenyl with (R₁)ₚ]

[chemical structure: phenyl-thieno-thiophene with (R₁)ₚ]

[chemical structure: thiophene with (R₁)ₚ]

and t1+t2=p.

In embodiment 79, the compound according to any one of embodiments 1-61, wherein

[structure: ----B'—(A with (R₁)ₚ)ᵩ—B----]

is selected from the group consisting of:

[two thieno-thiophene structures with (R₁)t1 and (R₁)t2]

and t1+t2=p.

In embodiment 80, The compound according to any one of embodiments 1-61, wherein

[structure: ----B'—(A with (R₁)ₚ)ᵩ—B----]

is:

[thieno-thiophene structure with (R₁)t1 and (R₁)t2]

and t1+t2=p.

In embodiment 80a, the compound according to any one of embodiments 1-61, wherein

[structure: ----B'—(A with (R₁)ₚ)ᵩ—B----]

is:

[thieno-thiophene structure]

and t1+t2=p.

In embodiment 80b, the compound according to any one of embodiments 1-61, wherein

[structure: ----B'—(A with (R₁)ₚ)ᵩ—B----]

is:

[thieno-thiophene structure with (R₁)t1 and (R₁)t2]

and t1+t2=p.

In embodiment 80c, the compound according to any one of embodiment 1-61, wherein

[structure: ----B'—(A with (R₁)ₚ)ᵩ—B----]

is

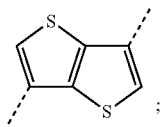

and t1+t2=p.

In embodiment 81, the compound according to any one of embodiments 1 to 80, wherein $R_1$ is halogen, $C_{1-4}$ alkyl which is unsubstituted or substituted one or more times by $R^{10}$, —C(=O)$OR_a$, —C(O)$NR_aR_b$, hydroxyl, cyano, or $C_{1-3}$ alkoxy.

In embodiment 82, The compound according to embodiment 81, wherein $R_1$ is chloro, fluoro, bromo, methyl, ethyl, propyl, butyl, —CH$_2$OH, difluoromethyl, trifluoromethyl, —C(=O)$OR_a$, hydroxyl, cyano, or methoxy.

In embodiment 83, the compound according to any one of embodiments 1 to 81, wherein each $R_2'$ is independently fluoro or methyl.

In embodiment 84, the compound according to embodiment 83, wherein s is 0.

In embodiment 85, the compound according to any one of embodiments 1 to 84, wherein each $R_2$ is independently fluoro or methyl.

In embodiment 86, the compound according to embodiment 85, wherein s is 0.

In embodiment 87, The compound according to any one of embodiments 1 to 86, wherein $R_3$ and $R_3'$ are H or methyl.

In embodiment 88, the compound according to any one of embodiments 1 to 87, wherein $R_4$ and $R_4'$ are each independently halogen, methyl, ethyl, isopropyl, di-fluoromethyl, di-fluoroethyl, trifluoromethyl, tri-fluoroethyl, —CH$_2$OH, —$NR_aN_b$, t-butoxy-, or hydroxyl; or two $R_4$ groups together with the atoms to which they are attached form fused cyclopropyl, spiro cyclopropyl or

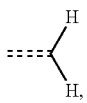

two $R_4'$ groups together with the atoms to which they are attached form fused cyclopropyl, spiro cyclopropyl or

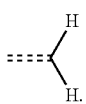

In embodiment 89, the compound according to embodiment 88, wherein $R_4$ and $R_4'$ are each independently methyl, ethyl, methoxy, di-fluoromethyl, trifluoromethyl, or two $R_4$ groups together with the atoms to which they are attached form fused cyclopropyl or spiro cyclopropyl or two $R_4'$ groups together with the atoms to which they are attached form fused cyclopropyl or spiro cyclopropyl.

In embodiment 90, the compound according to embodiment 89, wherein $R_4$ and $R_4'$ are methyl.

In embodiment 91. the compound according to anyone of embodiments 1 to 91, wherein m and n are independently 1 or 2.

In embodiment 92, the compound according to embodiment 91, wherein m and n are 1.

In embodiment 93, the compound according to any one of embodiments 1 to 92, wherein X and Y are

In embodiment 94, the compound according to any one of embodiments 1 to 93, wherein $R_5$ and $R_5'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

In embodiment 95, the compound according to embodiment 94, wherein $R_5$ and $R_5'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 membered heteroaryl which is unsubstituted or substituted one or more times by $R^{11}$, 6-7 membered heteroaralkyl which is unsubstituted or substituted one or more times by $R^{11}$, 5-6 membered heterocycle which is unsubstituted or substituted one or more times by $R^{12}$, or 6-7 membered heterocycle-alkyl which is unsubstituted or substituted one or more times by $R^{12}$.

In embodiment 96, the compound according to embodiment 95, wherein $R_5$ and $R_5'$ are each independently, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$.

In embodiment 97, the compound according to embodiments 1-93, wherein $R_5$ and $R_5'$ are each independently methyl, ethyl, propyl, isopropyl, butyl, sec-butyl, tert-butyl, pentyl, 2-methylbutane, 3-methylbutane, cyclopropyl, cyclobutyl, cyclopentyl, cyclohexyl, or cyclohexyl(CH$_2$)—, which are unsubstituted or substituted one or more times by $R^{10}$.

In embodiment 98, the compound according to embodiment 97, wherein $R_5$ and $R_5'$ are each independently phenyl which is unsubstituted or substituted one or more times by $R^{11}$.

In embodiment 99, the compound according to embodiment 98, wherein $R_5$ and $R_5'$ are each independently benzyl which is unsubstituted or substituted one or more times by $R^{11}$.

In embodiment 100, the compound according to any one of embodiments 1 to 99, wherein $R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=NOR$_c$)$R_a$, —C(=N$R_c$)$NR_aR_b$, —$NR_dC$(=O)$NR_aR_b$, —$NR_bC$(=O)$R_a$, —$NR_dC$ (=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, or —NR$_b$SO$_2$NR$_a$R$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

In embodiment 101, the compound according to embodiment 100 wherein R$^{10}$ is —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, or —NR$_b$SO$_2$NR$_a$R$_b$.

In embodiment 102, the compound according to embodiment 101, wherein R$^{10}$ is —NR$_a$R$_b$, —NR$_d$C(=O)NR$_a$R$_b$, —NR$_b$C(=O)R$_a$, —NR$_b$C(=O)OR$_a$, or —NR$_b$SO$_2$R$_a$.

In embodiment 103, the compound according to any one of embodiment 1 to 102, wherein R$_a$-R$_d$ are each independently H, C$_{1-6}$ alkyl, C$_{2-6}$ alkenyl, C$_{2-6}$ alkynyl, phenyl, C$_{7-8}$ aralkyl, 5-6 membered heteroaryl, 6-8 membered heteroaralkyl, 5-6 membered heterocycle, or 6-8 membered heterocycle-alkyl.

In embodiment 104, the compound according to embodiment 103, wherein R$_a$ and R$_c$ are each independently H, C$_{1-6}$ alkyl, C$_{2-6}$ alkenyl, C$_{2-6}$ alkynyl, phenyl, C$_{7-8}$ aralkyl, 5-6 membered heteroaryl, 6-8 membered heteroaralkyl, 5-6 membered heterocycle, or 6-8 membered heterocycle-alkyl, and R$_b$, and R$_d$ are each independently H or C$_{1-3}$ alkyl.

In embodiment 105, the compound according to embodiment 104, wherein R$_a$-R$_d$ are each independently H or C$_{1-3}$ alkyl.

In embodiment 106, the compound according to any one of embodiments 1 to 105, wherein said compound is of formula (IVA):

alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl; and m and n combined are 0, 1, 2, 3 or 4.

In embodiment 107, the compound according to embodiment 106, wherein R$_8$ and R$_8$' are each independently —NR$_a$R$_b$, —NR$_b$C(=O)R$_a$, —NR$_b$C(=O)OR$_a$, wherein R$_a$-R$_b$ are each independently H, C$_{1-6}$ alkyl, phenyl, benzyl, 5-6 membered heteroaryl, 6-8 membered heteroaralkyl, 5-6 membered heterocycle, or 6-8 membered heterocycle-alkyl.

In embodiment 108, the compound according to embodiment 107, wherein R$_8$ and R$_8$' in formulas (IV), are each independently —NR$_b$C(=O)OR$_a$, wherein R$_a$-R$_b$ are each independently H, C$_{1-6}$ alkyl, phenyl, tetrahydrofuran, or benzyl.

In embodiment 109, the compound according to any one of embodiments 107 to 108, wherein R$_7$ and R$_7$' are each independently phenyl which is unsubstituted or substituted one or more times by R$^{11}$.

In embodiment 110, the compound according to any one of embodiments 108 to 109, wherein R$_7$ and R$_7$' are each independently, C$_{1-6}$ alkyl which is unsubstituted or substituted one or more times by R$^{10}$.

In embodiment 111, the compound according to embodiment 110 wherein R$_7$ and R$_7$' are each independently methyl, ethyl, propyl, isopropyl, methoxyisopropyl, butyl, sec-butyl, tert-butyl, pentyl, 2-methylbutane, 3-methylbutane, cyclopropyl, cyclobutyl, cyclopentyl, or cyclohexyl.

In embodiment 112, the compound according to any one of embodiments 1 to 111, wherein R$_7$ and R$_8$ or R$_7$' and R$_8$' together with the carbon to which they are attached are each independently:

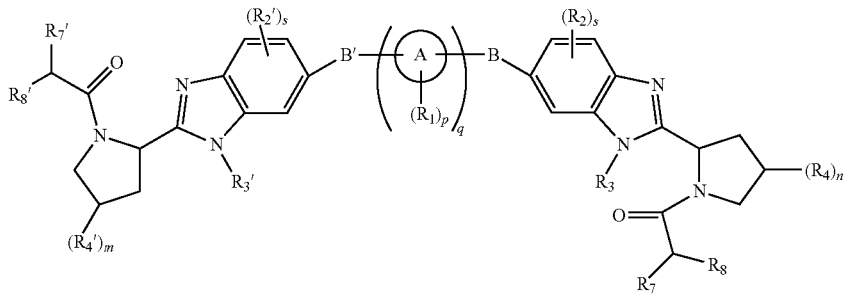

or a pharmaceutically acceptable salt thereof wherein

R$_7$ and R$_7$' are each independently C$_{1-8}$ alkyl which is unsubstituted or substituted one or more times by R$^{10}$, C$_{2-8}$ alkenyl which is unsubstituted or substituted one or more times by R$^{10}$, C$_{2-8}$ alkynyl which is unsubstituted or substituted one or more times by R$^{10}$, phenyl which is unsubstituted or substituted one or more times by R$^{11}$, benzyl which is unsubstituted or substituted one or more times by R$^{11}$, 5-6 membered heteroaryl which is unsubstituted or substituted one or more times by R$^{11}$, 6-7 membered heteroaralkyl which is unsubstituted or substituted one or more times by R$^{11}$, 3-6 membered heterocycle which is unsubstituted or substituted one or more times by R$^{12}$, or 4-7 membered heterocycle-alkyl which is unsubstituted or substituted one or more times by R$^{12}$;

R$_8$ and R$_8$' are each independently —NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —NR$_b$SO$_2$R$_a$, or —NR$_b$SO$_2$NR$_a$R$_b$, wherein R$_a$-R$_d$ are each independently H, C$_{1-12}$ alkyl, C$_{2-12}$

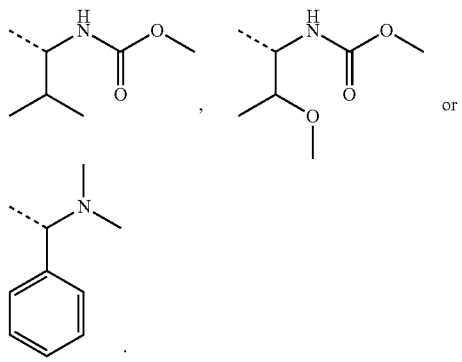

In embodiment 113, the compound according to any one of embodiments 1 to 112, wherein said compound is of formula (VA):

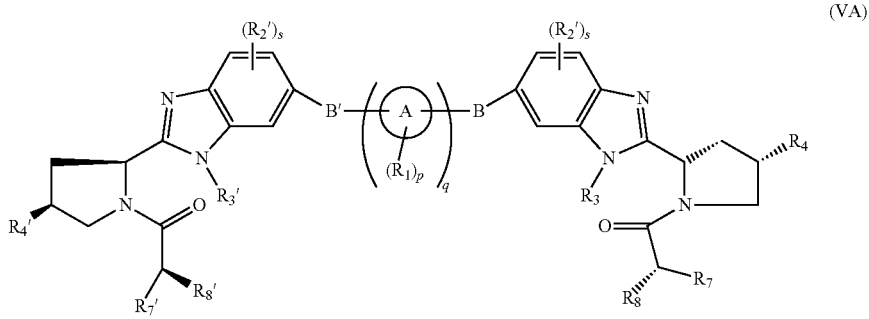

(VA)

or a pharmaceutically acceptable salt thereof.

In one embodiment, the present invention provides a compound according to the invention described herein for treating or preventing a Flaviviridae viral infection in a host.

In one embodiment, the present invention provides a pharmaceutical composition comprising at least one compound according to the invention described herein and at least one pharmaceutically acceptable carrier or excipient.

In one embodiment, the present invention provides a pharmaceutical composition comprising at least one compound according to the invention described herein and at least one pharmaceutically acceptable carrier or excipient, for treating or preventing a Flaviviridae viral infection in a host.

In one embodiment, the present invention provides a pharmaceutical composition comprising at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In another embodiment, there is provided a combination comprising a least one compound according to the invention described herein and one or more additional agents.

In another embodiment, there is provided a combination comprising a least one compound according to the invention described herein and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In one combination embodiment, the compound and additional agent are administered sequentially.

In another combination embodiment, the compound and additional agent are administered simultaneously.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The additional agents for the compositions and combinations include, for example, ribavirin, amantadine, merimepodib, Levovirin, Viramidine, and maxamine.

The term "viral serine protease inhibitor" as used herein means an agent that is effective to inhibit the function of the viral serine protease including HCV serine protease in a mammal. Inhibitors of HCV serine protease include, for example, those compounds described in WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006039488 (Vertex), WO 2005077969 (Vertex), WO 2005035525 (Vertex), WO 2005028502 (Vertex) WO 2005007681 (Vertex), WO 2004092162 (Vertex), WO 2004092161 (Vertex), WO 2003035060 (Vertex), of WO 03/087092 (Vertex), WO 02/18369 (Vertex), or WO98/17679 (Vertex).

Specific examples of viral serine protease inhibitors include Telaprevir (VX-950, Vertex), VX-500 (Vertex), VX-813 (Vertex), VX-985 (Vertex), TMC435350 (Tibotec/Medivir), MK-7009 (Merck), ITMN-191 (R7227, InterMune/Roche) and Boceprevir (SCH503034, Schering).

The term "viral polymerase inhibitors" as used herein means an agent that is effective to inhibit the function of a viral polymerase including an HCV polymerase in a mammal. Inhibitors of HCV polymerase include non-nucleosides, for example, those compounds described in:

WO 03/010140 (Boehringer Ingelheim), WO 03/026587 (Bristol Myers Squibb); WO 02/100846 A1, WO 02/100851 A2, WO 01/85172 A1 (GSK), WO 02/098424 A1 (GSK), WO 00/06529 (Merck), WO 02/06246 A1 (Merck), WO 01/47883 (Japan Tobacco), WO 03/000254 (Japan Tobacco) and EP 1 256 628 A2 (Agouron).

Furthermore other inhibitors of HCV polymerase also include nucleoside analogs, for example, those compounds described in: WO 01/90121 A2 (Idenix), WO 02/069903 A2 (Biocryst Pharmaceuticals Inc.), and WO 02/057287 A2 (Merck/Isis) and WO 02/057425 A2 (Merck/Isis).

Specific examples of inhibitors of an HCV polymerase, include VCH-759 (ViroChem Pharma), VCH-916 (ViroChem Pharma), VCH-222 (ViroChem Pharma), R1626 (Roche), R7128 (Roche/Pharmasset), PF-868554 (Pfizer), MK-0608 (Merck/Isis), MK-3281 (Merck), A-837093 (Abbott), GS 9190 (Gilead), ana598 (Anadys), HCV-796 (Viropharma) and GSK625433 (GlaxoSmithKline).

The term "viral helicase inhibitors" as used herein means an agent that is effective to inhibit the function of a viral helicase including a Flaviviridae helicase in a mammal.

"Immunomodulatory agent" as used herein means those agents that are effective to enhance or potentiate the immune system response in a mammal. Immunomodulatory agents include, for example, class I interferons (such as α-, β-, δ- and Ω-interferons, τ-interferons, consensus interferons and asialo-interferons), class II interferons (such as γ-interferons) and pegylated interferons.

Specific examples of Immunomodulatory agent as used herein include IL-29 (PEG-Interferon Lambda, ZymoGenetics), Belerofon (Nautilus Biotech) injectable or oral, Oral Interferon alpha (Amarillo Biosciences), BLX-883 (Locteron, Biolex Therapeutics/Octoplus), Omega Interferon (Intarcia Therapeutics), multiferon (Viragen), Albuferon (Human Genome Sciences), consensus Interferon (Infergen, Three Rivers Pharmaceuticals), Medusa Interferon (Flamel Technologies), NOV-205 (Novelos Therapeutics), Oglufanide disodium (Implicit Bioscience), SCV-07 (SciClone), Zadaxin® (thymalfasin, SciClone/Sigma-Tau), AB68 (XTL bio) and Civacir (NABI).

The term "class I interferon" as used herein means an interferon selected from a group of interferons that all bind to receptor type 1. This includes both naturally and synthetically produced class I interferons. Examples of class I interferons include α-, β-, δ- and Ω-interferons, τ-interferons, consensus interferons and asialo-interferons. The term "class II interferon" as used herein means an interferon selected from a group of interferons that all bind to receptor type II. Examples of class II interferons include γ-interferons.

Antisense agents include, for example, ISIS-14803.

Inhibitors of internal ribosome entry site (IRES) include ISIS-14803 (ISIS Pharmaceuticals) and those compounds described in WO 2006019831 (PTC therapeutics).

In one embodiment, the additional agent is interferon α, ribavirin, silybum marianum, interleukine-12, amantadine, ribozyme, thymosin, N-acetyl cysteine or cyclosporin.

In one embodiment, the additional agent is interferon α, or ribavirin.

In one embodiment, the additional agent is interferon α 1A, interferon α 1B, interferon α 2A, or interferon α 2B.

Interferon is available in pegylated and non pegylated forms. Pegylated interferons include PEGASYS™ and Peg-intron™.

In one embodiment, the additional agent is interferon α 1A, interferon α 1B, interferon α 2A (Roferon), PEG-interferon α 2A (Pegasys), interferon α 2B (Intron A) or PEG-interferon α 2B (Peg-Intron).

In one embodiment, the additional agents is standard or pegylated interferon α (Roferon, Pegasys, Intron A, Peg-Intron) in combination with ribavirin.

In one embodiment, the additional agent is chosen from A-831 (AZD0530, Arrow Therapeutics acquired by Astra-Zeneca), TLR9 agonist: IMO-2125 (Idera Pharmaceuticals), PYN17 (Phynova), Vavituximab (Tarvacin, Peregrine), DEBIO-025 (DEBIO), NIM-811 (Novartis), SCY635 (Scynexis), PF-03491390 (IDN-6556, Pfizer), Suvus (formerly BIVN-401, Virostat, Bioenvision), MX-3253 (Celgosivir, Migenix), Viramidine (Taribavirin, Valeant Pharmaceuticals), Hepaconda (Giaconda), TT033 (Benitec/Tacere Bio/Pfizer), SIRNA-034 (Sirna Therapeutics acquired by Merck) and EHC-18 (Enzo Biochem), ACH-1095 (Achillion/Gilead), JKB-022 (Jenkin), CTS-1027 (Conatus), MitoQ (mitoquinone, Antipodean Pharmaceuticals), Alinia (nitazoxanide, Romark Laboratories) and Bavituximab (Peregrine Pharm).

In one embodiment, the additional agent is a therapeutic vaccine chosen from CSL123 (Chiron/CSL), IC41 (Intercell Novartis), GI 5005 (Globeimmune), TG4040 (Transgene), Chronvac C (Tripep/Inovio), GNI-103 (GENimmune), HCV/MF59 (Chiron/Novartis), PeviPRO™ (Pevion biotect).

The recommended dose of PEGASYS™ monotherapy for chronic hepatitis C is 180 mg (1.0 mL vial or 0.5 mL prefilled syringe) once weekly for 48 weeks by subcutaneous administration in the abdomen or thigh.

The recommended dose of PEGASYS™ when used in combination with ribavirin for chronic hepatitis C is 180 mg (1.0 mL vial or 0.5 mL prefilled syringe) once weekly.

The daily dose of Ribavirin is 800 mg to 1200 mg administered orally in two divided doses. The dose should be individualized to the patient depending on baseline disease characteristics (e.g., genotype), response to therapy, and tolerability of the regimen.

The recommended dose of PEG-Intron™ regimen is 1.0 mg/kg/week subcutaneously for one year. The dose should be administered on the same day of the week.

When administered in combination with ribavirin, the recommended dose of PEG-Intron is 1.5 micrograms/kg/week.

In one embodiment, viral serine protease inhibitor is a flaviviridae serine protease inhibitor.

In one embodiment, viral polymerase inhibitor is a flaviviridae polymerase inhibitor.

In one embodiment, viral helicase inhibitor is a flaviviridae helicase inhibitor.

In further embodiments:

viral serine protease inhibitor is HCV serine protease inhibitor;

viral polymerase inhibitor is HCV polymerase inhibitor;

viral helicase inhibitor is HCV helicase inhibitor.

In one embodiment, the present invention provides a method for treating or preventing a Flaviviridae viral infection in a host comprising administering to the host a therapeutically effective amount of at least one compound according to formula (I), (II), (III), or (IV).

In one embodiment, the viral infection is chosen from *Flavivirus* infections.

In one embodiment, the *Flavivirus* infection is Hepatitis C virus (HCV), bovine viral diarrhea virus (BVDV), hog cholera virus, dengue fever virus, Japanese encephalitis virus or yellow fever virus.

In one embodiment, the Flaviviridea viral infection is hepatitis C viral infection (HCV).

In one embodiment, the host is human.

In one embodiment, the present invention provides a method for treating or preventing a Flaviviridae viral infection in a host comprising administering to the host a therapeutically effective amount of at least one compound according to the invention described herein, and further comprising administering at least one additional agent.

In one embodiment, the present invention provides a method for treating or preventing a Flaviviridae viral infection in a host comprising administering to the host a therapeutically effective amount of at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual components for use in the method of the present invention or combinations of the present invention may be administered either sequentially or simultaneously in separate or combined pharmaceutical formulations.

In one embodiment, the present invention provides the use of a compound according to the invention described herein for treating or preventing Flaviviridae viral infection in a host.

In one embodiment, the present invention provides the use of a compound according to the invention described herein and further comprising at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). for treating or preventing Flaviviridae viral infection in a host.

In one embodiment, the present invention provides the use of a compound according to the invention described herein for the manufacture of a medicament.

In one embodiment, the present invention provides the use of a compound according to the invention described herein for the manufacture of a medicament for treating or preventing a viral Flaviviridae infection in a host.

In one embodiment, the present invention provides the use of a compound according to the invention described herein and further comprising at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES). for the manufacture of a medicament for treating or preventing a viral Flaviviridae infection in a host.

It will be appreciated by those skilled in the art that the compounds in accordance with the present invention can exists as stereoisomers (for example, optical (+ and −), geometrical (cis and trans) and conformational isomers (axial and equatorial). All such stereoisomers are included in the scope of the present invention.

It will be appreciated by those skilled in the art that the compounds in accordance with the present invention can contain a chiral center. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In one embodiment, the compounds of the present invention are provided in the form of a single stereoisomer at least 95%, at least 97% and at least 99% free of the corresponding stereoisomers.

In a further embodiment the compound of the present invention are in the form of a single stereoisomer at least 95% free of the corresponding stereoisomers.

In a further embodiment the compound of the present invention are in the form of a single stereoisomer at least 97% free of the corresponding stereoisomers.

In a further embodiment the compound of the present invention are in the form of a single stereoisomer at least 99% free of the corresponding stereoisomers.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-arginine, L-Lysine).

Salts derived from appropriate bases include alkali metals (e.g. sodium, lithium, potassium) and alkaline earth metals (e.g. calcium, magnesium).

A reference hereinafter to a compound according to the invention includes that compound and its pharmaceutically acceptable salts.

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19, the disclosure of which is incorporated herein by reference.

It will be appreciated by those skilled in the art that the compounds in accordance with the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

In addition to the compounds of this invention, pharmaceutically acceptable derivatives or prodrugs, and esters, of the compounds of this invention may also be employed in compositions to treat or prevent the herein identified disorders.

Also included in the present invention are isotopically labeled compounds, wherein, for example, one or more hydrogen atoms in the compounds described herein are replaced with deuterium or tritium.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, hexenyl, butadienyl, pentenyl, pentadienyl, hexenyl, heptenyl, heptadienyl, heptatrienyl, octenyl, propynyl, butynyl, pentynyl, hexynyl, cyclopropyl, cyclobutyl, cyclohexenyl, cyclohexdienyl and cyclohexyl. The terms alkyl, alkenyl, and alkynyl, also include combinations of linear and branched groups, e.g., cyclopropylmethyl, cyclohexylethyl, etc. The term alkenyl also includes C1 alkenyl where the one carbon atom is attached to the remainder of the molecule via a double bond.

Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$) NR$_a$R$_b$, —NR$_b$C(=O)OR$_a$, —OC(=O)NR$_a$R$_b$, —OC (=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The terms "cycloalkyl", and "cycloalkenyl" represent a cyclic hydrocarbon alkyl or alkenyl, respectively, and are meant to include monocyclic (e.g., cyclopropyl, cyclobutyl, cyclohexyl), spiro (e.g., Spiro[2.3]hexanyl), fused (e.g., bicyclo[4.4.0]decanyl), and bridged (e.g., bicyclo[2.2.1]heptanyl)hydrocarbon moieties.

The terms "alkoxy," "alkenyloxy," and "alkynyloxy" represent an alkyl, alkenyl or alkynyl moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. Like the alkyl, alkenyl and alkynyl groups, where indicated the alkoxy, alkenyloxy, and alkynyloxy groups can be optionally substituted by, for example, halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$) NR$_a$R$_b$, —NR$_d$C(=O)NR$_a$R$_b$, —NR$_b$C(=O)R$_a$, —NR$_d$C (=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted where indicated by, for example, halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O) NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "aralkyl" represents an aryl group attached to the adjacent atom by an alkyl, alkenyl or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted one or more times by, for example, halogen, —OR$_a$, —NR$_a$R$_b$, —C(=O) OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O) NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "heterocycle" represents a non aromatic, saturated or partially saturated cyclic moiety wherein said cyclic moiety is interrupted by at least one heteroatom selected from oxygen (O), sulfur (S) or nitrogen (N). Heterocycles may be monocyclic or polycyclic rings. Examples include but are not limited to azetidinyl, dioxolanyl, morpholinyl, morpholino, oxetanyl, piperazinyl, piperidyl, piperidinyl, cyclopentapyrazolyl, cyclopentaoxazinyl, cyclopentafuranyl, tetrahydrofuranyl, thiazolinyl, oxazolinyl, pyranyl, aziridinyl, azepinyl, dioxazepinyl, diazepinyl, oxyranyl, oxazinyl, pyrrolidinyl, and thiopyranyl, thiolanyl, pyrazolidinyl, dioxanyl, and imidazolidinyl. Where indicated, the heterocyclic groups can be optionally substituted one or more times by, for example, halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$) R$_a$, —C(=NR$_c$)NR$_a$R$_b$, —NR$_d$C(=O)NR$_a$R$_b$, —NR$_b$C (=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "heterocycle-alkyl" represents heterocycle group attached to the adjacent atom by an alkyl, alkenyl or alkynyl group. It is understood that in, for example, a 4-18 member heterocycle-alkyl moiety, the 4-18 member represent the total of the ring atoms present in the heterocycle moiety and the carbon atoms present in the alkyl, alkenyl or alkynyl group. For example, the following groups are encompassed by a 7 member heterocycle-alkyl (* represents the attachment point):

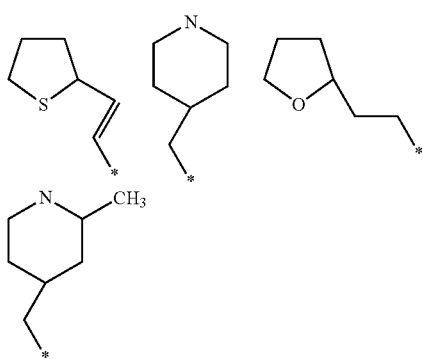

Where indicated the heterocycle-alkyl groups can be optionally substituted one or more times by, for example, halogen, —OR$_a$, oxo, —NR$_a$R$_b$, =NO—R$_c$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "heteroaryl" represents an aromatic cyclic moiety wherein said cyclic moiety is interrupted by at least one heteroatom selected from oxygen (O), sulfur (S) or nitrogen (N). Heteroaryls may be monocyclic or polycyclic rings wherein at least one ring in the polycyclic ring system is aromatic and at least one ring (not necessarily the same ring contains a heteroatom. Examples include but are not limited to dithiadiazinyl, furanyl, isooxazolyl, isothiazolyl, imidazolyl, oxadiazolyl, oxazolyl, pyrazinyl, pyridazinyl, pyrimidinyl, pyridyl, pyrazolyl, pyrrolyl, thiatriazolyl, tetrazolyl, thiadiazolyl, triazolyl, thiazolyl, thienyl, tetrazinyl, thiadiazinyl, triazinyl, thiazinyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, benzodioxolyl, dihydrobenzodioxinyl, benzothiadiazolyl, thienofuranyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl, chromen, benzodiazinyl. Where indicated the heteroaryl groups can be optionally substituted one or more times by, for example, halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl.

The term "heteroaralkyl" represents an optionally substituted heteroaryl group attached to the adjacent atom by an alkyl, alkenyl or alkynyl group. Where indicated the heteroaralkyl groups can be optionally substituted one or more times by, for example, halogen, —OR$_a$, —NR$_a$R$_b$, —C(=O)OR$_a$, —C(O)NR$_a$R$_b$, —C(=O)OH, —C(=O)R$_a$, —C(=NOR$_c$)R$_a$, —C(=NR$_c$)NR$_a$R$_b$, —NR$_d$C(=O)NR$_a$R$_b$, —NR$_b$C(=O)R$_a$, —NR$_d$C(=NR$_c$)NR$_a$R$_b$, —NR$_b$C(=O)OR$_a$, —OC(=O)NR$_a$R$_b$, —OC(=O)R$_a$, —OC(=O)OR$_a$, hydroxyl, nitro, azido, cyano, —S(O)$_{0-3}$R$_a$, —SO$_2$NR$_a$R$_b$, —NR$_b$SO$_2$R$_a$, —NR$_b$SO$_2$NR$_a$R$_b$, or —P(=O)OR$_a$OR$_b$, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl, wherein R$_a$-R$_d$ are each independently H, C$_{1-12}$ alkyl, C$_{2-12}$ alkenyl, C$_{2-12}$ alkynyl, C$_{6-12}$ aryl, C$_{7-16}$ aralkyl, 5-12 membered heteroaryl, 6-18 membered heteroaralkyl, 3-12 membered heterocycle, or 4-18 membered heterocycle-alkyl. It is understood that in, for example, a 6-18 member heteroaralkyl moiety, the 6-18 member represents the total of the ring atoms present in the heterocycle moiety and the carbon atoms in the alkyl, alkenyl or alkynyl groups. For example, the following groups are encompassed by a 7 member heteroaralkyl (* represents the attachment point):

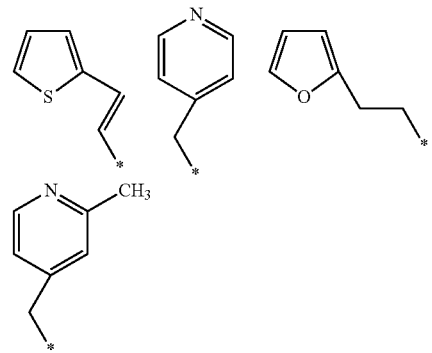

"Halogen atom" is specifically a fluorine atom, chlorine atom, bromine atom or iodine atom.

The term "oxo" represents =O.

A dash ("-") that is not between two letters or symbols is used to indicate a point of attachment for a substitutent. For example, —CONR$_d$R$_e$ is attached through the carbon of the amide.

A dash line ("- - - - -") is used to indicate the point of attachment for the group. For example, A is attached through the carbon at position 1 and 4 in the following representation:

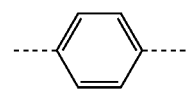

When there is a sulfur atom present, the sulfur atom can be at different oxidation levels, i.e., S, SO, or $SO_2$. All such oxidation levels are within the scope of the present invention.

The term "independently" means that a substituent can be the same or a different definition for each item.

In general, the term "substituted," whether preceded by the term "optionally" or not, refers to the replacement of hydrogen radicals on a carbon or nitrogen atom in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. For example, the language, "which is unsubstituted or substituted one or more times by $R^{10}$" means that when the group is substituted with more than one $R^{10}$ group, the $R^{10}$ groups can be different from each other. A ring substituent, such as a heterocycle, can be bound to another ring, such as a cycloalkyl, to form a spiro-bicyclic ring system, e.g., both rings share one common atom.

As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In certain embodiments, a compound represented by:

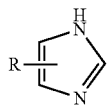

also includes where the R group replaces the H on the nitrogen atom.

Additionally, unless otherwise stated, structures depicted herein are also meant to include compounds that differ only in the presence of one or more isotopically enriched atoms. For example, compounds of this invention, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or antiviral compounds with improved therapeutic profile.

The terms "host" or "patient" mean human male or female, for example child, adolescent or adult.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, about 2 to 50 µM, about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When the compounds of the present invention or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

While it is possible that, for use in therapy, a compound of the invention may be administered as the raw chemical it is preferable to present the active ingredient as a pharmaceutical composition. The invention thus further provides a pharmaceutical composition comprising compounds of the present invention or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The following general schemes and examples are provided to illustrate various embodiments of the present invention and shall not be considered as limiting in scope. It will be appreciated by those of skill in the art that other compounds of the present invention can be obtained by substituting the generically or specifically described reactants and/or operating conditions used in the following examples.

In the foregoing and in the following examples, all temperatures are set forth uncorrected in degrees Celsius; and, unless otherwise indicated, all parts and percentages are by weight.

Analytical HPLC is carried out under standard conditions using a Varian Pursuit XRs C18 column, 50×4.6 mm, 3 μm for methods A and E and a Phenomenex Gemini C18 column, 250×4.6 mm, 3 μm, 110 Å for methods B, C and D. Elution is performed using a linear gradient with a flow rate of 1 mL/min. as described in the following table (Solvent A is 0.01% TFA in $H_2O$; solvent B is 0.01% TFA in $CH_3CN$):

| | Methods | | | | |
|---|---|---|---|---|---|
| | A | B | C | D | E |
| Solvent B | 30 to 75% over 15 min | 20 to 60% over 40 min | 30 to 70% over 40 min | 10 to 50% over 40 min | 15 to 60% over 15 min |

The following abbreviations may be used as follows:
Ac acetyl
AcOH acetic acid
aq aqueous
$(Boc)_2O$ di-tert-butyldicarbonate
DCM dichloromethane
DIPEA Diisopropylethylamine
DME 1,2-dimethoxyethane
DMF dimethylformamide
DMSO Dimethylsulfoxide
DBU 1,8-diazabicyclo[5.4.0]undec-7-ene
$Et_2O$ Diethyl ether
EtOAc Ethyl acetate
HATU O-(7-Azabenzotriazol-1-yl)-N,N,N',N'-tetramethyluronium hexafluorophosphate
$H_2O$ water
MeCN Acetonitrile
MeOH Methanol
Moc Methoxycarbonyl
$PdCl_2$dppf (1,1'-Bis-(diphenylphosphino)-ferrocene)palladium(II)dichloride
$Pd(PPh_3)_4$ Tetrakis(triphenylphosphine) palladium
rt room temperature
TEA Triethylamine
TFA Trifluoroacetic acid
THF Tetrahydrofuran The compounds of this invention may be prepared in light of the specification using steps generally known to those of ordinary skill in the art. Those compounds may be analyzed by known methods, including but not limited to LCMS (liquid chromatography mass spectrometry) HPLC and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

General Schemes:

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture. Method A: Column gradient conditions were 5%-100% acetonitrile-methanol over 3.5 mins gradient time and 4.8 mins run time on an ACE5C8 3.0×75 mm column. Flow rate was 1.2 ml/min. Method B: Column gradient were 5%-100% acetonitrile-methanol over 10 mins gradient time and 12 mins run time on a ACE5C8 4.6×150 mm column. Flow rate was 1.5 mL/min. As used herein, the term "Rt(min)" refers to the LCMS retention time, in minutes, associated with the compound. Unless otherwise indicated, the LCMS method utilized to obtain the reported retention time is as detailed above. If the Rt(min) is <5 min method A was used, if the Rt(min) is >5 min then method B was used.

1H-NMR spectra were recorded at 400 MHz using a Bruker DPX 400 instrument.

General Procedure 1

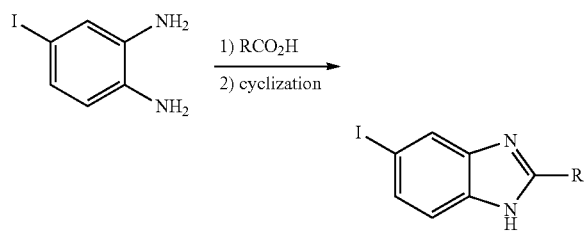

The benzimidazole is formed by coupling the diamino compound with the appropriate carboxylic acid, preactivated carboxylic acid, mixed anhydride or anhydride in solvents such as THF, DMF or DCM and in the presence of a base such as TEA or DIPEA to form the corresponding amide. The amide is than treated with an acid at 40-80° C. for 2-24 hours.

Intermediate 1

(S)-2-(5-Iodo-1H-benzoimidazol-2-yl)-pyrrolidine-1-carboxylic acid tert-butyl ester

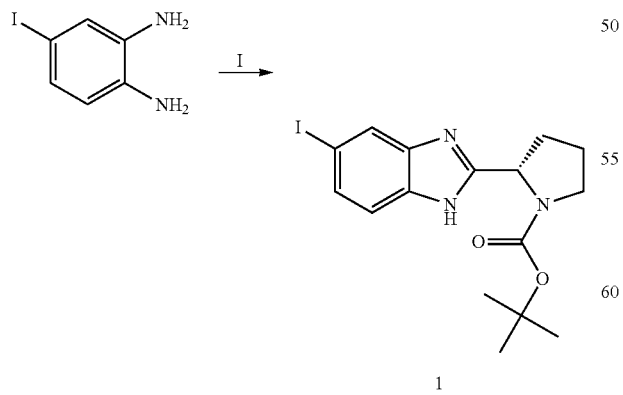

To a dry 1000 mL round bottom flask under Nitrogen, is added 4-Iodo-benzene-1,2-diamine (45 g), (S)-Pyrrolidine-1,2-dicarboxylic acid 1-tert-butyl ester (41.39 g) and THF (450 ml). The reaction mixture is stirred until complete dissolution then cool to 0-2° C. Diisopropylethylamine (50.17 ml) is added dropwise to control the exotherm then HATU (80.38 g) is added in one portion. The reaction mixture is stirred in an ice bath for 3 hours and follows by HPLC to monitor completion of reaction. To this solution are added 500 ml of water then 500 ml of ethyl acetate. The aqueous phase extracted twice with ethyl acetate. The organic phases are combined and evaporated half. To the organic phase is added 450 ml of acetic acid and the mixture is evaporated to 300 ml. This procedure is repeated 3 times for a residual of ~470 ml, and the mixture is then heated at 50° C. over night. Toluene (200 ml) is added and evaporated to a small residue (repeat 6 times). To this solution is added 450 ml of ethyl acetate. The organic phase is washed with saturated sodium carbonate, dried over sodium sulfate, filtered and evaporated to dryness. The residue is purified on a pad of silica using 25% ethyl acetate/hexane mixture to give compound (67 g) as a beige powder.

$^1$H NMR (400 MHz, MeOD): δ [ppm] 8.0-7.7 (bs, 1 H), 7.5 (m, 1 H), 7.4-7.1 (bs, 1 H), 5.1-4.9 (m, 1H), 3.8-3.6 (m, 1H), 3.6-3.4 (m, 1 H), 2.6-2.2 (m, 1 H), 2.2-1.8 (m, 3 H), 1.4 (s, 3 H), 1.1 (s, 6 H)

LC/MS: m/z=413.95 (M+H$^+$).

General Procedure 2

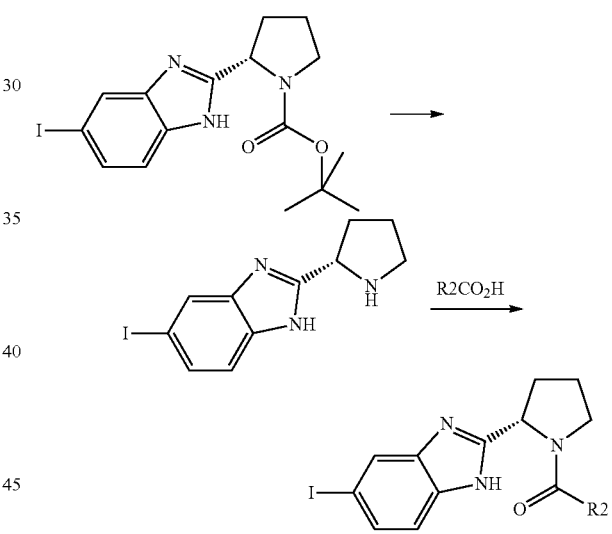

Intermediate 3

{(S)-1-[(S)-2-(5-iodo-1H-benzoimidazol-2-yl)-pyrrolidine-1-carbonyl]-2-methyl-propyl}-carbamic acid methyl ester

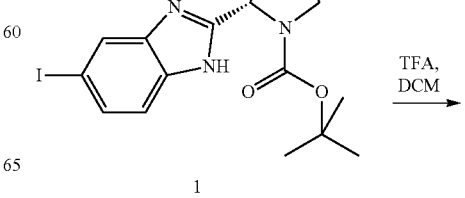

309

-continued

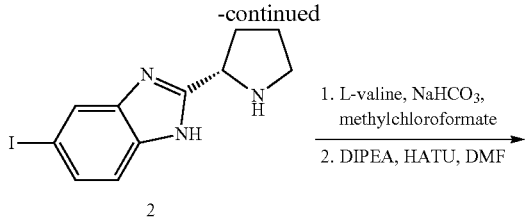

1. L-valine, NaHCO₃, methylchloroformate
2. DIPEA, HATU, DMF

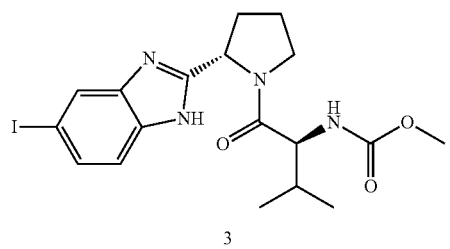

310

Intermediate 7

{(S)-1-[(S)-4,4-Difluoro-2-(5-iodo-1H-benzoimidazol-2-yl)-pyrrolidine-1-carbonyl]-2-methyl-propyl}-carbamic acid methyl ester

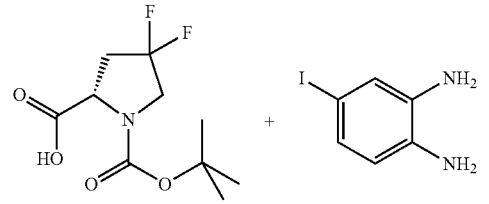

HATU + DIPEA $\xrightarrow{\text{1. DMF}}{\text{2. AcOH}}$

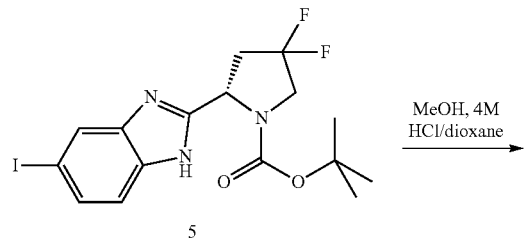

MeOH, 4M HCl/dioxane →

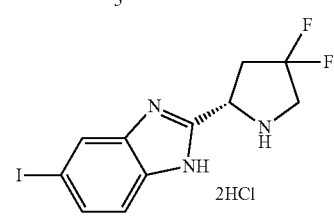

+ HATU + DIPEA $\xrightarrow{\text{1. DMF}}$

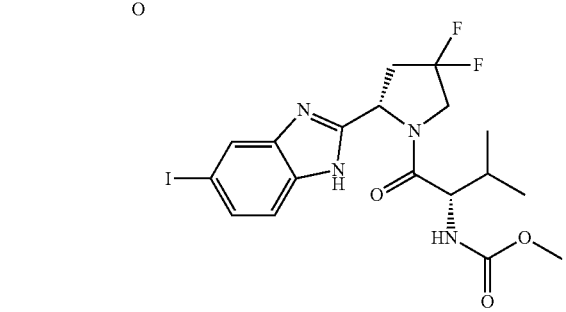

Step 1

To a stirring mixture of compound 1 (20 g, 48 mmol) in DCM (200 mL) at 0° C. is added TFA (200 mL). The reaction mixture is stirred at room temperature for 2 hours and concentrated in vacuum. The residue is dissolved in DCM and saturated aqueous NaHCO₃, the organic layer is washed with saturated aqueous NaHCO₃, dried over sodium sulfate and concentrated in vacuum to afford compound 2 (12 g).

¹H NMR (400 MHz, CDCl₃): δ [ppm] 8.40 (br s, 2H), 7.82 (s, 1H), 7.45 (d, 1H), 7.26 (d, 1H), 4.66 (t, 1H), 3.10 (m, 2H), 2.30 (m, 1H), 2.18 (m, 1H), 1.90 (m, 2H).

Step 2-1

To a mixture of L-valine (220 mg, 1.9 mmol) and NaHCO₃ (482 mg, 5.6 mmol) in H₂O (6 mL) at 0° C. is added dropwise methylchloroformate (0.25 mL, 3.25 mmol). The reaction mixture is stirred for 2 hours at 0-5° C. The mixture is diluted with water and washed with Et₂O. The aqueous layer is acidified with 1N HCl to pH 3 and the product is extracted with EtOAc. The combined organic layers are washed with brine, dried over sodium sulfate and concentrated in vacuum. The residue is triturated with hexanes-Et₂O to give (R)-2-methoxycarbonylamino-3-methyl-butyric acid (248 mg, 75%).

¹H NMR (400 MHz, CDCl₃): δ [ppm] 5.12 (m, 1H), 4.30 (m, 1H), 3.70 (s, 3H), 2.22 (m, 1H), 1.00 (d, 3H), 0.93 (d, 3H).

Step 2-2

To a mixture of (R)-2-methoxycarbonylamino-3-methyl-butyric acid (68 mg, 0.39 mmol) and compound 2 (100 mg, 0.32 mmol) in anhydrous DMF (2 mL) is added DIPEA (0.25 mL, 1.43 mmol) followed by HATU (142 mg, 0.37 mmol) The reaction mixture is stirred for 4 hours at room temperature. Ice is added and the product is extracted with EtOAc. The combined organic layers are washed with brine, dried over sodium sulfate and concentrated in vacuum. The residue is purified by flash column chromatography on silica gel (EtOAc/MeOH 0% to 10%) to give compound 3 (150 mg).

¹H NMR (400 MHz, DMSO) 12.25 (d, 1H), 7.8 (d, 1H), 7.45-7.33 (m, 1H), 7.33-7.15 (m, 2), 5.1-5.2 (m, 1H), 3.9-3.7 (m, 2H), 3.5 (s, 3H), 2.25-2.05 (m, 2H), 2.05-1.8 (m, 3H), 0.8 (m, 7H)

LC/MS: m/z=470.90 (M+H⁺).

HPLC (Method C): $t_R$=7.78 min.

Step 1

Compound 4 (0.493 mg, 1.96 mmol), 4-Iodo-benzene-1,2-diamine (677 mg, 2.94 mmol), HATU (1.12 g, 2.9 mmol) and DIPEA (1.02 mL, 5.88 mmol) are added to 5 mL of DMF. The mixture is stirred overnight at rt and concentrated under reduced pressure. The residue is diluted in 5 mL of AcOH, stirred overnight at 50° C., and concentrated to dryness. The resulting residue is purified by flash chromatography on silica gel (MeOH/DCM, 0 to 5%) to give compound 5 (800 mg).

Step 2

Compound 5 (160 mg) is dissolved in 5 mL of MeOH and the solution is added in 4M HCl/dioxane (1 mL). The mixture is stirred overnight at rt and concentrated under vacuum to dryness to give compound 6.

Step 3

Compound 6 (132 mg, 0.31 mmol), valine (71 mg, 0.41 mmol), HATU (154 mg, 0.41 mmol) and DIPEA (0.22 mL, 1.25 mmol) are added to 5 mL of DMF. The mixture is stirred overnight at rt. The solvent is removed reduced pressure, and the residue is purified by flash chromatography on silica gel (methanol/DCM, 0 to 5%) to give compound 7 (155 mg).

$^1$H NMR (400 MHz, CDCl$_3$): δ [ppm] 10.65 (bs, 1H), 7.30-7.85 (m, 3H), 5.53 (m, 2H), 3.55-4.41 (m, 6H), 2.85 (m, 2H), 1.90 (m, 1H), 0.83-1.42 (m, 6H).

LC/MS: m/z 507.06 (M+H$^+$).

Intermediate 12

(S)-2-Ethyl-5-(5-iodo-1H-benzoimidazol-2-yl)-pyrrolidine-1-carboxylic acid tert-butyl ester

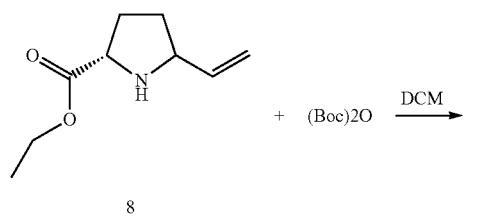

8

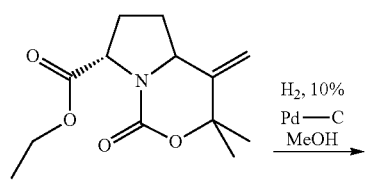

9

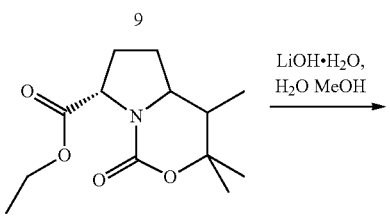

10

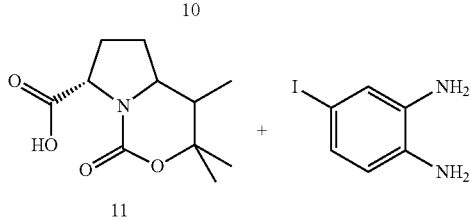

11

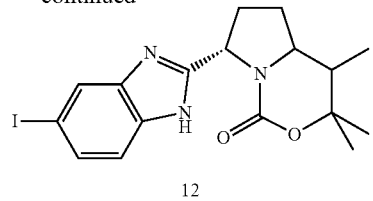

12

Step 1

Compound 8 (500 mg, 2.91 mmol) and (Boc)$_2$O (709 mg, 3.2 mmol) are added to 10 mL of DCM. The mixture is stirred overnight at rt. The mixture is concentrated under reduced pressure and the residue is purified by flash chromatography on silica gel (ethyl acetate/hexane, 0 to 15%) to give compound 9 (650 mg).

Step 2

To a mixture of compound 9 in 10 mL of MeOH is added 10% Pd—C (50 mg). The reaction mixture is stirred 1 hour under hydrogen atmosphere. The mixture is filtered and concentrated to dryness to give compound 10 (650 mg).

Step 3

Compound 10 (650 mg, 2.4 mmol) and LiOH.H$_2$O (302 mg, 7.2 mmol) are added to a solution of 10 mL of MeOH and 2 mL of water. The reaction mixture is stirred overnight at rt and acidified with 2N HCl to pH 2. The mixture is extracted with DCM (3×10 mL), dried over sodium sulfate, and concentrated to dryness to give compound 11.

Step 4

Compound 11 (593 mg, 2 mmol), 4-Iodo-benzene-1,2-diamine (685 mg, 2.4 mmol), HATU (1.12 g, 2.4 mmol) and DIPEA (0.85 mL, 4 mmol) are added to 10 mL of DMF. The mixture is stirred overnight at rt and solvent is removed under reduced pressure. The residue is dissolved in 10 mL of AcOH and stirred overnight at 50° C. The mixture is concentrated under vacuum and the residue is purified by flash chromatography on silica gel (MeOH/DCM, 0 to 5%) to give compound 12 (600 mg).

$^1$H NMR (400 MHz, CD$_3$OD): δ [ppm] 7.30-7.85 (m, 3H), 5.00 (m, 1H), 4.10 (m, 1H), 2.45 (m, 1H), 2.19 (m, 1H), 1.89 (m, 3H), 0.83-1.42 (m, 13H).

LC/MS: m/z 441.85 (M+H$^+$).

Intermediate 13

(S)-tert-Butyl-2-(5-(4,4,5,5-tetramethyl-1,3,2-dioxaborolan-2-yl)-1H-benzo[d]imidazol-2-yl)pyrrolidine-1-carboxylate

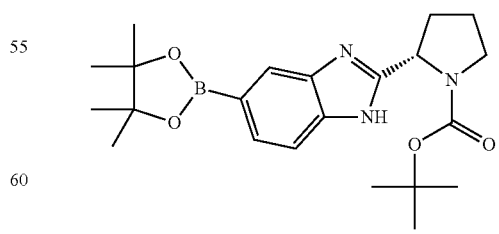

13

To a stirred solution of tert-butyl (2S)-2-(5-iodo-1H-benzimidazol-2-yl)pyrrolidine-1-carboxylate (2.64 g, 6.388 mmol) and 4,4,5,5-tetramethyl-2-(4,4,5,5-tetramethyl-1,3,2-dioxaborolan-2-yl)-1,3,2-dioxaborolane (2.433 g, 9.582 mmol) in DMSO (5 mL) is added potassium acetate (1.880 g, 19.16 mmol) and 1-cyclopenta-1,4-dienyl-diphenyl-phosphane dichloropalladium iron (467.4 mg, 0.6388 mmol). The reaction mixture is stirred 12 hours at 100° C. The reaction is cooled to rt and poured into EtOAc and water (20 ml/20 ml). The organic layer is washed with water (20 ml), brine (20 ml) and dried over $Na_2SO_4$. The solvent is removed and the residue is purified by flash chromatography on silica gel (EtOAc/hexane, 10%-90%) to give compound 13 (1.67 g) as a white solid.

LC/MS: 10-90% MeOH 3/5 min(grad/run): R.T.=3.30 min, m/z=414.24 (M+H$^+$).

Intermediate 14

{(S)-1-[(S)-2-(6-Ethynyl-1H-benzoimidazol-2-yl)-pyrrolidine-1-carbonyl]-2-methyl-propyl}-carbamic acid methyl ester

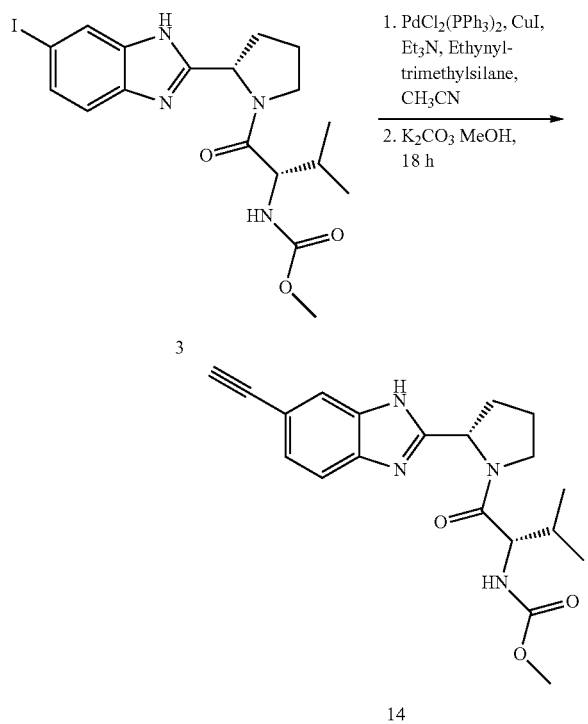

Step 1-1

To a solution of compound 3 (100 mg, 0.213 mmol), Bis(triphenylphosphine)palladium (II) (7.5 mg, 0.011 mmol) and copper(I) iodide (4.0 mg, 0.021 mmol) in 1.0 mL of anhydrous acetonitrile are added Ethynyltrimethylsilane (60 µL, 0.42 mmol), and triethylamine (74 µL, 0.53 mmol). The reaction mixture is stirred for 18 hours at room temperature and 3 hours at 36° C. The mixture is filtrated through a pad of celite using about 50 mL of EtOAc and the filtrate is concentrated under vacuum.

Step 1-2

The crude brown material is diluted in 1.0 mL of MeOH and Potassium carbonate (58 mg, 0.42 mmol) is added. The mixture is stirred at rt for 18 hours. The mixture is diluted with 15 mL of dichloromethane, washed with 10 mL of water, dried over anhydrous sodium sulfate and concentrated under vacuum. The residue is purified by flash chromatography on silica gel (MeOH/EtOAc, 0% to 6%) to give compound 14 (38 mg) as a pale yellow solid.

$^1$H NMR (400 MHz, CDCl$_3$): δ [ppm] 10.69 (br s, 0.65H), 7.88 (br s, 0.35H), 7.64-7.70 (m, 1H), 7.39-7.57 (m, 1H), 7.34 (d, 1H), 5.60 (d, 1H), 5.40 (br d, 1H), 4.33 (dd, 1H), 3.87 (q, 1H), 3.63-3.76 (m, 1H), 3.69 (s, 3H), 3.02-3.04 (br m, 2H), 2.34-2.41 (m, 1H), 2.11-2.28 (m, 2H), 1.92-2.04 (m, 1H), 0.84-0.93 (m, 6H).

LC/MS: m/z=368.97 (M+H$^+$).

Intermediate 15

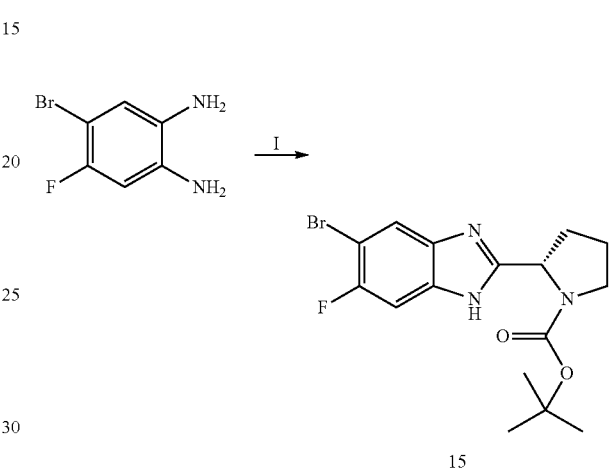

Step 1

To a cold (0-4° C.) solution of 4-bromo-5-fluoro-benzene-1,2-diamine (1 g, 4.877 mmol) and (2S)-1-tert-butoxycarbonylpyrrolidine-2-carboxylic acid (Boc-Pro-OH) (1.050 g, 4.877 mmol) in DMF (9.754 mL) are sequentially added HATU (2.040 g, 5.365 mmol) and 2,4,6-collidine (886.5 mg, 966.7 µL, 7.316 mmol). The reaction mixture is slowly warmed up to rt, stirred overnight, and diluted with water (20 mL). The resulting suspension is extracted with EtOAc (3×25 mL), and the combined extracts are washed with saturated bicarbonate solution, and brine. The organic phase is dried over sodium sulfate, and concentrated under vacuum to give crude amide (2.35 g, contaminated with 2,4,6-collidine). The residue is dissolved in acetic acid (15 mL), stirred at 50° C. for 8 h, and concentrated to dryness. The residue is diluted with ethyl acetate (25 mL), washed with aq. NaHCO$_3$ solution, and brine. The organic phase is dried over sodium sulfate, concentrated under vacuum and the residue is purified by silica gel chromatography (ethyl acetate/hexanes, 40 to 60%) to give 15 (1.74 g) as light brown solid.

$^1$H NMR spectra in CDCl$_3$ and CD$_3$OD showed 1.2:1 and 2:1 ratio of isomeric mixture (exchange of imidazole nitrogen). 19F spectra also showed mixture of two isomers.

$^1$H NMR (400 MHz, CDCl$_3$, 1.2:1 ratio of isomers): Peaks for the major isomer, δ [ppm] 7.86 (d, J=6.2, 1H), 7.45 (d, J=9.2, 1 H), 6.77 (s, 0.35 H), 5.02 (m, 1 H), 3.41 (m, 2 H), 2.2-1.9 (m, 2H), 1.49 (s, 3 H). LC/MS: m/z=303.78 (M–100+H$^+$).

$^{19}$F NMR (400 MHz, CDCl3), δ [ppm] −113.4 (t), −115.7 (t).

Intermediate 16

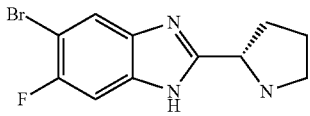

Step 2

To a solution of intermediate 15 (1 g, 2.442 mmol) in DCM (10 mL) at rt is added TFA (5 mL, 64.90 mmol). The reaction mixture is stirred 45 minutes and solvent is removed under vacuum. The residue is neutralized with saturated bicarbonate solution, and the resulting solid is extracted with ethyl acetate (3×15 mL). The combined organic phases are washed with brine, dried over sodium sulfate, and concentrated under vacuum to give 16 (292 mg, 1.028 mmol) as a brown gum.

Intermediate 17

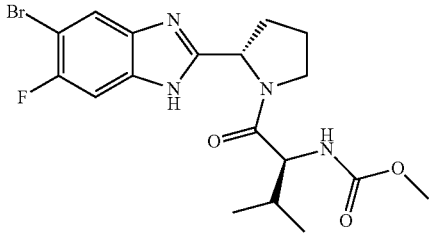

To a cold (0-4° C.) solution of intermediate 16 (298 mg, 1.049 mmol) and (2S)-2-(methoxycarbonylamino)-3-methyl-butanoic acid (202.2 mg, 1.154 mmol) in DMF (5.0 mL) are sequentially added HATU (438.8 mg, 1.154 mmol) and 2,4,6-collidine (279.7 mg, 305.0 μL, 2.308 mmol). The reaction mixture is slowly warmed up to rt during 4.5 hours, diluted with water (10 mL), and extracted with ethyl acetate (3×20 mL). The combined organic phases are washed with aq. 1N HCl, saturated bicarbonate solution, and brine. The organic phase is dried over sodium sulfate, concentrated under vacuum, and purified by silica gel chromatography (MeOH/ethyl acetate, 0 to 10%) to give intermediate 17 (130 mg) as light yellow solid.

$^1$H NMR (400 MHz, CD$_3$OD, 5:1 ratio of rotamers): Peaks for the major isomer, δ [ppm] 7.7 (brs, 1H), 7.33 (d, J=8.4, 1 H), 7.0 (d, J=8.4, 0.5 H), 5.19 (dd, J=7.8, 5.1, 1 H), 4.24-4.18 (m, 1 H), 4.06-3.8 (m, 2 H), 3.63 (s, 3 H), 2.45-1.9 (m, 5 H), 0.895 (d, J=6.8, 3 H), 0.85 (d, J=6.6, 3 H).

LC/MS: m/z=442.87 (M+H$^+$).

Intermediate 19

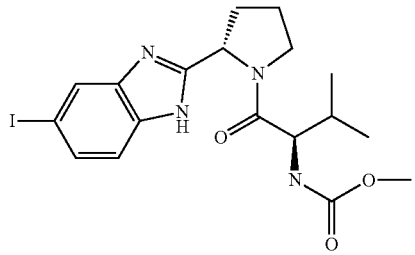

+

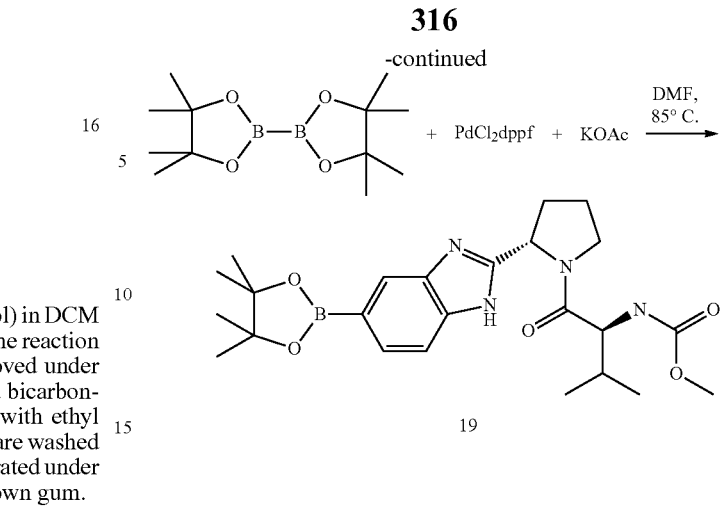

Compound 3 (2.23 g, 4.74 mmol), 4,4,4',4',5,5,5',5'-octamethyl-2,2'; bi(1,3,2-dioxaborolane (3.61 g, 14.22 mmol), PdCl$_2$dppf (193 mg), and potassium acetate (1.53 g, 15.64 mmol) are added to 40 mL of dry DMF. The mixture is purged twice with nitrogen and is stirred overnight at 85° C. After removal of the solvent under reduced pressure, the residue is purified on flash chromatography on silica gel (methanol/DCM, 0 to 5%) to give 1.5 g of Intermediate 19.

$^1$H NMR (400 MHz, CDCl$_3$): δ [ppm] 7.60-7.95 (m, 3H), 5.82 (m, 1H), 5.42 (m, 1H), 4.29 (m, 1H), 3.63-3.75 (m, 6H), 3.04 (m, 1H), 1.91-2.40 (m, 5H), 1.26-1.34 (m, 12H), 0.79-1.03 (m, 6H).

LC/MS: m/z 471.19 (M+H$^+$).

Intermediate 20

{(S)-1-[(S)-2-(6-Azido-1H-benzoimidazol-2-yl)-pyrrolidine-1-carbonyl]-2-methyl-propyl}-carbamic acid methyl ester

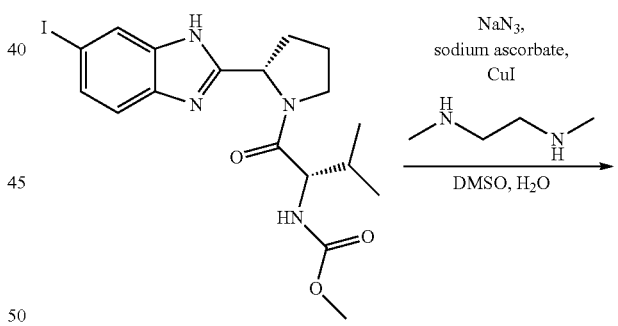

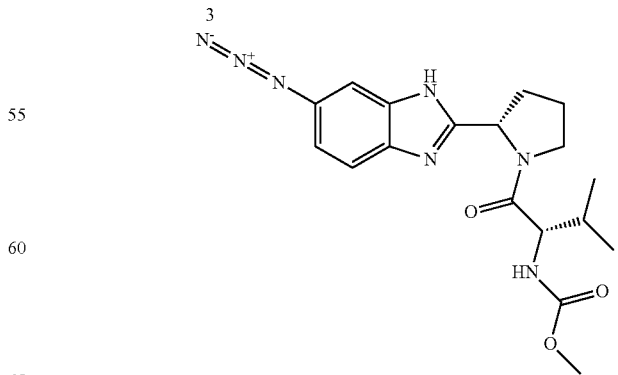

Step 1

Compound 3 (100 mg, 0.213 mmol), sodium azide (21 mg, 0.32 mmol), sodium L-ascorbate (4.2 mg, 0.021 mmol) and copper(I) iodide (8.1 mg, 0.042 mmol) are dissolved in a mixture of 1.0 mL of DMSO and 0.2 mL of water. N,N'-dimethylethane-1,2-diamine is added and the reaction mixture is stirred for one hour at room temperature. A portion of 50 mL of EtOAc is added and the mixture is washed with three portions of 40 mL of water. The organic portion is dried over anhydrous sodium sulfate, concentrated and purified by flash ichromatography on silica gel (MeOH/EtOAc 0% to 10%) to give (50 mg) of intermediate 20 as a yellow gum.

$^1$H NMR (400 MHz, CDCl$_3$): δ [ppm] 10.68 (s, 1H), 7.66 (d, 0.55H), 7.41 (s, 0.55H), 7.21 (d, 0.45H), 6.84-6.90 (m, 1.45H), 5.59 (br d, 1H), 5.38-5.40 (m, 1H), 4.35 (dd, 1H), 3.89 (q, 1H), 3.65-3.78 (m, 1H), 3.70 (s, 3H), 2.99 (br s, 1H), 2.33-2.44 (m, 1H), 2.22-2.28 (m, 1H), 2.07-2.20 (m, 1H), 1.96-2.04 (m, 1H), 0.86-0.93 (m, 6H).

LC/MS: m/z=385.94 (M+H$^+$).

Intermediate 21

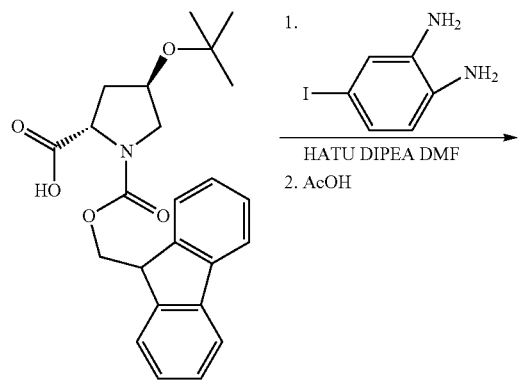

Step 1-1

To a stirring solution of 4-iodobenzene-1,2-diamine (570 mg, 2.43 mmol) and (2S,4R)-4-tert-butoxy-1-(9H-fluoren-9-ylmethoxycarbonyl)pyrrolidine-2-carboxylic acid (998 mg, 2.437 mmol) in DMF (7 mL) are added HATU (1.01 g, 2.68 mmol), and DIPEA (0.85 mL, 4.87 mmol) at 0° C. The reaction mixture is stirred for 3 hours, diluted with water (100 mL) with fast stirring, and a beige solid crashed out in the mixture. The suspension is filtered to give 1.59 g of solid.

Step 1-2

The solid is dissolved in acetic acid, stirred overnight at 50° C., and concentrated to dryness under vacuum. The residue is purified by flash chromatography on silica gel (EtOAc/Hexanes, 30% to 100%) to give intermediate 21 (1.31 g).

Intermediate 22

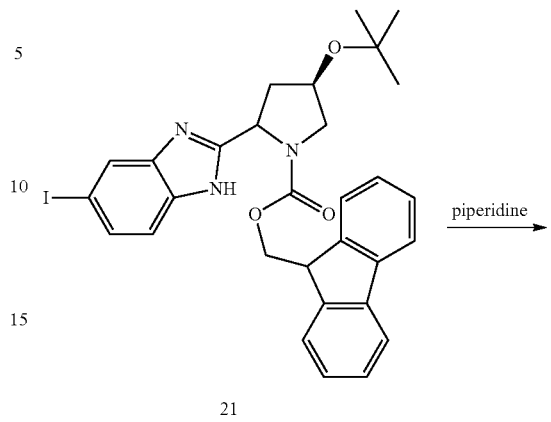

To a solution of intermediate 21 (1.31 g, 2.15 mmol) in DMF (4.75 mL) is added piperidine (1 mL) at 0° C. The reaction mixture is stirred for 30 minutes at rt and is concentrated to dryness. The residue is purified by flash chromatography on silica gel (MeOH/CH$_2$Cl$_2$, 1% to 10%) to give intermediate 22 (701 mg).

Intermediate 23

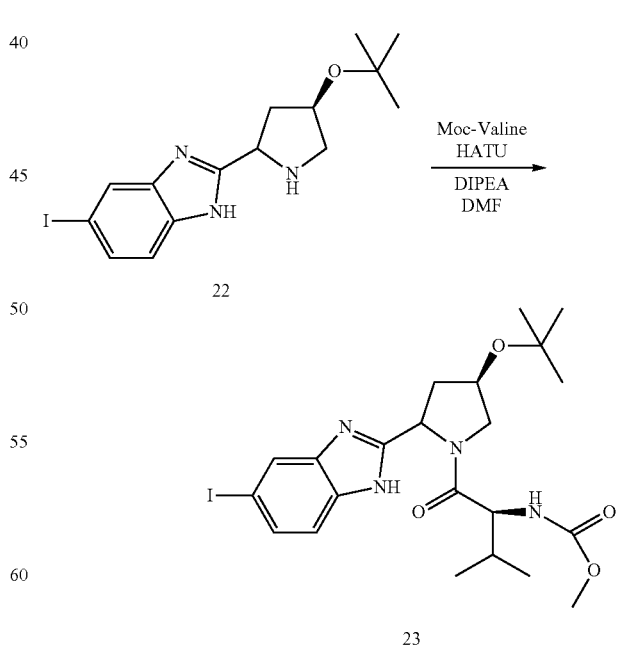

To a solution of intermediate 22 (691 mg, 1.79 mmol) and Moc-Valine (384 mg, 1.97 mmol) in DMF (5 mL) are added HATU (750 mg, 1.97 mmol) and DIPEA (620 uL, 3.58 mmol) at 0° C. The reaction mixture is stirred overnight at rt, diluted with water (100 mL) with fast stirring, and a white solid crashed out from the solution. The solid is filtered to give intermediate 23 (947 mg).

Intermediate 24

(S)-2-(5-Iodo-1H-benzoimidazol-2-yl)-piperidine-1-carboxylic acid benzyl ester

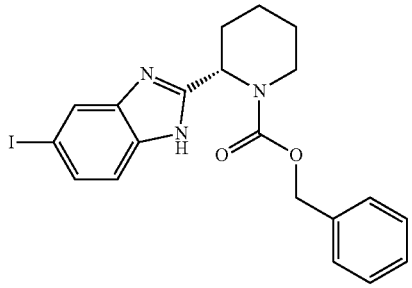 [SMILES: O=C(OCc1ccccc1)N1CCCC[C@H]1c1nc2cc(I)ccc2[nH]1]

To a mixture of 4-iodo-benzene-1,2-diamine (1.5 g, 6.4 mmol) and (S)-N-Cbz-2-piperidine-carboxylic acid (available commercially at Aldrich) (1.7 g, 6.4 mmol) in DMF (20 mL) at 0° C. is added DIPEA (3.3 mL, 19.2 mmol) followed by HATU (3.0 g, 7.69 mmol). The reaction mixture is stirred at 0° C., brought to room temperature and stirred overnight. The reaction mixture is than concentrated in vacuum and the residue is dissolved in AcOH (15 mL) and stirred at 60° C. for 4 hours. The mixture is concentrated in vacuum and the residue is dissolved in EtOAc and washed with water, 1N HCl and brine, dried over sodium sulfate and concentrated in vacuum. The residue is purified by flash column chromatography on silica gel (MeOH/DCM 0% to 20%) to give the title compound (1.4 g, 47%).

$^1$H NMR (400 MHz, CD$_3$OD): δ [ppm] 7.98 (s, 1H), 7.71 (d, 1H), 7.43 (d, 1H), 7.30 (br m, 5H), 5.76 (br s, 1H), 5.20 (m, 2H), 4.18 (br d, 1H), 3.00 (m, 1H), 2.43 (br d, 1H), 2.05 (m, 1H), 1.78 (m, 1H), 1.56 (m, 3H).
LC/MS: m/z=462.00 (M+H$^+$).

Intermediate 25

(S)-2-(5-Iodo-1H-benzoimidazol-2-yl)-piperazine-1,4-dicarboxylic acid 1-benzyl ester 4-tert-butyl ester

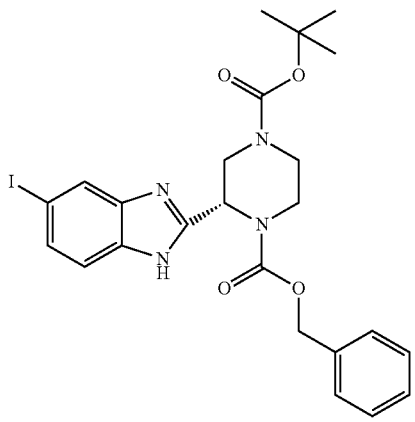 [SMILES: CC(C)(C)OC(=O)N1CCN(C(=O)OCc2ccccc2)[C@H](c2nc3cc(I)ccc3[nH]2)C1]

This intermediate is synthesized as described for Intermediate 24

The (S)-piperazine-1,2,4-tricarboxylic acid 4-tert-butyl ester 1-benzyl ester is commercially available at Astatech.
LC/MS: m/z=563.15 (M+H$^+$).

Intermediate 26

(S)-2-(5-Iodo-1H-benzoimidazol-2-yl)-pyrrolidine-1-carboxylic acid benzyl ester

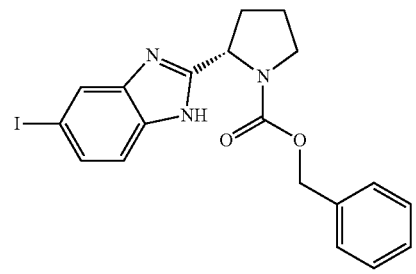 [SMILES: O=C(OCc1ccccc1)N1CCC[C@H]1c1nc2cc(I)ccc2[nH]1]

This intermediate is synthesized as described for Intermediate 24

$^1$H NMR (400 MHz, CDCl$_3$): δ [ppm] 7.48 (d, 1H), 7.40-7.16 (m, 7H), 5.20 (m, 3H), 3.50 (m, 3H), 3.03 (m, 1H), 2.19 (m, 1H), 2.00 (m, 1H).

Intermediate 27

(S)-2-(5-Iodo-1H-benzoimidazol-2-yl)-pyrrolidine-1-carboxylic acid tert-butyl ester

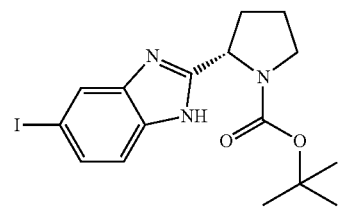 [SMILES: CC(C)(C)OC(=O)N1CCC[C@H]1c1nc2cc(I)ccc2[nH]1]

This intermediate is synthesized as described for Intermediate 24
LC/MS: m/z=413.95 (M$^+$).

General Procedure for Intermediate 28

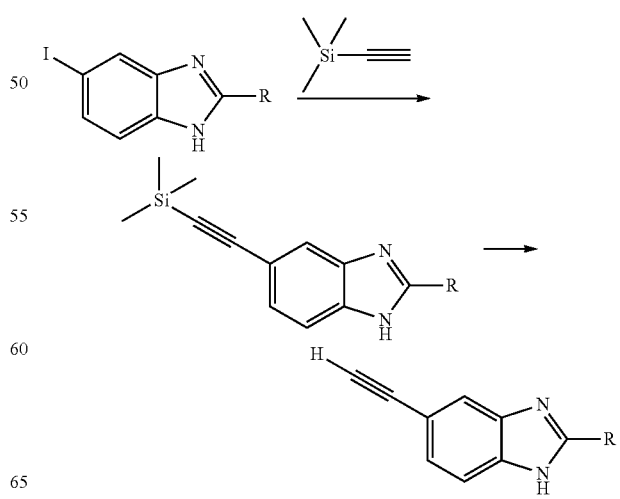

Step 1: The acetylene group is introduced by Sonogoshira coupling using copper and palladium catalysts in solvents such as DMF in presence of base such as TEA or DIPEA.

Step 2: The removal of the silyl group is obtained by a base such as potassium carbonate in MeOH or by using TBAF conditions.

Intermediate 28

(S)-2-(5-Ethynyl-1H-benzoimidazol-2-yl)-piperidine-1-carboxylic acid benzyl ester

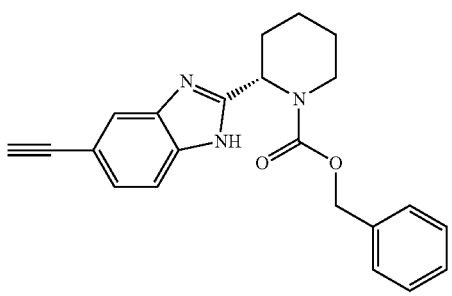 [SMILES: C#Cc1ccc2[nH]c([C@@H]3CCCCN3C(=O)OCc3ccccc3)nc2c1]

Step 1

To a stirring solution of (S)-2-(5-iodo-1H-benzoimidazol-2-yl)-piperidine-1-carboxylic acid benzyl ester (524 mg, 1.135 mmol), CuI (22 mg, 0.114 mmol) and bis(triphenylphosphine)palladium(II)dichloride (40 mg, 0.056 mmol) in DMF (4 mL) is added TEA (0.47 mL, 3.4 mmol) followed by ethynyl-trimethylsilane (0.17 mL, 1.25 mmol). The reaction mixture is stirred at room temperature overnight and concentrated in vacuum to dryness. The residue is purified by flash column chromatography on silica gel (EtOAc/hexanes 5% to 100%) to give a yellow residue which is triturated twice with DCM to afford the title compound (S)-2-(5-trimethylsilanylethynyl-1H-benzoimidazol-2-yl)-piperidine-1-carboxylic acid benzyl ester (340 mg, 70%).

$^1$H NMR (400 MHz, CD$_3$OD): δ [ppm] 7.50-7.00 (m, 8H), 5.42 (d, 1H), 4.94 (m, 2H), 3.98 (br d, 1H), 2.75 (m, 1H), 2.30 (m, 1H), 1.70 (m, 1H), 1.55-1.20 (m, 4H), 0.02 (s, 9H).

LC/MS: m/z=432.18 (M+H$^+$).

Step 2

To a stirring solution of compound (S)-2-(5-trimethylsilanylethynyl-1H-benzoimidazol-2-yl)-piperidine-1-carboxylic acid benzyl ester (85.3 mg, 0.197 mmol) in MeOH (2 mL) is added potassium carbonate (27.3 mg, 0.197 mmol). The reaction mixture is stirred at room temperature for 3 hours and concentrated in vacuum to dryness. The residue obtained is used directly in the next step.

LC/MS: m/z=359.87 (M$^+$).

Intermediate 29

(S)-2-(5-Ethynyl-1H-benzoimidazol-2-yl)-piperazine-1,4-dicarboxylic acid 1-benzyl ester 4-tert-butyl ester

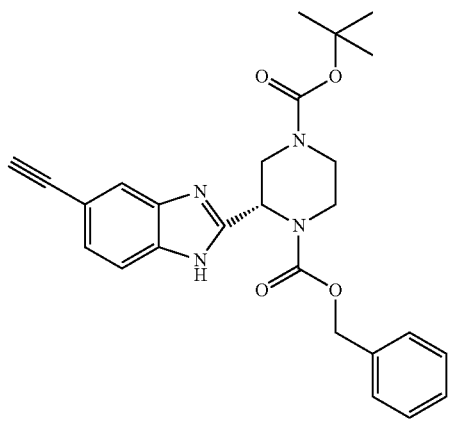 [SMILES: C#Cc1ccc2[nH]c([C@@H]3CN(C(=O)OC(C)(C)C)CCN3C(=O)OCc3ccccc3)nc2c1]

This intermediate is synthesized as described for Intermediate 28

LC/MS: m/z=461.05 (M+H$^+$).

Intermediate 30

(S)-2-(5-Ethynyl-1H-benzoimidazol-2-yl)-pyrrolidine-1-carboxylic acid benzyl ester

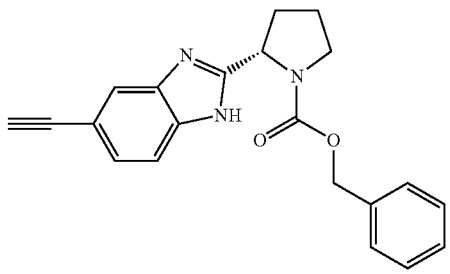 [SMILES: C#Cc1ccc2[nH]c([C@@H]3CCCN3C(=O)OCc3ccccc3)nc2c1]

This intermediate is synthesized as described for Intermediate 28

$^1$H NMR (400 MHz, CDCl$_3$) mixture of rotamers: δ [ppm] 7.90 (m, 1H), 7.74 (m, 1H), 7.45 (m, 1H), 7.38-7.18 (m, 3H), 7.10-6.86 (m, 2H), 5.50 (m, 1H), 5.20-4.90 (m, 2H), 4.00-3.50 (m, 2H), 3.10 (m, 1H), 2.58 (m, 1H), 2.32-1.92 (m, 2H), 1.65 (m, 1H).

Intermediate 31

(S)-2-(5-Ethynyl-1H-benzoimidazol-2-yl)-pyrrolidine-1-carboxylic acid tert-butyl ester

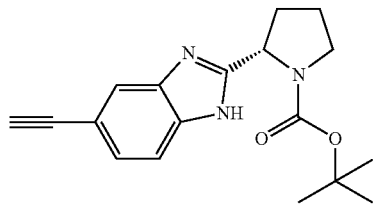 [SMILES: C#Cc1ccc2[nH]c([C@@H]3CCCN3C(=O)OC(C)(C)C)nc2c1]

This intermediate is synthesized as described for Intermediate 28

$^1$H NMR (400 MHz, CDCl$_3$): δ [ppm] 7.78 (m, 1H), 7.59 (m, 1H), 7.40 (d, 1H), 5.18 (d, 1H), 3.48 (m, 2H), 3.08 (m, 2H), 2.24 (m, 2H), 2.03 (m, 1H), 1.50 (s, 9H).

Intermediate 32

{(R)-2-[(S)-2-(5-Ethynyl-1H-benzoimidazol-2-yl)-pyrrolidin-1-yl]-2-oxo-1-phenyl-ethyl}-carbamic acid methyl ester

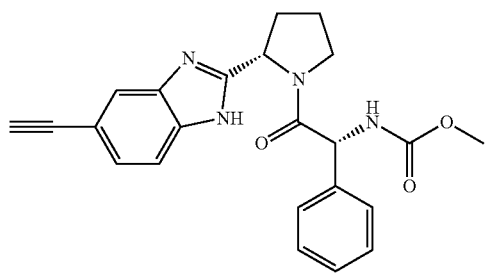 [SMILES: C#Cc1ccc2[nH]c([C@@H]3CCCN3C(=O)[C@H](NC(=O)OC)c3ccccc3)nc2c1]

This intermediate is synthesized as described for Intermediate 28

Intermediate 33

[(S)-2-(5-Ethynyl-1H-benzoimidazol-2-yl)-pyrrolidin-1-yl]-(R)-tetrahydro-furan-2-yl-methanone

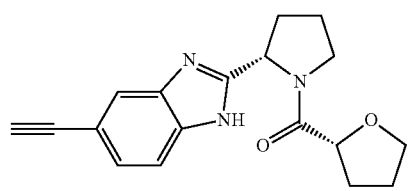 [SMILES: C#Cc1ccc2[nH]c([C@@H]3CCCN3C(=O)[C@H]3CCCO3)nc2c1]

This intermediate is synthesized as described for Intermediate 28

$^1$H NMR (400 MHz, CDCl$_3$): δ [ppm] 7.62 (s, 1H), 7.49 (d, 1H), 7.29 (d, 1H), 5.52 (br m, 1H), 4.75 (br m, 1H), 3.90 (m, 3H), 3.58 (m, 1H), 3.10 (s, 1H), 2.78 (br m, 1H), 2.30 (m, 3H), 2.20-1.80 (m, 4H).

Example 1

((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

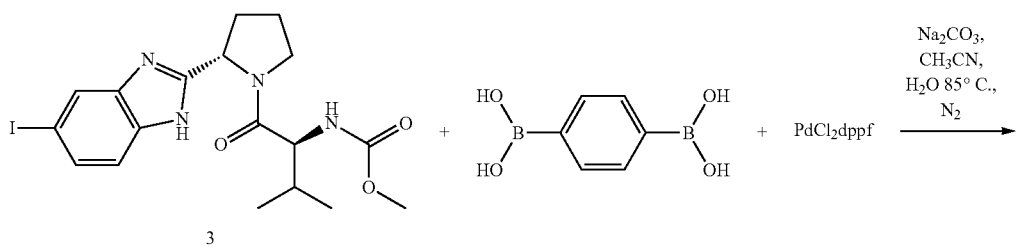

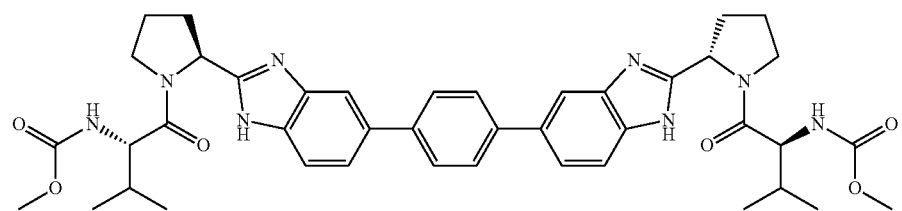

Compound 3 (216 mg, 0.46 mmol), (4-boronophenyl)boronic acid (33 mg, 0.2 mmol), PdCl₂dppf (16 mg, 10 mol %), and Na₂CO₃ (1M, 1 mL) are added to 5 mL of acetonitrile. The mixture is purged with nitrogen and stirred overnight at 85° C. After removal of the solvent under reduced pressure, the residue is purified by flash chromatography on silica gel (methanol/DCM, 0 to 5%). The resulting compound is further purified by reverse phase HPLC to obtain 34 mg of title compound.

$^1$H NMR (400 MHz, CDCl$_3$): δ [ppm] 7.40-7.90 (m, 10H), 5.5 (bs, 2H), 5.42 (m, 2H), 4.34 (m, 2H), 3.63-3.75 (m, 10H), 2.95 (bs, 2H), 2.00-2.45 (m, 10H), 0.90-1.06 (m, 12H).

LC/MS: m/z 763.58 (M+H$^+$).

The following compounds are synthesized as described in Example 1

Example 2

((S)-1-{(S)-2-[5-(3-{2-[(S)-1-((S)-2-Methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

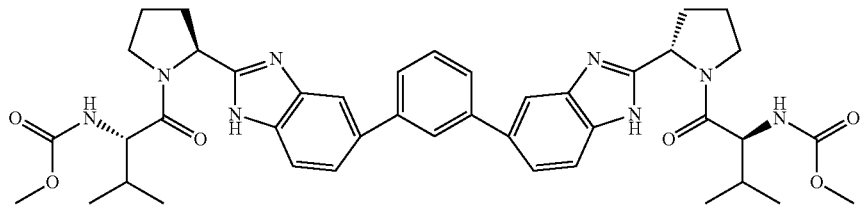 [SMILES: COC(=O)N[C@H](C(=O)N1CCC[C@H]1c1nc2cc(-c3cccc(-c4ccc5[nH]c([C@@H]6CCCN6C(=O)[C@@H](NC(=O)OC)C(C)C)nc5c4)c3)ccc2[nH]1)C(C)C]

$^1$H NMR (400 MHz, CD$_3$OD): δ [ppm] 7.50-7.90 (m, 10H), 5.26 (m, 2H), 4.20 (d, 2H), 4.01 (m, 2H), 3.91 (m, 2H), 3.63 (s, 6H), 2.01-2.41 (m, 10H), 0.85-0.97 (m, 12H).

LC/MS: m/z 763.58 (M+H$^+$).

Example 3

((S)-1-{(S)-2-[5-(4-{2-[(S)-4,4-Difluoro-1-((S)-2-methoxycarbonylamino-3-methyl-butyryl)-pyrrolidin-2-yl]-1H-benzoimidazol-5-yl}-phenyl)-1H-benzoimidazol-2-yl]-4,4-difluoro-pyrrolidine-1-carbonyl}-2-methyl-propyl)-carbamic acid methyl ester

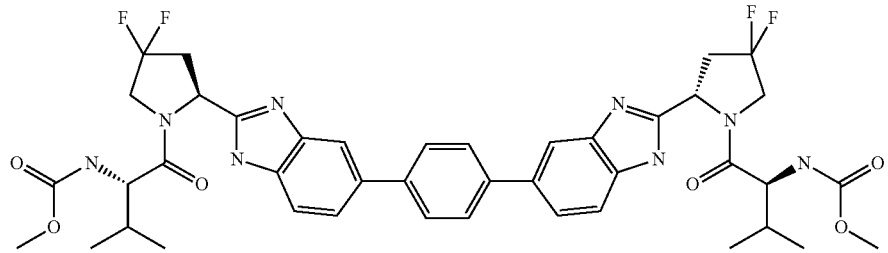 [SMILES: COC(=O)N[C@H](C(=O)N1CC(F)(F)C[C@H]1c1nc2cc(-c3ccc(-c4ccc5[nH]c([C@@H]6CC(F)(F)CN6C(=O)[C@@H](NC(=O)OC)C(C)C)nc5c4)cc3)ccc2[nH]1)C(C)C]

$^1$H NMR (400 MHz, CD$_3$OD): δ [ppm] 7.59-7.90 (m, 10H), 5.48 (m, 2H), 4.58 (m, 2H), 4.09-4.28 (m, 4H), 3.91 (m, 2H), 3.64 (s, 6H), 2.80-3.05 (m, 4H), 1.99 (m, 2H), 0.84-0.99 (m, 12H).

LC/MS: m/z 835.56 (M+H$^+$).

Example 4

[(S)-1-((S)-2-{5-[4-(2-{(S)-1-[(S)-2-(Methoxycarbonyl-methyl-amino)-3-methyl-butyryl]-pyrrolidin-2-yl}-1H-benzoimidazol-5-yl)-phenyl]-1H-benzoimidazol-2-yl}-pyrrolidine-1-carbonyl)-2-methyl-propyl]-methyl-carbamic acid methyl ester

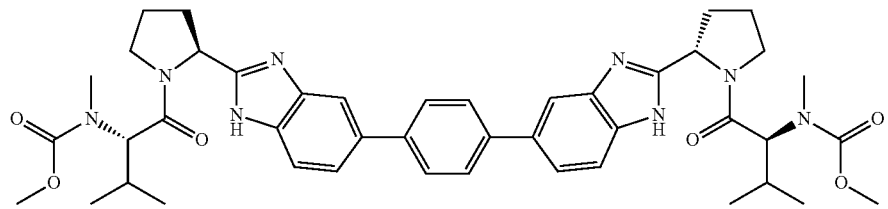 [SMILES: COC(=O)N(C)[C@H](C(=O)N1CCC[C@H]1c1nc2cc(-c3ccc(-c4ccc5[nH]c([C@@H]6CCCN6C(=O)[C@H](C(C)C)N(C)C(=O)OC)nc5c4)cc3)ccc2[nH]1)C(C)C]

δ (400 MHz, CD$_3$OD) δ [ppm] 7.56-7.90 (m, 10H), 5.25-5.55 (m, 2H), 4.45-4.67 (m, 2H), 4.34 (m, 2H), 3.63-3.95 (m, 10H), 2.85 (m, 6H), 1.90-2.45 (m, 10H), 0.73-0.96 (m, 12H). LC/MS: m/z 791.65 (M+H$^+$).

Example 5

((S)-1-{(S)-2-[5-(2-Cyano-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester $^1$H NMR (400 MHz, CD$_3$OD): δ [ppm] 7.45-8.09 (m, 9H), 5.30 (m, 2H), 4.34 (d, 2H), 3.91-4.02 (m, 4H), 3.64 (s, 6H), 2.03-2.40 (m, 10H), 0.86-0.98 (m, 12H).

LC/MS: m/z 788.64 (M+H$^+$).

The following compounds are synthesized as described in Example 5

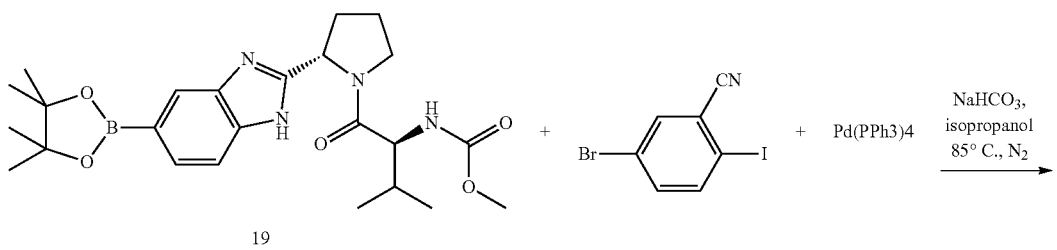

19

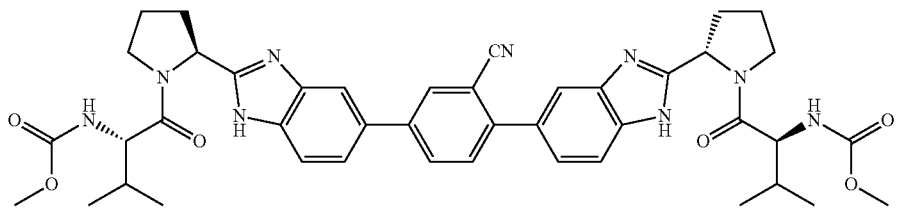

Intermediate 19 (103 mg, 0.22 mmol), 5-bromo-2-iodo-benzonitrile (0.1 mmol, 0.1 mmol), 1M aq NaHCO$_3$ solution (0.5 mL, 0.5 mmol), and Pd(PPh$_3$)$_4$ (11.5 mg, 10 mol %) are suspended into 2.5 mL of isopropanol in a microwave vial. The mixture is purged with nitrogen, heated to 85° C., and stirred overnight. The mixture is concentrated under vacuum and the residue is purified by flash chromatography on silica gel (methanol/DCM, 0 to 6%) to give a white solid. This solid is further purified on reverse phase HPLC to give title compound (9.3 mg).

Example 6

((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyridin-2-yl)-1H-benzoimidazol-2-yl]-pyrrolidine-1-carbonyl}-2-methyl-propyl)-carbamic acid methyl ester

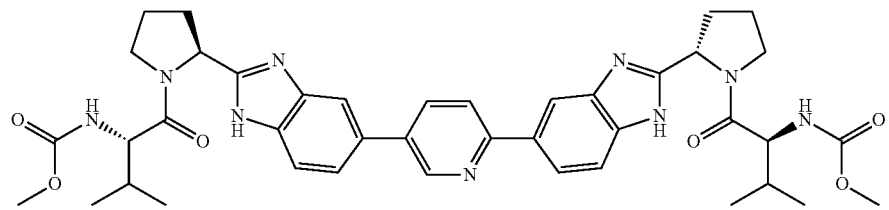 [SMILES: COC(=O)N[C@H](C(=O)N1CCC[C@H]1c1nc2cc(-c3ccc(-c4ccc5[nH]c([C@@H]6CCCN6C(=O)[C@@H](NC(=O)OC)C(C)C)nc5c4)nc3)ccc2[nH]1)C(C)C]

¹H NMR (400 MHz, CD₃OD): δ [ppm] 7.57-8.87 (m, 9H), 5.27 (m, 2H), 4.25 (d, 2H), 3.91-4.02 (m, 4H), 3.64 (s, 6H), 2.03-2.40 (m, 10H), 0.86-0.98 (m, 12H).

LC/MS: m/z 764.65 (M+H⁺).

Example 7

((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2-methyl-phenyl)-1H-benzoimidazol-2-yl]-pyrrolidine-1-carbonyl}-2-methyl-propyl)-carbamic acid methyl ester

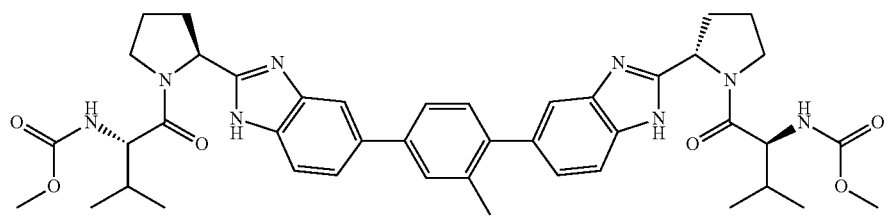 [SMILES: COC(=O)N[C@H](C(=O)N1CCC[C@H]1c1nc2cc(-c3ccc(-c4ccc5[nH]c([C@@H]6CCCN6C(=O)[C@@H](NC(=O)OC)C(C)C)nc5c4)c(C)c3)ccc2[nH]1)C(C)C]

¹H NMR (400 MHz, CD₃OD): δ [ppm] 7.21-7.54 (m, 9H), 5.27 (m, 2H), 4.25 (d, 2H), 3.91-4.02 (m, 4H), 3.64 (s, 6H), 2.03-2.40 (m, 10H), 0.86-0.98 (m, 12H).
LC/MS: m/z 777.60 (M+H⁺).

Example 8

((S)-1-{(S)-2-[5-(2-Methoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

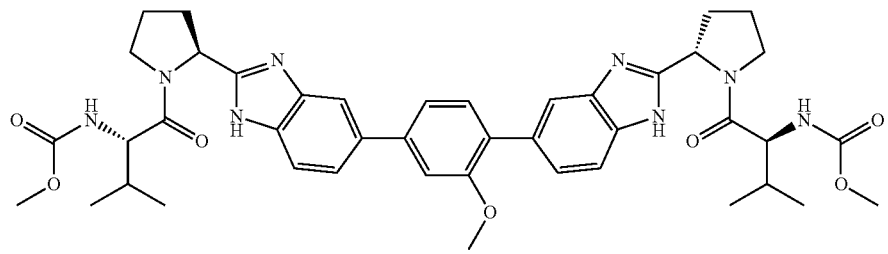 [SMILES: COC(=O)N[C@H](C(=O)N1CCC[C@H]1c1nc2cc(-c3ccc(-c4ccc5[nH]c([C@@H]6CCCN6C(=O)[C@@H](NC(=O)OC)C(C)C)nc5c4)c(OC)c3)ccc2[nH]1)C(C)C]

¹H NMR (400 MHz, CD₃OD): δ [ppm] 7.28-7.80 (m, 9H), 5.27 (m, 2H), 4.25 (d, 2H), 3.86-4.10 (m, 7H), 3.64 (s, 6H), 2.03-2.40 (m, 10H), 0.86-0.98 (m, 12H).
LC/MS: m/z 793.58 (M+H⁺).

Example 9

((S)-1-{(S)-2-[5-(2-Fluoro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

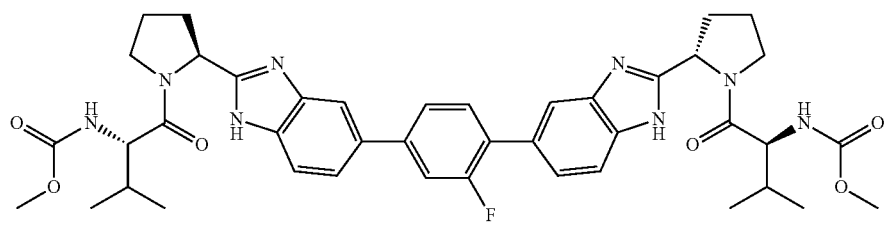 [SMILES: COC(=O)N[C@H](C(=O)N1CCC[C@H]1c1nc2cc(-c3ccc(-c4ccc5[nH]c([C@@H]6CCCN6C(=O)[C@@H](NC(=O)OC)C(C)C)nc5c4)c(F)c3)ccc2[nH]1)C(C)C]

¹H NMR (400 MHz, CD₃OD): δ [ppm] 7.46-7.80 (m, 9H), 5.27 (m, 2H), 4.25 (d, 2H), 3.90-4.10 (m, 4H), 3.64 (s, 6H), 2.03-2.40 (m, 10H), 0.86-0.98 (m, 12H).

LC/MS: m/z 781.56 (M+H⁺).

Example 10

((S)-1-{(S)-2-[5-(2-Chloro-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

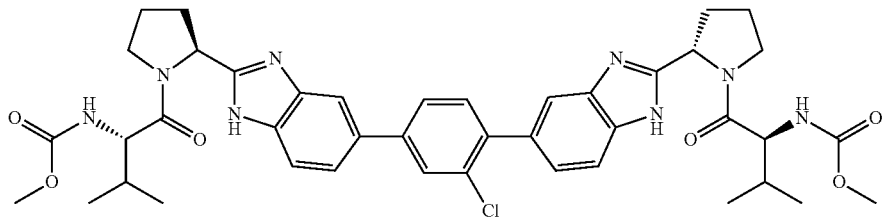 [SMILES: COC(=O)N[C@H](C(=O)N1CCC[C@H]1c1nc2cc(-c3ccc(-c4ccc5[nH]c([C@@H]6CCCN6C(=O)[C@@H](NC(=O)OC)C(C)C)nc5c4)c(Cl)c3)ccc2[nH]1)C(C)C]

To a mixture of Intermediate 19 (135 mg, 0.24 mmol), 2,5-diiodo-chlorobenzene (39 mg, 0.10 mmol) and Pd(PPh₃)₄ (12.4 mg, 0.010 mmol) in 2.5 ml of isopropanol is added 0.53 ml of 1M aq NaHCO₃ solution. This mixture is heated under microwave at 150° C. for 300 seconds and concentrated under vacuum. The residue is purified by flash chromatography on silica gel (MeOH/CH₂Cl₂, 0% to 6%), and further purified by reverse phase HPLC using a gradient of acetonitrile/water to give title compound (18.3 mg)

¹H NMR (400 MHz, CD₃OD): δ [ppm] 7.80-7.30 (m, 9H), 5.28 (dd, 2H), 4.24 (d, 2H), 4.1-3.85 (m, 4H), 3.64 (s, 6H), 2.46-2.00 (m, 10H), 0.90 (d, 6H), 0.88 (d, 6H).

LC/MS: m/z=797.5 (M+H⁺).

The following compounds are synthesized as described in Example 10

Example 11

((S)-1-{(S)-2-[5-(2-Cyano-6-{2-[(S)-1-((S)-2-methoxycarbonylamino-3-methyl-butyryl)-pyrrolidin-2-yl]-1H-benzoimidazol-5-yl}-pyridin-3-yl)-1H-benzoimidazol-2-yl]-pyrrolidine-1-carbonyl}-2-methyl-propyl)-carbamic acid methyl ester ¹H NMR (400 MHz, CD₃OD): δ [ppm] 8.62 (d, 2H), 7.64 (d, 2H), 7.45-6.94 (m, 4H), 5.10 (m, 2H), 4.18 (d, 2H), 3.90-3.75 (m, 8H), 3.58 (s, 6H), 2.40-1.80 (m, 10H), 1.80-1.60 (m, 12H).

LC/MS: m/z=789.6 (M+H⁺).

Example 12

(S)-1-{(S)-2-[5-(2,5-Dimethoxy-4-{2-[(S)-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester $^1$H NMR (400 MHz, CD$_3$OD): δ [ppm] 8.75-7.30 (m, 6H), 6.96 (s, 2H), 5.20 (dd, 2H), 4.16 (d, 2H), 4.00-3.80 (m, 4H), 3.68 (s, 6H), 3.56 (s, 6H), 2.40-1.90 (m, 10H), 0.84 (d, 6H), 0.80 (d, 6H).

LC/MS: m/z=823.6 (M+H$^+$).

Example 13

((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,3-dimethyl-phenyl)-1H-benzoimidazol-2-yl]-pyrrolidine-1-carbonyl}-2-methyl-propyl)-carbamic acid methyl ester

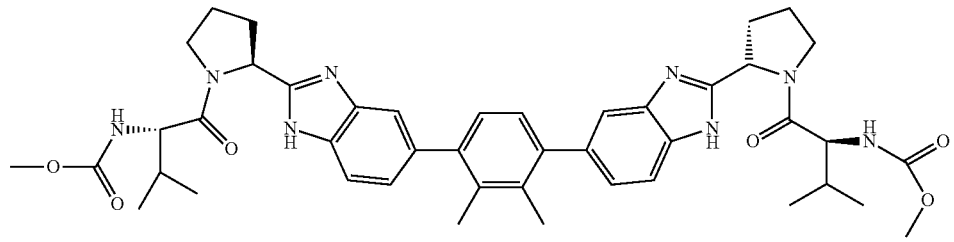

To a mixture of Intermediate 19 (60 mg, 0.12 mmol), 1,4-dibromo-2,3-dimethyl-benzene (14.6 mg, 0.055 mmol) and PdCl$_2$dppf-DCM (4.5 mg, 0.0055 mmol) in 0.5 ml of 1,2-dimethoxyethane is added 0.25 ml of a 2M aq Na$_2$CO$_3$ solution. This mixture is heated under microwave at 150° C. for 20 minutes. The brown biphasic solution is diluted with EtOAc, washed by H$_2$O and brine. The organic phase is dried over sodium sulfate, filtered and concentrated under vacuum. The residue is purified by flash chromatography on silica gel (MeOH/DCM, 2% to 30%) to give title compound (19 mg) of a beige powder.

$^1$H NMR (400 MHz, CD$_3$OD): δ [ppm] 7.57-7.36 (m, 4H), 7.17-7.15 (d, 2H), 7.08 (s, 2H), 5.27 (m, 2H), 4.24 (d, 2H), 4.1-3.99 (m, 2H), 3.93-3.91 (m, 2H), 3.64 (s, 6H), 2.46-2.23 (m, 5H), 2.19 (s, 6H), 2.13-2.028 (m, 5H), 0.96-0.92 (d, 6H), 0.88-0.86 (d, 6H).

LC/MS: m/z=791.6 (M+H$^+$).

The following compounds are synthesized as described in Example 13

Example 14

((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-dimethyl-phenyl)-1H-benzoimidazol-2-yl]-pyrrolidine-1-carbonyl}-2-methyl-propyl)-carbamic acid methyl ester

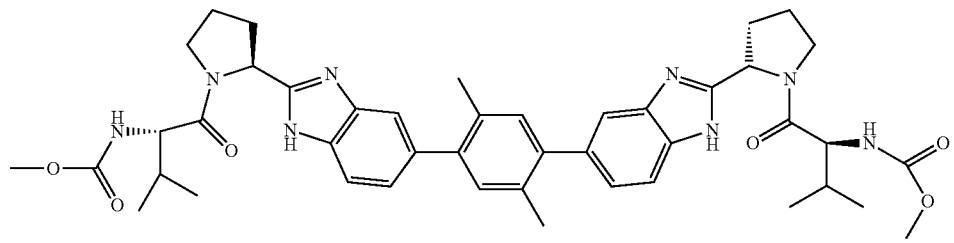

$^1$H NMR (400 MHz, CD$_3$OD): δ [ppm] 7.65-7.39 (m, 6H), 7.19 (d, 1H), 7.12 (s, 1H), 5.27 (m, 2H), 4.24 (d, 2H), 4.1-3.9 (m, 2H), 3.93-3.89 (m, 2H), 3.64 (s, 6H), 2.46-2.25 (m, 5H), 2.22 (s, 6H), 2.15-2.011 (m, 5H), 0.96-0.92 (d, 6H), 0.88-0.86 (d, 6H).

LC/MS: m/z=791.6 (M+H$^+$).

Example 15

((S)-1-{(S)-2-[5-(5-{2-[(S)-1-((S)-2-Methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester

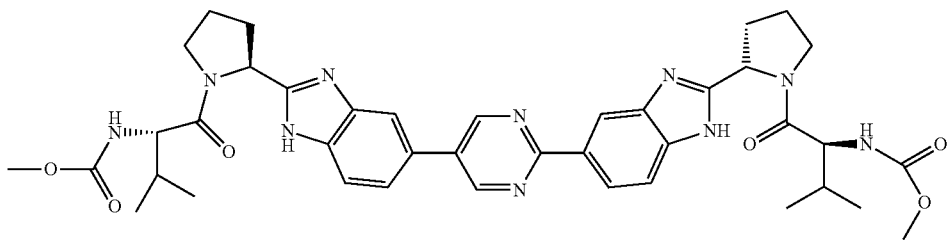

$^1$H NMR (400 MHz, CD$_3$OD): δ [ppm] 9.10 (d, 2H), 8.71-8.38 (m, 3H), 7.91-7.60 (m, 3H), 5.25 (m, 2H), 4.25 (dd, 2H), 4.04-4.02 (m, 2H), 3.93-3.88 (m, 2H), 3.64 (s, 6H), 2.68-1.99 (m, 10H), 0.92 (d, 6H), 0.87 (d, 6H).

LC/MS: m/z=765.6 (M+H$^+$).

Example 16

(2S,2'S)-tert-butyl-2,2'-(5,5'-(thiophene-2,5-diyl)bis(1H-benzo[d]imidazole-5,2-diyl))dipyrrolidine-1-carboxylate

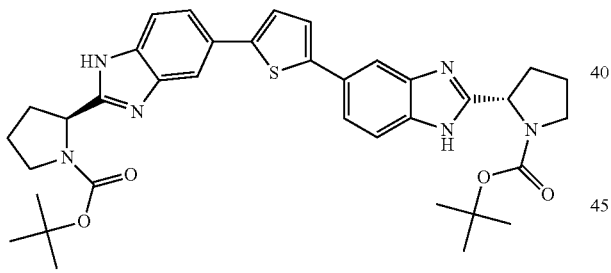

To a solution of (S)-tert-Butyl-2-(5-(4,4,5,5-tetramethyl-1,3,2-dioxaborolan-2-yl)-1H-benzo[d]imidazol-2-yl)pyrrolidine-1-carboxylate (322 mg, 0.7791 mmol) in DME (6 ml) is added 2,5-dibromothiophene (94.26 mg, 43.90 μL, 0.3896 mmol), Tetrakis(triphenylphosphane) palladium (0) (180.0 mg, 0.1558 mmol) and 2M aq Na$_2$CO$_3$ (1.168 mL, 2.337 mmol). The reaction is purged with nitrogen for several minutes and sealed in a reaction tube. The reaction is stirred overnight at 90° C. The reaction is cooled to room temperature and the mixture is extracted with EtOAc (5 ml×3). The combined organic layer is dried over sodium sulfate and concentrated. The crude is purified over silica gel to afford 325 mg of desired title product.

LC/MS: 10-90% MeOH 3/5 min(grad/run): R.T.=3.16 min, M+1=655.63

Example 17

Dimethyl-(2S,2'S)-1,1'-((2S,2'S)-2,2'-(5,5'-(thiophene-2,5-diyl)bis(1H-benzo[d]imidazole-5,2-diyl))bis(pyrrolidine-2,1-diyl))bis(3-methyl-1-oxobutane-2,1-diyl)dicarbamate tert-butyl-(2S)-2-[5-[5-[2-[(2S)-1-tert-butoxycarbonylpyrrolidin-2-yl]-1H-benzimidazol-5-yl]-2-thienyl]-1H-benzimidazol-2-yl]pyrrolidine-1-carboxylate (205 mg, 0.3131 mmol) is dissolved in DCM (10 mL) and HCl 4 M in dioxane (2.348 mL, 9.393 mmol) is added into the solution. The reaction is stirred at room temperature for 30 minutes and the solvent is removed to afforded 185 mg of desired tetra HCl salt. This salt (57 mg, 0.09493 mmol) is dissolved in DMF (2 ml) and 4-methylmorpholine (76.81 mg, 83.49 µL, 0.7594 mmol), (2R)-2-(methoxycarbonylamino)-3-methyl-butanoic acid (83.14 mg, 0.4746 mmol) are added into this solution. The mixture is stirred at room temperature for 30 minutes. Propylphosphonic anhydride (302.0 mg, 0.4746 mmol) is added into the reaction and the reaction is stirred at room temperature for 3 hours. The reaction is diluted with 20 ml EtOAc and washed with water (5 ml×2), saturated aq NaHCO$_3$ and brine. The organic layer is concentrated under vacuum and purified by reverse phase HPLC to give 28.6 mg of bis HCl salt of title compound.

LC/MS: 10-90% MeOH 3/5 min(grad/run): R.T.=3.09 min, M+1=769.85

DMSO-d6: 7.92 (bs, 2H); 7.77 (m, 4H); 7.66 (s, 2H); 7.30 (m, 2H); 5.20 (m, 2H); 4.10 (m, 2H); 3.83 (m, 4H); 2.20-1.88 (m, 6H); 1.70-1.40 (m, 4H); 1.00-0.80 (m, 12H)

Example 18
methyl N-[(1S)-1-[(2S)-2-[5-[4-[2-[(2S)-1-[(2S)-2-(methoxycarbonylamino)-3-methyl-butanoyl]pyrrolidin-2-yl]-1H-benzimidazol-5-yl]-2-thienyl]-1H-benzimidazol-2-yl]pyrrolidine-1-carbonyl]-2-methyl-propyl]carbamate Step 1:

Intermediate 19 (236 mg, 0.454 mmol), 2,4-dibromothiophene (50 mg, 0.2067 mmol) and Pd(PPh$_3$)$_4$ (23.89 mg, 0.02067 mmol) are added in isopropanol (2.000 mL) and 1M aq NaHCO$_3$ (0.5 mL). Then, the mixture is purged with nitrogen and stirred for 5 minutes at 150° C. in the microwave. The reaction mixture is diluted with water (5 mL) and EtOAc (15 mL) and filtered off insoluble materials. Then, the filtrate is washed with water, dried over sodium sulfate, and concentrated under vacuum. The residue is purified by silica gel thin layer chromatography plate (methanol-EtOAc, 1 to 10%) to give title compound (6.0 mg).

$^1$H NMR (400 MHz, DMSO): δ [ppm] 12.5 (s, 1H), 9.44 (s, 1H), 8.25 (d, 1H), 7.80-7.40 (m, 2H), 7.27 (br s, 1H), 7.14 (d, 1H), 6.86 (s, 1H), 4.96 (s, 1H), 3.92 (s, 3H), 3.48 (m, 1H), 2.95-2.61 (m, 3H), 2.04-1.38 (m, 14H), 1.09 (d, 3H), 0.99 (d, 3H)

LC/MS: m/z=769.59 (M+H$^+$).

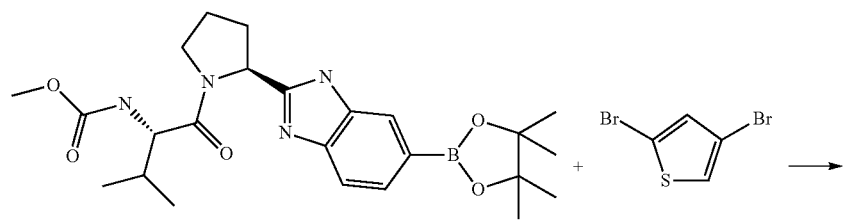

19

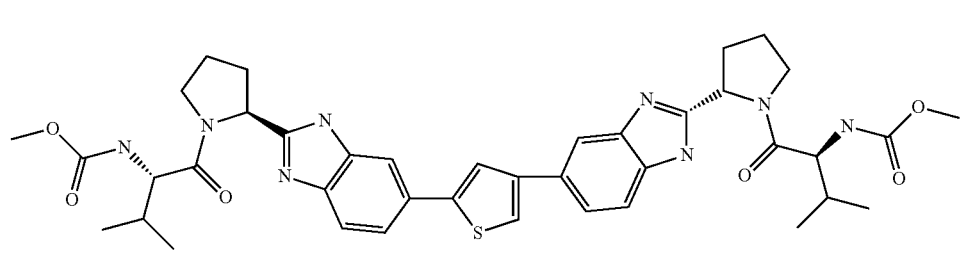

Example 19

((S)-1-{(S)-2-[5-(4-Benzyloxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester

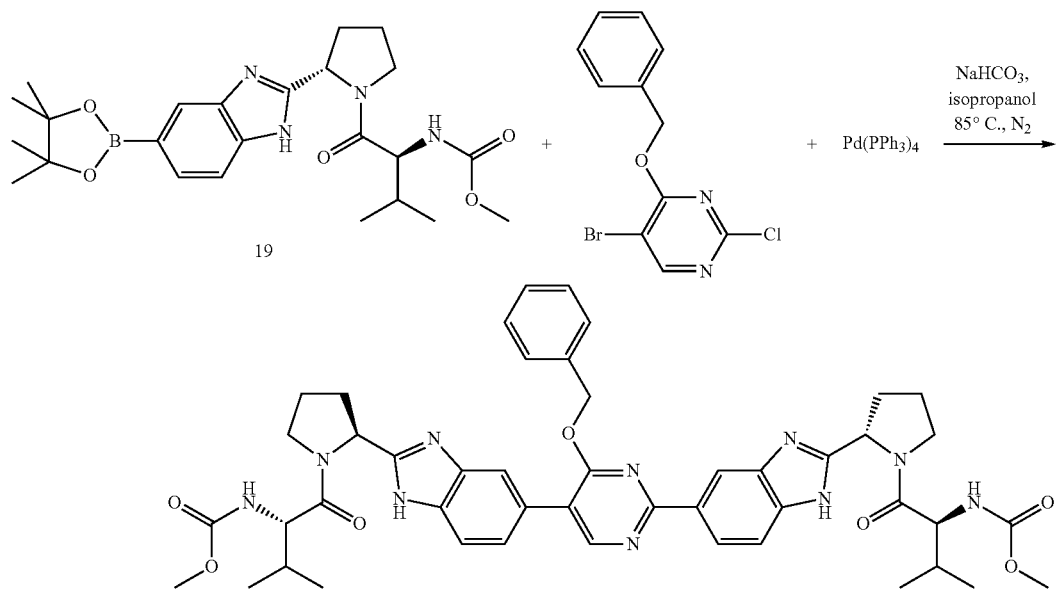

Step 1

Title compound is prepared using a similar procedure as described in Example 5.

$^1$H NMR (400 MHz, CD$_3$OD): δ [ppm] 8.35-8.65 (m, 3H), 7.27-7.90 (m, 9H), 5.69 (s, 2H), 5.27 (m, 2H), 4.25 (m, 2H), 3.90-4.10 (m, 4H), 3.64 (s, 6H), 2.03-2.40 (m, 10H), 0.86-0.98 (m, 12H).

LC/MS: m/z 871.56 (M+H$^+$).

Example 20

((S)-1-{(S)-2-[5-(4-Hydroxy-5-{2-[(S)-1-((S)-2-methoxycarbonylamino-3-methyl-butyryl)-pyrrolidin-2-yl]-1H-benzoimidazol-5-yl}-pyrimidin-2-yl)-1H-benzoimidazol-2-yl]-pyrrolidine-1-carbonyl}-2-methyl-propyl)-carbamic acid methyl ester

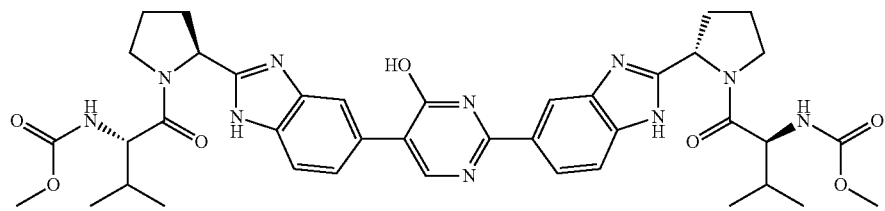 [SMILES: COC(=O)N[C@H](C(=O)N1CCC[C@H]1c1nc2cc(-c3ncc(-c4ccc5[nH]c([C@@H]6CCCN6C(=O)[C@@H](NC(=O)OC)C(C)C)nc5c4)c(O)n3)ccc2[nH]1)C(C)C]

Step 1

To a solution of compound from example 19 (15 mg) in 3 mL of methanol is added Pd—C 10% (5 mg). The reaction is stirred for 30 minutes under hydrogen atmosphere. The reaction mixture is filtered, concentrated to dryness and the residue is purified by reverse phase HPLC to give title compound as a white solid (8 mg).

$^1$H NMR (400 MHz, CD$_3$OD): δ [ppm] 8.24 (s, 2H), 7.95 (s, 2H), 7.54 (m, 3H), 5.27 (m, 2H), 4.25 (d, 2H), 3.90-4.10 (m, 4H), 3.64 (s, 6H), 2.03-2.40 (m, 10H), 0.86-0.98 (m, 12H).

LC/MS: m/z 781.60 (M+H$^+$).

Example 21

((S)-1-{(S)-2-[6-(1-{2-[(S)-1-((S)-2-Methoxycarbonylamino-3-methyl-butyryl)-pyrrolidin-2-yl]-3H-benzoimidazol-5-yl}-1H-[1,2,3]triazol-4-yl)-1H-benzoimidazol-2-yl]-pyrrolidine-1-carbonyl}-2-methyl-propyl)-carbamic acid methyl ester

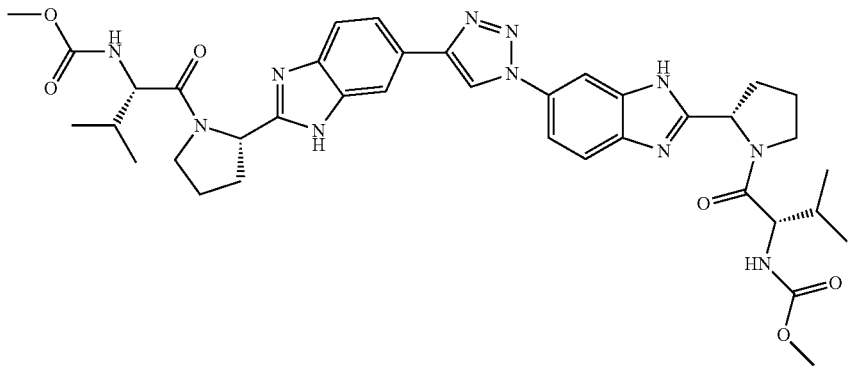 [SMILES: COC(=O)N[C@H](C(=O)N1CCC[C@H]1c1nc2ccc(-c3cn(-c4ccc5nc([C@@H]6CCCN6C(=O)[C@@H](NC(=O)OC)C(C)C)[nH]c5c4)nn3)cc2[nH]1)C(C)C]

DBU (154 µL, 1.03 mmol) is diluted in 0.5 mL of anhydrous toluene. Copper(I) iodide (5.9 mg, 0.031 mmol) is added followed by a solution of {(S)-1-[(S)-2-(6-Ethynyl-1H-benzoimidazol-2-yl)-pyrrolidine-1-carbonyl]-2-methyl-propyl}-carbamic acid methyl ester intermediate 14 (38 mg, 0.10 mmol) in 0.5 mL of toluene and a solution of {(S)-1-[(S)-2-(6-Azido-1H-benzoimidazol-2-yl)-pyrrolidine-1-carbonyl]-2-methyl-propyl}-carbamic acid methyl ester intermediate 20 (50 mg, 0.13 mmol) in 1.0 mL of toluene. The resulting mixture is submitted to microwave for 30 minutes at normal power. The final mixture is filtrated through a pad of celite using DCM. The filtrate is concentrated and purified by flash chromatography on silica gel (MeOH/CH$_2$Cl$_2$, 0% to 15%) The compound is further purified by reverse phase HPLC to give title compound (6.5 mg) as a white solid.

$^1$H NMR (400 MHz, dmso-d$_6$): δ [ppm] 12.56 (br s, 1H), 12.32 (br s, 1H), 9.23 (br s, 1H), 8.05 (br d, 2H), 7.54-7.78 (br m, 4H), 7.34 (dd, 2H), 5.18-5.23 (m, 2H), 4.09 (t, 2H), 3.86 (br s, 4H), 3.54 (s, 6H), 2.24-2.30 (br m, 4H), 1.92-2.04 (br m, 6H), 0.82-0.91 (m, 12H).

LC/MS: m/z=754.57 (M+H$^+$).

Example 22

(2R,2'R,5S,5'S)-tert-butyl 5,5'-(6,6'-(1,4-phenylene)bis(1H-benzo[d]imidazole-6,2-diyl))bis(2-ethylpyrrolidine-1-carboxylate)

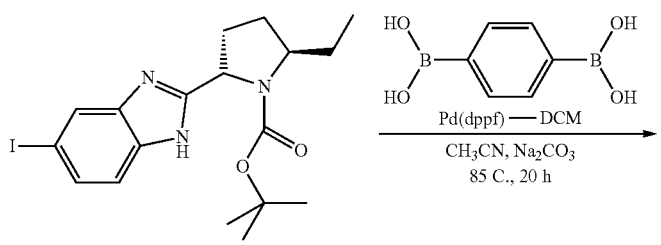

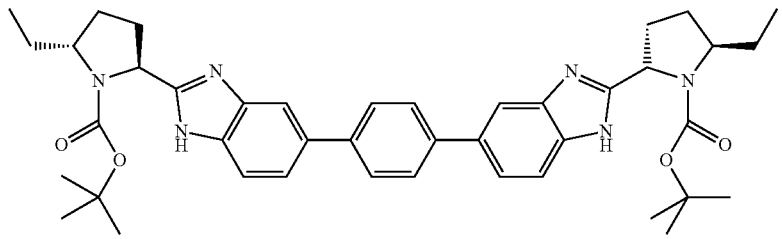

Step 1

To a mixture of compound 12 (61 mg, 0.14 mmol), (4-boronophenyl)boronic acid (9.9 mg, 0.06 mmol) and pd(DPPF)CL$_2$-DCM (4.9 mg, 0.006 mmol) in 0.5 ml of acetonitrile is added 0.3 ml of a 2M aq Na$_2$CO$_3$. This mixture is stirred at 85° C. for 20 hours and diluted with EtOAc. The organic phase is washed with H$_2$O, brine, dried over sodium sulfate, and concentrated under vacuum. The residue is purified by flash chromatography by silica gel (MeOH/CH$_2$Cl$_2$, 1% to 30%) to give title compound (13.7 mg).

LC/MS: m/z=705.6 (M+H$^+$).

Example 23

1,4-bis(2-((2S,5R)-5-ethylpyrrolidin-2-yl)-1H-benzo[d]imidazol-6-yl)benzene

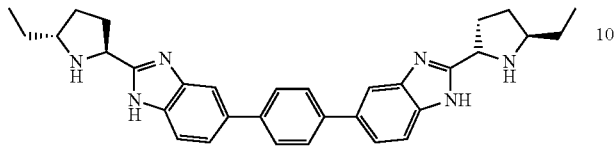

Step 2

To a solution of compound from Example 22 (13 mg, 0.018 mmol) in CH$_2$Cl$_2$ (0.1 ml) is added TFA (50 μl). The reaction mixture is stirred at rt for 3 hours and concentrated to dryness. The residue is diluted with a solution of 2% MeOH in CH$_2$Cl$_2$, and washed by an aqueous saturated NaHCO$_3$ solution. The aqueous phase is extracted twice by CH$_2$Cl$_2$ and the combined organic phases are dried over Na$_2$SO$_4$, filtered and concentrated under vacuum to give title compound (8 mg).
LC/MS: m/z=505.3 (M+H$^+$).

Example 24

((S)-1-{(2R,5S)-2-Ethyl-5-[5-(4-{2-[(2S,5R)-5-ethyl-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

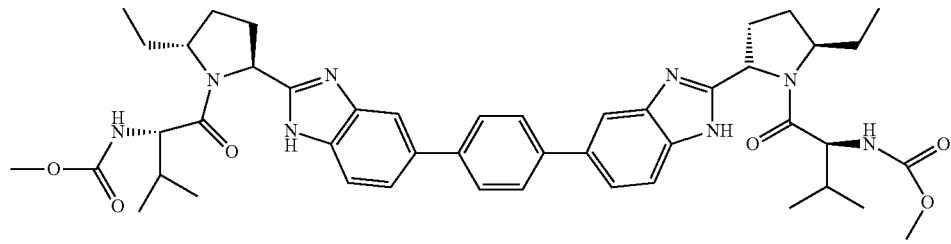

To a solution compound from Example 23 (8 mg, 0.015 mmol), Moc-Valine (4.16 mg, 0.023 mmol), and 2,4,6-collidine (6.2 ul, 0.047 mmol) in DMF (5 mL) is added HATU (9 mg, 0.023 mmol) at 0 C. The reaction mixture is stirred at rt overnight, diluted with EtOAc, and washed with brine. The organic phase is dried over Na$_2$SO$_4$, filtered and concentrated. The residue is purified by reverse phase HPLC to give title compound (4.3 mg).
$^1$H NMR (400 MHz, CD$_3$OD): δ [ppm] 7.71-7.54 (m, 12H), 5.44 (d, 1H), 5.26 (d, 1H), 4.4 (m, 1H), 4.36 (d, 1H), 4.13 (m, 1H), 3.93 (m, 1H), 3.63 (s, 3H), 3.059 (s, 3H), 2.61-1.26 (m, 10H), 0.52-0.75 (m, 22H).
LC/MS: m/z=820.6 (M+H$^+$).

Example 25

((S)-1-{(2S,4R)-4-tert-butoxy-2-[5-(4-{2-[(2S,4R)-4-tert-butoxy-1-((S)-2-methoxycarbonylamino-3-methyl-butyryl)-pyrrolidin-2-yl]-1H-benzoimidazol-5-yl]-phenyl)-1H-benzoimidazol-2-yl]-pyrrolidine-1-carbonyl}-2-methyl-propyl)-carbamic acid methyl ester

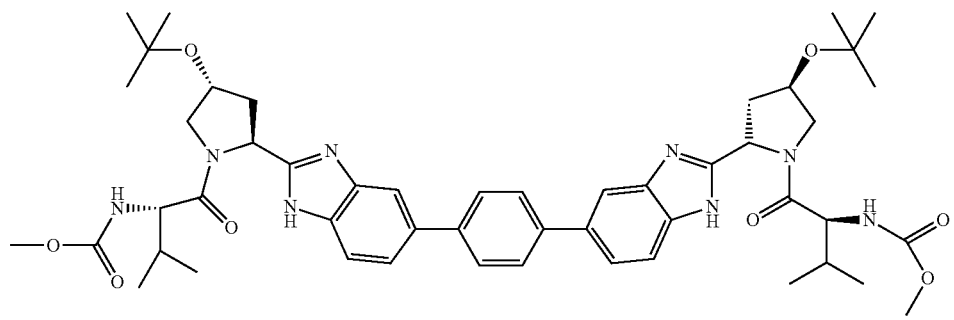

To a mixture of Intermediate 23 (447 mg, 0.82 mmol), (4-boronophenyl)boronic acid (59 mg, 0.35 mmol) and pd(DPPF)CL$_2$-DCM (29 mg, 0.035 mmol) in 3 ml of acetonitrile is added 1.8 ml of a 2M aq Na$_2$CO$_3$. This mixture is stirred 20 hours at 85° C. The resulted solution is diluted with EtOAc, washed by H$_2$O and brine. The organic phase is dried over sodium sulfate, filtered and concentrated. The residue is purified by flash chromatography on silica gel (MeOH/CH$_2$Cl$_2$, 1% to 10%) and further purified by reverse phase HPLC to give title compound (47.5 mg).

$^1$H NMR (400 MHz, CD$_3$OD): δ [ppm] 7.90-7.50 (m, 10H), 5.32 (t, 2H), 4.66 (m, 2H), 4.20 (d, 2H), 4.22 (dd, 2H), 3.88 (dd, 2H), 3.66 (s, 6H), 2.56-2.28 (m, 4H), 2.00 (m, 2H), 1.26 (s, 18H), 0.88 (d, 6H), 0.86 (d, 6H).
LC/MS: m/z=907.6 (M+H$^+$).

Example 26

((S)-1-{(2S,4R)-4-Hydroxy-2-[5-(4-{2-[(2S,4R)-4-hydroxy-1-((S)-2-methoxycarbonylamino-3-methyl-butyryl)-pyrrolidin-2-yl]-1H-benzoimidazol-5-yl}-phenyl)-1H-benzoimidazol-2-yl]-pyrrolidine-1-carbonyl}-2-methyl-propyl)-carbamic acid methyl ester

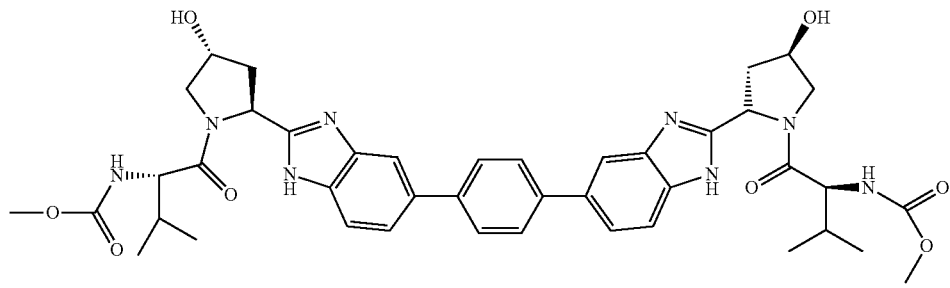

To a solution of compound from example 25 (15 mg, 0.015 mmol) is added TFA (0.3 mL) at 0° C. The reaction mixture is stirred 1 hour at rt, concentrated to dryness, and triturated with DCM (3×) to give title compound (16 mg).

$^1$H NMR (400 MHz, CD$_3$OD): δ [ppm] 7.92 (d, 2H), 7.84 (m, 2H), 7.78 (m, 6H), 5.38 (m, 2H), 4.60 (m, 2H), 4.18 (d, 2H), 3.98 (m, 4H), 3.58 (s, 6H), 2.50 (m, 2H), 2.30 (m, 2H), 1.96 (m, 2H), 0.80 (d, 6H), 0.78 (d, 6H).

LC/MS: m/z=795.6 (M+H$^+$).

Example 27

Dimethyl (2S,2'S)-1,1'-((2S,2'S)-2,2'-(5,5'-(1,4-phenylene)bis(6-fluoro-1H-benzo[d]imidazole-5,2-diyl))bis(pyrrolidine-2,1-diyl))bis(3-methyl-1-oxobutane-2,1-diyl)dicarbamate

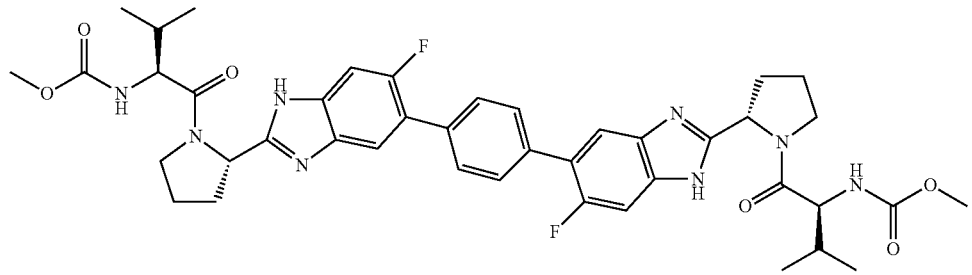

To a solution intermediate 17 (117.2 mg, 0.2655 mmol) and (4-boronophenyl)boronic acid (20 mg, 0.1207 mmol) in acetonitrile (2.5 mL) under nitrogen atmosphere are sequentially added Pd(dppf)Cl2-DCM (9.857 mg, 0.01207 mmol) and sodium bicarbonate (603.5 µL of 1 M, 0.6035 mmol). The resultant suspension is heated in microwave at 150° C. for 6 minutes, concentrated under vacuum, and dissolved in a solution of 10% MeOH in CH$_2$Cl$_2$. The suspension is filtered and the filtrate concentrated under vacuum. The residue is purified by silica gel chromatography (MeOH/ethyl acetate, 0 to 10%) and further purified by reverse phase HPLC to give title compound (48 mg) as white solid.

$^1$H NMR (400 MHz, CD$_3$OD, 5:1 ratio of rotamers): Peaks for the major isomer, δ [ppm] 7.6-7.2 (m, 4 H), 5.25 (dd, J=7.8, 5.1, 1 H), 4.24 (d, J=7.4, 1 H), 4.1-3.8 (m, 2 H), 3.64 (s, 3 H), 2.5-1.9 (m, 5 H), 0.92 (d, J=6.6, 3 H), 0.87 (d, J=6.6, 3 H).

LC/MS: m/z=799.6 (M+H$^+$).

General Procedure for Example 28:

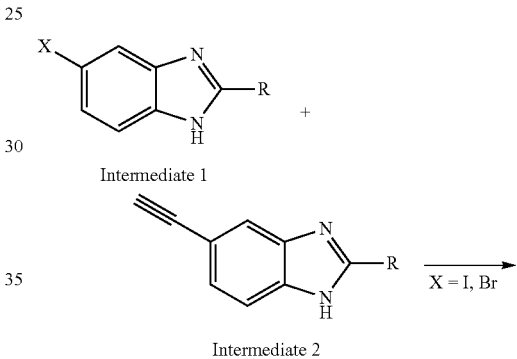

-continued

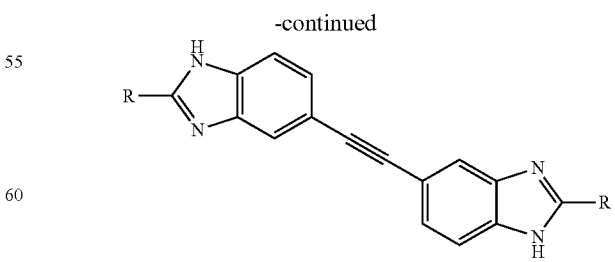

The dimer is formed by Sonogoshira coupling using copper and palladium catalysts in solvents such as DMF in presence of base such as TEA or DIPEA.

Example 28

(S)-2-{5-[2-((S)-1-Benzyloxycarbonyl-piperidin-2-yl)-1H-benzoimidazol-5-ylethynyl]-1H-benzoimidazol-2-yl}-piperazine-1,4-dicarboxylic acid 1-benzyl ester 4-tert-butyl ester

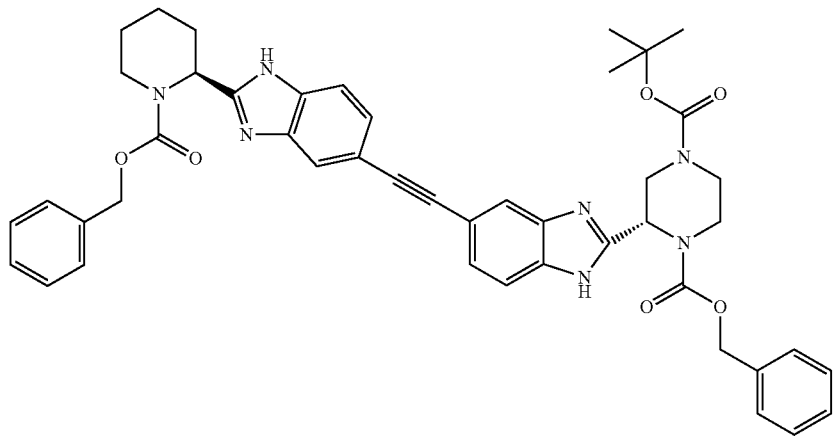 [SMILES: CC(C)(C)OC(=O)N1CCN(C(=O)OCc2ccccc2)[C@H](c2nc3cc(C#Cc4ccc5[nH]c([C@@H]6CCCCN6C(=O)OCc6ccccc6)nc5c4)ccc3[nH]2)C1]

To a stirring solution of (S)-2-(5-ethynyl-1H-benzoimidazol-2-yl)-piperazine-1,4-dicarboxylic acid 1-benzyl ester 4-tert-butyl ester (77 mg, 0.16 mmol), (S)-2-(5-iodo-1H-benzoimidazol-2-yl)-piperidine-1-carboxylic acid benzyl ester (70 mg, 0.15 mmol), CuI (3 mg, 0.015 mmol) and bis(triphenylphosphine)palladium(II)dichloride (10.6 mg, 0.015 mmol) in DMF (2 mL) is added TEA (0.1 mL, 0.76 mmol). The reaction mixture is stirred at room temperature for 2 hours, diluted with EtOAc and water. The mixture is filtered to remove insoluble material and the layers of the filtrate are separated. The organic layer is dried over sodium sulfate and concentrated in vacuum to dryness. The residue is purified by flash column chromatography on silica gel (MeOH/DCM 0% to 20%) and repurified by reverse phase HPLC using a gradient of $CH_3CN$/water to give the title compound (9.4 g, 7%).

LC/MS: m/z=795.27 (M+H$^+$).

HPLC (Method A): $t_R$=10.48 min.

Example 29

(S)-2-{5-[2-((S)-1-Benzyloxycarbonyl-4-tert-butyloxycarbonyl-piperazin-2-yl)-1H-benzoimidazol-5-ylethynyl]-1H-benzoimidazol-2-yl}-piperazine-1,4-dicarboxylic acid 1-benzyl ester 4-tert-butyl ester

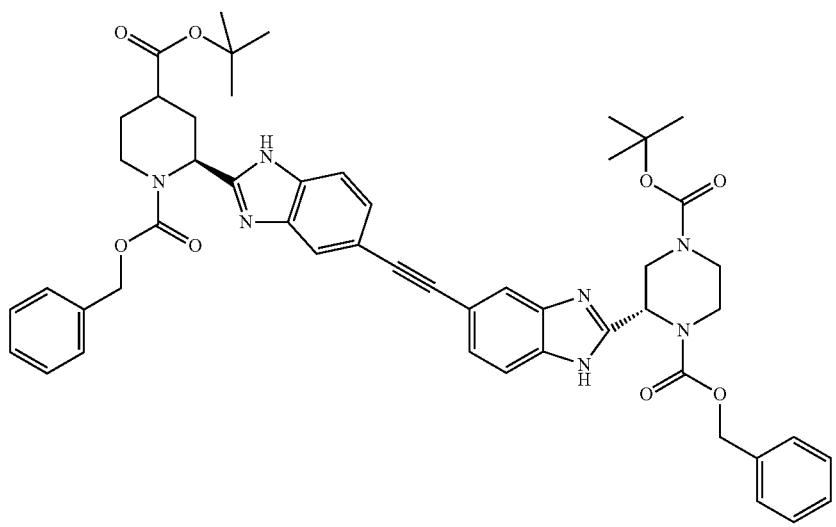 [SMILES: CC(C)(C)OC(=O)C1CCN(C(=O)OCc2ccccc2)[C@H](c2nc3cc(C#Cc4ccc5[nH]c([C@@H]6CN(C(=O)OC(C)(C)C)CCN6C(=O)OCc6ccccc6)nc5c4)ccc3[nH]2)C1]

This compound is prepared as described in example 28

LC/MS: m/z=896.74 (M+H$^+$).

HPLC (Method A): $t_R$=11.95 min.

Example 30

(S)-2-{5-[2-((S)-1-Benzyloxycarbonyl-piperidin-2-yl)-1H-benzoimidazol-5-ylethynyl]-1H-benzoimidazol-2-yl}-piperidine-1-carboxylic acid benzyl ester

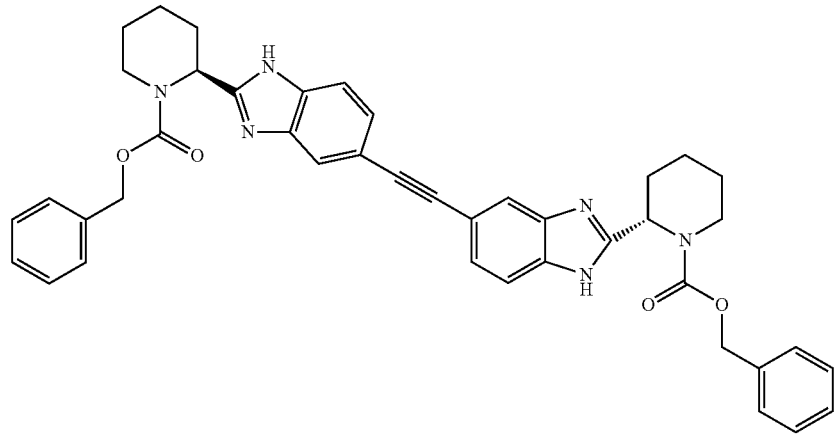 [SMILES: O=C(OCc1ccccc1)N1CCCC[C@H]1c1nc2cc(C#Cc3ccc4[nH]c([C@@H]5CCCCN5C(=O)OCc5ccccc5)nc4c3)ccc2[nH]1]

This compound is prepared as described in example 28
LC/MS: m/z=693.82 (M+H$^+$).
HPLC (Method A): t$_R$=8.85 min.

Example 31

(S)-2-{5-[2-((S)-1-Benzyloxycarbonyl-pyrrolidin-2-yl)-1H-benzoimidazol-5-ylethynyl]-1H-benzoimidazol-2-yl}-pyrrolidine-1-carboxylic acid benzyl ester

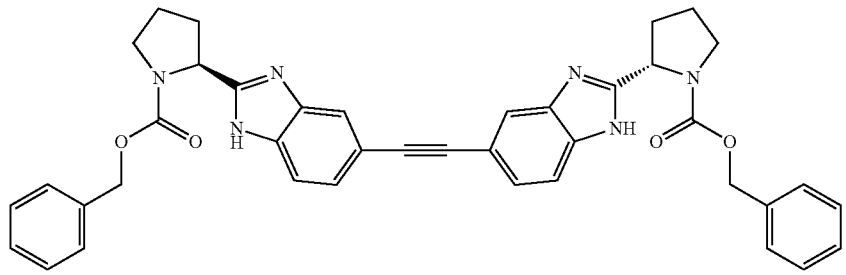 [SMILES: O=C(OCc1ccccc1)N1CCC[C@H]1c1nc2cc(C#Cc3ccc4[nH]c([C@@H]5CCCN5C(=O)OCc5ccccc5)nc4c3)ccc2[nH]1]

This compound is prepared as described in example 28
$^1$H NMR (400 MHz, DMSO-d$_6$): δ [ppm] 7.85 (d, 2H), 7.67 (d x d, 2H), 7.56 (br s, 2H), 7.40-7.27 (m, 4H), 7.10 (t, 2H), 6.97 (t, 2H), 6.82 (t, 2H), 5.19 (m, 2H), 5.08 (m, 2H), 4.85 (m, 2H), 3.68 (m, 2H), 2.54 (m, 2H), 2.40 (m, 2H), 2.10 (m, 2H), 1.95 (m, 4H).
LC/MS: m/z=665.52 (M+H$^+$).

Example 32

[(S)-5-(5-{2-[(S)-1-((R)-tetrahydro-furan-2-carbonyl)-pyrrolidin-2-yl]-1H-benzoimidazol-5-ylethynyl}-1H-benzoimidazol-2-yl)-pyrrolidin-1-yl]-(R)-tetrahydro-furan-2-yl-methanone

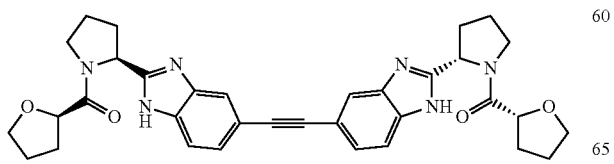

This compound is prepared as described in example 28
$^1$H NMR (400 MHz, DMSO-d$_6$) mixture of rotamers: δ [ppm] 7.91 (br m, 1.52H), 7.81 (br m, 0.48H), 7.72 (m, 1.52H), 7.59 (m, 2H), 7.47 (br m, 0.48H), 5.57 (m, 0.48H), 5.20 (m, 1.52H), 4.62 (br m, 1.52H), 4.25 (m, 0.48H), 3.88 (m, 2H), 3.80-3.30 (m, 8H), 2.33 (m, 2H), 2.10 (m, 6H), 1.97-1.70 (m, 6H).
LC/MS: m/z=593.24 (M+H$^+$).

Example 33

{(R)-2-[(S)-2-(5-{2-[(S)-1-((R)-2-Methoxycarbony-lamino-2-phenyl-acetyl)-pyrrolidin-2-yl]-1H-ben-zoimidazol-5-ylethynyl}-1H-benzoimidazol-2-yl)-pyrrolidin-1-yl]-2-oxo-1-phenyl-ethyl}-carbamic acid methylester

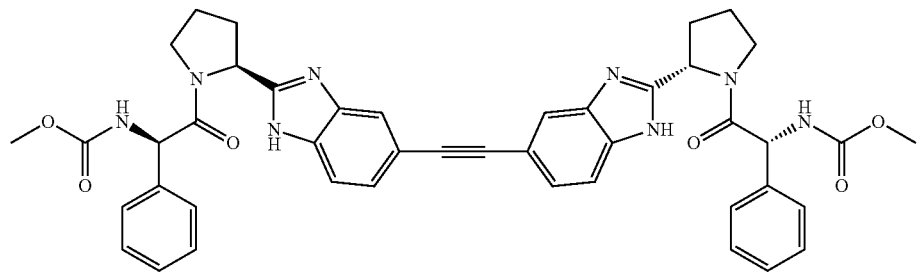

This compound is prepared as described in example 28
$^1$H NMR (400 MHz, DMSO-d$_6$): δ [ppm] 7.87 (br s, 2H), 7.70 (d, 4H), 7.56 (m, 2H), 7.47-7.28 (m, 8H), 6.82 (m, 2H), 5.50 (d, 2H), 5.22 (d, 2H), 3.92 (m, 2H), 3.50 (s, 6H), 3.18 (m, 2H), 2.22 (m, 2H), 2.05 (m, 4H), 1.88 (m, 2H).
LC/MS: m/z=779.38 (M+H$^+$).

Example 34

(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carboxylic acid tert-butyl ester

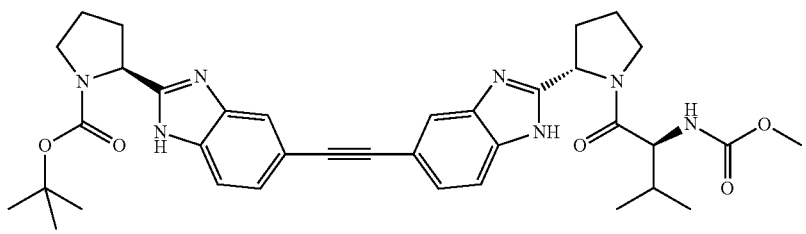 [SMILES: COC(=O)N[C@H](C(=O)N1CCC[C@H]1c1nc2cc(C#Cc3ccc4[nH]c([C@@H]5CCCN5C(=O)OC(C)(C)C)nc4c3)ccc2[nH]1)C(C)C]

This compound is prepared as described in example 28
LC/MS: m/z=654.31 (M+H$^+$).
HPLC (Method B): t$_R$=13.94 min.

General Procedure for Example 35 and 36

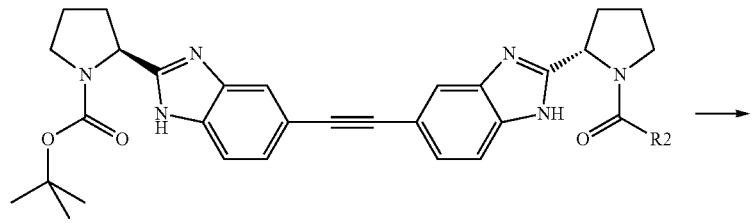

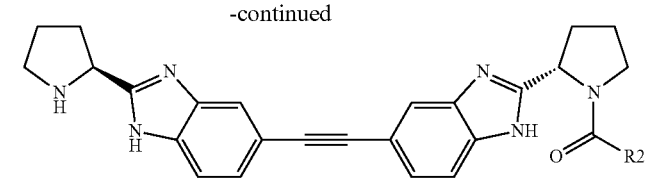

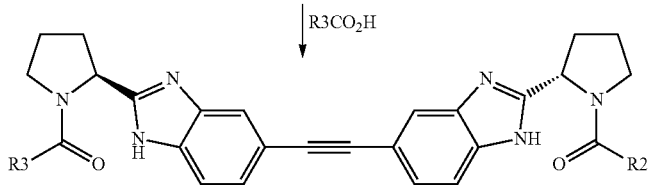

Example 35

((S)-2-Methyl-1-{(S)-2-[5-((S)-2-pyrrolidin-2-yl-1H-benzoimidazol-5-ylethynyl)-1H-benzoimidazol-2-yl]-pyrrolidine-1-carbonyl}-propyl)-carbamic acid methyl ester

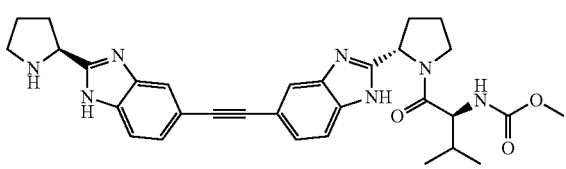 [SMILES: COC(=O)N[C@H](C(=O)N1CCC[C@H]1c1nc2cc(C#Cc3ccc4[nH]c([C@@H]5CCCN5)nc4c3)ccc2[nH]1)C(C)C]

This compound is prepared as described in example 34

$^1$H NMR (400 MHz, CD$_3$OD): δ [ppm] 7.69 (m, 2H), 7.52 (m, 2H), 7.38 (m, 2H), 7.15 (m, 2H), 5.22 (m, 1H), 4.58 (m, 2H), 4.23 (m, 2H), 4.02 (m, 1H), 3.90 (m, 1H), 3.63 (s, 3H), 2.48-1.90 (m, 9H), 0.95 (m, 6H).

Example 36

{(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2,2-dimethyl-propyl}-carbamic acid methyl ester

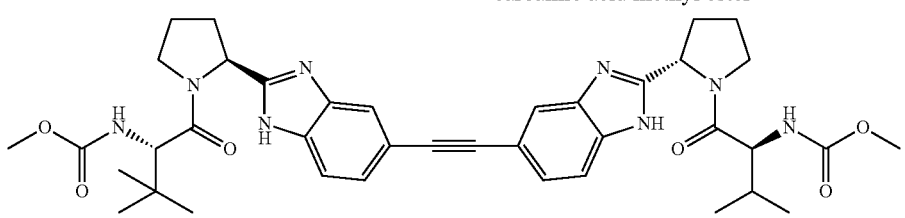

Step 2

This compound is prepared as described in example 34

$^1$H NMR (400 MHz, DMSO-d$_6$): δ [ppm] 12.30 (m, 2H), 7.65 (m, 1H), 7.60 (m, 1H), 7.49 (m, 1H), 7.44 (m, 1H), 7.30-7.22 (m, 3H), 7.13 (m, 1H), 5.12 (m, 2H), 4.20 (m, 1H), 4.03 (m, 1H), 3.80 (m, 2H), 3.51 (s, 3H), 3.49 (s, 3H), 2.20 (m, 4H), 2.10-1.80 (m, 5H), 1.21 (m, 2H), 0.86 (s, 9H), 0.80 (m, 6H).

LC/MS: m/z=725.47 (M+H$^+$).

HPLC (Method B): t$_R$=15.45 min.

Example 37

{(S)-1-[(S)-2-(5-{2-[(S)-1-((S)-2-Methoxycarbonylamino-3-methyl-butyryl)-pyrrolidin-2-yl]-1H-benzoimidazol-5-ylethynyl}-1H-benzoimidazol-2-yl)-pyrrolidine-1-carbonyl]-2-methyl-propyl}-carbamic acid methyl ester

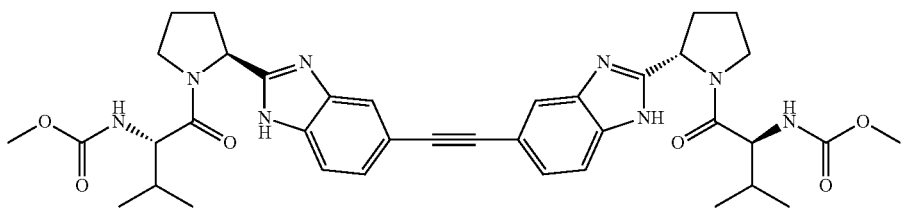

This compound is prepared as described in example 34

¹H NMR (400 MHz, DMSO-d₆): δ [ppm] 12.30 (d, 2H), 7.62 (m, 2H), 7.46 (m, 2H), 7.30 (m, 4H), 5.12 (m, 2H), 4.03 (m, 2H), 3.80 (m, 4H), 3.52 (s, 6H), 2.20 (m, 4H), 2.06-1.80 (m, 6H), 1.80 (m, 12H).

LC/MS: m/z=711.44 (M+H⁺).

HPLC (Method D): $t_R$=22.88 min.

Example 38

{(S)-2-Methyl-1-[(S)-2-(5-{2-[(S)-1-((R)-tetrahydro-furan-2-carbonyl)-pyrrolidin-2-yl]-1H-benzoimida-zol-5-ylethynyl}-1H-benzoimidazol-2-yl)-pyrroli-dine-1-carbonyl]-propyl}-carbamic acid methyl ester

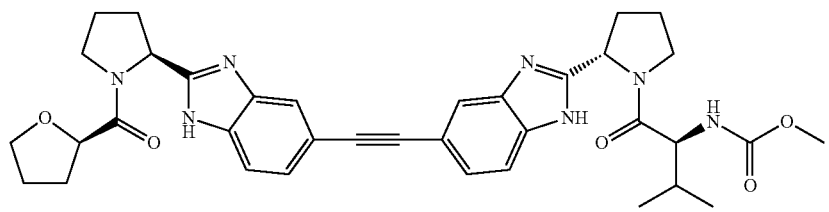 [SMILES: COC(=O)N[C@H](C(=O)N1CCC[C@H]1c1nc2cc(C#Cc3ccc4[nH]c([C@@H]5CCCN5C(=O)[C@H]5CCCO5)nc4c3)ccc2[nH]1)C(C)C]

This compound is prepared as described in example 34.

¹H NMR (400 MHz, DMSO-d₆): δ [ppm] 12.30 (m, 2H), 7.68 (m, 1H), 7.62-7.40 (m, 3H), 7.30 (m, 3H), 5.47 (d, 1H), 5.10 (m, 2H), 4.59 (t, 1H), 4.23 (m, 1H), 4.03 (t, 1H), 3.77 (m, 3H), 3.60 (m, 1H), 3.50 (s, 3H), 2.30-1.70 (m, 11H), 1.20 (m, 2H), 0.90 (m, 6H).

LC/MS: m/z=652.41 (M+H⁺).

Example 39

{(S)-1-[(S)-2-(5-{2-[(S)-1-((R)-2-Methoxycarbony-lamino-2-phenyl-acetyl)-pyrrolidin-2-yl]-1H-ben-zoimidazol-5-ylethynyl}-1H-benzoimidazol-2-yl)-pyrrolidine-1-carbonyl]-2-methyl-propyl}-carbamic acid methyl ester

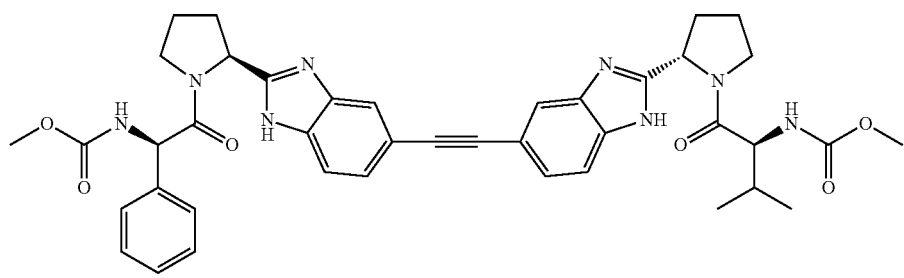

This compound is prepared as described in example 34

¹H NMR (400 MHz, DMSO-d₆): δ [ppm] 7.87 (d, 2H), 7.69 (m, 3H), 7.55 (m, 2H), 7.34 (m, 5H), 6.82 (m, 1H), 5.50 (d, 1H), 5.20 (m, 2H), 4.10 (t, 1H), 3.93 (m, 1H), 3.85 (m, 1H), 3.51 (s, 3H), 3.49 (s, 3H), 3.19 (m, 1H), 2.32 (m, 2H) 2.20 (m, 2H), 2.16-1.80 (m, 6H), 0.92 (d, 3H), 0.88 (d, 3H).

LC/MS: m/z=745.46 (M+H⁺).

HPLC (Method E): $t_R$=8.48 min.

General Procedure for Synthesis of Compounds for Example 40:

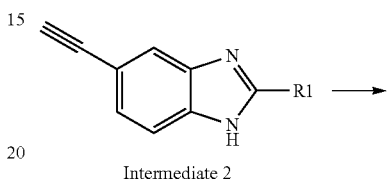

Intermediate 2

-continued

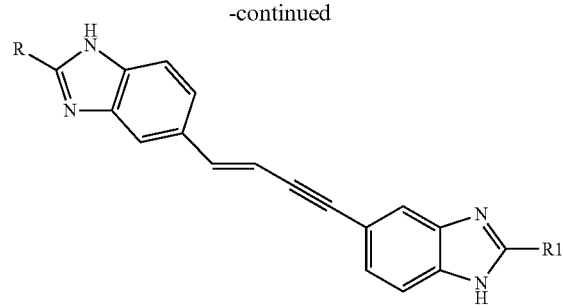

Example 40

(S)-2-(5-{(E)-4-[2-((S)-1-Benzyloxycarbonyl-piperidin-2-yl)-1H-benzoimidazol-5-yl]-but-1-en-3-ynyl}-1H-benzoimidazol-2-yl)-piperidine-1-carboxylic acid benzyl ester

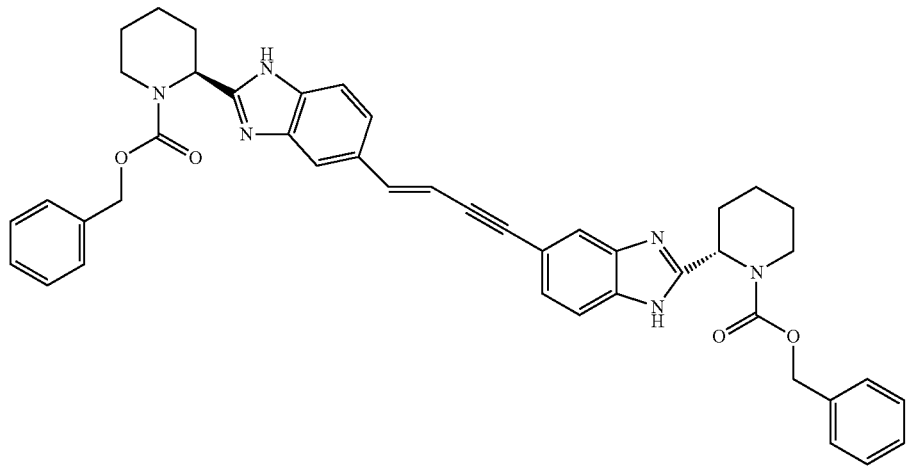 [SMILES: O=C(OCc1ccccc1)N1CCCC[C@H]1c1nc2cc(C#C/C=C/c3ccc4[nH]c([C@@H]5CCCCN5C(=O)OCc5ccccc5)nc4c3)ccc2[nH]1]

A mixture of (S)-2-(5-ethynyl-1H-benzoimidazol-2-yl)-piperidine-1-carboxylic acid benzyl ester (41 mg, 0.115 mmol) and dichloro(p-cymene)ruthenium(II) dimer (5 mg) is purged with $N_2$. AcOH (1 mL) is added and the mixture is stirred at room temperature overnight and concentrated in vacuum to dryness. The residue is purified by flash column chromatography on silica gel (EtOAc/hexanes 5% to 100%) and repurified by reverse phase HPLC using a gradient of $CH_3CN$/water to afford the title compound (5.9 mg, 7%).

$^1$H NMR (400 MHz, $CD_3OD$): δ [ppm] 7.77 (m, 3H), 7.72-7.50 (m, 4H), 7.34 (m, 9H), 7.25 (d, 1H), 6.66 (d, 1H), 5.85 (m, 2H), 5.20 (m, 4H), 4.18 (m, 2H), 3.04 (m, 2H), 2.45 (m, 2H), 2.10 (m, 2H), 1.83 (m, 2H), 1.70-1.44 (m, 6H).

LC/MS: m/z=719.96 (M+H$^+$).

General Procedure for Example 42

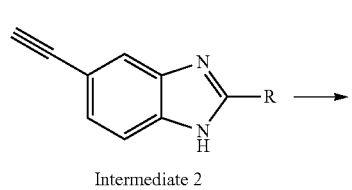

Intermediate 2

⟶

-continued

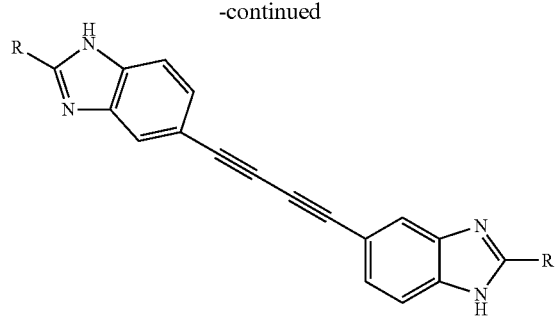

Example 41

(S)-2-(5-{4-[2-((S)-1-Benzyloxycarbonyl-piperidin-2-yl)-1H-benzoimidazol-5-yl]-buta-1,3-diynyl}-1H-benzoimidazol-2-yl)-piperidine-1-carboxylic acid benzyl ester

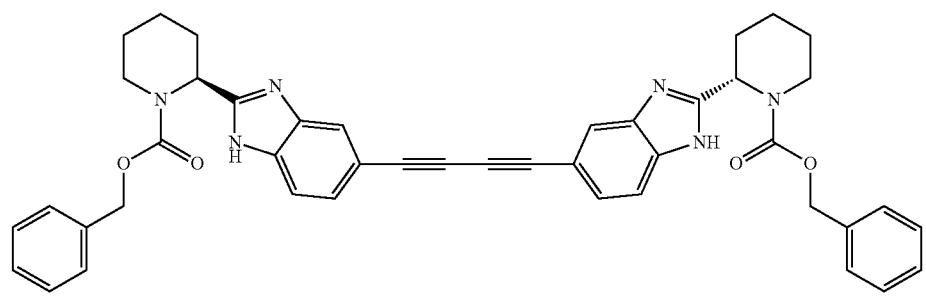 [SMILES: O=C(OCc1ccccc1)N1CCCC[C@H]1c1nc2cc(C#CC#Cc3ccc4[nH]c([C@@H]5CCCCN5C(=O)OCc5ccccc5)nc4c3)ccc2[nH]1]

To a stirring solution of (S)-2-(5-ethynyl-1H-benzoimidazol-2-yl)-piperidine-1-carboxylic acid benzyl ester (26 mg, 0.0723 mmol), CuI (3 mg) and bis(triphenylphosphine)palladium(II)dichloride (8 mg) in THF (1.5 mL) is added TEA (30 μL, 3.4 mmol). The reaction mixture is stirred at room temperature for 12 hours and filtered through celite and the filtrate is concentrated in vacuum to dryness. The residue is purified by flash column chromatography on silica gel (EtOAc/hexanes 0% to 100%) to give the title compound (S)-2-(5-{4-[2-((S)-1-benzyloxycarbonyl-piperidin-2-yl)-1H-benzoimidazol-5-yl]-buta-1,3-diynyl}-1H-benzoimidazol-2-yl)-piperidine-1-carboxylic acid benzyl ester (10 mg, 39%).

$^1$H NMR (400 MHz, DMSO-d$_6$): δ [ppm] 12.59 (d, 2H), 7.84 (s, 2H), 7.66 (s, 2H), 7.60 (d, 2H), 7.46 (d, 2H), 7.40-7.10 (m, 10H), 5.54 (m, 2H), 5.08 (m, 4H), 4.01 (m, 2H), 3.05 (m, 2H), 2.38 (m, 2H), 1.80 (m, 2H), 1.59 (m, 4H), 1.38 (m, 4H).
LC/MS: m/z=717.96 (M+H$^+$).

Example 42

((S)-1-{(S)-2-[5-(4-{2-[(S)-1-((S)-2-Methoxycarbonylamino-3-methyl-butyryl)-pyrrolidin-2-yl]-1H-benzoimidazol-5-yl}-2,5-difluoro-phenyl)-1H-benzoimidazol-2-yl]-pyrrolidine-1-carbonyl}-2-methyl-propyl)-carbamicacid methyl ester

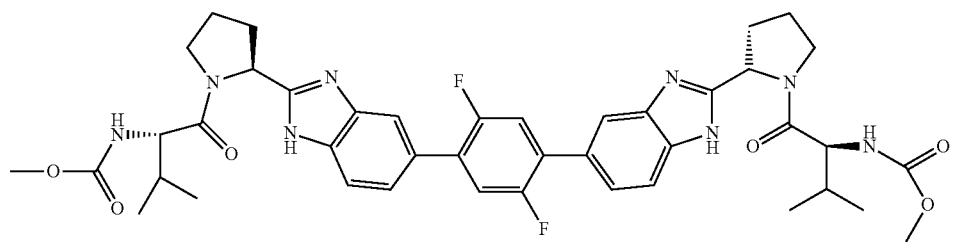

This compound is prepared as described in example 13
$^1$H NMR (400 MHz, CD$_3$OD): δ [ppm] 7.80-7.52 (m, 6H), 7.42 (d, 1H), 7.38 (m, 1H), 5.25 (m, 2H), 4.24 (d, 2H), 4.1-3.9 (m, 2H), 3.95-3.90 (m, 2H), 3.64 (s, 6H), 2.50-2.00 (m, 10H), 0.98 (d, 6H), 0.90 (d, 6H).
LC/MS: m/z=799.6 (M+H$^+$).

Example 43

Methyl N-[(1S)-1-[(2S)-2-[5-[5-[2-[(2S)-1-[(2S)-2-(methoxycarbonylamino)-3-methyl-butanoyl]pyrrolidin-2-yl]-1H-benzimidazol-5-yl]-3-methyl-2-pyridyl]-1H-benzimidazol-2-yl]pyrrolidine-1-carbonyl]-2-methyl-propyl]carbamate

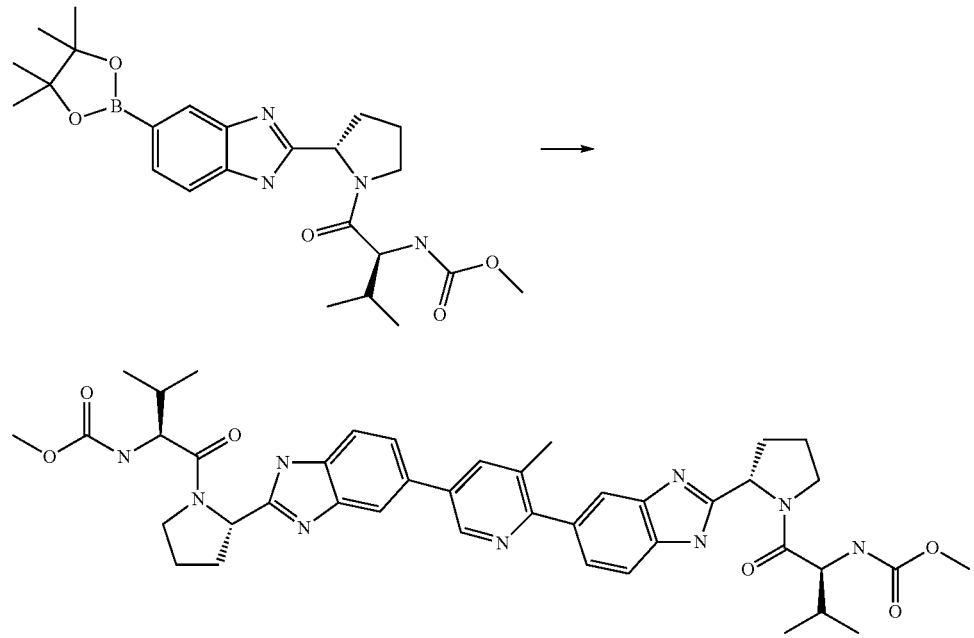

Suzuki coupling of solution of methyl N-[(1S)-2-methyl-1-[(2S)-2-[6-(4,4,5,5-tetramethyl-1,3,2-dioxaborolan-2-yl)-1H-benzimidazol-2-yl]pyrrolidine-1-carbonyl]propyl]carbamate (139.0 mg, 0.2955 mmol) and 5-bromo-2-iodo-3-methyl-pyridine (40.00 mg, 0.1343 mmol) in acetonitrile (2.5 mL) is carried out using Pd(dppf)Cl2-DCM (16 mg, 0.01959 mmol) and sodium bicarbonate (671.5 µL of 1 M, 0.6715 mmol) as described for Example 28 to methyl N-[(1S)-1-[(2S)-2-[5-[5-[2-[(2S)-1-[(2S)-2-(methoxycarbonylamino)-3-methyl-butanoyl]pyrrolidin-2-yl]-1H-benzimidazol-5-yl]-3-methyl-2-pyridyl]-1H-benzimidazol-2-yl]pyrrolidine-1-carbonyl]-2-methyl-propyl]carbamate (47.7 mg, 0.06018 mmol, 44.80%) as white solid.

Rf=0.24 (1:5; MeOH:Ethyl acetate).

1H NMR (400 MHz, CD$_3$OD, 5:1 mixture of rotamers): Peaks for the major isomer, 8.66 (brd, 1 H), 8.02 (br s, 1 H), 7.9-7.5 (m, 5 H), 7.37 (dd, 1 H), 5.3-5.25 (m, 2 H), 4.25 (d, 2 H), 4.1-3.7 (m, 4 H), 3.64 (s, 6 H), 2.5-1.9 (m, 13 H), 0.923 (d, 6 H), 0.867 (d, 6 H). LC/MS: m/z=778.63 (M+H+).

Example 44

Dimethyl-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate

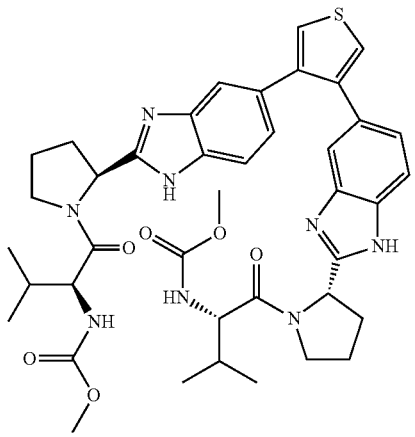 [SMILES: COC(=O)N[C@H](C(=O)N1CCC[C@H]1c1nc2cc(-c3cscc3-c3ccc4[nH]c([C@@H]5CCCN5C(=O)[C@@H](NC(=O)OC)C(C)C)nc4c3)ccc2[nH]1)C(C)C]

This compound is made using the procedure described for example 17.

LC/MS: 10-90% MeOH 3/5 min(grad/run): R.T.=2.63 min, M+1=769.60

DMSO-d6: 7.70-7.00 (m, 10H); 5.20 (m, 2H); 4.20 (m, 2H); 3.70 (m, 4H); 3.55 (m, 6H); 2.40-1.80(m, 10H); 1.70-1.30 (m, 6H); 1.00-0.65 (m, 12H)

Example 45 bis((S)-tetrahydrofuran-3-yl)-(2S,2'S)-1,1'-((2S,2'S)-2,2'-(5,5'-(thiophene-3,4-diyl)bis(1H-benzo[d]imidazole-5,2-diyl))bis(pyrrolidine-2,1-diyl))bis(3-methyl-1-oxobutane-2,1-diyl)dicarbamate

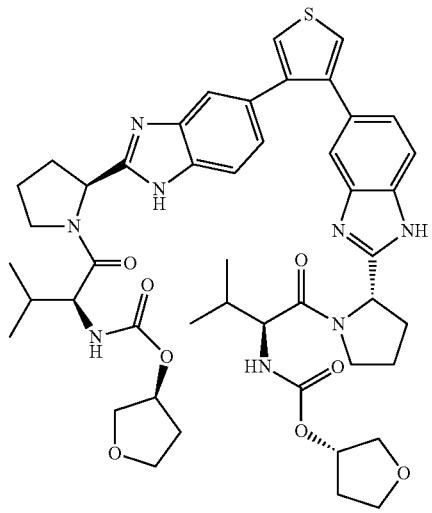 [SMILES: CC(C)[C@H](NC(=O)O[C@H]1CCOC1)C(=O)N1CCC[C@H]1c1nc2cc(-c3cscc3-c3ccc4[nH]c([C@@H]5CCCN5C(=O)[C@@H](NC(=O)O[C@H]5CCOC5)C(C)C)nc4c3)ccc2[nH]1]

This compound is made using the procedure described for example 17.

LC/MS: 10-90% MeOH 3/5 min(grad/run): R.T.=2.55 min, M+1=881.60

DMSO-d6: 7.70-6.95 (m, 10H); 5.10 (m, 2H); 4.10-3.00 (m, 14H); 2.70 (m, 2H); 2.40-1.30 (m, 16H); 1.00-0.65 (m, 12H)

Example 46

Dimethyl-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate

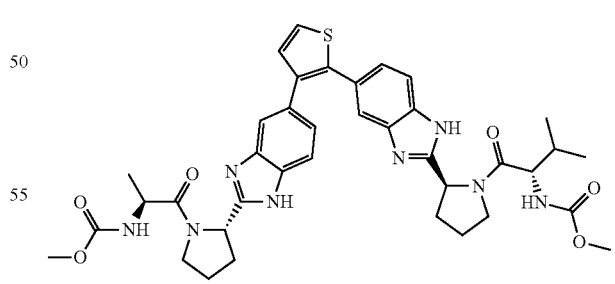

This compound is made using the procedure described for example 17.

LC/MS: 10-90% MeOH 3/5 min(grad/run): R.T.=2.99 min, M+1=769.57

DMSO-d6: 7.70-7.20 (m, 10H); 5.20 (m, 2H); 4.15 (m, 2H); 3.85 (m, 4H); 3.60 (m, 6H); 2.40-1.40 (m, 16H); 1.00-0.65 (m, 12H)

Example 47 bis((S)-tetrahydrofuran-3-yl)-(2S,2'S)-1,1'-((2S,2'S)-2,2'-(5,5'-(thiophene-2,3-diyl)bis(1H-benzo[d]imidazole-5,2-diyl))bis(pyrrolidine-2,1-diyl))bis(3-methyl-1-oxobutane-2,1-diyl)dicarbamate

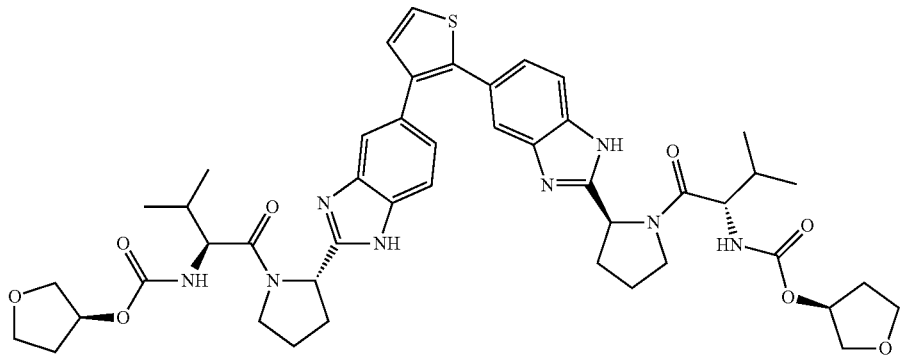 [SMILES: CC(C)[C@H](NC(=O)O[C@H]1CCOC1)C(=O)N1CCC[C@H]1c1nc2cc(-c3ccsc3-c3ccc4[nH]c([C@@H]5CCCN5C(=O)[C@@H](NC(=O)O[C@H]5CCOC5)C(C)C)nc4c3)ccc2[nH]1]

This compound is made using the procedure described for example 17.

LC/MS: 10-90% MeOH 3/5 min(grad/run): R.T.=3.03 min, M+1=881.5

DMSO-d6: 7.70-7.20 (m, 10H); 5.20-5.10 (m, 4H); 415-3.5-(m, 14H); 2.40-1.30 (m, 16H); 1.00-0.65 (m, 12H)

Example 48

Synthesis of 4-methyl-N-(t-butoxycarbonyl)-(2S)-prolinol Compound

The process for synthesizing compounds of the invention uses 4-methyl-N-(t-butoxycarbonyl)-(2S)-prolinol as a starting material. Scheme 1 illustrates the process of this invention as employed to synthesize 4-methyl-N-(t-butoxycarbonyl)-(2S)-prolinol 7. As shown in Scheme 1, the process includes multiple steps in converting the preferred starting material L-pyroglutamic acid 1, to the enantiomerically and diastereomerically pure 4-methyl-N-(t-butoxycarbonyl)-(2S)-prolinol. The process includes first protecting the carboxylic acid as an ester (e.g. ethyl ester), followed by protection of the nitrogen with a protecting group (e.g. t-butoxylcarbonyl (BOC)). The protected pyroglutamate 3 is then converted to an enaminone 4, preferably by reacting with a nitrogen containing acetal or orthoester (e.g. 1-t-butoxy-N,N,N',N'-tetramethylmethanediamine (Bredereck's reagent)). This conversion is carried out at elevated temperatures between 60-150° C. either neat or with a solvent, preferably an ethereal solvent such as 1,2-dimethoxyethane. Enaminone 4 is hydrolyzed, preferably with a strong acid then reacted with a source of formaldehyde (e.g. 37 wt. % formaldehyde in water) to afford the desired 4-methylene pyroglutamate 5. The 4-methylene glutamate 5 is stereospecifically reduced to the 4-methylpyroglutamate 6 using and of the standard conditions for hydrogenation (e.g. hydrogen/10% palladium on carbon) known to those in the art. The amide carbonyl and the carboxylic acid ester of 4-methylpyroglutamate 6 are reduced either sequentially or simultaneously with reducing agents commonly used by those familiar with the art (e.g. sodium borohydride-boron trifluoride etherate) to produce the desired 4-methyl-N-(t-butoxycarbonyl)-(2S)-prolinol 7.

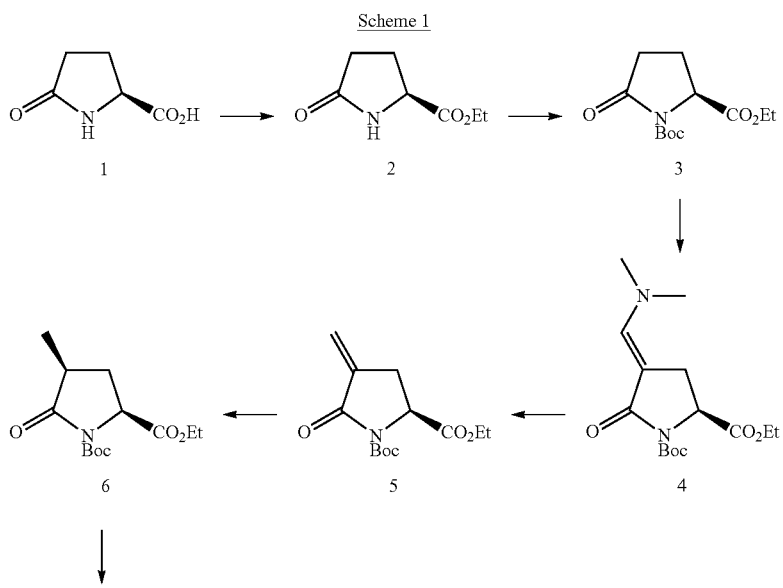

Scheme 1

-continued

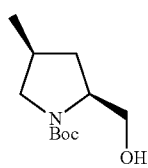

7

Similar synthetic procedures are described in Katoh, M. et al., Tetrahedron Letters, 46 (2005), p5161-5163, the entire teachings of which are incorporated herein by reference.

Example 49

Synthesis of 4(S)-methyl-L-BOC-proline (2)

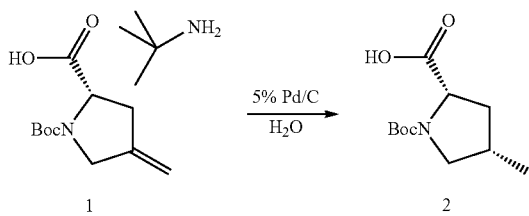

A solution of 1 (1000 g, 3.32 mol) in water (10 L) was charged to a 20 L hydrogenator along with 5% Palladium on Carbon (56% wet, 120 g, JM-JR537). The resulting mixture was hydrogenated for 8 hrs with rapid agitation under a 3.0 bar hydrogen pressure. The catalyst was removed by filtration through Celite and the resulting light yellow solution was acidified to pH 1.5 with 3N HCl in the presence of isopropyl acetate (16 L). The layers were separated and the aqueous layer was re-extracted with isopropyl acetate (8 L). The combined organic layers were then washed with water (16 L), followed by brine (8 L) and then distilled under reduced pressure to dryness. The crude product (695 g) was obtained as an off-white solid. Analysis by $^1$H-NMR indicated that the solid was a diastereomeric mixture of 9:1 cis/trans isomers (ratio of the methine proton alpha to the carbonyl). This mixture was upgraded to 20:1 cis/trans isomers by re-crystallizing twice from a 2:1 isopropyl acetate/heptane solvent mixture to obtain 459 g of solid (60% yield).

$^1$H-NMR (dmso$_{d6}$): 12.45(s, 1H); 4.03(t, 1H, J=10.5 Hz); 3.54(m, 1H); 2.77(m, 1H); 2.37(m, 1H); 2.17(m, 1H); 1.41 (m, 1H); 1.38(m, 9H); 0.97(t, 3H, J=8.0 Hz).

Example A

Cell-Based Luciferase Reporter HCV (Ib) RNA Replication Assay Cell Culture

Replicon cell lines Huh-7, 5.2 and ET which are derived from the Huh-7 hepatocarcinoma cell line are maintained in culture as generally described in Krieger, N; Lohmann, V; Bartenschlager, R. Enhancement of hepatitis C virus RNA replication by cell culture-adaptive mutations. J. Virol. 2001, 75, 4614-4624. The Huh-7, 5.2 cells contain the highly cell culture-adapted replicon I$_{389}$luc-ubi-neo/NS3-3'/5.1 construct that carries, in addition to the neomycin gene, an integrated copy to the firefly luciferase gene (Krieger, N; Lohmann, V; Bartenschlager, R. Enhancement of hepatitis C virus RNA replication by cell culture-adaptive mutations. J. Virol. 2001, 75, 4614-4624). This cell line allows measurement of HCV RNA replication and translation by measuring luciferase activity. It has been previously shown that the luciferase activity tightly follows the replicon RNA level in these cells (Krieger, N; Lohmann, V; Bartenschlager, R. Enhancement of hepatitis C virus RNA replication by cell culture-adaptive mutations. J. Virol. 2001, 75, 4614-4624). The Huh-7, ET cell line has the same features as those mentioned for Huh-7, 5.2 cell line, except that ET cells are more robust and contain an adaptative mutation in the HCV NS4B gene instead of NS5A. Both cell lines are maintained in cultures at a sub-confluent level (<85%) as the level of replicon RNA is highest in actively proliferating cells. The culture media used for cell passaging consist of DMEM (Gibco BRL Laboratories, Mississauga, ON, Canada) supplemented with 10% foetal bovine serum with 1% penicilin/streptomycin, 1% glutamine, 1% sodium pyruvate, 1% non-essential amino acids, and 180 ug/ml of G418 final concentration. Cells are incubated at 37° C., in an atmosphere of 5% $CO_2$ and passaged twice a week to maintain sub-confluence.

Approximately 3000 viable Huh-7, 5.2 or ET cells (100 µl) are plated per well in a white opaque 96-well microtiter plate. The cell culture media used for the assay is the same as described above except that it contains no G418 and no phenol red. After an incubation period of 3-4 hours at 37° C. in a 5% $CO_2$ incubator, compounds (100 µl) are added at various concentrations. Cells are then further incubated for 4 days at 37° C. in a 5% $CO_2$ incubator. Thereafter, the culture media is removed and cells are lysed by the addition of 95 µL of the luciferase buffer (luciferin substrate in buffered detergent). Cell lysates are incubated at room temperature and protected from direct light for at least 10 minutes. Plates are read for luciferase counts using a luminometer (Wallac MicroBeta Trilux, Perkin Elmer™, Mass, USA).

The 50% inhibitory concentrations ($IC_{50}$s) for inhibitory effect are determined from dose response curves using eleven concentrations per compound in duplicate. Curves are fitted to data points using nonlinear regression analysis, and $IC_{50}$s are interpolated from the resulting curve using GraphPad Prism software, version 2.0 (GraphPad Software Inc., San Diego, Calif., USA).

Table 2 show compounds representative of the present invention and the EC50 values against the HCV 1b genotype.

TABLE 2

| # | M + 1 (obs) | RT (min) | 1H-NMR | EC50_1b (uM) |
|---|---|---|---|---|
| 1 | | | | +++ |
| 2 | 762.9 | 7.64 | | ++ |
| 3 | 835.56 | 10.22 | | +++ |
| 4 | 790.9 | 8.36 | | +++ |
| 5 | 788.49 | 7.86 | | +++ |
| 6 | 763.9 | 6.4 | | +++ |
| 7 | 777.6 | 7.72 | | +++ |
| 8 | 792.9 | 7.47 | | +++ |

TABLE 2-continued

| # | M + 1 (obs) | RT (min) | 1H-NMR | EC50_1b (uM) |
|---|---|---|---|---|
| 9 | 780.9 | 7.87 | | +++ |
| 10 | 797.54 | 8.32 | | +++ |
| 11 | 789.6 | 6.95 | | ++ |
| 12 | 823.6 | 10.8 | | +++ |
| 13 | 791.6 | 7.9 | | +++ |
| 14 | 791.6 | 7.96 | | +++ |
| 15 | 765.6 | 7.3 | | +++ |
| 16 | 655.57 | 3.12 | DMSO-d6: 12.2 (m, 2H); 7.8-7.5 (m, 8H); 4.90 (m, 2H); 3.50 (m, 2H); 3.35 (m, 2H); 2.39 (m, 2H); 1.80 (m, 2H); 1.35 (m, 4H); 1.10 (m, 18H) | ++ |
| 17 | 769.85 | 3.01 | DMSO-d6: 7.90 (bs, 2H); 7.78 (m, 4H); 7.68 (s, 2H); 7.30 (m, 2H); 5.22 (m, 2H); 4.10 (m, 2H); 3.85 (m, 4H); 2.20-1.90 (m, 6H); 1.70-1.40 (m, 4H); 1.00-0.80 (m, 12H) | +++ |
| 18 | 769.59 | 7.76 | | +++ |
| 19 | 871.59 | 8.94 | | +++ |
| 20 | 781.6 | 6.49 | | ++ |
| 21 | | | | +++ |
| 22 | | | | -- |
| 23 | | | | -- |
| 24 | 820.6 | 9.03 | | +++ |
| 25 | 907.64 | 10.12 | | +++ |
| 26 | 795.64 | 6.97 | | +++ |
| 27 | 799.59 | 9.1 | | +++ |
| 28 | | | | ++ |
| 29 | | | | + |
| 30 | | | | ++ |
| 31 | | | | ++ |
| 32 | | | | ++ |
| 33 | | | | +++ |
| 34 | | | | ++ |
| 35 | | | | -- |
| 36 | | | | +++ |
| 37 | 711.52 | 2.66 | | +++ |
| 38 | | | | +++ |
| 39 | | | | +++ |
| 40 | | | | ++ |
| 41 | | | | ++ |
| 42 | 799.6 | 8.34 | | +++ |
| 43 | 778.63 | 6.52 | | +++ |
| 44 | 769.6 | 2.63 | DMSO-d6: 7.70-7.00 (m, 10H); 5.20 (m, 2H); 4.20 (m, 2H); 3.70 (m, 4H); 3.55 (m, 6H); 2.40-1.80 (m, 10H); 1.70-1.30 (m, 6H); 1.00-0.65 (m, 12H) | +++ |
| 45 | 881.6 | 2.55 | DMSO-d6: 7.70-6.95 (m, 10H); 5.10 (m, 2H); 4.10-3.00 (m, 14H); 2.70 (m, 2H); 2.40-1.30 (m, 16H); 1.00-0.65 (m, 12H) | ++ |
| 46 | 797.61 | 3.24 | DMSO-d6: 7.70-7.20 (m, 10H); 5.20 (m, 2H); 4.60-3.80 (M, 10H); 3.60 (m, 3H); 2.75 (m, 3H); 2.45-1.30 (m, 12H); 1.00-0.65 (m, 12H) | ++ |
| 47 | 881.5 | 3.03 | DMSO-d6: 7.70-7.20 (m, 10H); 5.20-5.10 (m, 4H); 415-3.5-(m, 14H); 2.40-1.30 (m, 16H); 1.00-0.65 (m, 12H) | ++ |
| 48 | | | | + |
| 49 | | | | ++ |
| 50 | | | | +++ |
| 51 | | | | ++ |
| 52 | | | | +++ |
| 53 | | | | +++ |
| 54 | | | | +++ |
| 55 | | | | +++ |
| 56 | | | | +++ |
| 57 | | | | ++ |
| 58 | | | | +++ |
| 59 | | | | +++ |
| 60 | | | | +++ |
| 61 | | | | +++ |
| 62 | | | | +++ |
| 63 | 739.57 | 2.78 | | +++ |
| 64 | | | | +++ |
| 65 | | | | ++ |
| 66 | | | | ++ |
| 67 | | | | ++ |
| 68 | | | | +++ |
| 69 | | | | ++ |
| 70 | | | | ++ |
| 71 | | | | +++ |
| 72 | | | | +++ |
| 73 | | | | +++ |
| 74 | | | | +++ |
| 75 | | | | +++ |
| 76 | 655 | 2.92 | | +++ |
| 77 | 794.15 | 3.66 | | +++ |
| 78 | 654.94 | 2.91 | | +++ |
| 79 | 675.59 | 3.26 | | +++ |
| 80 | 703.67 | 3.45 | | + |
| 81 | 731.64 | 3.65 | | +++ |
| 82 | 823.82 | 3.71 | | ++ |
| 83 | 675.58 | 3.39 | | +++ |
| 84 | 759.9 | 3.7 | | +++ |
| 85 | 816 | 3.6 | | ++ |
| 86 | 619.7 | 3 | | + |
| 87 | 817.9 | 3.2 | | + |
| 88 | 835.9 | 3.6 | | ++ |
| 89 | 909.9 | 3.6 | | ++ |
| 90 | | | | +++ |
| 91 | | | | +++ |
| 92 | | | | +++ |
| 93 | | | | ++ |
| 94 | | | | ++ |
| 95 | | | | +++ |
| 96 | | | | ++ |
| 97 | | | | ++ |
| 98 | | | | ++ |
| 99 | 623.6 | 1.65 | | ++ |
| 100 | 623.53 | 1.63 | | + |
| 101 | 881.88 | 3.07 | | ++ |
| 102 | | | | +++ |
| 103 | 645.75 | 3.68 | | ++ |
| 104 | 651.8 | 3.3 | | ++ |
| 105 | 597.7 | 3.4 | | ++ |
| 106 | 649.8 | 3.4 | | ++ |
| 107 | 597.7 | 3.5 | | ++ |
| 108 | 561.8 | 3.6 | | ++ |
| 109 | 679.61 | 3.62 | | ++ |
| 110 | 647.59 | 3.31 | | + |
| 111 | 651.59 | 3.24 | | ++ |
| 112 | 684.74 | 4.64 | | ++ |
| 113 | 847.8 | 4.33 | | +++ |
| 114 | 864.13 | 4 | | ++ |
| 115 | 752.09 | 2.8 | | +++ |
| 116 | 715.76 | 2.28 | DMSO-d6: 7.65 (m, 4H); 7.42 (m, 2H); 7.32 (m, 2H); 5.20 (m, 2H); 4.12 (m, 2H); 3.90 (m, 2H); 4.80 (m, 2H); 3.50 (s, 6H); 3.10 (s, 4H); 2.42 (m, 2H); 2.15-2.05 (m, 8H); 0.90 (m, 2H); 0.75 (dd, 12H) | +++ |
| 117 | 726.05 | 2.71 | | +++ |
| 118 | 683.58 | 3.55 | | +++ |
| 119 | 863.34 | 4 | | +++ |
| 120 | 641.7 | 2.17 | | + |
| 121 | 848.02 | 4.32 | | ++ |
| 122 | 639.97 | 2.7 | | +++ |
| 123 | 680.03 | 2.8 | | ++ |
| 124 | 593.66 | 3.98 | | ++ |
| 125 | 617.67 | 4.1 | | ++ |
| 126 | 851.96 | 4.36 | | ++ |
| 127 | 795.78 | 4.11 | | ++ |
| 128 | 765.71 | 4.06 | | ++ |
| 129 | 763.64 | 3.87 | | + |
| 130 | 791.74 | 4.02 | | ++ |
| 131 | 761.8 | 3.98 | | ++ |
| 132 | 917.34 | 4.04 | | ++ |

TABLE 2-continued

| # | M + 1 (obs) | RT (min) | 1H-NMR | EC50_1b (uM) |
|---|---|---|---|---|
| 133 | 769.57 | 2.99 | DMSO-d6: 7.70-7.20 (m, 10H); 5.20 (m, 2H); 4.15 (m, 2H); 3.85 (m, 4H); 3.60 (m, 6H); 2.40-1.40 (m, 16H); 1.00-0.65 (m, 12H) | +++ |
| 134 | 565.61 | 2.65 | | ++ |
| 135 | 537.68 | 2.48 | | ++ |
| 136 | 589.6 | 2.76 | | ++ |
| 137 | 537.66 | 3.37 | | ++ |
| 138 | 621.71 | 2.68 | | ++ |
| 139 | 561.67 | 2.95 | | ++ |
| 140 | 565.7 | 4.13 | | ++ |
| 141 | 808.65 | 8.18 | | +++ |
| 142 | 763.67 | 3.89 | | +++ |
| 143 | 799.6 | 8.29 | | +++ |
| 144 | 791.95 | 7.72 | | +++ |
| 145 | 735.67 | 7.86 | | +++ |
| 146 | 806.9 | 7.83 | | +++ |
| 147 | 787.7 | 8.88 | | +++ |
| 148 | 791.7 | 9.84 | | +++ |
| 149 | 791.7 | 7.88 | | +++ |
| 150 | 841.63 | 7.23 | | +++ |
| 151 | 599.63 | 2.12 | | ++ |
| 152 | 675.53 | 3.39 | | ++ |
| 153 | 769.77 | 3.86 | | +++ |
| 154 | 822.83 | 3.88 | H NMR (300.0 MHz, DMSO) d 8.12 (d, J = 11.9 Hz, 1H), 8.00-7.85 (m, 5H), 7.69 (d, J = 8.3 Hz, 1H), 7.60 (d, J = 8.1 Hz, 1H), 5.27 (dd, J = 5.2, 8.0 Hz, 2H), 4.15 (d, J = 7.7 Hz, 2H), 3.91 (m, 4H), 3.56 (s, 6H), 2.43 (m, 2H), 2.28-1.90 (m, 8H), 0.85 (td, J = 17.2, 7.9 Hz, 12H) and 0.00 (TMS) ppm | +++ |
| 155 | 783.03 | 3.14 | DMSO-d6: 8.05-7.20 (m, 9H); 5.25 (m, 2H), 4.15 (m, 2H); 3.92 (m, 6H); 3.55-3.45 (m, 6H); 2.45-1.90 (m, 9H); 2.35 (s, 3H); 1.48 (m, 1H); 0.90-0.65 (m, 12H) | +++ |
| 156 | 895.28 | 3.1 | | ++ |
| 157 | 826 | 3.46 | | +++ |
| 158 | 937.29 | 3.48 | | +++ |
| 159 | 770.81 | 3.04 | | +++ |
| 160 | 882.24 | 3.07 | DMSO-d6: 8.40-7.00 (m, 11H); 5.30-5.-5 (m, 6H); 4.20-3.55 (m, 13H); 2.45-1.75 (m, 12H); 1.50 (m, 1H); 0.80-0.45 (m, 12H) | ++ |
| 161 | 793.64 | 6.92 | | +++ |
| 162 | 765.7 | 6.74 | | +++ |
| 163 | 814.67 | 7.05 | | +++ |
| 164 | 820.6 | 6.68 | | +++ |
| 165 | 799.69 | 8.11 | | +++ |
| 166 | 823.72 | 7.64 | | +++ |
| 167 | 825.64 | 8.84 | | +++ |
| 168 | 795.63 | 8.72 | | +++ |
| 169 | 799.63 | 7.5 | | +++ |
| 170 | 795.63 | 11.4 | | +++ |
| 171 | 763.67 | 7.8 | | ++ |
| 172 | 821.65 | 7.49 | | +++ |
| 173 | 804.62 | 7.64 | | +++ |
| 174 | 823.7 | 7.88 | | +++ |
| 175 | 834.8 | 6.93 | | +++ |
| 176 | 770.64 | 9.28 | | ++ |
| 177 | 831.66 | 8.43 | | +++ |
| 178 | 791.71 | 8.22 | | +++ |
| 179 | 799.65 | 7.68 | | +++ |
| 180 | 799.65 | 7.68 | | +++ |
| 181 | 821.7 | 7.51 | | +++ |
| 182 | 835.66 | 8.65 | | +++ |
| 183 | 766.9 | 3.11 | DMSO-d6: 9.80 (bs, 2H); 7.80-7.20 (m, 8H); 5.60 (m, 1H); 5.24 (m, 2H); 4.18 (m, 2H); 3.85 (m, 2H); 3.65 (m, 2H); 3.50 (m, 3H); 3.20 (m, 5H); 1.20 (m, 12H); 0.80 (m, 6H) | +++ |
| 184 | 769.85 | 3.4 | DMSO-d6: 8.40-7.20 (m, 10H); 5.25 (m, 2H); 4.10 (m, 2H); 3.85 (m, 4H); 3.44 (m, 5H); 2.40 (m, 1H); 2.10 (m, 6H); 1.50 (m, 4H); 1.20 (m, 1H); 1.20 (m, 1H); 1.0-0.75 (m, 12H) | +++ |
| 185 | 839.52 | 7.18 | | +++ |
| 186 | 791.63 | 8.09 | | +++ |
| 187 | 799.6 | 8.69 | | +++ |
| 188 | 836.65 | 6.97 | | +++ |
| 189 | 848.36 | 2.92 | | ++ |
| 190 | | | | +++ |
| 191 | 791.56 | 14.92 | | +++ |
| 192 | 673.75 | 2.47 | | ++ |
| 193 | 791.6 | 15.32 | | ++ |
| 194 | 809.61 | 7.83 | | +++ |
| 195 | 735.74 | 2.5 | | ++ |
| 196 | 792.08 | 2.67 | | ++ |
| 197 | 647.96 | 2.19 | | ++ |
| 198 | 807.6 | 7 | | +++ |
| 199 | 857.55 | 8.2 | | +++ |
| 200 | 767.6 | 15.1 | | ++ |
| 201 | 847.6 | 16.57 | | +++ |
| 202 | 753.63 | 6.36 | | ++ |
| 203 | 815.6 | 6.43 | | +++ |
| 204 | 733.7 | 6.71 | | +++ |
| 205 | 733.65 | 6.7 | | +++ |
| 206 | 743.55 | 17.18 | | +++ |
| 207 | 809.64 | 7.95 | | +++ |
| 208 | 779.63 | 8.09 | | +++ |
| 209 | 693.56 | 7.95 | | ++ |
| 210 | 725.48 | 2.58 | 1H NMR (300 MHz, DMSO) d 12.01 (s, 2H), 7.38 (s, 6H), 7.20-6.81 (m, 8H), 5.19-4.81 (m, 6H), 3.58 (d, J = 48.3 Hz, 4H), 3.27 (s, 8H), 2.28 (s, 2H), 2.00 (d, J = 8.1 Hz, 6H). | ++ |
| 211 | 777.56 | 12.7 | | +++ |
| 212 | 777.58 | 13.12 | | +++ |
| 213 | 791.6 | 8.9 | | +++ |
| 214 | 784.57 | 8.97 | | +++ |
| 215 | 807.57 | 8.52 | | +++ |
| 216 | 833.09 | 831.17 | | +++ |
| 217 | 851.91 | 4.22 | | +++ |
| 218 | 851.95 | 3.69 | H NMR (300.0 MHz, DMSO) d 7.85-7.79 (m, 4H), 7.55-7.47 (m, 4H), 5.30-5.26 (m, 2H), 4.36 (dd, J = 11.6, 16.4 Hz, 4H), 4.15 (d, J = 7.3 Hz, 2H), 3.91 (s, 4H), 3.37 (s, 6H), 2.40-1.90 (m, 10H) and 0.93-0.79 (m, 12H) ppm | +++ |
| 219 | 839.58 | 19.68 | | +++ |
| 220 | 795.58 | 8.73 | | +++ |
| 221 | 843.5 | 10.11 | | +++ |
| 222 | 823.63 | 8.1 | | +++ |
| 223 | 763.77 | 2.88 | H NMR (300.0 MHz, DMSO) d 9.42 (s, 2H), 8.49 (s, 2H), 8.29 (d, J = 8.1 Hz, 2H), 7.87 (d, J = 8.6 Hz, 2H), 5.27 (dd, J = 5.2, 8.0 Hz, 2H), 4.15 (d, J = 7.5 Hz, 2H), 3.95-3.65 (m, 4H), 3.54 (s, 6H), 2.45 (m, 2H), 2.30-1.98 (m, 6H), 1.56-1.44 (m, 4H) and 1.08-0.78 (m, 12H) ppm | +++ |
| 224 | 457.29 | 1.73 | | + |
| 225 | 677.6 | 2.72 | | + |
| 226 | 663 | 2.71 | | ++ |
| 227 | 477.8 | 2.32 | | + |
| 228 | 463.72 | 2.34 | | + |
| 229 | 771.65 | 2.14 | | +++ |
| 230 | 777.76 | 3.67 | | ++ |
| 231 | 792.01 | 2.61 | | + |
| 232 | 778.05 | 2.62 | | +++ |
| 233 | 853.49 | 9.42 | | +++ |
| 234 | 787.58 | 9.61 | | |

TABLE 2-continued

| # | M + 1 (obs) | RT (min) | 1H-NMR | EC50_1b (uM) |
|---|---|---|---|---|
| 235 | 795.6 | 6.66 | | +++ |
| 236 | 754.5 | 20.04 | | +++ |
| 237 | 805.68 | 8.38 | | +++ |
| 238 | 767.5 | 15.1 | | ++ |
| 239 | 739.64 | 8.23 | | +++ |
| 240 | 787.62 | 7.9 | | +++ |
| 241 | 783.5 | 7.77 | | +++ |
| 242 | 809.58 | 8.45 | | +++ |
| 243 | 787.62 | 8 | | +++ |
| 244 | 787.59 | 7.73 | | +++ |
| 245 | | | | +++ |
| 246 | 793.6 | 7.58 | | +++ |
| 247 | 820.6 | 9.01 | | +++ |
| 248 | 791.68 | 8.46 | | +++ |
| 249 | 791.65 | 7.41 | | +++ |
| 250 | 799.58 | 11.27 | | +++ |
| 251 | 763.65 | 9.92 | | +++ |
| 252 | 819.68 | 8.5 | | +++ |
| 253 | 806.7 | 8.66 | | +++ |
| 254 | 812.92 | 11.44 | | +++ |
| 255 | 777.72 | 2.88 | | +++ |
| 256 | 663.74 | 2.97 | | ++ |
| 257 | 677.7 | 2.96 | | ++ |
| 258 | 799.61 | 2.09 | | +++ |
| 259 | 791.63 | 1.6 | | +++ |
| 260 | 881.61 | 10.31 | | +++ |
| 261 | 805.68 | 8.53 | | +++ |
| 262 | 812.7 | 8.39 | | +++ |
| 263 | 867.77 | 9.58 | | +++ |
| 264 | 868.5 | 9.88 | | +++ |
| 265 | 809.61 | 7.19 | | +++ |
| 266 | 834.6 | 11.94 | | +++ |
| 267 | 791.7 | 8.03 | | +++ |
| 268 | 850.5 | 7.99 | | +++ |
| 269 | 792.5 | 8.74 | | +++ |
| 270 | 836.5 | 7.46 | | ++ |
| 271 | 791.67 | 2.94 | | +++ |
| 272 | 777.85 | 2.64 | | +++ |
| 273 | 671.4 | 2.4 | | + |
| 274 | 791.56 | 10.87 | | +++ |
| 275 | 671.57 | 2.42 | | ++ |
| 276 | 833.58 | 9 | | +++ |
| 277 | 847.53 | 9.44 | | +++ |
| 278 | 837.6 | 18.4 | | +++ |
| 279 | 875.59 | 10.42 | | +++ |
| 280 | 827.5 | 8.83 | | +++ |
| 281 | 841.5 | 9.28 | | +++ |
| 282 | 855.6 | 9.73 | | +++ |
| 283 | 671.16 | 1.84 | | + |
| 284 | 833.6 | 9.29 | | +++ |
| 285 | 823.58 | 8.9 | | +++ |
| 286 | 823.6 | 8.88 | | +++ |
| 287 | 787.47 | 7.34 | | +++ |
| 288 | 789.56 | 7.7 | | +++ |
| 289 | 826.7 | 8.69 | | +++ |
| 290 | 881.51 | 9.93 | | +++ |
| 291 | 705.91 | 1.94 | | ++ |
| 292 | 691.92 | 1.94 | | ++ |
| 293 | 820.28 | 2.06 | | +++ |
| 294 | 806.26 | 1.96 | | +++ |
| 295 | 848.39 | 1.96 | | +++ |
| 296 | 834.37 | 2.08 | | +++ |
| 297 | 819.54 | 8.9 | | +++ |
| 298 | 819.64 | 1.95 | | +++ |
| 299 | 877.52 | 9.25 | | +++ |
| 300 | 805.51 | 8.97 | | +++ |
| 301 | 805.48 | 9.11 | | +++ |
| 302 | 819.5 | 1.91 | 1H NMR (300 MHz, Acetone) d 11.30 (d, J = 9.5 Hz, 2H), 7.96-7.33 (m, 10H), 6.13 (d, J = 29.6 Hz, 2H), 5.30 (t, J = 7.7 Hz, 2H), 4.34 (t, J = 7.8 Hz, 4H), 3.58 (d, J = 20.9 Hz, 6H), 3.34 (t, J = 8.1 Hz, 2H), 2.58 (dt, J = 19.5, 9.8 Hz, 2H), 2.32 (t, J = 17.6 Hz, 4H), 1.60 (td, J = 13.5, 6.7 Hz, 4H), 1.04 (t, J = 7.4 Hz, 6H), 0.97-0.74 (m, 12H). | +++ |
| 303 | 855.54 | 2.16 | | +++ |
| 304 | 849.46 | 8.4 | | +++ |
| 305 | 803.45 | 8.11 | | +++ |
| 306 | 815.48 | 8.06 | | +++ |
| 307 | 793.51 | 7.72 | | +++ |
| 308 | 396.93 | 4.48 | | -- |
| 309 | 477.04 | 6.22 | | -- |
| 310 | 791.5 | 7.87 | | +++ |
| 311 | 820.7 | 9.61 | | +++ |
| 312 | 767.24 | 2.17 | | |
| 313 | 791.19 | 8.17 | | +++ |
| 314 | 827.5 | 9.53 | | +++ |
| 315 | 863.94 | 2.84 | | +++ |
| 316 | 899.67 | 3.1 | | +++ |
| 317 | 849.49 | 8.95 | | +++ |
| 318 | 835.45 | 8.76 | | +++ |
| 319 | 853.36 | 9.75 | | +++ |
| 320 | 791.68 | 8.27 | | +++ |
| 321 | 853.36 | 10.18 | | +++ |
| 322 | 809.35 | 16.6 | | +++ |
| 323 | 867.34 | 3.16 | | +++ |
| 324 | 763.23 | 11.09 | | +++ |
| 325 | 881.13 | 2.05 | 1H NMR (300 MHz, DMSO) d 7.99 (d, J = 11.6 Hz, 4H), 7.76 (s, 5H), 7.35 (d, J = 7.9 Hz, 2H), 5.25-5.15 (m, 2H), 4.03 (d, J = 8.0 Hz, 2H), 3.89 (d, J = 9.4 Hz, 2H), 3.59 (d, J = 9.7 Hz, 2H), 3.53 (s, 6H), 2.29-2.17 (m, 2H), 2.11-2.01 (m, 2H), 1.98-1.84 (m, 2H), 1.15 (d, J = 38.2 Hz, 12H), 0.80 (dd, J = 10.4, 6.8 Hz, 12H). | +++ |
| 326 | 785.26 | 1.73 | | +++ |
| 327 | 805 | 2.83 | | +++ |
| 328 | 785.4 | 1.81 | | +++ |
| 329 | 785 | 2.13 | | +++ |
| 330 | 841.69 | 8.88 | | +++ |
| 331 | 881.56 | 9.71 | | +++ |
| 332 | 853.7 | 9.26 | | +++ |
| 333 | | | | -- |
| 334 | | | | -- |
| 335 | | | | -- | uM: +++ <= 0.005 < ++ <= 5.0 < +

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of formula (IIB):

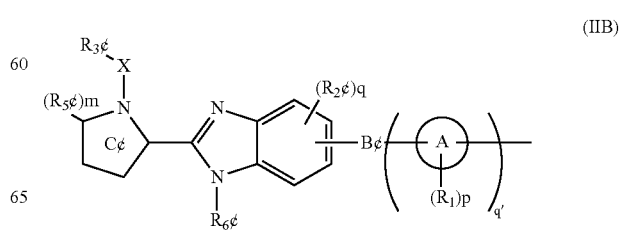

(IIB)

-continued

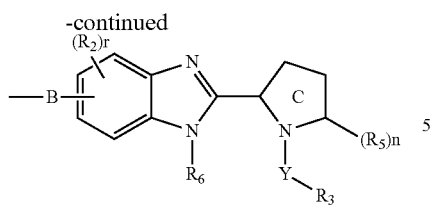

or pharmaceutically acceptable salts thereof, wherein
each A is independently $C_{6-14}$ aryl, 4-12 membered heterocycle, $C_{3-10}$ cycloalkyl, or 5-12 membered heteroaryl;
B and B' are each independently absent, $C_{1-6}$ alkyl, $C_{2-6}$ alkenyl, or $C_{2-6}$ alkynyl;
$R_1$ is halogen, $-OR_a$, $-NR_aR_b$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, $-P(=O)OR_aOR_b$, $C_{1-6}$ alkyl which is unsubstituted or substituted one or more times by $R^{10}$, $C_{2-6}$ alkenyl which is unsubstituted or substituted one or more times by $R^{10}$, $C_{2-6}$ alkynyl which is unsubstituted or substituted one or more times by $R^{10}$, or any two occurrences of $R_1$ can be taken together with the atoms to which they are attached to form a 5-7 cycloalkyl which is unsubstituted or substituted one or more times by $R^{11}$ or a 5-7 membered heterocycle which is unsubstituted or substituted one or more times by $R^{12}$;
$R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
$R_2$' and $R_2$ are each independently halogen, $C_{1-10}$ alkyl, $C_{1-6}$ halogenated alkyl, $-(CH_2)_{1-6}OH$, $-OR_a$, $-C(=O)OR_a$, $-NR_aR_b$, $-NR_bC(=O)R_a$, $-C(O)NR_aR_b$, $-S(O)_{0-3}R_a$, $C_{6-12}$ aryl, or 5-12 membered heteroaryl;
$R_3$ and $R_3$' are each independently H, $C_{1-18}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 membered heteroaryl which is unsubstituted or substituted one or more times by $R^{11}$, 6-18 membered heteroaralkyl which is unsubstituted or substituted one or more times by $R^{11}$, 3-12 membered heterocycle which is unsubstituted or substituted one or more times by $R^{12}$, or 4-18 membered heterocycle-alkyl which is unsubstituted or substituted one or more times by $R^{12}$;
X and Y are each independently

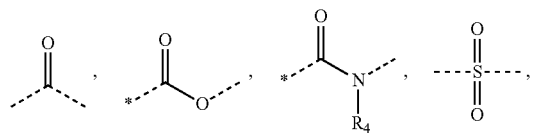

or a bond;
wherein the asterisk (*) indicates the point of attachment to the nitrogen of ring C or C';
$R_4$ is H, $C_{1-6}$alkyl, or halogenated $C_{1-6}$alky;

$R_5$ and $R_5$' are each independently halogen, $-NR_aR_b$, $-C(O)NR_aR_b$, $-(CH_2)_{1-6}OH$, $C_{1-6}$ alkyl, $C_{1-6}$ halogenated alkyl, hydroxyl, $C_{6-14}$ aryl, or $C_{1-6}$ alkoxy; wherein two occurrence of $R_4$ can be taken together with the atoms to which they are attached to form a $C_{1-6}$alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein two occurrence of $R_4$' can be taken together with the atoms to which they are attached to form a $C_{1-6}$ alkenyl which is unsubstituted or substituted one or more times by $R^{10}$, a 3-7 cycloalkyl which is unsubstituted or substituted one or more times by $R^{11}$ or a 4-7 membered heterocycle which is unsubstituted or substituted one or more times by $R^{12}$; wherein $R_a$-$R_b$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl;
$R_6$ and $R_6$' are each independently H, $C_{1-6}$alkyl, $-(CH_2)_{1-6}OH$, $C_{2-6}$alkenyl, or $C_{2-6}$alkynyl;
m, and n, combined are 1, 2, 3 or 4;
p is 0, 1, 2, 3 or 4;
q' is 0, 1 or 2;
q and r are each independently 0, 1, 2, 3 or 4;
$R^{10}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$;
$R^{11}$ is halogen, $-OR_a$, $-NR_aR_b$, $-C(=O)OR_a$, $C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl; and
$R^{12}$ is halogen, $-OR_a$, oxo, $-NR_aR_b$, $=NO-R_c$, $-C(=O)OR_a$, $-C(O)NR_aR_b$, $-C(=O)OH$, $-C(=O)R_a$, $-C(=NOR_c)R_a$, $-C(=NR_c)NR_aR_b$, $-NR_dC(=O)NR_aR_b$, $-NR_bC(=O)R_a$, $-NR_dC(=NR_c)NR_aR_b$, $-NR_bC(=O)OR_a$, $-OC(=O)NR_aR_b$, $-OC(=O)R_a$, $-OC(=O)OR_a$, hydroxyl, nitro, azido, cyano, $-S(O)_{0-3}R_a$, $-SO_2NR_aR_b$, $-NR_bSO_2R_a$, $-NR_bSO_2NR_aR_b$, or $-P(=O)OR_aOR_b$, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18membered heterocycle-alkyl.

2. The compound according to claim 1, wherein each A is independently cyclopropyl, cyclohexyl, pyrrolidinyl, pyrazolidinyl, imidazolidinyl, piperazinyl, piperadinyl, phenyl, naphthalenyl, thienyl, furanyl, pyrrolyl, pyrazolyl, imidazolyl, thiazolyl, thiadiazolyl, oxazolyl, oxadiazolyl, pyridyl, pyrimidyl, pyrazinyl, pyridazinyl, indolyl, indazolyl, benzimidazolyl, benzoxazolyl, benzodioxolyl, benzothiazolyl, benzothiadiazolyl, benzothiophenyl, dihydrobenzodioxinyl, thienofuranyl, thienothienyl, thienopyrrolyl, quinolinyl, quinoxalinyl, quinazolinyl, cinnolinyl, or triazolyl; and wherein each A is independently substituted with $(R_1)_p$.

3. The compound according to claim 2, wherein each A is independently piperazinyl, piperadinyl, thienyl, furanyl, pyrrolyl, pyrazolyl, imidazolyl, thiazolyl, oxazolyl, thiadiazolyl, pyrrolidinyl, pyridyl, pyrimidinyl, pyrazinyl, pyridazinyl, benzoxazolyl, benzodioxolyl, benzothiazolyl, benzothiadiazolyl, benzothiophenyl, dihydrobenzodioxinyl, thienofuranyl, thienothienyl, quinolinyl, or triazolyl, each of which is substituted with $(R_1)_p$.

4. The compound according to claim 1, wherein each A is independently a 5-12 membered heteroaryl wherein the heteroatom(s) are selected from the group consisting of oxygen and sulphur; wherein each A is independently substituted with $(R1)_p$.

5. The compound according to claim 1, wherein B and B' are independently absent, $C_{1-6}$ alkyl or $C_{2-6}$ alkynyl.

6. The compound according to claim 1, wherein

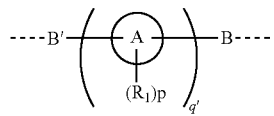

is selected from the group consisting of:

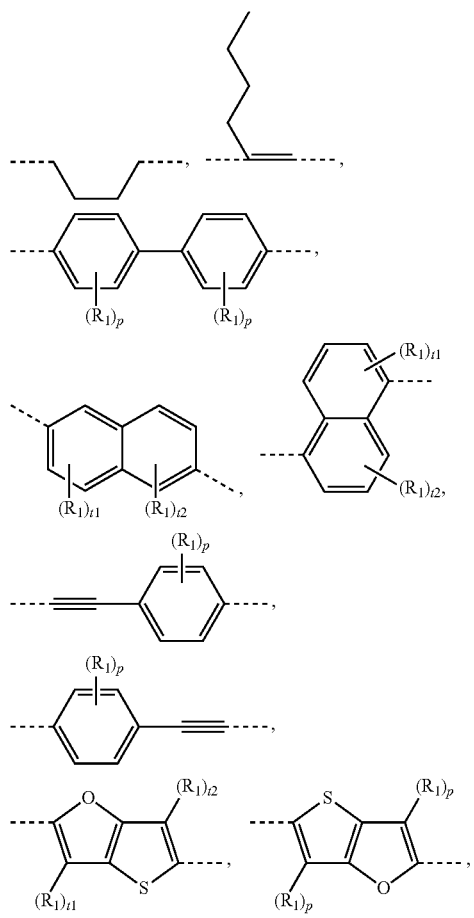

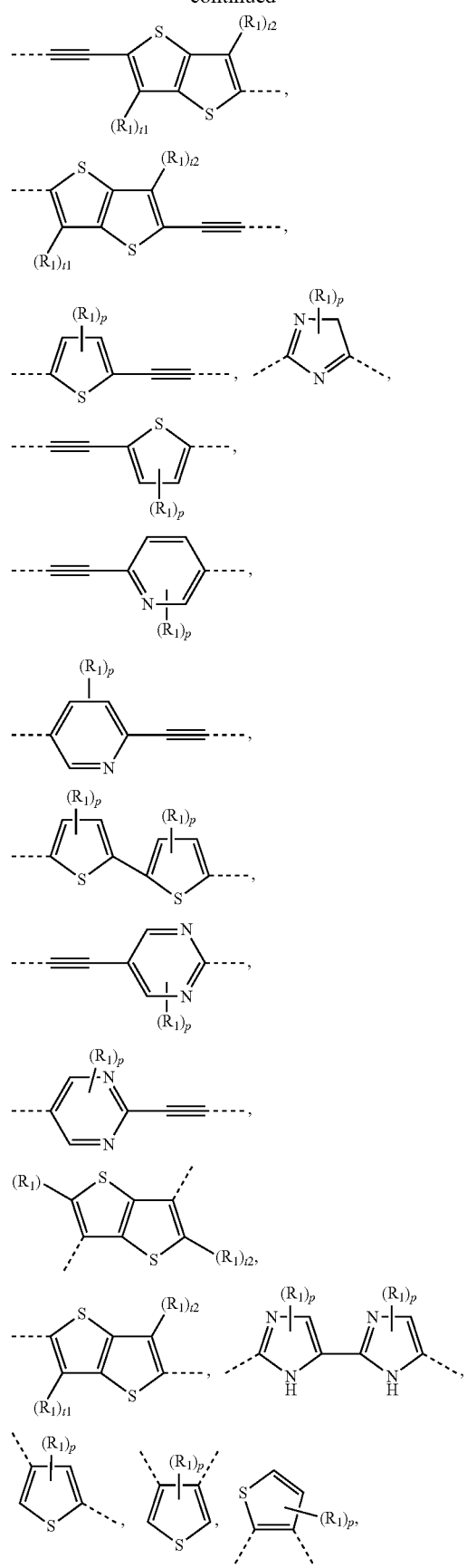

-continued
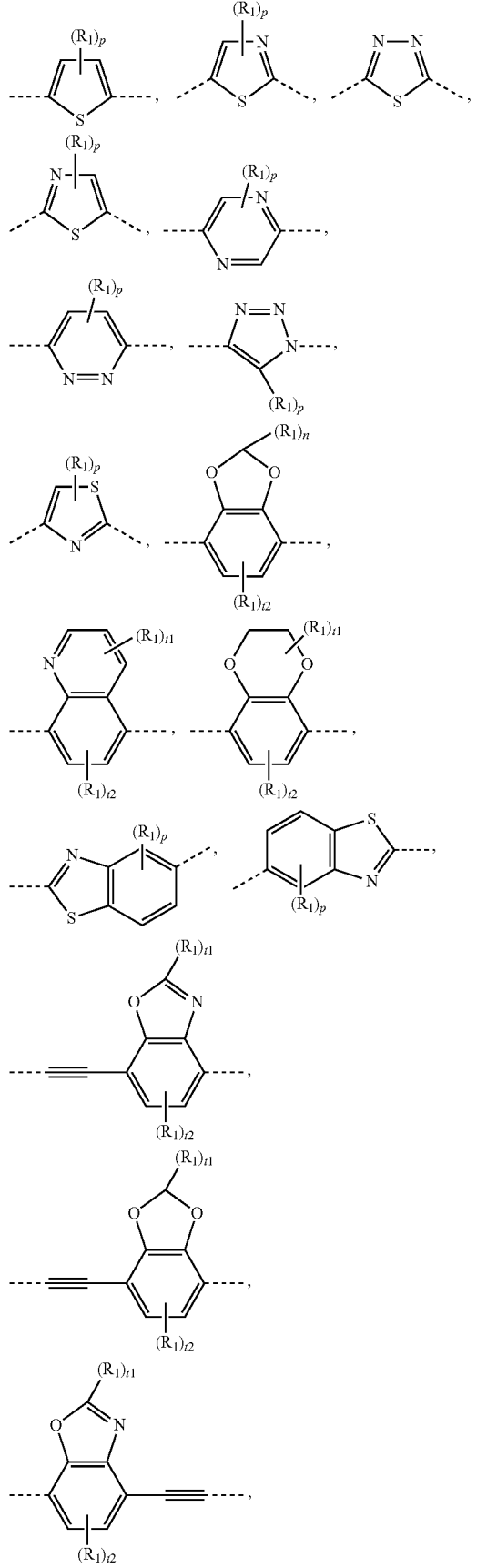
-continued
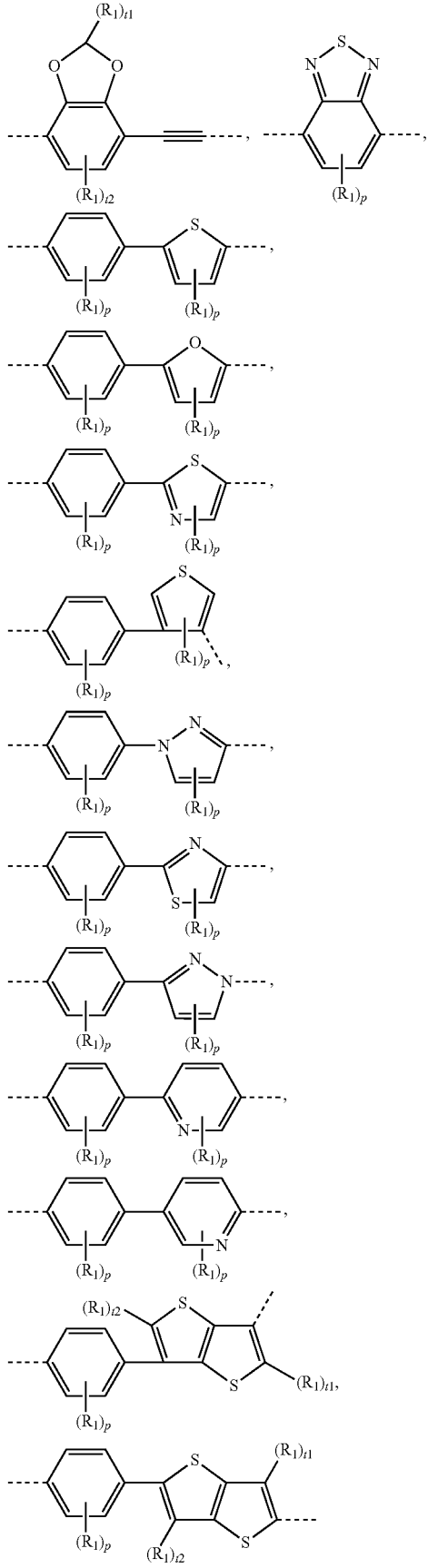

-continued

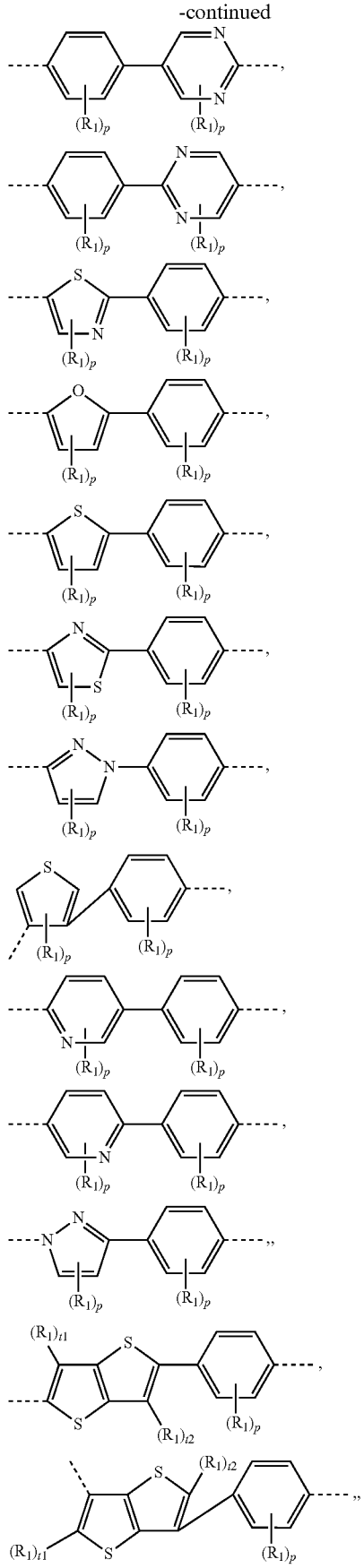

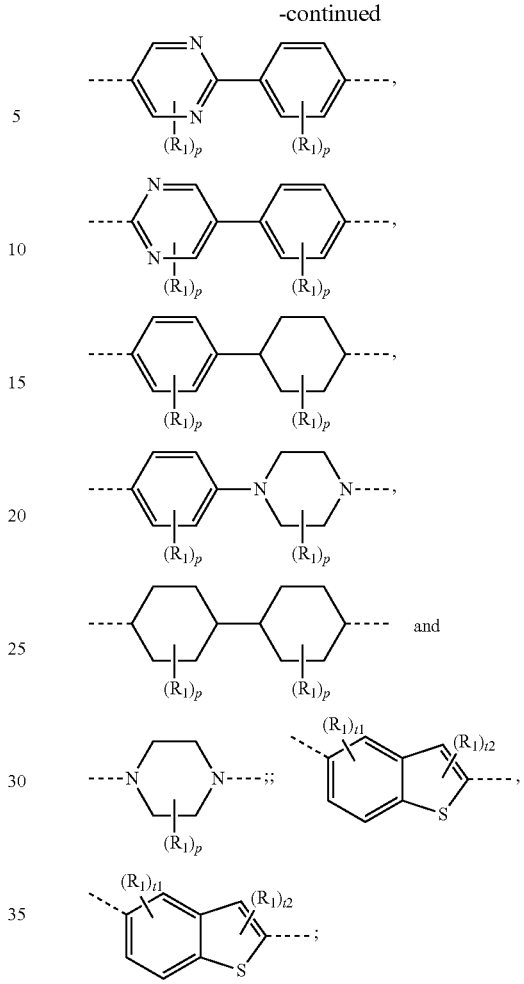

and t1+t2=p.

7. The compound according to claim 1, wherein $R_1$ is halogen, $C_{1-4}$ alkyl which is unsubstituted or substituted one or more times by $R^{10}$, —C(=O)$OR_a$, —C(O)$NR_aR_b$, hydroxyl, cyano, or $C_{1-3}$ alkoxy.

8. The compound according to claim 7, wherein $R_1$ is chloro, fluoro, bromo, methyl, ethyl, propyl, butyl, —$CH_2OH$, difluoromethyl, trifluoromethyl, hydroxyl, cyano, or methoxy.

9. The compound according to claim 1, wherein each $R_2'$ are independently fluoro or methyl.

10. The compound according to any one of claims 9, wherein q is 0.

11. The compound according to claim 1, wherein each $R_2$ are independently fluoro or methyl.

12. The compound according to claim 11, wherein r is 0.

13. The compound according to claim 1, wherein $R_6$ and $R_6'$ are H or methyl.

14. The compound according to claim 1, wherein $R_5$ and $R_5'$ in formula (IIB), are each independently halogen, methyl, ethyl, isopropyl, di-fluoromethyl, di-fluoroethyl, trifluoromethyl, tri-fluoroethyl, —$CH_2OH$, —$NR_aN_b$, t-butoxy-, or hydroxyl; or two $R_5$ groups together with the atoms to which they are attached form fused cyclopropyl, spiro cyclopropyl or

two $R_5'$ groups together with the atoms to which they are attached form fused cyclopropyl, spiro cyclopropyl or

15. The compound according to claim 1, wherein m and n are independently 1 or 2.

16. The compound according to claim 15, wherein m and n are 1.

17. The compound according to claim 1, wherein X and Y are

18. The compound according to claim 1, wherein $R_3$ and $R_3'$ are each independently, $C_{1-8}$ alkyl which is unsubstituted or substituted one or more times by $R^{10}$, $C_{2-8}$ alkenyl which is unsubstituted or substituted one or more times by $R^{10}$, $C_{2-8}$ alkynyl which is unsubstituted or substituted one or more times by $R^{10}$, phenyl which is unsubstituted or substituted one or more times by $R^{11}$, $C_{7-8}$ aralkyl which is unsubstituted or substituted one or more times by $R^{11}$, 5-6 membered heteroaryl which is unsubstituted or substituted one or more times by $R^{11}$, 6-8 membered heteroaralkyl which is unsubstituted or substituted one or more times by $R^{11}$, 3-6 membered heterocycle which is unsubstituted or substituted one or more times by $R^{12}$, or 4-8 membered heterocycle-alkyl which is unsubstituted or substituted one or more times by $R^{12}$.

19. The compound according to claim 1, wherein $R^{10}$ is halogen, —$OR_a$, oxo, —$NR_aR_b$, =NO—$R_c$, —C(=O)$OR_a$, —C(O)$NR_aR_b$, —C(=O)OH, —C(=O)$R_a$, —C(=$NOR_c$)$R_a$, —C(=$NR_c$)$NR_aR_b$, —$NR_dC$(=O)$NR_aR_b$, —$NR_bC$(=O)$R_a$, —$NR_dC$(=$NR_c$)$NR_aR_b$, —$NR_bC$(=O)$OR_a$, —OC(=O)$NR_aR_b$, —OC(=O)$R_a$, —OC(=O)$OR_a$, hydroxyl, nitro, azido, cyano, —S(O)$_{0-3}R_a$, —SO$_2NR_aR_b$, —$NR_bSO_2R_a$, or —$NR_bSO_2NR_aR_b$, wherein $R_a$-$R_d$ are each independently H, $C_{1-12}$ alkyl, $C_{2-12}$ alkenyl, $C_{2-12}$ alkynyl, $C_{6-12}$ aryl, $C_{7-16}$ aralkyl, 5-12 membered heteroaryl, 6-18 membered heteroaralkyl, 3-12 membered heterocycle, or 4-18 membered heterocycle-alkyl.

20. The compound according to claim 1, wherein $R_a$-$R_d$ are each independently H, $C_{1-6}$ alkyl, $C_{2-6}$ alkenyl, $C_{2-6}$ alkynyl, phenyl, $C_{7-8}$ aralkyl, 5-6 membered heteroaryl, 6-8 membered heteroaralkyl, 5-6 membered heterocycle, or 6-8 membered heterocycle-alkyl.

21. The compound according to claim 1, for treating or preventing a Hepatitis C viral infection in a human.

22. A pharmaceutical composition comprising at least one compound according to claim 1 and at least one pharmaceutically acceptable carrier or excipient.

* * * * *